Figure 1:
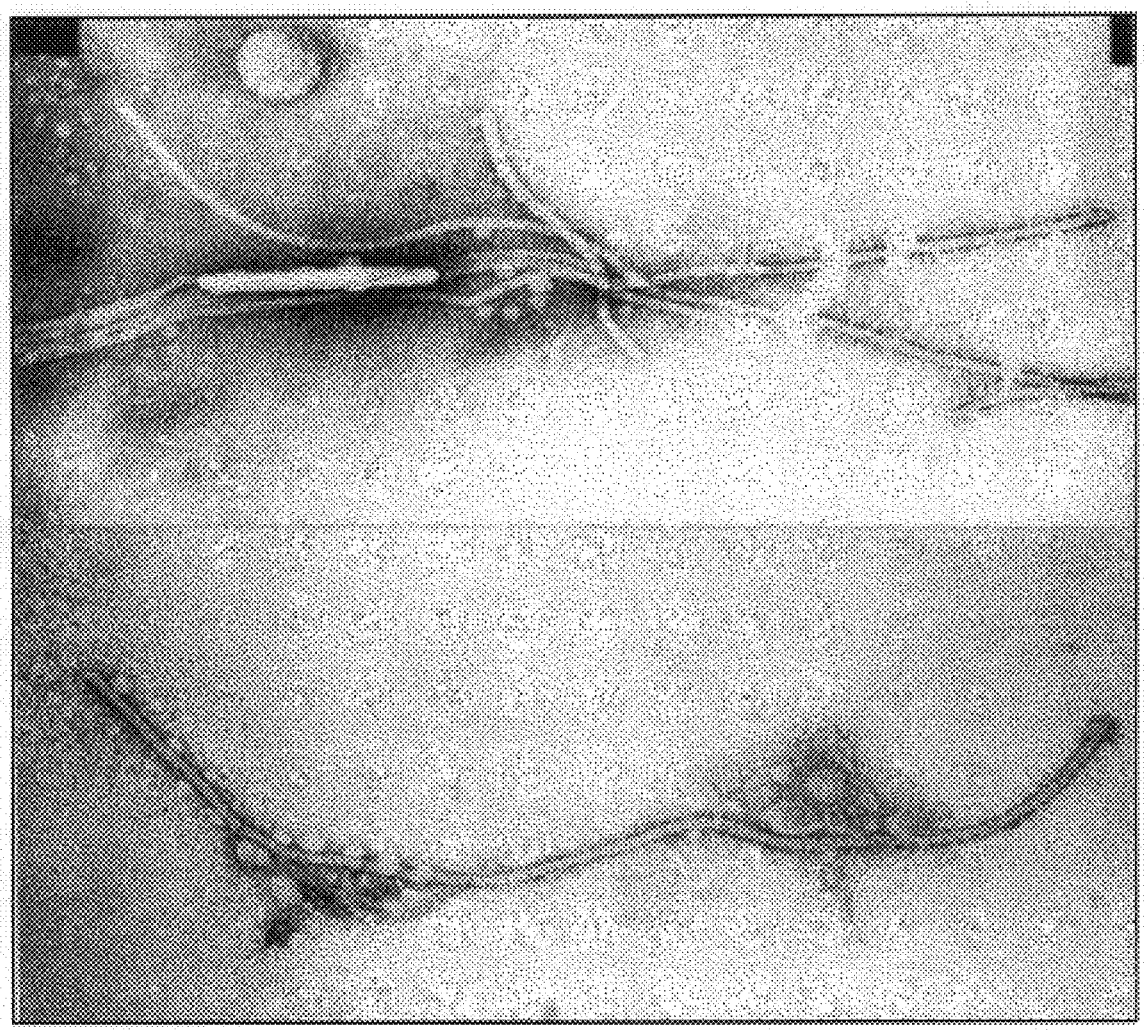

United States Patent [19]
Gonsalves et al.

[11] Patent Number: 5,907,085
[45] Date of Patent: May 25, 1999

[54] GRAPEVINE LEAFROLL VIRUS PROTEINS AND THEIR USES

[75] Inventors: Dennis Gonsalves; Kai-Shu Ling, both of Geneva, N.Y.

[73] Assignee: Cornell Research Foundation, Inc., Ithaca, N.Y.

[21] Appl. No.: 08/770,544

[22] Filed: Dec. 20, 1996

Related U.S. Application Data

[60] Provisional application No. 60/009,008, Dec. 21, 1995.

[51] Int. Cl.$^6$ ...................................................... A01H 1/04
[52] U.S. Cl. ........................ 800/205; 530/300; 530/350; 435/410; 435/419
[58] Field of Search .............................. 435/320.1, 172.3, 435/91.2, 410, 419; 530/300, 350; 800/205

[56] References Cited

U.S. PATENT DOCUMENTS

| | | | |
|---|---|---|---|
| 4,358,535 | 11/1982 | Falkow et al. | 435/5 |
| 4,480,040 | 10/1984 | Owens et al. | 435/6 |
| 5,043,272 | 8/1991 | Hartley | 435/5 |
| 5,104,792 | 4/1992 | Silver et al. | 435/6 |
| 5,106,727 | 4/1992 | Hartley et al. | 435/6 |
| 5,196,305 | 3/1993 | Findlay et al. | 435/6 |
| 5,288,611 | 2/1994 | Kohne | 435/6 |
| 5,322,770 | 6/1994 | Gelfand | 435/6 |
| 5,328,825 | 7/1994 | Warren, III et al. | 435/6 |

OTHER PUBLICATIONS

Zimmerman et al., "Characterization and Serological Detection of Four Closterovirus–like Particles Associated with Leafroll Disease on Grapevine," *Journal of Phytopathology*, 130:205–218 (1990).

Dolja et al., "Molecular Biology and Evolution of Closteroviruses: Sophisticated Build–up of Large RNA Genomes," *Annual Reviews on Phytopathology*, 32:261–285 (1994).

Ling et al., "Identification of a Coat Protein Gene and Partial Genome Organization of Grapevine Leafroll–Associated Closterovirus Type III," *Phytopathology* 84:1372 (1994) (Abstract).

Schell et al., "Transformation of 'Nova' Tangelo with the Coat Protein Gene of Citrus Tristeza Closterovirus," *Phytopathology*, 84:1076 (1994) (Abstract).

Habili et al., "Natural Spread and Molecular Analysis of Grapevine Leafroll–Associated Virus 3 in Australia," *Phytopathology*, 85:1418–1422 (1995).

Ling et al, "Partial Genome Organization of Grapevine Leafroll–Associated Closterovirus," *Phytopathology*, 85:1152 (1995) (Abstract).

(List continued on next page.)

*Primary Examiner*—James Ketter
*Assistant Examiner*—Irem Yucel
*Attorney, Agent, or Firm*—Nixon, Hargrave, Devans & Doyle LLP

[57] ABSTRACT

The present invention relates to an isolated protein or polypeptide corresponding to a coat protein or polypeptide of a grapevine leafroll virus. The encoding DNA molecule either alone in isolated form or in an expression system, a host cell, or a transgenic grape plant is also disclosed. Another aspect of the present invention relates to a method of imparting grapevine leafroll resistance to grape plants by transforming them with the DNA molecule of the present invention. A method for imparting tristeza virus resistance in citrus plants using the DNA molecule of the present invention is also disclosed.

34 Claims, 57 Drawing Sheets

OTHER PUBLICATIONS

Minafra et al., "Detection of grapevine closterovirus A in infected grapevine tissue by reverse transcription–polymerase chain reaction," *Vitis,* 31:221–227 (1992).

Wetzel et al., "A highly sensitive immunocapture polymerase chain reaction method for plum pox potyvirus detection," *Journal of Virological Methods,* 39:27–37 (1992).

Karasev et al., "Screening of the closterovirus genome by degenerate primer–mediated polymerase chain reaction," *Journal of General Virology,* 75:1415–1422 (1994).

Minafra et al., "Sensitive detection of grapevine virus A, B, or leafroll–associated III from viruliferous Mealybugs and infected tissue by cDNA amplification," *Journal of Virological Methods,* 47:175–188 (1994).

Saldarelli et al., "Detection of grapevine leafroll–associated closterovirus III by molecular hybridization," *Plant Pathology,* 43:91–96 (1994).

Krastanova et al. Plant Cell Reports, 1995, vol. 14, pp. 550–554.

Le Gall et al. Plant Science, 1994, vol. 102, pp. 161–170.

Beachy et al. Annual Review of Plant Pathology, 1990, vol. 28, pp. 451–474.

Candresse et al. Archives of Virology, 1995, Supplement 1, pp. 461–464.

Genbank accessions U22170 and U22158, submitted Mar. 1995.

```
BYV_p64     115_VGCKFNIQSVTEFVKKINGNVAEPSLVEHCWSLSNSCGELINPKDTKRFV
CTV_p61     108_VGCRFTLNDVESYLMSRGEDFADLAAVEHSWCLSNSCSRLLSSTEIDANK
LIYV_P59    131_EGCSFTEQQVVEKYPQVDSLVAKIL.....YRVCNSLGKLLDLKDFENKN
GLRaV3_p55  114_VDSNLPKKDRDDIME...ASRRLSPSDAAFCRAVSVQVGKYVDVTQNLEST

CONSENSUS       vgc-f----v-e---------a--------w--sns-g-l----d-----

BYV_p64         SLIFKGKDLAESTDEAIVS..SSYLDYLSHCLNLYETCNLSSNSGKKSLY
CTV_p61         TLVF.TKNFDSNISG..VT..TKLETYLSYCISLYKKHCM.KDDDYFNLI
LIYV_P59        ISGFEINTAQDSPTVADDN..ES.NDFFRECVNDQRYYSSLSGSKLGKAK
GLRaV3_p55      IVPLRVMEIKKRRGSAHVSLPKVVSAYVDFYTNLQELLSDEVTRARTDTV

CONSENSUS       ---f----------a-v--------yl--c-nl-----------------

BYV_p64         DEFLKHVIDYL...ENSDLEYRSPSDNPLVAGILYDMCFEYNTLKSTYLK
CTV_p61         LPMFNCLMKVL...ASLGLFYEKHADNPLLTGMLIEFCLENKVYYSTFKV
LIYV_P59        LEANAYIFKILLKSASGEFDIDRLSRNPLAISKFMNLYTNHVTDSETFKS
GLRaV3_p55      SAYATDSMAFLVKMLPLT......AREQWLKDVLGYLLVRRRPANFSYDV

CONSENSUS       ----------L-------l-------npl----l--lc--------t---

BYV_p64         NIESFDCFLSLYLPLLSEVFSMNWERPAPDVRLLFELDAAELLLKVPTIN
CTV_p61         NLDNVRLFKSKVLPVVLTVWDISEPDDPVDERVLIPFDPTDFVLDLPKLN
LIYV_P59        KFEALKSIKTPFASFIKKAFGIR..........LNFEDSKIFYALPKER
GLRaV3_p55      RVAWVYDVIATLKLVIRLFFNKDTPGGIKDLKPCVPIESFDPFHELS...

CONSENSUS       --e------------i---f----------d------f---d-f--lp---

BYV_p64         MHDST...FLYKNKLRYLESYFEDDSNELIKVKVDSLL
CTV_p61         IHDTM...VVVGNQIRQLEYVVESDALDDLSQHVDLRL
LIYV_P59        QSDVLSDDMMVESIVRDAASFTVVSDNNYLPERVDRFV
GLRaV3_p55      ...........SYFSRLSYEMTTGKGGKICPEIAEKL

CONSENSUS       --d------------r-l---------------vd--l
```

*FIG. 3*

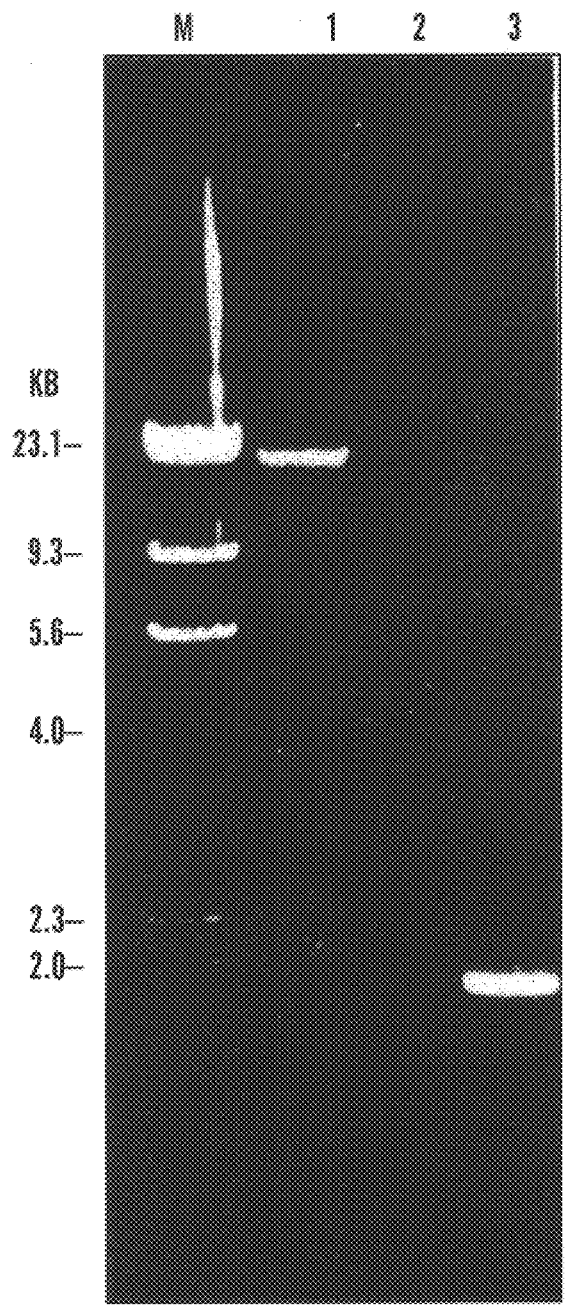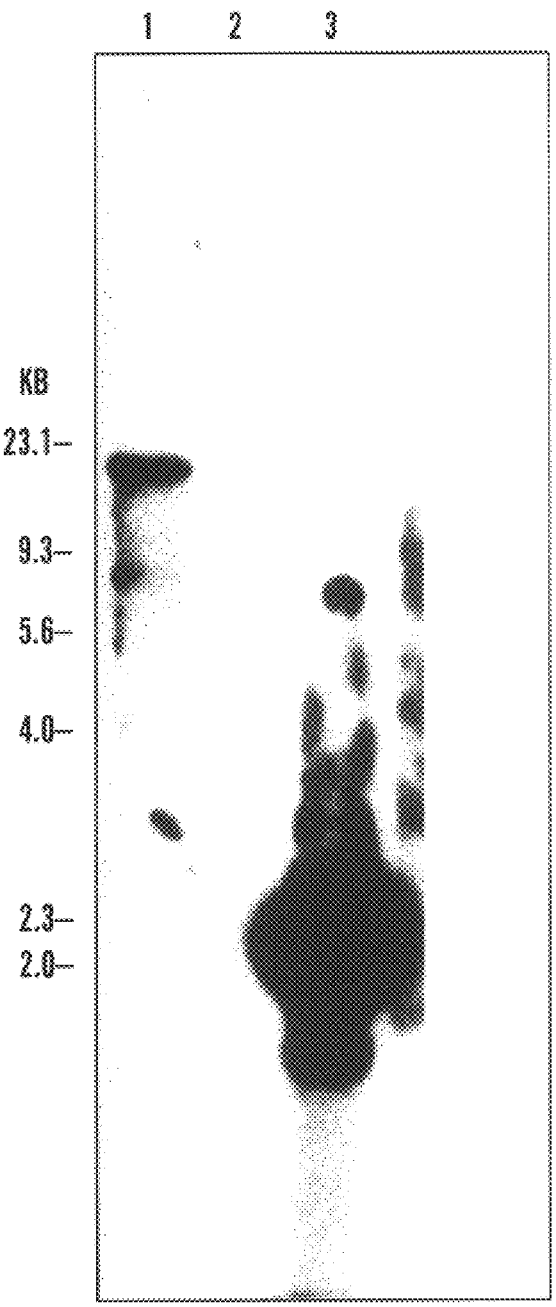
*FIG. 4A*  *FIG. 4B*

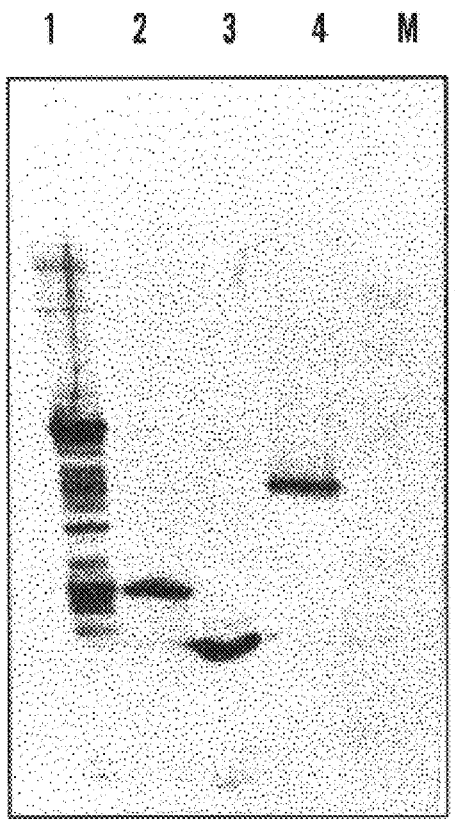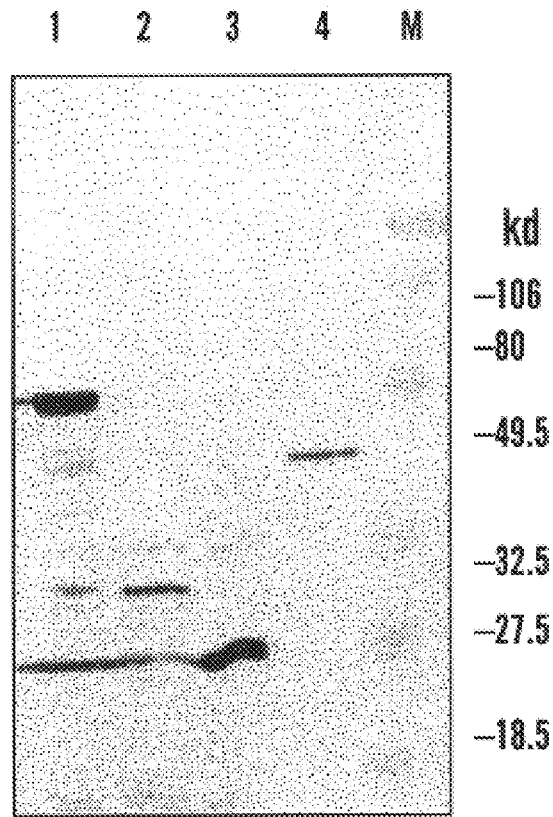
*FIG. 8A*  *FIG. 8B*

```
      ATGGCATTTGAACTGAAATTAGGGCAGATATATGAAGTCGTCCCCGAAAATAATTTGAGA
  1   ---------+---------+---------+---------+---------+---------+  60
      M  A  F  E  L  K  L  G  Q  I  Y  E  V  V  P  E  N  N  L  R   -

GTTAGAGTGGGGGATGCGGCACAAGGAAAATTTAGTAAGGCGAGTTTCTTAAAGTACGTT
 61   ---------+---------+---------+---------+---------+---------+ 120
      V  R  V  G  D  A  A  Q  G  K  F  S  K  A  S  F  L  K  Y  V   -

AAGGACGGGACACAGGCGGAATTAACGGGAATCGCCGTAGTGCCCGAAAAATACGTATTC
121   ---------+---------+---------+---------+---------+---------+ 180
      K  D  G  T  Q  A  E  L  T  G  I  A  V  V  P  E  K  Y  V  F   -

GCCACAGCAGCTTTGGCTACAGCGGCGCAGGAGCCACCTAGGCAGCCACCAGCGCAAGTG
181   ---------+---------+---------+---------+---------+---------+ 240
      A  T  A  A  L  A  T  A  A  Q  E  P  P  R  Q  P  P  A  Q  V   -

GCGGAACCACAGGAAACCGATATAGGGGTAGTGCCGGAATCTGAGACTCTCACACCAAAT
241   ---------+---------+---------+---------+---------+---------+ 300
      A  E  P  Q  E  T  D  I  G  V  V  P  E  S  E  T  L  T  P  N   -

AAGTTGGTTTTCGAGAAAGATCCAGACAAGTTCTTGAAGACTATGGGCAAGGGAATAGCT
301   ---------+---------+---------+---------+---------+---------+ 360
      K  L  V  F  E  K  D  P  D  K  F  L  K  T  M  G  K  G  I  A   -

TTGGACTTGGCGGGAGTTACCCACAAACCGAAAGTTATTAACGAGCCAGGGAAAGTATCA
361   ---------+---------+---------+---------+---------+---------+ 420
      L  D  L  A  G  V  T  H  K  P  K  V  I  N  E  P  G  K  V  S   -

GTAGAGGTGGCAATGAAGATTAATGCCGCATTGATGGAGCTGTGTAAGAAGGTTATGGGC
421   ---------+---------+---------+---------+---------+---------+ 480
      V  E  V  A  M  K  I  N  A  A  L  M  E  L  C  K  K  V  M  G   -

GCCGATGACGCAGCAACTAAGACAAAATTCTTCTTGTACGTGATGCAGATTGCTTGCACG
481   ---------+---------+---------+---------+---------+---------+ 540
      A  D  D  A  A  T  K  T  K  F  F  L  Y  V  M  Q  I  A  C  T   -

TTCTTTACATCGTCTTCGACGGAGTTCAAAGAGTTTGACTACATAGAAACCGATGATGGA
541   ---------+---------+---------+---------+---------+---------+ 600
      F  F  T  S  S  S  T  E  F  K  E  F  D  Y  I  E  T  D  D  G   -

AAGAAGATATATGCGGTGTGGGTATATGATTGCATTAAACAAGCTGCTGCTTCGACGGGT
601   ---------+---------+---------+---------+---------+---------+ 660
      K  K  I  Y  A  V  W  V  Y  D  C  I  K  Q  A  A  A  S  T  G   -

TATGAAAACCCGGTAAGGCAGTATCTAGCGTACTTCACACCAACCTTCATCACGGCGACC
661   ---------+---------+---------+---------+---------+---------+ 720
      Y  E  N  P  V  R  Q  Y  L  A  Y  F  T  P  T  F  I  T  A  T   -

CTGAATGGTAAACTAGTGATGAACGAGAAGGTTATGGCACAGCATGGAGTACCACCGAAA
721   ---------+---------+---------+---------+---------+---------+ 780
      L  N  G  K  L  V  M  N  E  K  V  M  A  Q  H  G  V  P  P  K   -

TTCTTTCCGTACACGATAGACTGCGTTCGTCCGACGTACGATCTGTTCAACAACGACGCA
781   ---------+---------+---------+---------+---------+---------+ 840
      F  F  P  Y  T  I  D  C  V  R  P  T  Y  D  L  F  N  N  D  A   -

ATATTAGCATGGAATTTAGCTAGACAGCAGGCGTTTAGAAACAAGACGGTAACGGCCGAT
841   ---------+---------+---------+---------+---------+---------+ 900
      I  L  A  W  N  L  A  R  Q  Q  A  F  R  N  K  T  V  T  A  D   -

AACACCTTACACAACGTCTTCCAACTATTGCAAAAGAAGTAG
901   ---------+---------+---------+---------+-- 942
      N  T  L  H  N  V  F  Q  L  L  Q  K  K  *
```

FIG. 10

```
              1                                                              50
BYV_CP        ..........  ..........  ..........  ..........  ..........
CTV_CP        ..........  ..........  ..........  ..........  ..........
LIYV_CP       ..........  ..........  ..........  ..........  ..........
GLRaV3_CP     MAFELKLGQI  YEVVPENNLR  VRVGDAAQGK  FSKASFLKYV  KDGTQAELTG

CONSENSUS     ----------  ----------  ----------  ----------  ----------

51                                                            100
BYV_CP        ..........  ..........  ..........  ..........  ..........
CTV_CP        ..........  ..........  ..........  ..........  MDDETKKLKN
LIYV_CP       ..........  ....MDTDGD  NDVFGSGNDT  RNNDDKKKEE  MKQNISDNSQ
GLRaV3_CP     IAVVPEKYVF  ATAALATAAQ  EPPRQPPAQV  AEPQETDIGV  VPESETLTPN

CONSENSUS     ----------  ----------  ----------  ----------  ----------

101                                                           150
BYV_CP        .....MGSAE  PISAIA..TF  ENVSL.AD.Q  TCLHGEDCDK  LRK......N
CTV_CP        KNKETKEGDD  VVAAES..SF  GSVNLHID.P  TLITMNDVRQ  LSTQQNAALN
LIYV_CP       IISTRDHEAD  IIGSISKEDL  SKIVVRVDRH  DALSANDVQS  FR...EAMIN
GLRaV3_CP     KLVFEKDPDK  FLKTMGKGIA  LDLAGVTHKP  KVI..NEPGK  VSVEVAMKIN

CONSENSUS     ---------d  -i-------f  --v----d--  -----nd---  l--------N 151                                                           200
BYV_CP        FEECLKLKG.  ...VPEDNLG  IALGLCLYSC  AT.IGTSNKV  NVQPTS.TFI
CTV_CP        RDLFLALKGK  YPNLPDKDKD  FHIAMMLYRL  AV.KSSSLQS  DDDTTGITYT
LIYV_CP       ...FMRDKDP  NRNQPSDKLI  IAMEVGVYQM  VINLGTSAKL  G.NANNLEFT
GLRaV3_CP     .AALMELCKK  VMGADDAATK  TKFFLYVMQI  ACTFFTS..S  STEFKEFDYI

CONSENSUS     ---f--lk--  ----pd----  ----l--y--  a----tS---  ----------

201                                                           250
BYV_CP        KASFGGGKEL  YLTHGELNSF  LGSQKLLEGK  PNKLRCFCRT  FQKDYISLRK
CTV_CP        R....EGVEV  DLSDKLWTDI  VYNSKGIGNR  TNALRVWGRT  NDALYLAFCR
LIYV_CP       IAYDQETRTY  KVAD..FVNY  MQSR..MRNS  PNVVRQYARA  MEKTINNIRS
GLRaV3_CP     ET..DDGKKI  Y..AVWVYDC  IKQAAASTGY  ENPVRQYLAY  FTPTFITATL

CONSENSUS     -----eg---  ----------  ----------  -N--R-y-r-  ----y-----

251                                                           300
BYV_CP        EYRGKLPPIA  RANRHGLPAE  DHYLAADF.I  STSTELTDLQ  QSRLLLAREN
CTV_CP        QNR.NLSYGG  RPLDAGIPAG  YHYLCADF.L  .TGAGLTDLE  CAVYIQAKEQ
LIYV_CP       AGIIN.SNGV  LAAKHGVLAS  YRNSYSDFAV  GFGNDTTDAQ  LTSLMLARKQ
GLRaV3_CP     NGKLVMNEKV  MA.QHGVPPK  FFPYTIDCVR  PTYDLFNNDA  ILAWNLARQQ

CONSENSUS     -----l----  -a--hGvpa-  y-----Df--  -t---ltd--  -----lAr-q 301              328
BYV_CP        ATH.TEFSSE  SPVTSLKQLG  RGLGTGR*..
CTV_CP        LLK.KRGADE  VVVTNVRQLG  K.FNTR*...
LIYV_CP       ALC.KGEGGS  VEHYNTMQLA  NLKHPC*...
GLRaV3_CP     AFRNKTVTAD  NTLHNVFQLL  QKK*......

CONSENSUS     al--k----e  ----n--QL-  --------
```

FIG. 11

FIG. 18A

ORF1a (HELICASE)

```
    GTGTCTACTTACGCGAAGAGTGTGATGAACGACAATTTCAATATCCTTGAGACCCTGGTA
  1 ---------+---------+---------+---------+---------+---------+ 60
    CACAGATGAATGCGCTTCTCACACTACTTGCTGTTAAAGTTATAGGAACTCTGGGACCAT
a    V  S  T  Y  A  K  S  V  M  N  D  N  F  N  I  L  E  T  L  V   -

ACTTTGCCCAAGTCCTTTATAGTCAAAGTACCTGGTTCGGTGCTGGTTAGCATAACCACT
 61 ---------+---------+---------+---------+---------+---------+ 120
    TGAAACGGGTTCAGGAAATATCAGTTTCATGGACCAAGCCACGACCAATCGTATTGGTGA
a    T  L  P  K  S  F  I  V  K  V  P  G  S  V  L  V  S  I  T  T   -

TCGGGCATTTCCGACAAACTTGAACTTCGGGGCGCGTTCGACGTTTCTAAAAAGAATTTC
121 ---------+---------+---------+---------+---------+---------+ 180
    AGCCCGTAAAGGCTGTTTGAACTTGAAGCCCCGCGCAAGCTGCAAAGATTTTTCTTAAAG
a    S  G  I  S  D  K  L  E  L  R  G  A  F  D  V  S  K  K  N  F   -

TCCAGGAGGTTACGTTCGAGTCGTTTGCGCGTATTTTCTAGGGCTATTGTGGAGGATACG
181 ---------+---------+---------+---------+---------+---------+ 240
    AGGTCCTCCAATGCAAGCTCAGCAAACGCGCATAAAAGATCCCGATAACACCTCCTATGC
a    S  R  R  L  R  S  S  R  L  R  V  F  S  R  A  I  V  E  D  T   -

ATCAAGGTTATGAAGGGCATGAAATCAGAGGATGGTAAACCACTCCCTATAGCCGAGGAT
241 ---------+---------+---------+---------+---------+---------+ 300
    TAGTTCCAATACTTCCCGTACTTTAGTCTCCTACCATTTGGTGAGGGATATCGGCTCCTA
a    I  K  V  M  K  G  M  K  S  E  D  G  K  P  L  P  I  A  E  D   -

TCCGTGTACGCGTTCATGACAGGCAATATGTCAAACGTTCATTGCACTAGGGCTGGTTTG
301 ---------+---------+---------+---------+---------+---------+ 360
    AGGCACATGCGCAAGTACTGTCCGTTATACAGTTTGCAAGTAACGTGATCCCGACCAAAC
a    S  V  Y  A  F  M  T  G  N  M  S  N  V  H  C  T  R  A  G  L   -

CTCGGGGGCTCAAAGGCTTGCGCGGCTTCTTTAGCTGTGAAGGGTGCAGCTTCACGCGCT
361 ---------+---------+---------+---------+---------+---------+ 420
    GAGCCCCCGAGTTTCCGAACGCGCCGAAGAAATCGACACTTCCCACGTCGAAGTGCGCGA
a    L  G  G  S  K  A  C  A  A  S  L  A  V  K  G  A  A  S  R  A   -

ACTGGAACAAAACTCTTTTCAGGTCTCACATCCTTTCTTTCCGCCGGTGGTCTGTTTTAC
421 ---------+---------+---------+---------+---------+---------+ 480
    TGACCTTGTTTTGAGAAAAGTCCAGAGTGTAGGAAAGAAAGGCGGCCACCAGACAAAATG
a    T  G  T  K  L  F  S  G  L  T  S  F  L  S  A  G  G  L  F  Y   -

GATGAAGGCTTGACGCCCGGAGAGAGGCTTGATGCACTAACGCGCCGTGAACATGCTGTG
481 ---------+---------+---------+---------+---------+---------+ 540
    CTACTTCCGAACTGCGGGCCTCTCTCCGAACTACGTGATTGCGCGGCACTTGTACGACAC
a    D  E  G  L  T  P  G  E  R  L  D  A  L  T  R  R  E  H  A  V   -

AATTCACCTGTAGGCCTCTTAGAACCTGGAGCTTCGGTTGCGAAGCGGGTCGTTTCCGGA
541 ---------+---------+---------+---------+---------+---------+ 600
    TTAAGTGGACATCCGGAGAATCTTGGACCTCGAAGCCAACGCTTCGCCCAGCAAAGGCCT
a    N  S  P  V  G  L  L  E  P  G  A  S  V  A  K  R  V  V  S  G   -

ACGAAAGCTTTTCTGTCAGAATTGTCATTGGAGGACTTCACCACTTTCGTCATAAAAAAT
601 ---------+---------+---------+---------+---------+---------+ 660
    TGCTTTCGAAAAGACAGTCTTAACAGTAACCTCCTGAAGTGGTGAAAGCAGTATTTTTTA
a    T  K  A  F  L  S  E  L  S  L  E  D  F  T  T  F  V  I  K  N   -
```

FIG. 18B

```
      AGGGTGCTTATTGGTGTTTTTACTCTTTCCATGGCTCTCACTCCGGTGGTCTGGAAGTAC
  661 ---------+---------+---------+---------+---------+---------+ 720
      TCCCACGAATAACCACAAAAATGAGAAAGGTACCGAGAGTGAGGCCACCAGACCTTCATG
a       R  V  L  I  G  V  F  T  L  S  M  A  L  T  P  V  V  W  K  Y  -

AGAAGGAATATCGCGCGAACTGGCGTGGATGTTTTCCACCGTGCTCGTTCGGGTACCGCG
  721 ---------+---------+---------+---------+---------+---------+ 780
      TCTTCCTTATAGCGCGCTTGACCGCACCTACAAAAGGTGGCACGAGCAAGCCCATGGCGC
a       R  R  N  I  A  R  T  G  V  D  V  F  H  R  A  R  S  G  T  A  -

GCCATCGGTTTACAATGTCTTAGTGGAGGAAGGTCGTTAGCTGGTGACGCTGCTCGTGGC
  781 ---------+---------+---------+---------+---------+---------+ 840
      CGGTAGCCAAATGTTACAGAATCACCTCCTTCCAGCAATCGACCACTGCGACGAGCACCG
a       A  I  G  L  Q  C  L  S  G  G  R  S  L  A  G  D  A  A  R  G  -

GCGTTAACAGTGACTCGAGGAGGGCTATCTTCGGCGGTTGCGGTGACCAGAAATACAGTG
  841 ---------+---------+---------+---------+---------+---------+ 900
      CGCAATTGTCACTGAGCTCCTCCCGATAGAAGCCGCCAACGCCACTGGTCTTTATGTCAC
a       A  L  T  V  T  R  G  G  L  S  S  A  V  A  V  T  R  N  T  V  -

GCTAGGCGTCAGGTACCATTGGCGTTGCTTTCGTTTTCCACGTCTTACGCAGTCAGTGGT
  901 ---------+---------+---------+---------+---------+---------+ 960
      CGATCCGCAGTCCATGGTAACCGCAACGAAAGCAAAAGGTGCAGAATGCGTCAGTCACCA
a       A  R  R  Q  V  P  L  A  L  L  S  F  S  T  S  Y  A  V  S  G  -

TGCACTTTGTTAGGTATTTGGGCTCATGCTCTCCCTAGGCATTTGATGTTCTTCTTTGGC
  961 ---------+---------+---------+---------+---------+---------+ 1020
      ACGTGAAACAATCCATAAACCCGAGTACGAGAGGGATCCGTAAACTACAAGAAGAAACCG
a       C  T  L  L  G  I  W  A  H  A  L  P  R  H  L  M  F  F  F  G  -

CTAGGGACGCTCTTCGGGGTGAGTGCCAGTACCAATTCTTGGTCGCTTGGGGGCTATACG
 1021 ---------+---------+---------+---------+---------+---------+ 1080
      GATCCCTGCGAGAAGCCCCACTCACGGTCATGGTTAAGAACCAGCGAACCCCCGATATGC
a       L  G  T  L  F  G  V  S  A  S  T  N  S  W  S  L  G  G  Y  T  -

AACAGTCTGTTCACCGTACCGGAATTAACTTGGGAAGGGAGGAGTTACAGATCTTTATTG
 1081 ---------+---------+---------+---------+---------+---------+ 1140
      TTGTCAGACAAGTGGCATGGCCTTAATTGAACCCTTCCCTCCTCAATGTCTAGAAATAAC
a       N  S  L  F  T  V  P  E  L  T  W  E  G  R  S  Y  R  S  L  L  -

CCCCAAGCAGCTTTAGGTATTTCTCTCGTTGTGCGCGGGTTGTTAAGTGAAACTGTGCCA
 1141 ---------+---------+---------+---------+---------+---------+ 1200
      GGGGTTCGTCGAAATCCATAAAGAGAGCAACACGCGCCCAACAATTCACTTTGACACGGT
a       P  Q  A  A  L  G  I  S  L  V  V  R  G  L  L  S  E  T  V  P  -

CAACTAACGTACGTACCGCCGATTGAAGGTCGGAATGTTTATGATCAGGCACTAAATTTT
 1201 ---------+---------+---------+---------+---------+---------+ 1260
      GTTGATTGCATGCATGGCGGCTAACTTCCAGCCTTACAAATACTAGTCCGTGATTTAAAA
a       Q  L  T  Y  V  P  P  I  E  G  R  N  V  Y  D  Q  A  L  N  F  -

TATCGCGACTTTGACTATGACGATGGTGCAGGCCCATCCGGGACGGCTGGTCAAAGCGAT
 1261 ---------+---------+---------+---------+---------+---------+ 1320
      ATAGCGCTGAAACTGATACTGCTACCACGTCCGGGTAGGCCCTGCCGACCAGTTTCGCTA
a       Y  R  D  F  D  Y  D  D  G  A  G  P  S  G  T  A  G  Q  S  D  -
```

FIG. 18C

```
     CCTGGAACCAATACTTCGGATACTTCTTCGGTTTTCTCTGACGATGGTTTGCCCGCTAGT
1321 ---------+---------+---------+---------+---------+---------+ 1380
     GGACCTTGGTTATGAAGCCTATGAAGAAGCCAAAAGAGACTGCTACCAAACGGGCGATCA
a     P  G  T  N  T  S  D  T  S  S  V  F  S  D  D  G  L  P  A  S  -

GGCGGTGGCTTCGACGCGCGCGTTGAGGCAGGTCCCAGCCATGCTGTTGATGAATCACCA
1381 ---------+---------+---------+---------+---------+---------+ 1440
     CCGCCACCGAAGCTGCGCGCGCAACTCCGTCCAGGGTCGGTACGACAACTACTTAGTGGT
a     G  G  G  F  D  A  R  V  E  A  G  P  S  H  A  V  D  E  S  P  -

AGGGGTAGTGTTGAGTTCGTCTACAGAGAACGTGTAGATGAACATCCGGCGTGTGGTGAA
1441 ---------+---------+---------+---------+---------+---------+ 1500
     TCCCCATCACAACTCAAGCAGATGTCTCTTGCACATCTACTTGTAGGCCGCACACCACTT
a     R  G  S  V  E  F  V  Y  R  E  R  V  D  E  H  P  A  C  G  E  -

GCTGAAGTTGAAAAGGATCTAATAACACCACTTGGTACAGCTGTCTTAGAGTCGCCCCCC
1501 ---------+---------+---------+---------+---------+---------+ 1560
     CGACTTCAACTTTTCCTAGATTATTGTGGTGAACCATGTCGACAGAATCTCAGCGGGGGG
a     A  E  V  E  K  D  L  I  T  P  L  G  T  A  V  L  E  S  P  P  -

GTAGGTCCTGAAGCTGGGAGCGCGCCCAACGTCGAGGACGGTTGTCCGGAGGTTGAAGCT
1561 ---------+---------+---------+---------+---------+---------+ 1620
     CATCCAGGACTTCGACCCTCGCGCGGGTTGCAGCTCCTGCCAACAGGCCTCCAACTTCGA
a     V  G  P  E  A  G  S  A  P  N  V  E  D  G  C  P  E  V  E  A  -

GAGAAATGTTCGGAGGTCATCGTTGACGTTCCTAGTTCAGAACCGCCGGTACAAGAAGTC
1621 ---------+---------+---------+---------+---------+---------+ 1680
     CTCTTTACAAGCCTCCAGTAGCAACTGCAAGGATCAAGTCTTGGCGGCCATGTTCTTCAG
a     E  K  C  S  E  V  I  V  D  V  P  S  S  E  P  P  V  Q  E  V  -

CTTGAATCAACCAATGGTGTCCAAGCTGCAAGAACTGAAGAGGTTGTGCAGGGCGACACA
1681 ---------+---------+---------+---------+---------+---------+ 1740
     GAACTTAGTTGGTTACCACAGGTTCGACGTTCTTGACTTCTCCAACACGTCCCGCTGTGT
a     L  E  S  T  N  G  V  Q  A  A  R  T  E  E  V  V  Q  G  D  T  -

TGTGGAGCTGGGGTAGCTAAATCAGAAGTGAGTCAACGTGTGTTTCCTGCGCAAGTACCC
1741 ---------+---------+---------+---------+---------+---------+ 1800
     ACACCTCGACCCCATCGATTTAGTCTTCACTCAGTTGCACACAAAGGACGCGTTCATGGG
a     C  G  A  G  V  A  K  S  E  V  S  Q  R  V  F  P  A  Q  V  P  -

GCACATGAAGCTGGTCTTGAGGCATCTAGTGGCGCGGTCGTGGAGCCATTGCAAGTTTCT
1801 ---------+---------+---------+---------+---------+---------+ 1860
     CGTGTACTTCGACCAGAACTCCGTAGATCACCGCGCCAGCACCTCGGTAACGTTCAAAGA
a     A  H  E  A  G  L  E  A  S  S  G  A  V  V  E  P  L  Q  V  S  -

GTGCCAGTAGCCGTAGAGAAAACTGTTTTATCTGTCGAGAAGGCGCGTGAGCTAAAGGCG
1861 ---------+---------+---------+---------+---------+---------+ 1920
     CACGGTCATCGGCATCTCTTTTGACAAAATAGACAGCTCTTCCGCGCACTCGATTTCCGC
a     V  P  V  A  V  E  K  T  V  L  S  V  E  K  A  R  E  L  K  A  -

GTAGATAAGGGCAAGGCGGTCGTGCACGCAAAGGAAGTCAAGAATGTACCGGTTAAGACG
1921 ---------+---------+---------+---------+---------+---------+ 1980
     CATCTATTCCCGTTCCGCCAGCACGTGCGTTTCCTTCAGTTCTTACATGGCCAATTCTGC
a     V  D  K  G  K  A  V  V  H  A  K  E  V  K  N  V  P  V  K  T  -
```

FIG. 18D

```
      TTACCACGAGGGGCTCTAAAAATTAGTGAGGATACCGTTCGTAAGGAATTGTGCATGTTT
1981  ------------+---------+---------+---------+---------+---------+ 2040
      AATGGTGCTCCCCGAGATTTTTAATCACTCCTATGGCAAGCATTCCTTAACACGTACAAA
a     L  P  R  G  A  L  K  I  S  E  D  T  V  R  K  E  L  C  M  F  -

AGAACGTGTTCCTGCGGCGTGCAGTTGGACGTGTACAATGAAGCGACCATCGCCACTAGG
2041  ------------+---------+---------+---------+---------+---------+ 2100
      TCTTGCACAAGGACGCCGCACGTCAACCTGCACATGTTACTTCGCTGGTAGCGGTGATCC
a     R  T  C  S  C  G  V  Q  L  D  V  Y  N  E  A  T  I  A  T  R  -

TTCTCAAATGCGTTTACCTTTGTCGATAGCTTGAAAGGGAGGAGTGCGGTCTTTTTCTCA
2101  ------------+---------+---------+---------+---------+---------+ 2160
      AAGAGTTTACGCAAATGGAAACAGCTATCGAACTTTCCCTCCTCACGCCAGAAAAAGAGT
a     F  S  N  A  F  T  F  V  D  S  L  K  G  R  S  A  V  F  F  S  -

AAGCTGGGTGAGGGGTATACCTATAATGGTGGTAGCCATGTTTCATCAGGGTGGCCTCGT
2161  ------------+---------+---------+---------+---------+---------+ 2220
      TTCGACCCACTCCCCATATGGATATTACCACCATCGGTACAAAGTAGTCCCACCGGAGCA
a     K  L  G  E  G  Y  T  Y  N  G  G  S  H  V  S  S  G  W  P  R  -

GCCCTAGAGGATATCTTAACGGCAATTAAGTACCCAAGCGTCTTCGACCACTGTTTAGTG
2221  ------------+---------+---------+---------+---------+---------+ 2280
      CGGGATCTCCTATAGAATTGCCGTTAATTCATGGGTTCGCAGAAGCTGGTGACAAATCAC
a     A  L  E  D  I  L  T  A  I  K  Y  P  S  V  F  D  H  C  L  V  -

CAGAAGTACAAGATGGGTGGAGGCGTACCATTCCACGCTGATGACGAGGAGTGCTATCCA
2281  ------------+---------+---------+---------+---------+---------+ 2340
      GTCTTCATGTTCTACCCACCTCCGCATGGTAAGGTGCGACTACTGCTCCTCACGATAGGT
a     Q  K  Y  K  M  G  G  G  V  P  F  H  A  D  D  E  E  C  Y  P  -

TCAGATAACCCTATCTTGACGGTCAATCTCGTGGGGAAGGCAAACTTCTCGACTAAGTGC
2341  ------------+---------+---------+---------+---------+---------+ 2400
      AGTCTATTGGGATAGAACTGCCAGTTAGAGCACCCCTTCCGTTTGAAGAGCTGATTCACG
a     S  D  N  P  I  L  T  V  N  L  V  G  K  A  N  F  S  T  K  C  -

AGGAAGGGTGGTAAGGTCATGGTCATAAACGTAGCTTCGGGTGACTATTTTCTTATGCCT
2401  ------------+---------+---------+---------+---------+---------+ 2460
      TCCTTCCCACCATTCCAGTACCAGTATTTGCATCGAAGCCCACTGATAAAAGAATACGGA
a     R  K  G  G  K  V  M  V  I  N  V  A  S  G  D  Y  F  L  M  P  -

TGCGGTTTTCAAAGGACGCACTTGCATTCAGTAAACTCCATCGACGAAGGGCGCATCAGT
2461  ------------+---------+---------+---------+---------+---------+ 2520
      ACGCCAAAAGTTTCCTGCGTGAACGTAAGTCATTTGAGGTAGCTGCTTCCCGCGTAGTCA
a     C  G  F  Q  R  T  H  L  H  S  V  N  S  I  D  E  G  R  I  S  -

TTGACGTTCAGGGCAACTCGGCGCGTCTTTGGTGTAGGCAGGATGTTGCAGTTAGCCGGC
2521  ------------+---------+---------+---------+---------+---------+ 2580
      AACTGCAAGTCCCGTTGAGCCGCGCAGAAACCACATCCGTCCTACAACGTCAATCGGCCG
a     L  T  F  R  A  T  R  R  V  F  G  V  G  R  M  L  Q  L  A  G  -

GGCGTGTCGGATGAGAAGTCACCAGGTGTTCCAAACCAGCAACCACAGAGCCAAGGTGCT
2581  ------------+---------+---------+---------+---------+---------+ 2640
      CCGCACAGCCTACTCTTCAGTGGTCCACAAGGTTTGGTCGTTGGTGTCTCGGTTCCACGA
a     G  V  S  D  E  K  S  P  G  V  P  N  Q  Q  P  Q  S  Q  G  A  -
```

FIG. 18E

```
        ACCAGAACAATCACACCAAAATCGGGGGGCAAGGCTCTATCTGAGGGAAGTGGTAGGGAA
   2641 ---------+---------+---------+---------+---------+---------+ 2700
        TGGTCTTGTTAGTGTGGTTTTAGCCCCCCGTTCCGAGATAGACTCCCTTCACCATCCCTT
 a       T  R  T  I  T  P  K  S  G  G  K  A  L  S  E  G  S  G  R  E   -

GTCAAGGGGAGGTCGACATACTCGATATGGTGCGAACAAGATTACGTTAGGAAGTGTGAG
   2701 ---------+---------+---------+---------+---------+---------+ 2760
        CAGTTCCCCTCCAGCTGTATGAGCTATACCACGCTTGTTCTAATGCAATCCTTCACACTC
 a       V  K  G  R  S  T  Y  S  I  W  C  E  Q  D  Y  V  R  K  C  E   -

TGGCTCAGGGCTGATAATCCAGTGATGGCTCTTRAACCTGGCTACACCCCAATGACATTT
   2761 ---------+---------+---------+---------+---------+---------+ 2820
        ACCGAGTCCCGACTATTAGGTCACTACCGAGAAYTTGGACCGATGTGGGGTTACTGTAAA
 a       W  L  R  A  D  N  P  V  M  A  L  ?  P  G  Y  T  P  M  T  F   -

GAAGTGGTTAAAGCCGGGACCTCTGAAGATGCCGTCGTGGAGTACTTGAAGTATCTGGCT
   2821 ---------+---------+---------+---------+---------+---------+ 2880
        CTTCACCAATTTCGGCCCTGGAGACTTCTACGGCAGCACCTCATGAACTTCATAGACCGA
 a       E  V  V  K  A  G  T  S  E  D  A  V  V  E  Y  L  K  Y  L  A   -

ATAGGCATTGGGAGGACATACAGGGCGTTGCTTATGGCTAGAAATATTGCCGTCACTACC
   2881 ---------+---------+---------+---------+---------+---------+ 2940
        TATCCGTAACCCTCCTGTATGTCCCGCAACGAATACCGATCTTTATAACGGCAGTGATGG
 a       I  G  I  G  R  T  Y  R  A  L  L  M  A  R  N  I  A  V  T  T   -

GCCGAAGGTGTTCTGAAAGTACCTAATCAAGTTTATGAATCACTACCGGGCTTTCACGTT
   2941 ---------+---------+---------+---------+---------+---------+ 3000
        CGGCTTCCACAAGACTTTCATGGATTAGTTCAAATACTTAGTGATGGCCCGAAAGTGCAA
 a       A  E  G  V  L  K  V  P  N  Q  V  Y  E  S  L  P  G  F  H  V   -

TACAAGTCGGGCACAGATCTCATTTTTCATTCAACACAAGACGGCTTGCGTGTGAGAGAC
   3001 ---------+---------+---------+---------+---------+---------+ 3060
        ATGTTCAGCCCGTGTCTAGAGTAAAAAGTAAGTTGTGTTCTGCCGAACGCACACTCTCTG
 a       Y  K  S  G  T  D  L  I  F  H  S  T  Q  D  G  L  R  V  R  D   -

CTACCGTACGTATTCATAGCTGAGAAAGGTATTTTTATCAAGGGCAAAGATGTCGACGCG
   3061 ---------+---------+---------+---------+---------+---------+ 3120
        GATGGCATGCATAAGTATCGACTCTTTCCATAAAAATAGTTCCCGTTTCTACAGCTGCGC
 a       L  P  Y  V  F  I  A  E  K  G  I  F  I  K  G  K  D  V  D  A   -

GTAGTAGCTTTGGGCGACAATCTGTCCGTATGTGATGATATATTGGTTTTCCATGATGCT
   3121 ---------+---------+---------+---------+---------+---------+ 3180
        CATCATCGAAACCCGCTGTTAGACAGGCATACACTACTATATAACCAAAAGGTACTACGA
 a       V  V  A  L  G  D  N  L  S  V  C  D  D  I  L  V  F  H  D  A   -

ATTAATTTGATGGGTGCACTGAAAGTTGCTCGATGTGGTATGGTGGGTGAATCATTTAAG
   3181 ---------+---------+---------+---------+---------+---------+ 3240
        TAATTAAACTACCCACGTGACTTTCAACGAGCTACACCATACCACCCACTTAGTAAATTC
 a       I  N  L  M  G  A  L  K  V  A  R  C  G  M  V  G  E  S  F  K   -

TCGTTCGAATACAAATGCTATAATGCTCCCCCAGGTGGCGGTAAGACGACGATGCTAGTG
   3241 ---------+---------+---------+---------+---------+---------+ 3300
        AGCAAGCTTATGTTTACGATATTACGAGGGGGTCCACCGCCATTCTGCTGCTACGATCAC
 a       S  F  E  Y  K  C  Y  N  A  P  P  G  G  G  K  T  T  M  L  V   -
```

FIG. 18F

```
      GACGAATTTGTCAAGTCACCCAATAGCACGGCCACCATTACGGCTAACGTGGGAAGTTCT
3301  ---------+---------+---------+---------+---------+---------+ 3360
      CTGCTTAAACAGTTCAGTGGGTTATCGTGCCGGTGGTAATGCCGATTGCACCCTTCAAGA
a      D  E  F  V  K  S  P  N  S  T  A  T  I  T  A  N  V  G  S  S   -

GAGGACATAAATATGGCGGTGAAGAAGAGAGATCCGAATTTGGAAGGTCTCAACAGTGCT
3361  ---------+---------+---------+---------+---------+---------+ 3420
      CTCCTGTATTTATACCGCCACTTCTTCTCTCTAGGCTTAAACCTTCCAGAGTTGTCACGA
a      E  D  I  N  M  A  V  K  K  R  D  P  N  L  E  G  L  N  S  A   -

ACCACAGTTAACTCCAGGGTGGTTAACTTTATTGTCAGGGGAATGTATAAAAGGGTTTTG
3421  ---------+---------+---------+---------+---------+---------+ 3480
      TGGTGTCAATTGAGGTCCCACCAATTGAAATAACAGTCCCCTTACATATTTTCCCAAAAC
a      T  T  V  N  S  R  V  V  N  F  I  V  R  G  M  Y  K  R  V  L   -

GTGGATGAGGTGTACATGATGCATCAAGGCTTACTACAACTAGGCGTCTTCGCAACCGGC
3481  ---------+---------+---------+---------+---------+---------+ 3540
      CACCTACTCCACATGTACTACGTAGTTCCGAATGATGTTGATCCGCAGAAGCGTTGGCCG
a      V  D  E  V  Y  M  M  H  Q  G  L  L  Q  L  G  V  F  A  T  G   -

GCGTCGGAAGGCCTCTTTTTTGGAGACATAAATCAGATACCATTCATAAACMGGGAGAAG
3541  ---------+---------+---------+---------+---------+---------+ 3600
      CGCAGCCTTCCGGAGAAAAAACCTCTGTATTTAGTCTATGGTAAGTATTTGKCCCTCTTC
a      A  S  E  G  L  F  F  G  D  I  N  Q  I  P  F  I  N  R  E  K   -

GTGTTTAGGATGGATTGTGCTGTATTTGTTCCAAAGAAGGAAAGCGTTGTATACACTTCT
3601  ---------+---------+---------+---------+---------+---------+ 3660
      CACAAATCCTACCTAACACGACATAAACAAGGTTTCTTCCTTTCGCAACATATGTGAAGA
a      V  F  R  M  D  C  A  V  F  V  P  K  K  E  S  V  V  Y  T  S   -

AAATCATACAGGTGTCCGTTAGATGTTTGCTACTTGTTGTCCTCAATGACCGTAAGGGGA
3661  ---------+---------+---------+---------+---------+---------+ 3720
      TTTAGTATGTCCACAGGCAATCTACAAACGATGAACAACAGGAGTTACTGGCATTCCCCT
a      K  S  Y  R  C  P  L  D  V  C  Y  L  L  S  S  M  T  V  R  G   -

ACGGAAAAGTGTTACCCTGAAAAGGTCGTTAGCGGTAAGGACAAACCAGTAGTAAGATCG
3721  ---------+---------+---------+---------+---------+---------+ 3780
      TGCCTTTTCACAATGGGACTTTTCCAGCAATCGCCATTCCTGTTTGGTCATCATTCTAGC
a      T  E  K  C  Y  P  E  K  V  V  S  G  K  D  K  P  V  V  R  S   -

CTGTCCAAAAGGCCAATTGGAACCACTGATGACGTAGCTGAAATAAACGCTGACGTGTAC
3781  ---------+---------+---------+---------+---------+---------+ 3840
      GACAGGTTTTCCGGTTAACCTTGGTGACTACTGCATCGACTTTATTTGCGACTGCACATG
a      L  S  K  R  P  I  G  T  T  D  D  V  A  E  I  N  A  D  V  Y   -

TTGTGCATGACCCAGTTGGAGAAGTCGGATATGAAGAGGTCGTTGAAGGGAAAAGGAAAA
3841  ---------+---------+---------+---------+---------+---------+ 3900
      AACACGTACTGGGTCAACCTCTTCAGCCTATACTTCTCCAGCAACTTCCCTTTTCCTTTT
a      L  C  M  T  Q  L  E  K  S  D  M  K  R  S  L  K  G  K  G  K   -

GAAACACCAGTGATGACAGTGCATGAAGCACAGGGAAAAACATTCAGTGATGTGGTATTG
3901  ---------+---------+---------+---------+---------+---------+ 3960
      CTTTGTGGTCACTACTGTCACGTACTTCGTGTCCCTTTTTGTAAGTCACTACACCATAAC
a      E  T  P  V  M  T  V  H  E  A  Q  G  K  T  F  S  D  V  V  L   -
```

FIG. 18G

```
       TTTAGGACGAAGAAAGCCGATGACTCCCTATTCACTAAACAACCGCATATACTTGTTGGT
  3961 ---------+---------+---------+---------+---------+---------+ 4020
       AAATCCTGCTTCTTTCGGCTACTGAGGGATAAGTGATTTGTTGGCGTATATGAACAACCA
a       F  R  T  K  K  A  D  D  S  L  F  T  K  Q  P  H  I  L  V  G  -

TTGTCGAGACACACACGCTCACTGGTTTATGCCGCTCTGAGCTCAGAGTTGGACGATAAG
  4021 ---------+---------+---------+---------+---------+---------+ 4080
       AACAGCTCTGTGTGTGCGAGTGACCAAATACGGCGAGACTCGAGTCTCAACCTGCTATTC
a       L  S  R  H  T  R  S  L  V  Y  A  A  L  S  S  E  L  D  D  K  -
                                       *  A  Q  S  W  T  I  R      -

(FRAMESHIFT)
       GTCGGCACATATATTAGCGACGCGTCGCCTCAATCAGTATCCGACGCTTTGCTTCACACG
  4081 ---------+---------+---------+---------+---------+---------+ 4140
       CAGCCGTGTATATAATCGCTGCGCAGCGGAGTTAGTCATAGGCTGCGAAACGAAGTGTGC
a       V  G  T  Y  I  S  D  A  S  P  Q  S  V  S  D  A  L  L  H  T  -
        S  A  H  I  L  A  T  R  H  L  N  Q  Y  P  T  L  C  F  T  R  -

ORF1b (RdRp)
       TTCGCCCCGGCTGGTTGCTTTCGAGGTATATGAGCGTATGAATTTTGGACCGACCTTCGA
  4141 ---------+---------+---------+---------+---------+---------+ 4200
       AAGCGGGGCCGACCAACGAAAGCTCCATATACTCGCATACTTAAAACCTGGCTGGAAGCT
a       F  A  P  A  G  C  F  R  G  I  *                              -
b       S  P  R  L  V  A  F  E  V  Y  E  R  M  N  F  G  P  T  F  E  -

AGGGGAGTTGGTACGGAAGATACCAACAAGTCATTTTGTAGCCGTGAATGGGTTTCTCGA
  4201 ---------+---------+---------+---------+---------+---------+ 4260
       TCCCCTCAACCATGCCTTCTATGGTTGTTCAGTAAAACATCGGCACTTACCCAAAGAGCT
b       G  E  L  V  R  K  I  P  T  S  H  F  V  A  V  N  G  F  L  E  -

GGACTTACTCGACGGTTGTCCGGCTTTCGACTATGACTTCTTTGAGGATGATTTCGAAAC
  4261 ---------+---------+---------+---------+---------+---------+ 4320
       CCTGAATGAGCTGCCAACAGGCCGAAAGCTGATACTGAAGAAACTCCTACTAAAGCTTTG
b       D  L  L  D  G  C  P  A  F  D  Y  D  F  F  E  D  D  F  E  T  -

TTCAGATCAGTCTTTCCTCATAGAAGATGTGCGCATTTCTGAATCTTTTTCTCATTTTGC
  4321 ---------+---------+---------+---------+---------+---------+ 4380
       AAGTCTAGTCAGAAAGGAGTATCTTCTACACGCGTAAAGACTTAGAAAAAGAGTAAAACG
b       S  D  Q  S  F  L  I  E  D  V  R  I  S  E  S  F  S  H  F  A  -

GTCGAAAATAGAGGATAGGTTTTACAGTTTTATTAGGTCTAGCGTAGGTTTACCAAAGCG
  4381 ---------+---------+---------+---------+---------+---------+ 4440
       CAGCTTTTATCTCCTATCCAAAATGTCAAAATAATCCAGATCGCATCCAAATGGTTTCGC
b       S  K  I  E  D  R  F  Y  S  F  I  R  S  S  V  G  L  P  K  R  -

CAACACCTTGAAGTGTAACCTCGTCACGTTTGAAAATAGGAATTCCAACGCCGATCGCGG
  4441 ---------+---------+---------+---------+---------+---------+ 4500
       GTTGTGGAACTTCACATTGGAGCAGTGCAAACTTTTATCCTTAAGGTTGCGGCTAGCGCC
b       N  T  L  K  C  N  L  V  T  F  E  N  R  N  S  N  A  D  R  G  -

TTGTAACGTGGGTTGTGACGACTCTGTGGCGCATGAACTGAAGGAGATTTTCTTCGAGGA
  4501 ---------+---------+---------+---------+---------+---------+ 4560
       AACATTGCACCCAACACTGCTGAGACACCGCGTACTTGACTTCCTCTAAAAGAAGCTCCT
b       C  N  V  G  C  D  D  S  V  A  H  E  L  K  E  I  F  F  E  E  -
```

FIG. 18H

```
         GGTCGTTAACAAAGCTCGTTTAGCAGAGGTGACGGAAAGCCATTTGTCCAGCAACACGAT
    4561 ---------+---------+---------+---------+---------+---------+ 4620
         CCAGCAATTGTTTCGAGCAAATCGTCTCCACTGCCTTTCGGTAAACAGGTCGTTGTGCTA
  b        V V N K A R L A E V T E S H L S S N T M  -

GTTGTTATCAGATTGGTTGGACAAAAGGGCACCTAACGCTTACAAGTCTCTCAAGCGGGC
    4621 ---------+---------+---------+---------+---------+---------+ 4680
         CAACAATAGTCTAACCAACCTGTTTTCCCGTGGATTGCGAATGTTCAGAGAGTTCGCCCG
  b        L L S D W L D K R A P N A Y K S L K R A  -

TTTAGGTTCGGTTGTCTTTCATCCGTCTATGTTGACGTCTTATACGCTCATGGTGAAAGC
    4681 ---------+---------+---------+---------+---------+---------+ 4740
         AAATCCAAGCCAACAGAAAGTAGGCAGATACAACTGCAGAATATGCGAGTACCACTTTCG
  b        L G S V V F H P S M L T S Y T L M V K A  -

AGACGTAAAACCCAAGTTGGACAATACGCCATTGTCGAAGTACGTAACGGGGCAGAATAT
    4741 ---------+---------+---------+---------+---------+---------+ 4800
         TCTGCATTTTGGGTTCAACCTGTTATGCGGTAACAGCTTCATGCATTGCCCCGTCTTATA
  b        D V K P L D N T P L S K Y V T G Q N I  -

AGTCTACCACGATAGGTGCGTAACTGCGCTTTTTTCTTGCATTTTTACTGCGTGCGTAGA
    4801 ---------+---------+---------+---------+---------+---------+ 4860
         TCAGATGGTGCTATCCACGCATTGACGCGAAAAAAGAACGTAAAAATGACGCACGCATCT
  b        V Y H D R C V T A L F S C I F T A C V E  -

GCGCTTAAAATACGTAGTGGACGAAAGGTGGCTCTTCTACCACGGGATGGACACTGCGGA
    4861 ---------+---------+---------+---------+---------+---------+ 4920
         CGCGAATTTTATGCATCACCTGCTTTCCACCGAGAAGATGGTGCCCTACCTGTGACGCCT
  b        R L K Y V V D E R W L F Y H G M D T A E  -

GTTGGCGGCTGCATTGAGGAACAATTTGGGGGACATCCGGCAATACTACACCTATGAACT
    4921 ---------+---------+---------+---------+---------+---------+ 4980
         CAACCGCCGACGTAACTCCTTGTTAAACCCCCTGTAGGCCGTTATGATGTGGATACTTGA
  b        L A A A L R N N L G D I R Q Y Y T Y E L  -

GGATATCAGTAAGTACGACAAATCTCAGAGTGCTCTCATGAAGCAGGTGGAGGAGTTGAT
    4981 ---------+---------+---------+---------+---------+---------+ 5040
         CCTATAGTCATTCATGCTGTTTAGAGTCTCACGAGAGTACTTCGTCCACCTCCTCAACTA
  b        D I S K Y D K S Q S A L M K Q V E E L I  -

ACTCTTGACACTTGGTGTTGATAGAGAAGTTTTGTCTACTTTCTTTTGTGGTGAGTATGA
    5041 ---------+---------+---------+---------+---------+---------+ 5100
         TGAGAACTGTGAACCACAACTATCTCTTCAAAACAGATGAAAGAAAACACCACTCATACT
  b        L L T L G V D R E V L S T F F C G E Y D  -

TAGCGTCGTGAGAACGATGACGAAGGAATTGGTGTTGTCTGTCGGCTCTCAGAGGCGCAG
    5101 ---------+---------+---------+---------+---------+---------+ 5160
         ATCGCAGCACTCTTGCTACTGCTTCCTTAACCACAACAGACAGCCGAGAGTCTCCGCGTC
  b        S V V R T M T K E L V L S V G S Q R R S  -

TGGTGGTGCTAACACGTGGTTGGGAAATAGTTTAGTCTTGTGCACCTTGTTGTCCGTAGT
    5161 ---------+---------+---------+---------+---------+---------+ 5220
         ACCACCACGATTGTGCACCAACCCTTTATCAAATCAGAACACGTGGAACAACAGGCATCA
  b        G G A N T W L G N S L V L C T L L S V V  -
```

FIG. 18I

```
      ACTTAGGGGATTAGATTATAGTTATATTGTAGTTAGCGGTGATGATAGCCTTATATTTAG
5221  ----------+---------+---------+---------+---------+---------+ 5280
      TGAATCCCCTAATCTAATATCAATATAACATCAATCGCCACTACTATCGGAATATAAATC
  b    L  R  G  L  D  Y  S  Y  I  V  V  S  G  D  D  S  L  I  F  S  -

TCGGCAGCCGTTGGATATTGATACGTCGGTTCTGAGCGATAATTTTGGTTTTGACGTAAA
5281  ----------+---------+---------+---------+---------+---------+ 5340
      AGCCGTCGGCAACCTATAACTATGCAGCCAAGACTCGCTATTAAAACCAAAACTGCATTT
  b    R  Q  P  L  D  I  D  T  S  V  L  S  D  N  F  G  F  D  V  K  -

GATTTTTAACCAAGCTGCTCCATATTTTTGTTCTAAGTTTTTAGTTCAAGTCGAGGATAG
5341  ----------+---------+---------+---------+---------+---------+ 5400
      CTAAAAATTGGTTCGACGAGGTATAAAAACAAGATTCAAAAATCAAGTTCAGCTCCTATC
  b    I  F  N  Q  A  A  P  Y  F  C  S  K  F  L  V  Q  V  E  D  S  -

TCTCTTTTTTGTTCCCGATCCACTTAAACTCTTCGTTAAGTTTGGAGCTTCCAAAACTTC
5401  ----------+---------+---------+---------+---------+---------+ 5460
      AGAGAAAAAACAAGGGCTAGGTGAATTTGAGAAGCAATTCAAACCTCGAAGGTTTTGAAG
  b    L  F  F  V  P  D  P  L  K  L  F  V  K  F  G  A  S  K  T  S  -

AGATATCGACCTTTTACATGAGATTTTTCAATCTTTCGTCGATCTTTCGAAGGGTTTCAA
5461  ----------+---------+---------+---------+---------+---------+ 5520
      TCTATAGCTGGAAAATGTACTCTAAAAAGTTAGAAAGCAGCTAGAAAGCTTCCCAAAGTT
  b    D  I  D  L  L  H  E  I  F  Q  S  F  V  D  L  S  K  G  F  N  -

TAGAGAGGACGTCATCCAGGAATTAGCTAAGCTGGTGACGCGGAAATATAAGCATTCGGG
5521  ----------+---------+---------+---------+---------+---------+ 5580
      ATCTCTCCTGCAGTAGGTCCTTAATCGATTCGACCACTGCGCCTTTATATTCGTAAGCCC
  b    R  E  D  V  I  Q  E  L  A  K  L  V  T  R  K  Y  K  H  S  G  -

ATGGACCTACTCGGCTTTGTGTGTCTTGCACGTTTTAAGTGCAAATTTTTCGCAGTTCTG
5581  ----------+---------+---------+---------+---------+---------+ 5640
      TACCTGGATGAGCCGAAACACACAGAACGTGCAAAATTCACGTTTAAAAAGCGTCAAGAC
  b    W  T  Y  S  A  L  C  V  L  H  V  L  S  A  N  F  S  Q  F  C  -

TAGGTTATATTACCACAATAGCGTGAATCTCGATGTGCGCCCTATTCAGAGGACCGAGTC
5641  ----------+---------+---------+---------+---------+---------+ 5700
      ATCCAATATAATGGTGTTATCGCACTTAGAGCTACACGCGGGATAAGTCTCCTGGCTCAG
  b    R  L  Y  Y  H  N  S  V  N  L  D  V  R  P  I  Q  R  T  E  S  -

GCTTTCCTTGCTGGCCTTGAAGGCAAGAATTTTAAGGTGGAAAGCTTCTCGTTTTGCCTT
5701  ----------+---------+---------+---------+---------+---------+ 5760
      CGAAAGGAACGACCGGAACTTCCGTTCTTAAAATTCCACCTTTCGAAGAGCAAAACGGAA
  b    L  S  L  L  A  L  K  A  R  I  L  R  W  K  A  S  R  F  A  F  -

TTCGATAAAGAGGGGTTAATCGCGTTGGCCACGCTATAGTGTTTCTGTGCCTCGGTTCTT
5761  ----------+---------+---------+---------+---------+---------+ 5820
      AAGCTATTTCTCCCCAATTAGCGCAACCGGTGCGATATCACAAAGACACGGAGCCAAGAA
  b    S  I  K  R  G  *                                            -

CGTGAGGTTAATACCGAAGGGTCGTCGTACTTATCTCAGTTATTTATTTTTTCGTCTTCT
5821  ----------+---------+---------+---------+---------+---------+ 5880
      GCACTCCAATTATGGCTTCCCAGCAGCATGAATAGAGTCAATAAATAAAAAGCAGAAGA

CTTAGGCGTGCCATCCGTGAAGTTAATACCGGTGGCACTCCTTCTCGAAGTGGGTATTAA
5881  ----------+---------+---------+---------+---------+---------+ 5940
      GAATCCGCACGGTAGGCACTTCAATTATGGCCACCGTGAGGAAGAGCTTCACCCATAATT
```

FIG. 18J

```
         AGACCAAAATTTTTTATTTGTGTGTACTTTTTGTTTTGTTCACACCGTGAGGACAAGACC
   5941  ------------+---------+---------+---------+---------+---------+ 6000
         TCTGGTTTTAAAAAATAAACACACATGAAAAACAAAACAAGTGTGGCACTCCTGTTCTGG

ORF2 (7K)
         GGTGGAACATGTACAGTAGAGGGTCTTTCTTTAAGTCTCGGGTTACCCTTCCTACTCTTG
   6001  ------------+---------+---------+---------+---------+---------+ 6060
         CCACCTTGTACATGTCATCTCCCAGAAAGAAATTCAGAGCCCAATGGGAAGGATGAGAAC
 C            M  Y  S  R  G  S  F  F  K  S  R  V  T  L  P  T  L  V  -

TCGGAGCATACATGTGGGAGTTTGAACTCCCGTATCTTACGGACAAGAGACACATCAGCT
   6061  ------------+---------+---------+---------+---------+---------+ 6120
         AGCCTCGTATGTACACCCTCAAACTTGAGGGCATAGAATGCCTGTTCTCTGTGTAGTCGA
 C            G  A  Y  M  W  E  F  E  L  P  Y  L  T  D  K  R  H  I  S  Y  -

ATAGCGCGCCAAGTGTCGCGACTTTTAGCCTTGTGTCGAGGTAGGATAGGGGCCAACAGG
   6121  ------------+---------+---------+---------+---------+---------+ 6180
         TATCGCGCGGTTCACAGCGCTGAAAATCGGAACACAGCTCCATCCTATCCCCGGTTGTCC
 C            S  A  P  S  V  A  T  F  S  L  V  S  R  *             -

TGACCAACAGCCTGCACTTAAGGTGCGCTGGAAGTGTTGGATTTGGTCTCAGTGTGCCAA
   6181  ------------+---------+---------+---------+---------+---------+ 6240
         ACTGGTTGTCGGACGTGAATTCCACGCGACCTTCACAACCTAAACCAGAGTCACACGGTT

ATATCCTTTTAGGCGATGTACAGGAGTCTAGTTTAGTGTGTCTTTGGGGGATGACGGGAG
   6241  ------------+---------+---------+---------+---------+---------+ 6300
         TATAGGAAAATCCGCTACATGTCCTCAGATCAAATCACACAGAAACCCCCTACTGCCCTC

CGACTAGGTTTAGGACTGTAGCTGCTATGTAAGTCGTGCATGCGGCATTGTGCGTAAGAC
   6301  ------------+---------+---------+---------+---------+---------+ 6360
         GCTGATCCAAATCCTGACATCGACGATACATTCAGCACGTACGCCGTAACACGCATTCTG

GTGCATGCATTTGGGCGAGTGCCCTAGGGCAGCGTCGGTCAGGTGACTAGCAGCCGGCTC
   6361  ------------+---------+---------+---------+---------+---------+ 6420
         CACGTACGTAAACCCGCTCACGGGATCCCGTCGCAGCCAGTCCACTGATCGTCGGCCGAG

TACGGAGCGCTGAAAGTGCTAGGTCCTGAAGGTACAGTTGGGCTGAGGCAGGACATGGTT
   6421  ------------+---------+---------+---------+---------+---------+ 6480
         ATGCCTCGCGACTTTCACGATCCAGGACTTCCATGTCAACCCGACTCCGTCCTGTACCAA

GAACGAGTTGACCGTGGGGACCAGCGGCGGTGACTCGGGCCGTAGCCACGCGCGGGGCGG
   6481  ------------+---------+---------+---------+---------+---------+ 6540
         CTTGCTCAACTGGCACCCCTGGTCGCCGCCACTGAGCCCGGCATCGGTGCGCGCCCCGCC

CAGGGCGTCTCGTGGTGTATCTGGGCAAGATACGGCTTTATTAGGCACCATAATATGGAG
   6541  ------------+---------+---------+---------+---------+---------+ 6600
         GTCCCGCAGAGCACCACATAGACCCGTTCTATGCCGAAATAATCCGTGGTATTATACCTC

CCCAAAGCGTCGGGGTCGGGAAACATCTCCATAGCTTAGTGGCAGCAGCCTAAGATAGGC
   6601  ------------+---------+---------+---------+---------+---------+ 6660
         GGGTTTCGCAGCCCCAGCCCTTTGTAGAGGTATCGAATCACCGTCGTCGGATTCTATCCG

TGGGAGGCCCGTTCCCTGTAGTAGTGGTGGGTTAGCATGCCACTAAGCGGTGCGGCGTGA
   6661  ------------+---------+---------+---------+---------+---------+ 6720
         ACCCTCCGGGCAAGGGACATCATCACCACCCAATCGTACGGTGATTCGCCACGCCGCACT
```

FIG. 18K

```
      TAAGGCGCCACCGTCCGTAGTTAGGCGACCCGTGTTTTAATAGGGTCTCTTTAGTTAAGT
 6721 ---------+---------+---------+---------+---------+---------+ 6780
      ATTCCGCGGTGGCAGGCATCAATCCGCTGGGCACAAAATTATCCCAGAGAAATCAATTCA

TTAGGCATGTCGTACAGTTAGGATTTCTTTTTAGATATTCTTTTATTTTTTATTGTTTGT
 6781 ---------+---------+---------+---------+---------+---------+ 6840
      AATCCGTACAGCATGTCAATCCTAAAGAAAAATCTATAAGAAAATAAAAAATAACAAACA

TAGTTTAGATGTACATTATTACGTAGGTTACTTTGGCGCTACGCCAGAGGTTTTTCCTCT
 6841 ---------+---------+---------+---------+---------+---------+ 6900
      ATCAAATCTACATGTAATAATGCATCCAATGAAACCGCGATGCGGTCTCCAAAAAGGAGA

TTGTGTGTAGCCTTTAATGTAGGTTTCTTTGTTTTATTTTTGCCTTTCAGGCGGCGCGTT
 6901 ---------+---------+---------+---------+---------+---------+ 6960
      AACACACATCGGAAATTACATCCAAAGAAACAAAATAAAAACGGAAAGTCCGCCGCGCAA

TCTTTTCTTCTATTTAGGTTTATCTTCTTTCCTTAGTGTTGTCGTATATGACGCTACGTC
 6961 ---------+---------+---------+---------+---------+---------+ 7020
      AGAAAAGAAGATAAATCCAAATAGAAGAAAGGAATCACAACAGCATATACTGCGATGCAG

CAAATTATGAATTTTCCTTCGTGTAGGCGTCGTTGAGTGCGTTCATCGGCGCTAGACGAG
 7021 ---------+---------+---------+---------+---------+---------+ 7080
      GTTTAATACTTAAAAGGAAGCACATCCGCAGCAACTCACGCAAGTAGCCGCGATCTGCTC

GTTTAGTGGCGACATAAATAGGTTTTTGCGCGAGATTGGGATAGAACGAGTTCGCCTTAA
 7081 ---------+---------+---------+---------+---------+---------+ 7140
      CAAATCACCGCTGTATTTATCCAAAAACGCGCTCTAACCCTATCTTGCTCAAGCGGAATT

AAGAGAAATCGGGGAAGGCGCCACGCGAATGACCTTCGTGCTGAGCGAAGGTAGTATCGT
 7141 ---------+---------+---------+---------+---------+---------+ 7200
      TTCTCTTTAGCCCCTTCCGCGGTGCGCTTACTGGAAGCACGACTCGCTTCCATCATAGCA

ORF3 (5K, Membrane protein)
      GATTTTATATTGAAGTAGGCGTATTTGTTTATGGATGATTTTAAACAGGCAATACTGTTG
 7201 ---------+---------+---------+---------+---------+---------+ 7260
      CTAAAATATAACTTCATCCGCATAAACAAATACCTACTAAAATTTGTCCGTTATGACAAC
a                                M   D   D   F   K   Q   A   I   L   L   -

CTAGTAGTCGATTTTGTCTTCGTGATAATTCTGCTGCTGGTTCTTACGTTCGTCGTCCCG
 7261 ---------+---------+---------+---------+---------+---------+ 7320
      GATCATCAGCTAAAACAGAAGCACTATTAAGACGACGACCAAGAATGCAAGCAGCAGGGC
a       L   V   V   D   F   V   F   V   I   I   L   L   L   V   L   T   F   V   V   P   -

AGGTTACAGCAAAGCTCCACCATTAATACAGGTCTTAGGACAGTGTGATTCCTCCTTTAG
 7321 ---------+---------+---------+---------+---------+---------+ 7380
      TCCAATGTCGTTTCGAGGTGGTAATTATGTCCAGAATCCTGTCACACTAAGGAGGAAATC
a       R   L   Q   Q   S   S   T   I   N   T   G   L   R   T   V   *   -

ORF4 (HSP70 Homolog)
      TTAGATATGGAAGTAGGTATAGATTTTGGAACCACTTTCAGCACAATCTGCTTTTCCCCA
 7381 ---------+---------+---------+---------+---------+---------+ 7440
      AATCTATACCTTCATCCATATCTAAAACCTTGGTGAAAGTCGTGTTAGACGAAAAGGGGT
a            M   E   V   G   I   D   F   G   T   T   F   S   T   I   C   F   S   P   -
```

FIG. 18L

```
         TCTGGGGTCAGCGGTTGTACTCCTGTGGCCGGTAGTGTTTACGTTGAAACCCAAATTTTT
   7441  ---------+---------+---------+---------+---------+---------+ 7500
         AGACCCCAGTCGCCAACATGAGGACACCGGCCATCACAAATGCAACTTTGGGTTTAAAAA
a         S  G  V  S  G  C  T  P  V  A  G  S  V  Y  V  E  T  Q  I  F  -

ATACCTGAAGGTAGCAGTACTTACTTAATTGGTAAAGCTGCGGGGAAAGCTTATCGTGAC
   7501  ---------+---------+---------+---------+---------+---------+ 7560
         TATGGACTTCCATCGTCATGAATGAATTAACCATTTCGACGCCCCTTTCGAATAGCACTG
a         I  P  E  G  S  S  T  Y  L  I  G  K  A  A  G  K  A  Y  R  D  -

GGTGTAGAGGGAAGGTTGTATGTTAACCCGAAAAGGTGGGCAGGTGTGACGAGGGATAAC
   7561  ---------+---------+---------+---------+---------+---------+ 7620
         CCACATCTCCCTTCCAACATACAATTGGGCTTTTCCACCCGTCCACACTGCTCCCTATTG
a         G  V  E  G  R  L  Y  V  N  P  K  R  W  A  G  V  T  R  D  N  -

GTCGAACGCTACGTCGAGAAATTAAAACCTACATACACCGTGAAGATAGACAGCGGAGGC
   7621  ---------+---------+---------+---------+---------+---------+ 7680
         CAGCTTGCGATGCAGCTCTTTAATTTTGGATGTATGTGGCACTTCTATCTGTCGCCTCCG
a         V  E  R  Y  V  E  K  L  K  P  T  Y  T  V  K  I  D  S  G  G  -

GCCTTATTAATTGGAGGTTTAGGTTCCGGACCAGACACCTTATTGAGGGTCGTTGACGTA
   7681  ---------+---------+---------+---------+---------+---------+ 7740
         CGGAATAATTAACCTCCAAATCCAAGGCCTGGTCTGTGGAATAACTCCCAGCAACTGCAT
a         A  L  L  I  G  G  L  G  S  G  P  D  T  L  L  R  V  V  D  V  -

ATATGTTTATTCTTGAGAGCCTTGATACTGGAGTGCGAAAGGTATACGTCTACGACGGTT
   7741  ---------+---------+---------+---------+---------+---------+ 7800
         TATACAAATAAGAACTCTCGGAACTATGACCTCACGCTTTCCATATGCAGATGCTGCCAA
a         I  C  L  F  L  R  A  L  I  L  E  C  E  R  Y  T  S  T  T  V  -

ACAGCAGCTGTTGTAACGGTACCGGCTGACTATAACTCCTTTAAACGAAGCTTCGTTGTT
   7801  ---------+---------+---------+---------+---------+---------+ 7860
         TGTCGTCGACAACATTGCCATGGCCGACTGATATTGAGGAAATTTGCTTCGAAGCAACAA
a         T  A  A  V  V  T  V  P  A  D  Y  N  S  F  K  R  S  F  V  V  -

GAGGCGCTAAAAGGTCTTGGTATACCGGTTAGAGGTGTTGTTAACGAACCGACGGCCGCA
   7861  ---------+---------+---------+---------+---------+---------+ 7920
         CTCCGCGATTTTCCAGAACCATATGGCCAATCTCCACAACAATTGCTTGGCTGCCGGCGT
a         E  A  L  K  G  L  G  I  P  V  R  G  V  V  N  E  P  T  A  A  -

GCCCTCTATTCCTTAGCTAAGTCGCGAGTAGAAGACCTATTATTAGCGGTTTTTGATTTT
   7921  ---------+---------+---------+---------+---------+---------+ 7980
         CGGGAGATAAGGAATCGATTCAGCGCTCATCTTCTGGATAATAATCGCCAAAAACTAAAA
a         A  L  Y  S  L  A  K  S  R  V  E  D  L  L  A  V  F  D  F  -

GGGGGAGGGACTTTCGACGTCTCATTCGTTAAGAAGAAGGGAAATATACTATGCGTCATC
   7981  ---------+---------+---------+---------+---------+---------+ 8040
         CCCCCTCCCTGAAAGCTGCAGAGTAAGCAATTCTTCTTCCCTTTATATGATACGCAGTAG
a         G  G  G  T  F  D  V  S  F  V  K  K  K  G  N  I  L  C  V  I  -

TTTTCAGTGGGTGATAATTTCTTGGGTGGTAGAGATATTGATAGAGCTATCGTGGAAGTT
   8041  ---------+---------+---------+---------+---------+---------+ 8100
         AAAAGTCACCCACTATTAAAGAACCCACCATCTCTATAACTATCTCGATAGCACCTTCAA
a         F  S  V  G  D  N  F  L  G  G  R  D  I  D  R  A  I  V  E  V  -
```

FIG. 18M

```
       ATCAAACAAAAGATCAAAGGAAAGGCGTCTGATGCCAAGTTAGGGATATTCGTATCCTCG
  8101 ---------+---------+---------+---------+---------+---------+ 8160
       TAGTTTGTTTTCTAGTTTCCTTTCCGCAGACTACGGTTCAATCCCTATAAGCATAGGAGC
a      I K Q K I K G K A S D A K L G I F V S S  -

ATGAAGGAAGACTTGTCTAACAATAACGCTATAACGCAACACCTTATCCCCGTAGAAGGG
  8161 ---------+---------+---------+---------+---------+---------+ 8220
       TACTTCCTTCTGAACAGATTGTTATTGCGATATTGCGTTGTGGAATAGGGGCATCTTCCC
a      M K E D L S N N N A I T Q H L I P V E G  -

GGTGTGGAGGTTGTGGATTTGACTAGCGACGAACTGGACGCAATCGTTGCACCATTCAGC
  8221 ---------+---------+---------+---------+---------+---------+ 8280
       CCACACCTCCAACACCTAAACTGATCGCTGCTTGACCTGCGTTAGCAACGTGGTAAGTCG
a      G V E V V D L T S D E L D A I V A P F S  -

GCTAGGGCTGTGGAAGTATTCAAAACTGGTCTTGACAACTTTTACCCAGACCCGGTTATT
  8281 ---------+---------+---------+---------+---------+---------+ 8340
       CGATCCCGACACCTTCATAAGTTTTGACCAGAACTGTTGAAAATGGGTCTGGGCCAATAA
a      A R A V E V F K T G L D N F Y P D P V I  -

GCCGTTATGACTGGGGGGTCAAGTGCTCTAGTTAAGGTCAGGAGTGATGTGGCTAATTTG
  8341 ---------+---------+---------+---------+---------+---------+ 8400
       CGGCAATACTGACCCCCCAGTTCACGAGATCAATTCCAGTCCTCACTACACCGATTAAAC
a      A V M T G G S S A L V K V R S D V A N L  -

CCGCAGATATCTAAAGTCGTGTTCGACAGTACCGATTTTAGATGTTCGGTGGCTTGTGGG
  8401 ---------+---------+---------+---------+---------+---------+ 8460
       GGCGTCTATAGATTTCAGCACAAGCTGTCATGGCTAAAATCTACAAGCCACCGAACACCC
a      P Q I S K V V F D S T D F R C S V A C G  -

GCTAAGGTTTACTGCGATACTTTGGCAGGTAATAGCGGACTGAGACTGGTGGACACTTTA
  8461 ---------+---------+---------+---------+---------+---------+ 8520
       CGATTCCAAATGACGCTATGAAACCGTCCATTATCGCCTGACTCTGACCACCTGTGAAAT
a      A K V Y C D T L A G N S G L R L V D T L  -

ACGAATACGCTAACGGACGAGGTAGTGGGTCTTCAGCCGGTGGTAATTTTCCCGAAAGGT
  8521 ---------+---------+---------+---------+---------+---------+ 8580
       TGCTTATGCGATTGCCTGCTCCATCACCCAGAAGTCGGCCACCATTAAAAGGGCTTTCCA
a      T N T L T D E V V G L Q P V V I F P K G  -

AGTCCAATACCCTGTTCATATACTCATAGATACACAGTGGGTGGTGGAGATGTGGTATAC
  8581 ---------+---------+---------+---------+---------+---------+ 8640
       TCAGGTTATGGGACAAGTATATGAGTATCTATGTGTCACCCACCACCTCTACACCATATG
a      S P I P C S Y T H R Y T V G G G D V V Y  -

GGTATATTTGAAGGGGAGAATAACAGAGCTTTTCTAAATGAGCCGACGTTCCGGGGCGTA
  8641 ---------+---------+---------+---------+---------+---------+ 8700
       CCATATAAACTTCCCCTCTTATTGTCTCGAAAAGATTTACTCGGCTGCAAGGCCCCGCAT
a      G I F E G E N N R A F L N E P T F R G V  -

TCGAAACGTAGGGGAGACCCAGTAGAGACCGACGTGGCGCAGTTTAATCTCTCCACGGAC
  8701 ---------+---------+---------+---------+---------+---------+ 8760
       AGCTTTGCATCCCCTCTGGGTCATCTCTGGCTGCACCGCGTCAAATTAGAGAGGTGCCTG
a      S K R R G D P V E T D V A Q F N L S T D  -
```

FIG. 18N

```
            GGAACGGTGTCTGTTATCGTTAATGGTGAGGAAGTAAAGAATGAATATCTGGTACCCGGG
      8761  ---------+---------+---------+---------+---------+---------+ 8820
            CCTTGCCACAGACAATAGCAATTACCACTCCTTCATTTCTTACTTATAGACCATGGGCCC
a            G  T  V  S  V  I  V  N  G  E  E  V  K  N  E  Y  L  V  P  G   -

ACAACAAACGTACTGGATTCATTGGTCTATAAATCTGGGAGAGAAGATTTAGAGGCTAAG
      8821  ---------+---------+---------+---------+---------+---------+ 8880
            TGTTGTTTGCATGACCTAAGTAACCAGATATTTAGACCCTCTCTTCTAAATCTCCGATTC
a            T  T  N  V  L  D  S  L  V  Y  K  S  G  R  E  D  L  E  A  K   -

GCAATACCAGAGTACTTGACCACACTGAATATTTTGCACGATAAGGCTTTCACGAGGAGA
      8881  ---------+---------+---------+---------+---------+---------+ 8940
            CGTTATGGTCTCATGAACTGGTGTGACTTATAAAACGTGCTATTCCGAAAGTGCTCCTCT
a            A  I  P  E  Y  L  T  T  L  N  I  L  H  D  K  A  F  T  R  R   -

AACCTGGGTAACAAAGATAAGGGGTTCTCGGATTTAAGGATAGAAGAAAATTTTTTAAAA
      8941  ---------+---------+---------+---------+---------+---------+ 9000
            TTGGACCCATTGTTTCTATTCCCCAAGAGCCTAAATTCCTATCTTCTTTTAAAAAATTTT
a            N  L  G  N  K  D  K  G  F  S  D  L  R  I  E  E  N  F  L  K   -

ORF5 (HSP90 Homolog)
            TCCGCCGTAGATACAGACACGATTTTGAATGGATAAATATATTTATGTAACGGGGATATT
      9001  ---------+---------+---------+---------+---------+---------+ 9060
            AGGCGGCATCTATGTCTGTGCTAAAACTTACCTATTTATATAAATACATTGCCCCTATAA
a            S  A  V  D  T  D  T  I  L  N  G  *
b                                           M  D  K  Y  I  Y  V  T  G  I  L  -

AAACCCTAACGAGGCTAGAGACGAGGTATTCTCGGTAGTGAATAAGGGATATATTGGACC
      9061  ---------+---------+---------+---------+---------+---------+ 9120
            TTTGGGATTGCTCCGATCTCTGCTCCATAAGAGCCATCACTTATTCCCTATATAACCTGG
b            N  P  N  E  A  R  D  E  V  F  S  V  V  N  K  G  Y  I  G  P   -

GGGAGGGCGCTCCTTTTCGAATCGTGGTAGTAAGTACACCGTCGTCTGGGAAAACTCTGC
      9121  ---------+---------+---------+---------+---------+---------+ 9180
            CCCTCCCGCGAGGAAAAGCTTAGCACCATCATTCATGTGGCAGCAGACCCTTTTGAGACG
b            G  G  R  S  F  S  N  R  G  S  K  Y  T  V  V  W  E  N  S  A   -

TGCGAGGATTAGTGGATTTACGTCGACTTCGCAATCTACGATAGATGCTTTCGCGTATTT
      9181  ---------+---------+---------+---------+---------+---------+ 9240
            ACGCTCCTAATCACCTAAATGCAGCTGAAGCGTTAGATGCTATCTACGAAAGCGCATAAA
b            A  R  I  S  G  F  T  S  T  S  Q  S  T  I  D  A  F  A  Y  F   -

CTTGTTGAAAGGCGGATTGACTACCACGCTCTCTAACCCAATAAACTGTGAGAATTGGGT
      9241  ---------+---------+---------+---------+---------+---------+ 9300
            GAACAACTTTCCGCCTAACTGATGGTGCGAGAGATTGGGTTATTTGACACTCTTAACCCA
b            L  L  K  G  G  L  T  T  T  L  S  N  P  I  N  C  E  N  W  V   -

CAGGTCATCTAAGGATTTAAGCGCGTTTTTCAGGACCCTAATTAAAGGTAAGATTTATGC
      9301  ---------+---------+---------+---------+---------+---------+ 9360
            GTCCAGTAGATTCCTAAATTCGCGCAAAAAGTCCTGGGATTAATTTCCATTCTAAATACG
b            R  S  S  K  D  L  S  A  F  F  R  T  L  I  K  G  K  I  Y  A   -

ATCGCGTTCTGTGGACAGCAATCTTCCAAAGAAAGACAGGGATGACATCATGGAAGCGAG
      9361  ---------+---------+---------+---------+---------+---------+ 9420
            TAGCGCAAGACACCTGTCGTTAGAAGGTTTCTTTCTGTCCCTACTGTAGTACCTTCGCTC
b            S  R  S  V  D  S  N  L  P  K  K  D  R  D  D  I  M  E  A  S   -
```

FIG. 18O

```
          TCGACGACTATCGCCATCGGACGCCGCCTTTTGCAGAGCAGTGTCGGTTCAGGTAGGGAA
     9421 ---------+---------+---------+---------+---------+---------+ 9480
          AGCTGCTGATAGCGGTAGCCTGCGGCGGAAAACGTCTCGTCACAGCCAAGTCCATCCCTT
   b        R  R  L  S  P  S  D  A  A  F  C  R  A  V  S  V  Q  V  G  K  -

GTATGTGGACGTAACGCAGAATTTAGAAAGTACGATCGTGCCGTTAAGAGTTATGGAAAT
     9481 ---------+---------+---------+---------+---------+---------+ 9540
          CATACACCTGCATTGCGTCTTAAATCTTTCATGCTAGCACGGCAATTCTCAATACCTTTA
   b        Y  V  D  V  T  Q  N  L  E  S  T  I  V  P  L  R  V  M  E  I  -

AAAGAAAAGACGAGGATCAGCACATGTTAGTTTACCGAAGGTGGTATCCGCTTACGTAGA
     9541 ---------+---------+---------+---------+---------+---------+ 9600
          TTTCTTTTCTGCTCCTAGTCGTGTACAATCAAATGGCTTCCACCATAGGCGAATGCATCT
   b        K  K  R  R  G  S  A  H  V  S  L  P  K  V  V  S  A  Y  V  D  -

TTTTTATACGAACTTGCAGGAATTGCTGTCGGATGAAGTAACTAGGGCCAGAACCGATAC
     9601 ---------+---------+---------+---------+---------+---------+ 9660
          AAAAATATGCTTGAACGTCCTTAACGACAGCCTACTTCATTGATCCCGGTCTTGGCTATG
   b         F  Y  T  N  L  Q  E  L  L  S  D  E  V  T  R  A  R  T  D  T  -

AGTTTCGGCATACGCTACCGACTCTATGGCTTTCTTAGTTAAGATGTTACCCCTGACTGC
     9661 ---------+---------+---------+---------+---------+---------+ 9720
          TCAAAGCCGTATGCGATGGCTGAGATACCGAAAGAATCAATTCTACAATGGGGACTGACG
   b        V  S  A  Y  A  T  D  S  M  A  F  L  V  K  M  L  P  L  T  A  -

TCGTGAGCAGTGGTTAAAAGACGTGCTAGGATATCTGCTGGTACGGAGACGACCAGCAAA
     9721 ---------+---------+---------+---------+---------+---------+ 9780
          AGCACTCGTCACCAATTTTCTGCACGATCCTATAGACGACCATGCCTCTGCTGGTCGTTT
   b        R  E  Q  W  L  K  D  V  L  G  Y  L  L  V  R  R  R  P  A  N  -

TTTTTCCTACGACGTAAGAGTAGCTTGGGTATATGACGTGATCGCTACGCTCAAGCTGGT
     9781 ---------+---------+---------+---------+---------+---------+ 9840
          AAAAAGGATGCTGCATTCTCATCGAACCCATATACTGCACTAGCGATGCGAGTTCGACCA
   b        F  S  Y  D  V  R  V  A  W  V  Y  D  V  I  A  T  L  K  L  V  -

CATAAGATTGTTTTTCAACAAGGACACACCCGGGGGTATTAAAGACTTAAAACCGTGTGT
     9841 ---------+---------+---------+---------+---------+---------+ 9900
          GTATTCTAACAAAAAGTTGTTCCTGTGTGGGCCCCCATAATTTCTGAATTTTGGCACACA
   b        I  R  L  F  F  N  K  D  T  P  G  G  I  K  D  L  K  P  C  V  -

GCCTATAGAGTCATTCGACCCCTTTCACGAGCTTTCGTCCTATTTCTCTAGGTTAAGTTA
     9901 ---------+---------+---------+---------+---------+---------+ 9960
          CGGATATCTCAGTAAGCTGGGGAAAGTGCTCGAAAGCAGGATAAAGAGATCCAATTCAAT
   b        P  I  E  S  F  D  P  F  H  E  L  S  S  Y  F  S  R  L  S  Y  -

CGAGATGACGACAGGTAAAGGGGGAAAGATATGCCCGGAGATCGCCGAGAAGTTGGTGCG
     9961 ---------+---------+---------+---------+---------+---------+ 10020
          GCTCTACTGCTGTCCATTTCCCCCTTTCTATACGGGCCTCTAGCGGCTCTTCAACCACGC
   b        E  M  T  T  G  K  G  G  K  I  C  P  E  I  A  E  K  L  V  R  -

CCGTCTAATGGAGGAAAACTATAAGTTAAGATTGACCCCAGTGATGGCCTTAATAATTAT
    10021 ---------+---------+---------+---------+---------+---------+ 10080
          GGCAGATTACCTCCTTTTGATATTCAATTCTAACTGGGGTCACTACCGGAATTATTAATA
   b        R  L  M  E  E  N  Y  K  L  R  L  T  P  V  M  A  L  I  I  I  -
```

FIG. 18P

```
          ACTGGTATACTACTCCATTTACGGCACAAACGCTACCAGGATTAAAAGACGCCCGGATTT
   10081  ----------+---------+---------+---------+---------+---------+ 10140
          TGACCATATGATGAGGTAAATGCCGTGTTTGCGATGGTCCTAATTTTCTGCGGGCCTAAA
 b          L  V  Y  Y  S  I  Y  G  T  N  A  T  R  I  K  R  R  P  D  F  -

CCTCAATGTGAGGATAAAGGGAAGAGTCGAGAAGGTTTCGTTACGGGGGGTAGAAGATCG
   10141  ----------+---------+---------+---------+---------+---------+ 10200
          GGAGTTACACTCCTATTTCCCTTCTCAGCTCTTCCAAAGCAATGCCCCCCATCTTCTAGC
 b          L  N  V  R  I  K  G  R  V  E  K  V  S  L  R  G  V  E  D  R  -

TGCCTTTAGAATATCAGAAAAGCGCGGGATAAACGCTCAACGTGTATTATGTAGGTACTA
   10201  ----------+---------+---------+---------+---------+---------+ 10260
          ACGGAAATCTTATAGTCTTTTCGCGCCCTATTTGCGAGTTGCACATAATACATCCATGAT
 b          A  F  R  I  S  E  K  R  G  I  N  A  Q  R  V  L  C  R  Y  Y  -

TAGCGATCTCACATGTCTGGCTAGGCGACATTACGGCATTCGCAGGAACAATTGGAAGAC
   10261  ----------+---------+---------+---------+---------+---------+ 10320
          ATCGCTAGAGTGTACAGACCGATCCGCTGTAATGCCGTAAGCGTCCTTGTTAACCTTCTG
 b          S  D  L  T  C  L  A  R  R  H  Y  G  I  R  R  N  N  W  K  T  -

GCTGAGTTATGTAGACGGGACGTTAGCGTATGACACGGCTGATTGTATAACTTCTAAGGT
   10321  ----------+---------+---------+---------+---------+---------+ 10380
          CGACTCAATACATCTGCCCTGCAATCGCATACTGTGCCGACTAACATATTGAAGATTCCA
 b          L  S  Y  V  D  G  T  L  A  Y  D  T  A  D  C  I  T  S  K  V  -

GAGAAATACGATCAACACCGCAGATCACGCTAGCATTATACACTATATCAAGACGAACGA
   10381  ----------+---------+---------+---------+---------+---------+ 10440
          CTCTTTATGCTAGTTGTGGCGTCTAGTGCGATCGTAATATGTGATATAGTTCTGCTTGCT
 b          R  N  T  I  N  T  A  D  H  A  S  I  I  H  Y  I  K  T  N  E  -

AAACCAGGTTACCGGAACTACTCTACCACACCAGCTTTAAAGCTGCGTGTAGTATGCGAC
   10441  ----------+---------+---------+---------+---------+---------+ 10500
          TTTGGTCCAATGGCCTTGATGAGATGGTGTGGTCGAAATTTCGACGCACATCATACGCTG
 b          N  Q  V  T  G  T  T  L  P  H  Q  L  *                       -

GATGTTTCTCGTATTAGTTTTATAAAAATTTTTAATTGCTCTGTGTGTGGTTTTTGTTGA
   10501  ----------+---------+---------+---------+---------+---------+ 10560
          CTACAAAGAGCATAATCAAAATATTTTTAAAAATTAACGAGACACACACCAAAAACAACT

ORF6 (Coat protein)
          GTGAACGCGATGGCATTTGAACTGAAATTAGGGCAGATATATGAAGTCGTCCCCGAAAAT
   10561  ----------+---------+---------+---------+---------+---------+ 10620
          CACTTGCGCTACCGTAAACTTGACTTTAATCCCGTCTATATACTTCAGCAGGGGCTTTTA
 a                    M  A  F  E  L  K  L  G  Q  I  Y  E  V  V  P  E  N  -

AATTTGAGAGTTAGAGTGGGGGATGCGGCACAAGGAAAATTTAGTAAGGCGAGTTTCTTA
   10621  ----------+---------+---------+---------+---------+---------+ 10680
          TTAAACTCTCAATCTCACCCCCTACGCCGTGTTCCTTTTAAATCATTCCGCTCAAAGAAT
 a          N  L  R  V  R  V  G  D  A  A  Q  G  K  F  S  K  A  S  F  L  -

AAGTACGTTAAGGACGGGACACAGGCGGAATTAACGGGAATCGCCGTAGTGCCCGAAAAA
   10681  ----------+---------+---------+---------+---------+---------+ 10740
          TTCATGCAATTCCTGCCCTGTGTCCGCCTTAATTGCCCTTAGCGGCATCACGGGCTTTTT
 a          K  Y  V  K  D  G  T  Q  A  E  L  T  G  I  A  V  V  P  E  K  -
```

FIG. 18Q

```
         TACGTATTCGCCACAGCAGCTTTGGCTACAGCGGCGCAGGAGCCACCTAGGCAGCCACCA
   10741 ---------+---------+---------+---------+---------+---------+ 10800
         ATGCATAAGCGGTGTCGTCGAAACCGATGTCGCCGCGTCCTCGGTGGATCCGTCGGTGGT
a         Y  V  F  A  T  A  A  L  A  T  A  A  Q  E  P  P  R  Q  P  P   -

GCGCAAGTGGCGGAACCACAGGAAACCGATATAGGGGTAGTGCCGGAATCTGAGACTCTC
   10801 ---------+---------+---------+---------+---------+---------+ 10860
         CGCGTTCACCGCCTTGGTGTCCTTTGGCTATATCCCCATCACGGCCTTAGACTCTGAGAG
a         A  Q  V  A  E  P  Q  E  T  D  I  G  V  V  P  E  S  E  T  L   -

ACACCAAATAAGTTGGTTTTCGAGAAAGATCCAGACAAGTTCTTGAAGACTATGGGCAAG
   10861 ---------+---------+---------+---------+---------+---------+ 10920
         TGTGGTTTATTCAACCAAAAGCTCTTTCTAGGTCTGTTCAAGAACTTCTGATACCCGTTC
a         T  P  N  K  L  V  F  E  K  D  P  D  K  F  L  K  T  M  G  K   -

GGAATAGCTTTGGACTTGGCGGGAGTTACCCACAAACCGAAAGTTATTAACGAGCCAGGG
   10921 ---------+---------+---------+---------+---------+---------+ 10980
         CCTTATCGAAACCTGAACCGCCCTCAATGGGTGTTTGGCTTTCAATAATTGCTCGGTCCC
a         G  I  A  L  D  L  A  G  V  T  H  K  P  K  V  I  N  E  P  G   -

AAAGTATCAGTAGAGGTGGCAATGAAGATTAATGCCGCATTGATGGAGCTGTGTAAGAAG
   10981 ---------+---------+---------+---------+---------+---------+ 11040
         TTTCATAGTCATCTCCACCGTTACTTCTAATTACGGCGTAACTACCTCGACACATTCTTC
a         K  V  S  V  E  V  A  M  K  I  N  A  A  L  M  E  L  C  K  K   -

GTTATGGGCGCCGATGACGCAGCAACTAAGACAGAATTCTTCTTGTACGTGATGCAGATT
   11041 ---------+---------+---------+---------+---------+---------+ 11100
         CAATACCCGCGGCTACTGCGTCGTTGATTCTGTCTTAAGAAGAACATGCACTACGTCTAA
a         V  M  G  A  D  D  A  A  T  K  T  E  F  F  L  Y  V  M  Q  I   -

GCTTGCACGTTCTTTACATCGTCTTCGACGGAGTTCAAAGAGTTTGACTACATAGAAACC
   11101 ---------+---------+---------+---------+---------+---------+ 11160
         CGAACGTGCAAGAAATGTAGCAGAAGCTGCCTCAAGTTTCTCAAACTGATGTATCTTTGG
a         A  C  T  F  F  T  S  S  S  T  E  F  K  E  F  D  Y  I  E  T   -

GATGATGGAAAGAAGATATATGCGGTGTGGGTATATGATTGCATTAAACAAGCTGCTGCT
   11161 ---------+---------+---------+---------+---------+---------+ 11220
         CTACTACCTTTCTTCTATATACGCCACACCCATATACTAACGTAATTTGTTCGACGACGA
a         D  D  G  K  K  I  Y  A  V  W  V  Y  D  C  I  K  Q  A  A  A   -

TCGACGGGTTATGAAAACCCGGTAAGGCAGTATCTAGCGTACTTCACACCAACCTTCATC
   11221 ---------+---------+---------+---------+---------+---------+ 11280
         AGCTGCCCAATACTTTTGGGCCATTCCGTCATAGATCGCATGAAGTGTGGTTGGAAGTAG
a         S  T  G  Y  E  N  P  V  R  Q  Y  L  A  Y  F  T  P  T  F  I   -

ACGGCGACCCTGAATGGTAAACTAGTGATGAACGAGAAGGTTATGGCACAGCATGGAGTA
   11281 ---------+---------+---------+---------+---------+---------+ 11340
         TGCCGCTGGGACTTACCATTTGATCACTACTTGCTCTTCCAATACCGTGTCGTACCTCAT
a         T  A  T  L  N  G  K  L  V  M  N  E  K  V  M  A  Q  H  G  V   -

CCACCGAAATTCTTTCCGTACACGATAGACTGCGTTCGTCCGACGTACGATCTGTTCAAC
   11341 ---------+---------+---------+---------+---------+---------+ 11400
         GGTGGCTTTAAGAAAGGCATGTGCTATCTGACGCAAGCAGGCTGCATGCTAGACAAGTTG
a         P  P  K  F  F  P  Y  T  I  D  C  V  R  P  T  Y  D  L  F  N   -
```

FIG. 18R

```
       AACGACGCAATATTAGCATGGAATTTAGCTAGACAGCAGGCGTTTAGAAACAAGACGGTA
11401  ---------+---------+---------+---------+---------+---------+ 11460
       TTGCTGCGTTATAATCGTACCTTAAATCGATCTGTCGTCCGCAAATCTTTGTTCTGCCAT
a       N  D  A  I  L  A  W  N  L  A  R  Q  Q  A  F  R  N  K  T  V  -

ACGGCCGATAACACCTTACACAACGTCTTCCAACTATTGCAAAAGAAGTAGCTACGATCG
11461  ---------+---------+---------+---------+---------+---------+ 11520
       TGCCGGCTATTGTGGAATGTGTTGCAGAAGGTTGATAACGTTTTCTTCATCGATGCTAGC
a       T  A  D  N  T  L  H  N  V  F  Q  L  L  Q  K  K  *          -

ORF7 (CPr)
       ATGTCTATAAATTGGTGAAAAATTTAGAAATATTTACCTTTTATTGATAATTCATGGGAG
11521  ---------+---------+---------+---------+---------+---------+ 11580
       TACAGATATTTAACCACTTTTTAAATCTTTATAAATGGAAAATAACTATTAAGTACCCTC
a       M  S  I  N  W  *                                           -
c                                                         M  G  A -

CTTATACACATGTAGACTTTCATGAGTCGCGGTTGCTGAAAGACAAACAAGACTATCTTT
11581  ---------+---------+---------+---------+---------+---------+ 11640
       GAATATGTGTACATCTGAAAGTACTCAGCGCCAACGACTTTCTGTTTGTTCTGATAGAAA
c         Y  T  H  V  D  F  H  E  S  R  L  L  K  D  K  Q  D  Y  L  S -

CTTTCAAGTCAGCGGATGAAGCTCCTCCTGATCCTCCCGGATACGTTCGCCCAGATAGTT
11641  ---------+---------+---------+---------+---------+---------+ 11700
       GAAAGTTCAGTCGCCTACTTCGAGGAGGACTAGGAGGGCCTATGCAAGCGGGTCTATCAA
c         F  K  S  A  D  E  A  P  P  D  P  P  G  Y  V  R  P  D  S  Y -

ATGTGAGGGCTTATTTGATACAAAGAGCAGACTTTCCCAATACTCAAAGCTTATCAGTTA
11701  ---------+---------+---------+---------+---------+---------+ 11760
       TACACTCCCGAATAAACTATGTTTCTCGTCTGAAAGGGTTATGAGTTTCGAATAGTCAAT
c         V  R  A  Y  L  I  Q  R  A  D  F  P  N  T  Q  S  L  S  V  T -

CGTTATCGATAGCCAGTAATAAGTTAGCTTCAGGTCTTATGGGAAGCGACGCAGTATCAT
11761  ---------+---------+---------+---------+---------+---------+ 11820
       GCAATAGCTATCGGTCATTATTCAATCGAAGTCCAGAATACCCTTCGCTGCGTCATAGTA
c         L  S  I  A  S  N  K  L  A  S  G  L  M  G  S  D  A  V  S  S -

CGTCGTTTATGCTGATGAACGACGTGGGAGATTACTTCGAGTGCGGCGTGTGTCACAACA
11821  ---------+---------+---------+---------+---------+---------+ 11880
       GCAGCAAATACGACTACTTGCTGCACCCTCTAATGAAGCTCACGCCGCACACAGTGTTGT
c         S  F  M  L  M  N  D  V  G  D  Y  F  E  C  G  V  C  H  N  K -

AACCCTACTTAGGACGGGAAGTTATCTTCTGTAGGAAATACATAGGTGGGAGAGGAGTGG
11881  ---------+---------+---------+---------+---------+---------+ 11940
       TTGGGATGAATCCTGCCCTTCAATAGAAGACATCCTTTATGTATCCACCCTCTCCTCACC
c         P  Y  L  G  R  E  V  I  F  C  R  K  Y  I  G  G  R  G  V  E -

AGATCACCACTGGTAAGAACTACACGTCGAACAATTGGAACGAGGCGTCGTACGTAATAC
11941  ---------+---------+---------+---------+---------+---------+ 12000
       TCTAGTGGTGACCATTCTTGATGTGCAGCTTGTTAACCTTGCTCCGCAGCATGCATTATG
c         I  T  T  G  K  N  Y  T  S  N  N  W  N  E  A  S  Y  V  I  Q -

AAGTGAACGTAGTCGATGGGTTAGCACAGACCACTGTTAATTCTACTTATACGCAAACGG
12001  ---------+---------+---------+---------+---------+---------+ 12060
       TTCACTTGCATCAGCTACCCAATCGTGTCTGGTGACAATTAAGATGAATATGCGTTTGCC
c         V  N  V  V  D  G  L  A  Q  T  T  V  N  S  T  Y  T  Q  T  D -
```

FIG. 18S

```
        ACGTTAGTGGTCTACCCAAAAATTGGACGCGTATCTACAAAATAACAAAGATAGTGTCCG
12061   ---------+---------+---------+---------+---------+---------+ 12120
        TGCAATCACCAGATGGGTTTTTAACCTGCGCATAGATGTTTTATTGTTTCTATCACAGGC
  c        V  S  G  L  P  K  N  W  T  R  I  Y  K  I  T  K  I  V  S  V -

TAGATCAGAACCTCTACCCTGGTTGTTTCTCAGACTCGAAACTGGGTGTAATGCGTATAA
12121   ---------+---------+---------+---------+---------+---------+ 12180
        ATCTAGTCTTGGAGATGGGACCAACAAAGAGTCTGAGCTTTGACCCACATTACGCATATT
  c        D  Q  N  L  Y  P  G  C  F  S  D  S  K  L  G  V  M  R  I  R -

GGTCACTGTTAGTTTCCCCAGTGCGCATCTTCTTTAGGGATATCTTATTGAAACCTTTGA
12181   ---------+---------+---------+---------+---------+---------+ 12240
        CCAGTGACAATCAAAGGGGTCACGCGTAGAAGAAATCCCTATAGAATAACTTTGGAAACT
  c        S  L  L  V  S  P  V  R  I  F  F  R  D  I  L  L  K  P  L  K -

AGAAATCGTTCAACGCAAGAATCGAGGATGTGCTGAATATTGACGACACGTCGTTGTTAG
12241   ---------+---------+---------+---------+---------+---------+ 12300
        TCTTTAGCAAGTTGCGTTCTTAGCTCCTACACGACTTATAACTGCTGTGCAGCAACAATC
  c        K  S  F  N  A  R  I  E  D  V  L  N  I  D  D  T  S  L  L  V -

TACCGAGTCCTGTCGTACCAGAGTCTACGGGAGGTGTAGGTCCATCAGAGCAGCTGGATG
12301   ---------+---------+---------+---------+---------+---------+ 12360
        ATGGCTCAGGACAGCATGGTCTCAGATGCCCTCCACATCCAGGTAGTCTCGTCGACCTAC
  c        P  S  P  V  V  P  E  S  T  G  G  V  G  P  S  E  Q  L  D  V -

TAGTGGCTTTAACGTCCGACGTAACGGAATTGATCAACACTAGGGGGCAAGGTAAGATAT
12361   ---------+---------+---------+---------+---------+---------+ 12420
        ATCACCGAAATTGCAGGCTGCATTGCCTTAACTAGTTGTGATCCCCCGTTCCATTCTATA
  c        V  A  L  T  S  D  V  T  E  L  I  N  T  R  G  Q  G  K  I  C -

GTTTTCCAGACTCAGTGTTATCGATCAATGAAGCGGATATCTACGATGAGCGGTATTTGC
12421   ---------+---------+---------+---------+---------+---------+ 12480
        CAAAAGGTCTGAGTCACAATAGCTAGTTACTTCGCCTATAGATGCTACTCGCCATAAACG
  c        F  P  D  S  V  L  S  I  N  E  A  D  I  Y  D  E  R  Y  L  P -

CGATAACGGAAGCTCTACAGATAAACGCAAGACTACGCAGACTCGTTCTTTCGAAAGGCG
12481   ---------+---------+---------+---------+---------+---------+ 12540
        GCTATTGCCTTCGAGATGTCTATTTGCGTTCTGATGCGTCTGAGCAAGAAAGCTTTCCGC
  c        I  T  E  A  L  Q  I  N  A  R  L  R  R  L  V  L  S  K  G  G -

GGAGTCAAACACCACGAGATATGGGGAATATGATAGTGGCCATGATACAACTTTTCGTAC
12541   ---------+---------+---------+---------+---------+---------+ 12600
        CCTCAGTTTGTGGTGCTCTATACCCCTTATACTATCACCGGTACTATGTTGAAAAGCATG
  c        S  Q  T  P  R  D  M  G  N  M  I  V  A  M  I  Q  L  F  V  L -

TCTACTCTACTGTAAAGAATATAAGCGTCAAAGACGGGTATAGGGTGGAGACCGAATTAG
12601   ---------+---------+---------+---------+---------+---------+ 12660
        AGATGAGATGACATTTCTTATATTCGCAGTTTCTGCCCATATCCCACCTCTGGCTTAATC
  c        Y  S  T  V  K  N  I  S  V  K  D  G  Y  R  V  E  T  E  L  G -

GTCAAAAGAGAGTCTACTTAAGTTATTCGGAAGTAAGGGAAGCTATATTAGGAGGGAAAT
12661   ---------+---------+---------+---------+---------+---------+ 12720
        CAGTTTTCTCTCAGATGAATTCAATAAGCCTTCATTCCCTTCGATATAATCCTCCCTTTA
  c        Q  K  R  V  Y  L  S  Y  S  E  V  R  E  A  I  L  G  G  K  Y -
```

FIG. 18T

```
           ACGGTGCGTCTCCAACCAACACTGTGCGATCCTTCATGAGGTATTTTGCTCACACCACTA
    12721  ---------+---------+---------+---------+---------+---------+ 12780
           TGCCACGCAGAGGTTGGTTGTGACACGCTAGGAAGTACTCCATAAAACGAGTGTGGTGAT
  c          G  A  S  P  T  N  T  V  R  S  F  M  R  Y  F  A  H  T  T  I -

TTACTCTACTTATAGAGAAGAAAATTCAGCCAGCGTGTACTGCCCTAGCTAAGCACGGCG
    12781  ---------+---------+---------+---------+---------+---------+ 12840
           AATGAGATGAATATCTCTTCTTTTAAGTCGGTCGCACATGACGGGATCGATTCGTGCCGC
  c          T  L  L  I  E  K  K  I  Q  P  A  C  T  A  L  A  K  H  G  V -

TCCCGAAGAGGTTCACTCCGTACTGCTTCGACTTCGCACTACTGGATAACAGATATTACC
    12841  ---------+---------+---------+---------+---------+---------+ 12900
           AGGGCTTCTCCAAGTGAGGCATGACGAAGCTGAAGCGTGATGACCTATTGTCTATAATGG
  c          P  K  R  F  T  P  Y  C  F  D  F  A  L  L  D  N  R  Y  Y  P -

CGGCGGACGTGTTGAAGGCTAACGCAATGGCTTGCGCTATAGCGATTAAATCAGCTAATT
    12901  ---------+---------+---------+---------+---------+---------+ 12960
           GCCGCCTGCACAACTTCCGATTGCGTTACCGAACGCGATATCGCTAATTTAGTCGATTAA
  c          A  D  V  L  K  A  N  A  M  A  C  A  I  A  I  K  S  A  N  L -

ORF8
           TAAGGCGTAAAGGTTCGGAGACGTATAACATCTTAGAAAGCATTTGATTATCTAAAGATG
    12961  ---------+---------+---------+---------+---------+---------+ 13020
           ATTCCGCATTTCCAAGCCTCTGCATATTGTAGAATCTTTCGTAAACTAATAGATTTCTAC
  a                                                                    M -
  c          R  R  K  G  S  E  T  Y  N  I  L  E  S  I  *

GAATTCAGACCAGTTTTAATTACAGTTCGCCGTGATCCCGGCGTAAACACTGGTAGTTTG
    13021  ---------+---------+---------+---------+---------+---------+ 13080
           CTTAAGTCTGGTCAAAATTAATGTCAAGCGGCACTAGGGCCGCATTTGTGACCATCAAAC
  a          E  F  R  P  V  L  I  T  V  R  R  D  P  G  V  N  T  G  S  L -

AAAGTGATAGCTTATGACTTACACTACGACAATATATTCGATAACTGCGCGGTAAAGTCG
    13081  ---------+---------+---------+---------+---------+---------+ 13140
           TTTCACTATCGAATACTGAATGTGATGCTGTTATATAAGCTATTGACGCGCCATTTCAGC
  a          K  V  I  A  Y  D  L  H  Y  D  N  I  F  D  N  C  A  V  K  S -

TTTCGAGACACCGACACTGGATTCACTGTTATGAAAGAATACTCGACGAATTCAGCGTTC
    13141  ---------+---------+---------+---------+---------+---------+ 13200
           AAAGCTCTGTGGCTGTGACCTAAGTGACAATACTTTCTTATGAGCTGCTTAAGTCGCAAG
  a          F  R  D  T  D  T  G  F  T  V  M  K  E  Y  S  T  N  S  A  F -

ATACTAAGTCCTTATAAACTGTTTTCCGCGGTCTTTAATAAGGAAGGTGAGATGATAAGT
    13201  ---------+---------+---------+---------+---------+---------+ 13260
           TATGATTCAGGAATATTTGACAAAAGGCGCCAGAAATTATTCCTTCCACTCTACTATTCA
  a          I  L  S  P  Y  K  L  F  S  A  V  F  N  K  E  G  E  M  I  S -

AACGATGTAGGATCGAGTTTCAGGGTTTACAATATCTTTTCGCAAATGTGTAAAGATATC
    13261  ---------+---------+---------+---------+---------+---------+ 13320
           TTGCTACATCCTAGCTCAAAGTCCCAAATGTTATAGAAAGCGTTTACACATTTCTATAG
  a          N  D  V  G  S  S  F  R  V  Y  N  I  F  S  Q  M  C  K  D  I -

AACGAGATCAGCGAGATACAACGCGCCGGTTACCTAGAAACATATTTAGGAGACGGGCAG
    13321  ---------+---------+---------+---------+---------+---------+ 13380
           TTGCTCTAGTCGCTCTATGTTGCGCGGCCAATGGATCTTTGTATAAATCCTCTGCCCGTC
  a          N  E  I  S  E  I  Q  R  A  G  Y  L  E  T  Y  L  G  D  G  Q -
```

FIG. 18U

```
        GCTGACACTGATATATTTTTTGATGTCTTAACCAACAACAAAGCAAAGGTAAGGTGGTTA
 13381  ---------+---------+---------+---------+---------+---------+ 13440
        CGACTGTGACTATATAAAAAACTACAGAATTGGTTGTTGTTTCGTTTCCATTCCACCAAT
a        A  D  T  D  I  F  F  D  V  L  T  N  N  K  A  K  V  R  W  L  -

GTTAATAAAGACCATAGCGCGTGGTGTGGGATATTGAATGATTTGAAGTGGGAAGAGAGC
 13441  ---------+---------+---------+---------+---------+---------+ 13500
        CAATTATTTCTGGTATCGCGCACCACACCCTATAACTTACTAAACTTCACCCTTCTCTCG
a        V  N  K  D  H  S  A  W  C  G  I  L  N  D  L  K  W  E  E  S  -

AACAAGGAGAAATTTAAGGGGAGAGACATACTAGATACTTACGTTTTATCGTCTGATTAT
 13501  ---------+---------+---------+---------+---------+---------+ 13560
        TTGTTCCTCTTTAAATTCCCCTCTCTGTATGATCTATGAATGCAAAATAGCAGACTAATA
a        N  K  E  K  F  K  G  R  D  I  L  D  T  Y  V  L  S  S  D  Y  -

ORF9
        CCAGGGTTTAAATGAAGTTGCTTTCGCTCCGCTATCTTATCTTAAGGTTGTCAAAGTCGC
 13561  ---------+---------+---------+---------+---------+---------+ 13620
        GGTCCCAAATTTACTTCAACGAAAGCGAGGCGATAGAATAGAATTCCAACAGTTTCAGCG
a        P  G  F  K  *
c                      M  K  L  L  S  L  R  Y  L  I  L  R  L  S  K  S  L -

TTAGAACGAACGATCACTTGGTTTTAATACTTATAAAGGAGGCGCTTATAAACTATTACA
 13621  ---------+---------+---------+---------+---------+---------+ 13680
        AATCTTGCTTGCTAGTGAACCAAAATTATGAATATTTCCTCCGCGAATATTTGATAATGT
c        R  T  N  D  H  L  V  L  I  L  I  K  E  A  L  I  N  Y  Y  N  -

ACGCCTCTTTCACCGATGAGGGTGCCGTATTAAGAGACTCTCGCGAAAGTATAGAGAATT
 13681  ---------+---------+---------+---------+---------+---------+ 13740
        TGCGGAGAAAGTGGCTACTCCCACGGCATAATTCTCTGAGAGCGCTTTCATATCTCTTAA
c        A  S  F  T  D  E  G  A  V  L  R  D  S  R  E  S  I  E  N  F  -

TTCTCGTAGCCAGGTGCGGTTCGCAAAATTCCTGCCGAGTCATGAAGGCTTTGATCACTA
 13741  ---------+---------+---------+---------+---------+---------+ 13800
        AAGAGCATCGGTCCACGCCAAGCGTTTTAAGGACGGCTCAGTACTTCCGAAACTAGTGAT
c        L  V  A  R  C  G  S  Q  N  S  C  R  V  M  K  A  L  I  T  N  -

ACACAGTCTGTAAGATGTCGATAGAAACAGCCAGAAGTTTTATCGGAGACTTAATACTCG
 13801  ---------+---------+---------+---------+---------+---------+ 13860
        TGTGTCAGACATTCTACAGCTATCTTTGTCGGTCTTCAAAATAGCCTCTGAATTATGAGC
c        T  V  C  K  M  S  I  E  T  A  R  S  F  I  G  D  L  I  L  V  -

TCGCCGACTCCTCTGTTTCAGCGTTGGAAGAAGCGAAATCAATTAAAGATAATTTCCGCT
 13861  ---------+---------+---------+---------+---------+---------+ 13920
        AGCGGCTGAGGAGACAAAGTCGCAACCTTCTTCGCTTTAGTTAATTTCTATTAAAGGCGA
c        A  D  S  S  V  S  A  L  E  E  A  K  S  I  K  D  N  F  R  L  -

TAAGAAAAAGGAGAGGCAAGTATTATTATAGTGGTGATTGTGGATCCGACGTTGCGAAAG
 13921  ---------+---------+---------+---------+---------+---------+ 13980
        ATTCTTTTTCCTCTCCGTTCATAATAATATCACCACTAACACCTAGGCTGCAACGCTTTC
c         R  K  R  R  G  K  Y  Y  Y  S  G  D  C  G  S  D  V  A  K  V  -

TTAAGTATATTTTGTCTGGGGAGAATCGAGGATTGGGGTGCGTAGATTCCTTGAAGCTAG
 13981  ---------+---------+---------+---------+---------+---------+ 14040
        AATTCATATAAAACAGACCCCTCTTAGCTCCTAACCCCACGCATCTAAGGAACTTCGATC
c         K  Y  I  L  S  G  E  N  R  G  L  G  C  V  D  S  L  K  L  V -
```

FIG. 18V

```
         TTTGCGTAGGTAGACAAGGAGGTGGAAACGTACTACAGCACCTACTAATCTCATCTCTGG
  14041  ---------+---------+---------+---------+---------+---------+  14100
         AAACGCATCCATCTGTTCCTCCACCTTTGCATGATGTCGTGGATGATTAGAGTAGAGACC
c         C  V  G  R  Q  G  G  G  N  V  L  Q  H  L  L  I  S  S  L  G -

ORF10
         GTTAAAGCATCATGGACCTATCGTTTATTATTGTGCAGATCCTTTCCGCCTCGTACAATA
  14101  ---------+---------+---------+---------+---------+---------+  14160
         CAATTTCGTAGTACCTGGATAGCAAATAATAACACGTCTAGGAAAGGCGGAGCATGTTAT
c            *     M  D  L  S  F  I  I  V  Q  I  L  S  A  S  Y  N  N -

ATGACGTGACAGCACTTTACACTTTGATTAACGCGTATAATAGCGTTGATGATACGACGC
  14161  ---------+---------+---------+---------+---------+---------+  14220
         TACTGCACTGTCGTGAAATGTGAAACTAATTGCGCATATTATCGCAACTACTATGCTGCG
c            D  V  T  A  L  Y  T  L  I  N  A  Y  N  S  V  D  D  T  T  R -

GCTGGGCAGCGATAAACGATCCGCAAGCTGAGGTTAACGTCGTGAAGGCTTACGTAGCTA
  14221  ---------+---------+---------+---------+---------+---------+  14280
         CGACCCGTCGCTATTTGCTAGGCGTTCGACTCCAATTGCAGCACTTCCGAATGCATCGAT
c            W  A  A  I  N  D  P  Q  A  E  V  N  V  V  K  A  Y  V  A  T -

CTACAGCGACGACTGAGCTGCATAGAACAATTCTCATTGACAGTATAGACTCCGCCTTCG
  14281  ---------+---------+---------+---------+---------+---------+  14340
         GATGTCGCTGCTGACTCGACGTATCTTGTTAAGAGTAACTGTCATATCTGAGGCGGAAGC
c            T  A  T  T  E  L  H  R  T  I  L  I  D  S  I  D  S  A  F  A -

CTTATGACCAAGTGGGGTGTTTGGTGGGCATAGCTAGAGGTTTGCTTAGACATTCGGAAG
  14341  ---------+---------+---------+---------+---------+---------+  14400
         GAATACTGGTTCACCCCACAAACCACCCGTATCGATCTCCAAACGAATCTGTAAGCCTTC
c            Y  D  Q  V  G  C  L  V  G  I  A  R  G  L  L  R  H  S  E  D -

ATGTTCTGGAGGTCATCAAGTCGATGGAGTTATTCGAAGTGTGTCGTGGAAAGAGGGGAA
  14401  ---------+---------+---------+---------+---------+---------+  14460
         TACAAGACCTCCAGTAGTTCAGCTACCTCAATAAGCTTCACACAGCACCTTTCTCCCCTT
c            V  L  E  V  I  K  S  M  E  L  F  E  V  C  R  G  K  R  G  S -

GCAAAAGATATCTTGGATACTTAAGTGATCAATGCACTAACAAATACATGATGCTAACTC
  14461  ---------+---------+---------+---------+---------+---------+  14520
         CGTTTTCTATAGAACCTATGAATTCACTAGTTACGTGATTGTTTATGTACTACGATTGAG
c            K  R  Y  L  G  Y  L  S  D  Q  C  T  N  K  Y  M  M  L  T  Q -

AGGCCGGACTGGCCGCAGTTGAAGGAGCAGACATACTACGAACGAATCATCTAGTCAGTG
  14521  ---------+---------+---------+---------+---------+---------+  14580
         TCCGGCCTGACCGGCGTCAACTTCCTCGTCTGTATGATGCTTGCTTAGTAGATCAGTCAC
c            A  G  L  A  A  V  E  G  A  D  I  L  R  T  N  H  L  V  S  G -

GTAATAAGTTCTCTCCAAATTTCGGGATCGCTAGGATGTTGCTCTTGACGCTTTGTTGCG
  14581  ---------+---------+---------+---------+---------+---------+  14640
         CATTATTCAAGAGAGGTTTAAAGCCCTAGCGATCCTACAACGAGAACTGCGAAACAACGC
c            N  K  F  S  P  N  F  G  I  A  R  M  L  L  L  T  L  C  C  G -

GAGCACTATAAAAATGTTATGTTGTTCAGCCAGTGTCAAATTTTCAAACGGGTTACAATT
  14641  ---------+---------+---------+---------+---------+---------+  14700
         CTCGTGATATTTTTACAATACAACAAGTCGGTCACAGTTTAAAAGTTTGCCCAATGTTAA
c            A  L  *
```

FIG. 18W

```
            ATCGCTACTTATTTGCGCATGTTTGTTAGCGGTGCTAATTGTTAGCTTTTGTAGAAGGCG
    14701   ---------+---------+---------+---------+---------+---------+ 14760
            TAGCGATGAATAAACGCGTACAAACAATCGCCACGATTAACAATCGAAAACATCTTCCGC

ORF11
            ATGAGGCACTTAGAAAAACCCATCAGAGTAGCGGTACACTATTGCGTCGTGCGAAGTGAC
    14761   ---------+---------+---------+---------+---------+---------+ 14820
            TACTCCGTGAATCTTTTTGGGTAGTCTCATCGCCATGTGATAACGCAGCACGCTTCACTG
a           M  R  H  L  E  K  P  I  R  V  A  V  H  Y  C  V  V  R  S  D  -

GTTTGTGACGGGTGGGATGTATTTATAGGCGTAACGTTAATCGGTATGTTTATTAGTTAC
    14821   ---------+---------+---------+---------+---------+---------+ 14880
            CAAACACTGCCCACCCTACATAAATATCCGCATTGCAATTAGCCATACAAATAATCAATG
a           V  C  D  G  W  D  V  F  I  G  V  T  L  I  G  M  F  I  S  Y  -

TATTTATATGCTCTAATTAGCATATGTAGAAAAGGAGAAGGTTTAACAACCAGTAATGGG
    14881   ---------+---------+---------+---------+---------+---------+ 14940
            ATAAATATACGAGATTAATCGTATACATCTTTTCCTCTTCCAAATTGTTGGTCATTACCC
a           Y  L  Y  A  L  I  S  I  C  R  K  G  E  G  L  T  T  S  N  G  -

TAAAAATCCTTCAATAAATTTGAAATAAACAAAAGTAAGAAAAATGAAATAATTAGGCTA
    14941   ---------+---------+---------+---------+---------+---------+ 15000
            ATTTTTAGGAAGTTATTTAAACTTTATTTGTTTTCATTCTTTTTACTTTATTAATCCGAT
a           *                                                           -

GTCTTTTTGTTCGTCTTTCGCTTTTGTAGAATAGGTTTTATTTCGAGGTAAGATGACTAA
    15001   ---------+---------+---------+---------+---------+---------+ 15060
            CAGAAAAACAAGCAGAAAGCGAAAACATCTTATCCAAAATAAAGCTCCATTCTACTGATT

ACTCTACCTCACGGTTTAATACTCTGATATTTGTAAAATTAGTCCGTAAAGTCAGATAGT
    15061   ---------+---------+---------+---------+---------+---------+ 15120
            TGAGATGGAGTGCCAAATTATGAGACTATAAACATTTTAATCAGGCATTTCAGTCTATCA

GATATTATATTAGTATAGTATAATAAACGCCAAAATCCAATCAAAGTTTGGGACCTAGGC
    15121   ---------+---------+---------+---------+---------+---------+ 15180
            CTATAATATAATCATATCATATTATTTGCGGTTTTAGGTTAGTTTCAAACCCTGGATCCG

GGGCCTCTTATGAGGCTAACTTATCGACAATAAGTTAGGTCCGCCAC
    15181   ---------+---------+---------+-------  15227
            CCCGGAGAATACTCCGATTGAATAGCTGTTATTCAATCCAGGCGGTG
```

FIG. 20

```
                        _____I(A)_____                     _____Ia____
      BYV_HEL     FTFTNLSANV LLYEAPPGGG KTTTLIKVFC ETFSK.VNSL ILTANKSSRE
      CTV_HEL     LTFTNEEHSL IVYEAPPGGG KTHSLVNSYA DYCVK.VSCL VVTANKNSQT
      GLRaV3_HEL  VGESFKSFEY KCYNAPPGGG KTT....MLV DEFVKSPNST ATITANVGSS
      LIYV_HEL    MVRRPDVNGL KFYNKPPGAG KTTTIAKLMS KDLKNKVKCL ALSYTKVGRL

CONSENSUS   ---------- --Y-aPPGaG KTt------- d-f-k-v--l -----k----

__                                          ___II_
      BYV_HEL     EILAKVNRIV LD...EGDTP LQTRDRILTI DSYLMNNR.G LTCKVLYLDE
      CTV_HEL     EISQRISNEL MGRKLAAKYV TDAASRVFTV DSYLMNHL.R LTTQLLFIDE
      GLRaV3_HEL  EDINM....A VKKR...DPN LEGLNSATTV NSRVVNFIVR GMYKRVLVDE
      LIYV_HEL    ELIDKLKKDG IEKP...EKY VKTYDSFLMN NDNILEIV.. ....NLYCDE

CONSENSUS   E--------- -------d-- -------ltv -s--mn---- -----ly-DE

_                    ___III___
      BYV_HEL     CFMVHAGAAV ACIEFTKCDS AILFGDSRQI RYGRCSELDT AVLSDLNRFV
      CTV_HEL     CFMVHAGAIG AVVEFTSCKA VVFFGDSKQI HYIHRNDLGV SFVADIDAFI
      GLRaV3_HEL  VYMMHQG.LL QLGVFQPASE GLFFGDINQI PFINREKVFR MDCA..VXLP
      LIYV_HEL    VFMMHAGHFL TLLTKIAYQN GYCYGDVNQI PFINRDPYTP AYLS..REFF

CONSENSUS   -fM-HaG--- ----f--c-- --ffGD--QI --i-r----- --------f-

____IV____
      BYV_HEL     DDESRVYGEV SYRCPWDVCA WLSTF..... ...YPKTVAT TNLVSAGQSS
      CTV_HEL     QPEHRIYGEV SYRCPWDICE WLSEF..... ...YPRHVAT ANVGSIGKSS
      GLRaV3_HEL  KKESVVYTSK SYRCPLDVCY LLSSMTVRGT EKCYPEKVVS GKDK.PVVRS
      LIYV_HEL    RKQDLNYDTY TYRCPLDTCY LLSNLKDEMG NIIYAGGVKN VNEVYPTIRS

CONSENSUS   --e---vY--- sYRCP-DvC- -LS-f----- ---Yp--V-- -n-------S

BYV_HEL     MQVREIESVD DVEYSSEFVY LTMLQSEKKD LLKSFGK..R SRSSVEKPTV
      CTV_HEL     VSIEEINGCD DVPYDKAAKY IVYTQAEKND LQKHLGRLTV GRNKV.VPIV
      GLRaV3_HEL  LSKRPIGTTD DVAEINADVY LCMTQLEKSD MKRSLKGKGK .ETP.....V
      LIYV_HEL    LNLFGINVVG EVPVEYNAKY LTFTQDEKLN LQRHIDSQGG CRNA.....V

CONSENSUS   l----I---d dV-------Y l--tQ-EK-d l---l----- -r-------V

_____V_____                    _____VI_____
      BYV_HEL     LTVHEAQGET YRKVNLVRTK FQEDDPFRSE NHITVALSRH VESLTYSVLS
      CTV_HEL     NTVHEVQGET YKRVRLVRFK YQEDTPFSSK NHIVVALTRH VDSLVYSVLT
      GLRaV3_HEL  MTVHEAQGKT FSDVVLFRTK KADDSLFTKQ PHILVGLSRH TRSLVYAALS
      LIYV_HEL    STVNEAQGCT FSEVNLVRLV QFDNPVMSDI NQFVVAISRH TTTFKYFTPH

CONSENSUS   -TVhEaQG-T ---V-LvR-k ---d--f--- nhi-ValsRH --sl-Y--l-

BYV_HEL     SKRDDAIAQA I
      CTV_HEL     SRRYDDTATN I
      GLRaV3_HEL  SELDDKVGTY I
      LIYV_HEL    SRLNDRVSNA I

CONSENSUS   S---D-v--- I
```

FIG. 22

```
                      ___I___                        _____II_____
BYV_RdRp      ITTFKLMVKR DAKVKLDSSC LVKHPPAQNI MFHRKAVNAI FSPCFDEFKN
CTV_RdRp      ISNFKLMVKR DAKVKLDDSS LSKHPAAQNI MFHKKFINAI FSPCFDEFKN
GLRaV3_RdRp   LTSYTLMVKA DVKPKLDNTP LSKYVTGQNI VYHDRCVTAL FSCIFTACVE
LIYV_RdRp     FKTLNLMVKG ETKPKMDLST YDSYNAPANI VYYQQIVNLY FSPIFLECFA

CONSENSUS     ---f-LMVK- d-K-KlD-s- l-k----qNI --h---vna- FSp-F-e---

_____III____               _____IV_____
BYV_RdRp      RVITCTNSNI VFFTEMTNST LASIAKEMLG .SEHVYNVGE IDFSKFDKSQ
CTV_RdRp      RVLSSLNDNI VFFTEMTNAG LAEIIRRIIG .DDDNLFVGE VDFSKFDKSQ
GLRaV3_RdRp   RLKYVVDERW LFYHGMDTAE LAXALRNNLG .DIRQYYTYE LDISKYDKSQ
LIYV_RdRp     RLTYCLSDKI VLYSGMNTDV LAELIESKLP LGLNAYHTLE IDFSKFDKSQ

CONSENSUS     R-------d-i vf---M---- LA-------lg -----y---E iDfSKfDKSQ

BYV_RdRp      DAFIKSFERT LYSAFGFDED LLD.VWMQGE YTSNATTLDG QLSFSVDNQR
CTV_RdRp      DLFIKEYERT LYSEFGFDTE LLD.VWMEGE YRARATTLDG QLSFSVDGQR
GLRaV3_RdRp   SALMKQVEEL ILLTLGVDRE VLS.TFFCGE YDSVVRTMTK ELVLSVGSQR
LIYV_RdRp     GTCFKLYEEM MYKMFGFSPE LYDRDFKYTE YFCRAKA.TC GVDLELGTQR

CONSENSUS     --f-K-yE-- ly--fGfd-e lld-----gE Y---a-tl-- -l--sv--QR

_____V_____         _____VI_____
BYV_RdRp      KSGASNTWIG NSIETLGILS MFYYTNRFKA LFVSGDDSLI FSESPIRNSA
CTV_RdRp      RSGGSNTWIG NSLVTLGILS LYYDVSKFDL LLVSGDDSLI YSSEKISNFS
GLRaV3_RdRp   RSGGANTWLG NSLVLCTLLS VVLRGLDYSY IVVSGDDSLI FSRQPLDIDT
LIYV_RdRp     RTGSPNTWLS NTLVTLGMML SSYDIDDIDL LLVSGDDSLI FSRKHLPNKT

CONSENSUS     rsG--NTW-G Nslvtlg-ls --y----f-- llVSGDDSLI fS-----n--

___VII___              _____VIII_____
BYV_RdRp      DAMCTELGFE TKFLTPSVPY FCSKFFVMTG HDVFFVPDPY KLLVKLGAS.
CTV_RdRp      SEICLETGFE TKFMSPSVPY FCSKFVVQTG NKTCFVPDPY KLLVKLGAP.
GLRaV3_RdRp   SVLSDNFGFD VKIFNQAAPY FCSKFLVQVE DSLFFVPDPL KLFVKFGAS.
LIYV_RdRp     QEINKNFGME AKYIEKSSPY FCSKFIVELN GKLKVIPDPI RFFEKLSIPI

CONSENSUS     ------fGfe -Kf---s-PY FCSKF-V--- ----fvPDP- kl-vKlga--

BYV_RdRp      ..KDEVDDEF LFEVFTSFRD LTKDLVDERV IELLTHLVHS KYGYESGDTY
CTV_RdRp      ..QNKLTDVE LFELFTSFKD MTQDFGDQVV LEKLKLLVEA KYGFASGTTM
GLRaV3_RdRp   ..KTSDID.L LHEIFQSFVD LSKGFNREDV IQELAKLVTR KYK.HSGWTY
LIYV_RdRp     RQEDFVNGSV VKERFISFKD LMKEYDNDVA VIRIDEAVCY RYSIPVGCSY

CONSENSUS     -------d-- l-E-F-SF-D l-kdf--e-v i--l--lV-- kY---sG-ty

BYV_RdRp      AALCAIHCIR SNFSSFKKLY
CTV_RdRp      PALCAIHCVR SNFLSFERLF
GLRaV3_RdRp   SALCVLHVLS ANFSQFCRLY
LIYV_RdRp     AALCYIHCCM SNFVSFRRIY

CONSENSUS     -ALC-iHc-- sNF-sF-rly
```

```
GLRaV-3_HEL    S   P   Q   S   V   S   D   A   L   L
                               GLRaV-3_RdRp    T   R   S   P   R   L   V   A   F   E   V   Y

GLRaV-3 (nt)  TCg Cct CAA TCa GTa tcc GAC gcT tTg cTt c Aca cgT tcg ccc ccg ctg gtT GCt TTc GAg GTa TAT
LIYV (nt)     TCa Cta CAA TCt GTt agt GAt tTt gTt tTg a Aag acT atc att tta gac agT GCc TTt GAc GTg TAT LIYV_HEL       S   L   Q   S   V   S   D   F   V   L
                               LIYV_RdRp      K   T   I   I   L   D   S   A   F   D   V   Y
```

FIG. 24

```
                              transmembrane
           1                  ─────────────                                    54
BYV_p7K    MDCVLRSYLL LAFGFLICLF LFCLVVFIWF VYKQILFRTT AQSNEARHNH STVV*
LIYV_P5K   .......... .......... ..MSILLFFL MSILVWFIFT ILKLLFVNTD SEVNIPNKSR F*...
GLRaV3_p5K .......... .......MDD FKQAILLLVV DFVFVILLL  VLTFVVPRLQ QSSTINTGLR TV*..
CTV_p6K    MDCVIQGFLT FLVGIAVFCA FAGLIIVIT  IYRCTIKPVR SASPYGTHAT V*...

CONSENSUS  ---------- ---------- -------f-- ---il-f--- ---l

FIG. 26A

```
                         _____A_____
    BYV_p65    ..MVVFGLDF GTTFSSVCAY VGEELYLFKQ RDSAYIPTYV FLHSDTQEVA
    CTV_p65    ..MVLLGLDF GTTFSTVAMA TPSELVILKQ SNSSYIPTCL LLHAEPNSVS
    GLRaV3_p59 ...MEVGIDF GTTFSTICFS PSGVSGCTPV AGSVYVETQI FIPEGSSTYL
    LIYV_p62   MRDCKVGLDF GTTFSTVSTL VNNSMYVLRL GDSAYIPTCI AITPGGEAI.

CONSENSUS  ------GlDF GTTFStv--- ----l--l-- --S-YipTci f-------v-

BYV_p65    FGYDAEVLSN DLSVRGGFYR DLKRWIGCDE ENYRDYLEKL KPHYKTELLK
    CTV_p65    YGYDAEYLAA S.GESGSFYK DLKRWVGCTA KNYQTYLHKL SPSYKVIVKE
    GLRaV3_p59 IG.KAAGKAY RDGVEGRLYV NPKRWVGVTR DNVERYVEKL KPTYTVKM..
    LIYV_p62   IGGAAEVLSG DDTPHCFFY. DLKRWVGVDD NTFKFAMNKI RPKYVAELVE

CONSENSUS  -G--Ae-l-- -----g-fY- dlKRWvG--- -ny--yl-Kl -P-Y---l--

BYV_p65    VAQSSKSTVK LDCYSGTVPQ NATLPGLIAT FVKALISTAS EAFKCQCTGV
    CTV_p65    FGTKSVPVPY LSPLNNDLGL SVALPSLIAS YAKSILSDAE RVFNVSCTGV
    GLRaV3_p59 ...DSGGALL IGGLGSGPDT LLRVVDVICL FLRALILECE RYTSTTVTAA
    LIYV_p62   ......GEVY LTGINKGFSI KLSVKQLIKA YIETIVRLLA SSYSLRVIDL

CONSENSUS  ----s----- l--------- ------lI-- -----i---- --f----T--

_____B_____
    BYV_p65    ICSVPANYNC LQRSFTESCV NLSGYPCVYM VNEPSAAALS ACSRIKGATS
    CTV_p65    ICSVPAGYNT LQRAFTQQSI SMSGYSCVYI INEPSAAAYS TLPKLNSADK
    GLRaV3_p59 VVTVPADYNS FKRSFVVEAL KGLGIPVRGV VNEPTAAALY SLAKSRVEDL
    LIYV_p62   NQSVPADYKN AQRLAARSVL KALSFPCRRI INEPSAAAVY CVSRYPNYNY

CONSENSUS  i-sVPA-Yn- lqR-f----- ---gypc--i -NEPsAAA-- ----------

____C____            ____D____
    BYV_p65    PVLVYDFGGG TFDVSVISAL NNTFVVRASG GDMNLGGRDI DKAFVEHLYN
    CTV_p65    YLAVYDFGGG TFDVSIVSVR LPTFAVRSSS GDMNLGGRDI DKKLSDKIYE
    GLRaV3_p59 LLAVFDFGGG TFDVSFVKKK GNILCVIFSV GDNFLGGRDI DRAIVEVIKQ
    LIYV_p62   FL.VYDFGGG TFDVSLIGKY KSYVTVIDTE GDSFLGGRDI DKSIEDYLVG

CONSENSUS  -l-VyDFGGG TFDVS----- ---f-V--s- GD--LGGRDI Dk--------

BYV_p65    KAQ...LPVN YKIDISFLKE SLSKKVSFLN FPVVSEQGVR VDVLVNVSEL
    CTV_p65    MAD...FVPQ KELNVSSLKE ALSLQTDPVK YT.VNHYGMS ETVSIDQTVL
    GLRaV3_p59 KIKGKASDAK LGIFVSSMKE DLSNNNAITQ HLIPVEGGVE V.VDLTSDEL
    LIYV_p62   KYNIKKVIP. .ATYLALIKE E.CNNTNKSI FTILFDDGSV QVVEFSKSEL

CONSENSUS  k--------- ----vs-lKE -ls------- f-i--e-G-- --V-----eL

____E____
    BYV_p65    AEVAAPFVER TIKIVKEVY. .EKYCSSMRL EPNVKAKLLM VGGSSYLPGL
    CTV_p65    REIASVFINR TIDILTQV.. ..KVKSSMPE SQSL..KLVV VGGSSYLPGL
    GLRaV3_p59 DAIVAPFSAR AVEVFKTGP. .DNFYPDPVI A.......VM TGGSSALVKV
    LIYV_p62   EKCVRPFVER SIKLINDVVV RNKLTSGV.. ......IYM VGGSSLLQPV

CONSENSUS  --i--pFv-R -i-i---v-- --k-s---- ---------m vGGSS-L---
```

FIG. 26B

```
                                            F
    BYV_p65   LSRLSSIPFV DEC.L.VLPD ARAAVAGGCA LYSACLRNDS PMLLVDCAAH
    CTV_p65   LDALATVPFV SGI.V.PVED ARTAVARGCA LYSECLDGRS KALLIDCITH
 GLRaV3_p59   RSDVANLPQI SKV.VFDSTD FRCSVACGAK VYCDTLAGNS GLRLVDTLTN
   LIYV_p62   QDMVRSYAST KGLTLVADQD MRSAVSYGCS VLHK.LEDNK EIVYIDCNSH

CONSENSUS   -------p-v ---------D -R-aVa-Gc- -y---L---s ---l-Dc--h

G
    BYV_p65   NLSISSKYCE SIVCVPAGSP IPFTGVRTVN MTGSNASAVY SAALFEGDFV
    CTV_p65   HLSVTTFSAD SVVVAAAGSP IPFEGERKLT LRKCVSTSNY QARMFEGDYE
 GLRaV3_p59   TLTDEVVGLQ PVVIFPKGSP IPCSYTHRYT V....GGGDV VYGIFEGE..
   LIYV_p62   PLSDISFNCD PEPIIRKPMS IPYTHTVKMR HDRPLKT... IVNIYEGSNL

CONSENSUS   -Ls------d -vvi---gsp IPf------- ---------- ----fEGd--

H
    BYV_p65   KCRLNKRIFF GDVVLGNVGV TGSATRTVPL TLEINVSSVG TISFSLVGPT
    CTV_p65   KVFRNERIYA ASVSLFTLGV NWSVPNDVEM TLVTKVDSMG KVEFYLKGPS
 GLRaV3_p59   ....NNRAFL NEPTFRGVSK RRGDPVETDV A.QFNLSTDG TVSVIVNGEE
   LIYV_p62   FMPENDWLIS SNINTTDFAK .....VGEEY SKVYEYDIDG IITLKIRNEV

CONSENSUS   ----N-r-f- --v-l----- --------e- ---------G ---f---g--

BYV_p65   GVKKLIGGNA AYDFSSYQLG ERVVADLHKH NSDKVKLIHA LTYQPFQRKK
    CTV_p65   GELVNVQGTS HYDYAGMPHP TRKLVRLSDY NVNSAALVLA LTLTREKREK
 GLRaV3_p59   VKNEYLVPGT TNVLDSL... ...VYKSGRE DLEAKAIPEY LTTLNILHDK
   LIYV_p62   TGKMFTLPNS FTKSDNIKPI TFKLTQLSNT D.DLATLTSL LGYHDKNFER

CONSENSUS   ---------- ---------- ------l--- --d---l--- Lt------ek

BYV_p65   LTDGDKALFL KRLTADYRRE ARKFSSY... ......DDAV LNSSELLLGR
    CTV_p65   FLLRT...LF DTLLADLRKT A.SLSEYSKK YPITRNDIDV VSSR...MGI
 GLRaV3_p59   AFTRRNLGNK DKGFSDLRIE ENFLKS.... ...AVDTDTI LNG*......
   LIYV_p62   FYG......L FNVPTILIKE IDKLGGFKTL YRRLKSMNAN F.........

CONSENSUS   f--------l -----dlr-e ---l--y--- ---------v l---------

BYV_p65   IIPKILRGSR VEKLDV*
    CTV_p65   VVSKVLRGSD LERIPL.
 GLRaV3_p59   .......... .......
   LIYV_p62   .......... .......

CONSENSUS   ---------- -------
```

FIG. 28A

```
   BYV_p61  MTTRFSTPAN YYWGELFRRF FGGQEW.... ....KNLMSE AASVSRPRYS
   CTV_p61  ......MSSH HVWGSLFRKF YGEAIW.... ....KEYLSE STRNFDERNV
  LIYV_P59  ..MLNDRIAV TCFQTLLKKS NVKHEMEQTN NYIVNNLADI NRNTFPALAG
GLRaV3_p55  .......MDK YIYVTGI..L NPNEARDEVF SVVNKGYIGP GGRSFSNRGS

CONSENSUS  ---------- --w--lf--f -----w---- ----k----- ----f--r--

BYV_p61  S.DFRFSDGV ILSRKTFGES TGES..FVRE FSLLLTFPKT YEVCKLCGVA
   CTV_p61  SLDHTLSSGV VVRRQSLLNA PQGT..FENE LALLYNSVVI NDFVELTGMP
  LIYV_P59  SVRIDFNSDY YISGGQIVVS PKDSNAYVKL LIVYLKYCYI N.YSAKTKYP
GLRaV3_p55  KYTVVWEN.. ..SAARISGL TSTSQSTIDA FAYFL..... ..LKGGLTTT

CONSENSUS  s----f---- --s------- ---s--fv-- ---ll----- ----------

BYV_p61  MELALNGMN. .RLSDYNVSE FN......IV DVKTVGCKFN IQSVTEFVKK
   CTV_p61  LKSLMTGIED RKVPD....E LI......SV DPHEVGCRFT LNDVESYLMS
  LIYV_P59  PQSLLAVLDY DSFKAKWVKY LDKSLTDYLD DNKTEGCSFT EQQVVEKYPQ
GLRaV3_p55  LSNPINCENW VRSSKDLSAF FRTLIKGKIY ASRSVDSNLP KKDRDDIME.

CONSENSUS  l---l----- ---------- ---------- d---vgc-f- ---v-e----

BYV_p61  INGNVAEPSL VEHCWSLSNS CGELINPKDT KRFVSLIFKG KDLAESTDEA
   CTV_p61  RGEDFADLAA VEHSWCLSNS CSRLLSSTEI DANKTLVF.T KNFDSNISG.
  LIYV_P59  VDSLVAKIL. ....YRVCNS LGKLLDLKDF ENKNISGFEI NTAQDSPTVA
GLRaV3_p55  .ASRRLSPSD AAFCRAVSVQ VGKYVDVTQN LESTIVPLRV MEIKKRRGSA

CONSENSUS  -----a---- ----w--sns -g-l----d- -------f-- ---------a

BYV_p61  IVS..SSYLD YLSHCLNLYE TCNLSSNSGK KSLYDEFLKH VIDYL...EN
   CTV_p61  .VT..TKLET YLSYCISLYK KHCM.KDDDY FNLILPMFNC LMKVL...AS
  LIYV_P59  DDN..ES.ND FFRECVNDQR YYSSLSGSKL GKAKLEANAY IFKILLKSAS
GLRaV3_p55  HVSLPKVVSA YVDFYTNLQE LLSDEVTRAR TDTVSAYATD SMAFLVKMLP

CONSENSUS  -v-------- yl--c-nl-- ---------- ---------- ----L-----

BYV_p61  SDLEYRSPSD NPLVAGILYD MCFEYNTLKS TYLKNIESFD CFLSLYLPLL
   CTV_p61  LGLFYEKHAD NPLLTGMLIE FCLENKVYYS TFKVNLDNVR LFKSKVLPVV
  LIYV_P59  GEFDIDRLSR NPLAISKFMN LYTNHVTDSE TFKSKFEALK SIKTPFASFI
GLRaV3_p55  LT......AR EQWLKDVLGY LLVRRRPANF SYDVRVAWVY DVIATLKLVI

CONSENSUS  --l------- npl----l-- lc-------- t-----e--- ---------i

I
   BYV_p61  SEVFSMNWER PAPDVRLLFE LDAAELLLKV PTINMHDST. ..FLYKNKLR
   CTV_p61  LTVWDISEPD DPVDERVLIP FDPTDFVLDL PKLNIHDTM. ..VVVGNQIR
  LIYV_P59  KKAFGIR... ........LN FEDSKIFYAL PKERQSDVLS DDMMVESIVR
GLRaV3_p55  RLFFNKDTPG GIKDLKPCVP IESFDPFHEL S......... ......SYFS
```

FIG. 28B

```
      BYV_p61   YLESYFEDDS NELIKVKVDS LLTRDNPEL. .KLAQRWV.. ...GFHCYYG
      CTV_p61   QLEYVVESDA LDDLSQHVDL RLAADNPDL. .RVGLRWA.. ...GMFVYYG
      LIYV_P59  DAASFTVVSD NNYLPERVDR FVTQLLLELF PKTKASFPNK IMFGFLHYFA
    GLRaV3_p55  RLSYEMTTGK GGKICPEIAE KLVRRLMEEN YKLRLT.PVM ALIIILVYYS

CONSENSUS   -l-------- -------vd- -l-----el- -k----w--- ---g-l-Yy-

____II____
      BYV_p61   VFRTAQTRKV KRDAEYKLPP AL......GE FVINMSGVEE FF.EELQKKM
      CTV_p61   VYRCVVDRAV ERPTLFRLPQ KLLSQDDGES CSLHMGSVEA LF.NLVQKVN
      LIYV_P59  LSTTNSKR.. .....FNDTQ ESTIEIEGET LKISLKFITS YLRNAIQSQH
    GLRaV3_p55  IYGTNATRIK RRPDFLNVRI KGRVE..... .KVSLRGVED ..RAFRISEK

CONSENSUS   vy-t---R-- -r---f---- ---------- --i----ve- -f----q---

BYV_p61   PSI...SVRR RFCGSLSHEA FSVFKRFGVG FPPITRLNVP VKYSYLNVDY
      CTV_p61   KDI...NVRR QFMGRHSEVA LRLYRNLGLR FPPISSVRLP AHHGYLYVDF
      LIYV_P59  PDYADSNIVR LWCNKRSNLA LGYFKSRNIQ LYLYS..KYP RLLNYMRFDY
    GLRaV3_p56  RGINAQRVLC RYYSDLTCLA RRHYGIRRNN WKTLSYVD.. GTLAYDTADC

CONSENSUS   --i----v-r -fc---s--A l--------- f---s----p ----Yl--Dy

BYV_p61   YRHVKRVGLT QDELTILSNI EFDVAEMCCE REVALQARRA QR....GEKP
      CTV_p61   YKRVPDGAVT ADELESLRQL RSSVDVMCKD R.VSITPPPF NRLRRGSSRT
      LIYV_P59  FKGLDMGKLT DEERLSIQTL RCITEDRS.E GTLATHNDLN SWILRP....
    GLRaV3_p55  ITSKVRNTIN TADHASIIHY IKTNENQVTG TTLPHQL*.. ..........

CONSENSUS   y--------t -de--s---- ----e----e ---------- -r--------

BYV_p61   FQGWKGTKNE ISPHARSSIR VKKNNDSLLN ILWKDVGARS QRRLNPLHRK
      CTV_p61   FRGR.GARGA SSRHMSRDVA TSGFNLPYHG RLYSTS*... ..........
      LIYV_P59  .......... .......... .......... .......... ..........
    GLRaV3_p55  .......... .......... .......... .......... ..........

CONSENSUS   ---------- ---------- ---------- ---------- ----------

BYV_p61   H*
      CTV_p61   ..
      LIYV_P59  ..
    GLRaV3_p55  ..

CONSENSUS   --
```

FIG. 29A

```
(5' primer, 93-224)
                NcoI
tacttatctagaacc
              ↘
       ↗─ATGGAAGCGAGTCGACGACTA
      ATGGAAGCGAGTCGACGACTATCGCCATCGGACGCCGCCTTTTGCAGAGCAGTGTCGGTT
9404------+---------+---------+---------+---------+---------+---
        M  E  A  S  R  R  L  S  P  S  D  A  A  F  C  R  A  V  S  V  -

CAGGTAGGGAAGTATGTGGACGTAACGCAGAATTTAGAAAGTACGATCGTGCCGTTAAGA
      ------+---------+---------+---------+---------+---------+---
        Q  V  G  K  Y  V  D  V  T  Q  N  L  E  S  T  I  V  P  L  R  -

GTTATGGAAATAAAGAAAAGACGAGGATCAGCACATGTTAGTTTACCGAAGGTGGTATCC
      ------+---------+---------+---------+---------+---------+---
        V  M  E  I  K  K  R  R  G  S  A  H  V  S  L  P  K  V  V  S  -

GCTTACGTAGATTTTTATACGAACTTGCAGGAATTGCTGTCGGATGAAGTAACTAGGGCC
      ------+---------+---------+---------+---------+---------+---
        A  Y  V  D  F  Y  T  N  L  Q  E  L  L  S  D  E  V  T  R  A  -

AGAACCGATACAGTTTCGGCATACGCTACCGACTCTATGGCTTTCTTAGTTAAGATGTTA
      ------+---------+---------+---------+---------+---------+---
        R  T  D  T  V  S  A  Y  A  T  D  S  M  A  F  L  V  K  M  L  -

CCCCTGACTGCTCGTGAGCAGTGGTTAAAAGACGTGCTAGGATATCTGCTGGTACGGAGA
      ------+---------+---------+---------+---------+---------+---
        P  L  T  A  R  E  Q  W  L  K  D  V  L  G  Y  L  L  V  R  R  -

CGACCAGCAAATTTTTCCTACGACGTAAGAGTAGCTTGGGTATATGACGTGATCGCTACG
      ------+---------+---------+---------+---------+---------+---
        R  P  A  N  F  S  Y  D  V  R  V  A  W  V  Y  D  V  I  A  T  -

CTCAAGCTGGTCATAAGATTGTTTTTCAACAAGGACACACCCGGGGGTATTAAAGACTTA
      ------+---------+---------+---------+---------+---------+---
        L  K  L  V  I  R  L  F  F  N  K  D  T  P  G  G  I  K  D  L  -

AAACCGTGTGTGCCTATAGAGTCATTCGACCCCTTTCACGAGCTTTCGTCCTATTTCTCT
      ------+---------+---------+---------+---------+---------+---
        K  P  C  V  P  I  E  S  F  D  P  F  H  E  L  S  S  Y  F  S  -

AGGTTAAGTTACGAGATGACGACAGGTAAAGGGGGAAAGATATGCCCGGAGATCGCCGAG
      ------+---------+---------+---------+---------+---------+---
        R  L  S  Y  E  M  T  T  G  K  G  G  K  I  C  P  E  I  A  E  -

AAGTTGGTGCGCCGTCTAATGGAGGAAAACTATAAGTTAAGATTGACCCCAGTGATGGCC
      ------+---------+---------+---------+---------+---------+---
        K  L  V  R  R  L  M  E  E  N  Y  K  L  R  L  T  P  V  M  A  -
```

FIG. 29B

```
TTAATAATTATACTGGTATACTACTCCATTTACGGCACAAACGCTACCAGGATTAAAAGA
------+---------+---------+---------+---------+---------+---
 L  I  I  I  L  V  Y  Y  S  I  Y  G  T  N  A  T  R  I  K  R   -

CGCCCGGATTTCCTCAATGTGAGGATAAAGGGAAGAGTCGAGAAGGTTTCGTTACGGGGG
------+---------+---------+---------+---------+---------+---
 R  P  D  F  L  N  V  R  I  K  G  R  V  E  K  V  S  L  R  G   -

GTAGAAGATCGTGCCTTTAGAATATCAGAAAAGCGCGGGATAAACGCTCAACGTGTATTA
------+---------+---------+---------+---------+---------+---
 V  E  D  R  A  F  R  I  S  E  K  R  G  I  N  A  Q  R  V  L   -

TGTAGGTACTATAGCGATCTCACATGTCTGGCTAGGCGACATTACGGCATTCGCAGGAAC
------+---------+---------+---------+---------+---------+---
 C  R  Y  Y  S  D  L  T  C  L  A  R  R  H  Y  G  I  R  R  N   -

AATTGGAAGACGCTGAGTTATGTAGACGGGACGTTAGCGTATGACACGGCTGATTGTATA
------+---------+---------+---------+---------+---------+---
 N  W  K  T  L  S  Y  V  D  G  T  L  A  Y  D  T  A  D  C  I   -

ACTTCTAAGGTGAGAAATACGATCAACACCGCAGATCACGCTAGCATTATACACTATATC
------+---------+---------+---------+---------+---------+---
 T  S  K  V  R  N  T  I  N  T  A  D  H  A  S  I  I  H  Y  I   -

AAGACGAACGAAAACCAGGTTACCGGAACTACTCTACCACACCAGCTTTAAAGCTGCGTG
------+---------+---------+---------+---------+---------+---
 K  T  N  E  N  Q  V  T  G  T  T  L  P  H  Q  L  *

TAGTATGCGACGATGTTTCT
------+---------+--- 10503
ATCATACGCTGCTACAAAGA
              ggtacctaggagttct
                  NcoI
            (3' primer, 93-225)
```

GRAPEVINE LEAFROLL VIRUS PROTEINS AND THEIR USES

This application claims the benefit of U.S. Provisional Patent Application Ser. No. 60/009,008, filed Dec. 21, 1995.

This work was supported by U.S.-Israel Binational Agricultural Research and Development Fund Grant No. US-1737-89 and by the U.S. Department of Agriculture Cooperative Agreement No. 58-2349-9-01. The Federal Government may have certain rights in the invention.

FIELD OF THE INVENTION

The present invention relates to grapevine leafroll virus proteins, DNA molecules encoding these proteins, and their uses.

BACKGROUND OF THE INVENTION

The world's most widely grown fruit crop, the grape (Vitis sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards are planted with traditional grapevine cultivars, which have been perpetuated for centuries by vegetative propagation. Several important grapevine virus and virus-like diseases, such as grapevine leafroll, corky bark, and Rupestris stem pitting, are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) the rugose wood complex (Martelli, ed., *Graft Transmissible Diseases of Grapevines, Handbook for Detection and Diagnosis*, FAO, UN, Rome, Italy (1993)).

Of the major virus diseases, the grapevine leafroll complex is the most widely distributed throughout the world. According to Goheen (Goheen, "Grape Leafroll," in Frazier et al., eds., *Virus Diseases of Small Fruits and Grapevines (A Handbook)*, University of California, Division of Agricultural Sciences, Berkeley, Calif., USA, pp. 209–212 (1970) ("Goheen (1970)"), grapevine leafroll-like disease was described as early as the 1850s in German and French literature. However, the virus nature of the disease was first demonstrated by Scheu (Scheu, "Die Rollkrankheit des Rebstockes (Leafroll of grapevine)," *D. D. Weinbau* 14:222–358 (1935) ("Scheu (1935)")). In 1946, Harmon and Snyder (Harmon et al., "Investigations on the Occurrence, Transmission, Spread and Effect of 'White' Fruit Colour in the Emperor Grape," *Proc. Am. Soc. Hort. Sci.* 74:190–194 (1946)) determined the virus nature of White Emperor disease in California. It was later proven by Goheen et al. (Goheen et al., "Leafroll (White Emperor Disease) of Grapes in California, *Phytopathology*, 48:51–54 (1958) ("Goheen (1958)")) that both leafroll and "White Emperor" diseases were the same, and only the name "leafroll" was retained.

Leafroll is a serious virus disease of grapes and occurs wherever grapes are grown. This wide distribution of the disease has come about through the propagation of diseased vines. It affects almost all cultivated and rootstock varieties of Vitis. Although the disease is not lethal, it causes yield losses and reduction of sugar content. Scheu estimated in 1936 that 80 percent of all grapevines planted in Germany were infected (Scheu, *Mein Winzerbuch*, Berlin:Reichsnahrstand-Verlags (1936)). In many California wine grape vineyards, the incidence of leafroll (based on a survey of field symptoms conducted in 1959) agrees with Scheu's initial observation in German vineyards (Goheen et al., "Studies of Grape Leafroll in California," *Amer. J. Enol. Vitic.*, 10:78–84 (1959)). The current situation on leafroll disease does not seem to be any better (Goheen, "Diseases Caused by Viruses and Viruslike Agents," *The American Phytopathological Society*, St. Paul, Minn.:APS Press, 1:47–54 (1988) ("Goheen (1988)"). Goheen also estimated that the disease causes an annual loss of about 5–20 percent of the total grape production (Goheen (1970) and Goheen (1988)). The amount of sugar in individual berries of infected vines is only about ½ to ⅔ that of berries from noninfected vines (Goheen (1958)).

Symptoms of leafroll disease vary considerably depending upon the cultivar, environment, and time of the year. On red or dark-colored fruit varieties, the typical downward rolling and interveinal reddening of basal, mature leaves is the most prevalent in autumn; but not in spring or early summer. On light-colored fruit varieties however, symptoms are less conspicuous, usually with downward rolling accompanied by interveinal chlorosis. Moreover, many infected rootstock cultivars do not develop symptoms. In these cases, the disease is usually diagnosed with a woody indicator indexing assay using *Vitis vivifera* cv. Carbernet Franc (Goheen (1988)).

Ever since Scheu demonstrated that leafroll was graft transmissible, a virus etiology has been suspected (Scheu (1935)). Several virus particle types have been isolated from leafroll diseased vines. These include potyvirus-like (Tanne et al., "Purification and Characterization of a Virus Associated with the Grapevine Leafroll Disease," *Phytopathology*, 67:442–447 (1977)), isometric virus-like (Castellano et al., "Virus-like Particles and Ultrastructural Modifications in the Phloem of Leafroll-affected Grapevines," *Vitis*, 22:23–39 (1983) ("Castellano (1983)") and Namba et al., "A Small Spherical Virus Associated with the Ajinashika Disease of Koshu Grapevine, *Ann. Phytopathol. Soc. Japan*, 45:70–73 (1979)), and closterovirus-like (Namba, "Grapevine Leafroll Virus, a Possible Member of Closteroviruses, *Ann. Phytopathol. Soc. Japan*, 45:497–502 (1979)) particles. In recent years, however, long flexuous closteroviruses ranging from 1,400 to 2,200 nm have been most consistently associated with leafroll disease (FIG. 1) (Castellano (1983), Faoro et al., "Association of a Possible Closterovirus with Grapevine Leafroll in Northern Italy," *Riv. Patol. Veg., Ser IV,* 17:183–189 (1981), Gugerli et al., "L'enroulement de la vigne: mise en évidence de particules virales et développement d'une méthode immuno-enzymatique pour le diagnostic rapide (Grapevine Leafroll: Presence of Virus Particles and Development of an Immuno-enzyme method for Diagnosis and Detection)," *Rev. Suisse Viticult. Arboricult. Hort.,* 16:299–304 (1984) ("Gugerli (1984)"), Hu et al., "Characterization of Closterovirus-like Particles Associated with Grapevine Leafroll Disease," *J. Phytopathol.,* 128:1–14 (1990) ("Hu (1990)"), Milne et al., "Closterovirus-like Particles of Two Types Associated with Diseased Grapevines," *Phytopathol. Z.,* 110:360–368 (1984), Zee et al., "Cytopathology of Leafroll-diseased Grapevines and the Purification and Serology of Associated Closteroviruslike Particles," *Phytopathology,* 77:1427–1434 (1987) ("Zee (1987)"), and Zimmermann et al., "Characterization and Serological Detection of Four Closterovirus-like Particles Associated with Leafroll Disease on Grapevine," *J. Phytopathol.,* 130:205–218 (1990) ("Zimmermann (1990)")). These closteroviruses are referred to as grapevine leafroll associated viruses ("GLRaV"). At least six serologically distinct types of GLRaV's (GLRaV-1 to -6) have been detected from leafroll diseased vines (Table 1) (Boscia et al., "Nomenclature of Grapevine Leafroll-associated Putative Closteroviruses, *Vitis,* 34:171–175 (1995) ("Boscia (1995)") and (Martelli, "Leafroll," pp. 37–44 in Martelli, ed., *Graft Transmissible Diseases of Grapevines, Handbook for Detection and Diagnosis,* FAO, Rome Italy, (1993) ("Martelli I")). The first five of these were confirmed in the 10th Meeting of the International Council for the Study of Virus and Virus Diseases of the Grapevine ("ICVG") (Volos, Greece, 1990).

TABLE 1

| Type | Particle length (nm) | Coat protein Mr (×10³) | Reference |
|---|---|---|---|
| GLRaV-1 | 1,400–2,200 | 39 | Gugerli (1984) |
| GLRaV-2 | 1,400–1,800 | 26 | Gugerli (1984) |
|  |  |  | Zimmermann (1990) |
| GLRaV-3 | 1,400–2,200 | 43 | Zee (1987) |
| GLRaV-4 | 1,400–2,200 | 36 | Hu (1990) |
| GLRaV-5 | 1,400–2,200 | 36 | Zimmermann (1990) |
| GLRaV-6 | 1,400–2,200 | 36 | Gugerli (1993) |

Through the use of monoclonal antibodies, however, the original GLRaV II described in Gugerli (1984) has been shown to be an apparent mixture of at least two components, IIa and IIb (Gugerli et al., "Grapevine Leafroll Associated Virus II Analyzed by Monoclonal Antibodies," 11*th Meeting of the International Council for the Study of Viruses and Virus Diseases of the Grapevine,* Montreux, Switzerland, pp. 23–24 (1993) ("Gugerli (1993)")). Recent investigation with comparative serological assays (Boscia (1995)) demonstrated that the IIb component of cv. Chasselas 8/22 is the same as the GLRaV-2 isolate from France (Zimmermann (1990)) which also include the isolates of grapevine corky bark associated closteroviruses from Italy (GCBaV-BA) (Boscia (1995)) and from the United States (GCBaV-NY) (Namba et al., "Purification and Properties of Closterovirus-like Particles Associated with Grapevine Corky Bark Disease," *Phytopathology,* 81:964–970 (1991) ("Namba (1991)")). The IIa component of cv. Chasselas 8/22 was given the provisional name of grapevine leafroll associated virus 6 (GLRaV-6). Furthermore, the antiserum to the CA-5 isolate of GLRaV-2 produced by Boscia et al. (Boscia et al., "Characterization of Grape Leafroll Associated Closterovirus (GLRaV) Serotype II and Comparison with GLRaV Serotype III," *Phytopathology,* 80:117 (1990)) was shown to contain antibodies to both GLRaV-2 and GLRaV-1, with a prevalence of the latter (Boscia (1995)).

Several shorter closteroviruses (particle length 800 nm long) have also been isolated from grapevines. One of these, called grapevine virus A ("GVA") has also been found associated, though inconsistently, with the leafroll disease (Agran et al., "Occurrence of Grapevine Virus A (GVA) and Other Closteroviruses in Tunisian Grapevines Affected by Leafroll Disease," *Vitis,* 29:43–48 (1990), Conti, et al., "Closterovirus Associated with Leafroll and Stem Pitting in Grapevine," *Phytopathol. Mediterr.,* 24:110–113 (1985), and Conti et al., "A Closterovirus from a Stem-pitting-diseased Grapevine," *Phytopathology,* 70:394–399 (1980)). The etiology of GVA is not really known; however, it appears to be more consistently associated with rugose wood sensu lato (Rosciglione at al., "Maladies de l'enroulement et du bois strié de la vigne: analyse microscopique et sérologique (Leafroll and Stem Pitting of Grapevine: Microscopical and Serological Analysis)," *Rev. Suisse Vitic Arboric. Hortic.,* 18:207–211 (1986) ("Rosciglione (1986)"), and Zimmermann (1990)). Moreover, another short closterovirus (800 nm long) named grapevine virus B ("GVB") has been isolated and characterized from corky bark-affected vines (Boscia et al., "Properties of a Filamentous Virus Isolated from Grapevines Affected by Corky Bark, *Arch. Virol.,* 130:109–120 (1993) and Namba (1991)).

As suggested by Martelli I, leafroll symptoms may be induced by more than one virus or they may be simply a general plant physiological response to invasion by an array of phloem-inhabiting viruses. Evidence accumulated in the last 15 years strongly favors the idea that grapevine leafroll is induced by one (or a complex) of long closteroviruses (particle length 1,400 to 2,200 nm).

Grapevine leafroll is transmitted primarily by contaminated scions and rootstocks. However, under field conditions, several species of mealybugs have been shown to be the vector of leafroll (Engelbrecht et al., "Transmission of Grapevine Leafroll Disease and Associated Closteroviruses by the Vine Mealybug *Planococcus-ficus,*" *Phytophylactica,* 22:341–346 (1990), Rosciglione, et al., "Transmission of Grapevine Leafroll Disease and an Associated Closterovirus to Healthy Grapevine by the Mealybug *Planococcus ficus,*" (Abstract), *Phytoparasitica,* 17:63–63 (1989), and Tanne, "Evidence for the Transmission by Mealybugs to Healthy Grapevines of a Closter-like Particle Associated with Grapevine Leafroll Disease," *Phytoparasitica,* 16:288 (1988)). Natural spread of leafroll by insect vectors is rapid in various parts of the world. In New Zealand, observations of three vineyards showed that the number of infected vines nearly doubled in a single year (Jordan et al., "Spread of Grapevine Leafroll and its Associated Virus in New Zealand Vineyards," 11*th Meeting of the International Council for the Study of Viruses and Virus Diseases of the Grapevine,* Montreux, Switzerland, pp. 113–114 (1993)). One vineyard became 90% infected 5 years after GLRaV-3 was first observed. Prevalence of leafroll worldwide may increase as chemical control of mealybugs becomes more difficult due to the unavailability of effective insecticides.

In view of the serious risk grapevine leafroll virus poses to vineyards and the absence of an effective treatment of it, the need to prevent this affliction continues to exist. The present invention is directed to overcoming this deficiency in the art.

SUMMARY OF INVENTION

The present invention relates to an isolated protein or polypeptide corresponding to a protein or polypeptide of a grapevine leafroll virus. The encoding RNA and DNA molecules, in either isolated form or incorporated in an expression system, a host cell, or a transgenic Vitis or citrus scion or rootstock cultivar, are also disclosed.

Another aspect of the present invention relates to a method of imparting grapevine leafroll virus resistance to Vitis scion or rootstock cultivars by transforming them with a DNA molecule encoding the protein or polypeptide corresponding to a protein or polypeptide of a grapevine leafroll virus. These DNA molecules can also be used in transformation of citrus scion or rootstock cultivar to impart tristeza virus resistance to such cultivars.

The present invention also relates to an antibody or binding portion thereof or probe which recognizes the protein or polypeptide.

Grapevine leafroll virus resistant transgenic variants of the current commercial grape cultivars and rootstocks allows for more complete control of the virus while retaining the varietal characteristics of specific cultivars. Furthermore, these variants permit control of GLRaV transmitted either by contaminated scions or rootstocks or by GLRaV-carrying mealy bugs. With respect to the latter mode of transmission, the present invention circumvents increased restriction of pesticide use which has made chemical control of mealy bug infestations increasingly difficult. In this manner, as well as others, the interests of the environment and the economics of grape cultivation and wine making are all benefited by the present invention.

BRIEF DESCRIPTION OF THE DRAWINGS

FIG. 1 is electron micrographs of GLRaV-3 particles of the NY1 isolate after negative staining with 1% uranyl acetate of a purified virus preparation (magnification 80,000×).

FIG. 2 shows the nucleotide and amino acid sequences of a PCR amplified fragment of the GLRaV-3 genome. The external and internal primers used for PCR are underlined and their orientations are indicated by arrows.

FIG. 3 compares the alignment of the amino acid sequence deduced from the PCR fragment of GLRaV-3 with respective regions of HSP90 homologues of beet yellow virus ("BYV") (p64), citrus tristeza virus ("CTV") (p61), and lettuce infectious yellow virus ("LIYV") (p59). Consensus amino acid residues are shown. Uppercase letters indicate identical amino acids, lowercase letters indicate at least three identical or functionally similar amino acids.

FIGS. 4A and 4B, panel B, is a Northern blot hybridization. Probe made from a clone insert gave positive reaction to itself (lane 3) as well as dsRNA from leafroll infected tissues (lane 1), but not to nucleic acids extracted from healthy grapevines (lane 2). Lane M contains a molecular weight marker (the Hind III digested fragments of lambda DNA). Panel A of FIG. 4 depicts an ethidium bromide stained agarose gel before transfer to a membrane.

FIG. 5 presents an analysis of GLRaV-3 dsRNA by electrophoresis on an ethidium bromide stained agarose gel. A dsRNA of ca. 16 kb was readily isolated from diseased grapevine (lane 6), but not from the healthy control (lane 5). Other samples that were used for control were tobacco mosaic virus dsRNA (lane 1); cucumber mosaic virus dsRNA (lane 2); pBluescript vector (lane 3) and an insert of clone pC4. λ Hind III digested fragment of lambda DNA was used as the molecular weight marker (lane M).

FIG. 6 is a secondary immunoscreening of plaques derived from three mother plaques that reacted to GLRaV-3 specific polyclonal antibody. Two filters each represent plaques from clones pCP5 (left), pCP8-4 (middle), and pCP10-1 (right).

FIG. 7 is a PCR analysis of immuno-positive clones with flanking vector primer (KS and SK). A similar size (1.0–1.1 kb) PCR product was produced in all three mother clones.

FIGS. 8A and 8B are Western blots of antibodies to GLRaV-3 that reacted to proteins produced by cDNA clones after IPTG induction in *E. coli.* Similar banding patterns were observed whether a polyclonal (panel A) or a monoclonal antibody (panel B) was used. Lane 1 shows clone pCP10-1; lane 2, pCP5; lane 3, pCP8-4; and lane 4, the native coat protein from GLRaV-3 infected tissue. Lane M is a prestained protein molecular weight marker.

FIG. 9 shows the cDNA clones containing the coding region for the coat protein of the NY1 isolate of GLRaV-3. Three clones (pCP8-4, pCP5, pCP10-1) were identified by immunoscreening of a cDNA library prepared in lambda ZAP II. Two other clones were aligned after plaque hybridization and nucleotide sequencing. An ORF encoding the coat protein is shown by an arrow in an open rectangle.

FIG. 10 shows the nucleotide and amino acid sequences of the coat protein gene of grapevine leafroll associated closterovirus-3, isolate NY1. Nucleotide sequencing was conducted by the procedure described in Example 1. The translated amino acid sequence is shown below the nucleotide sequence.

FIG. 11 compares the alignment of the coat protein of GLRaV-3 with respect to BYV, CTV, and LIYV. Consensus amino acid residues are shown. Uppercase letters indicate identical amino acids, and lowercase letters indicate at least three identical or functionally similar amino acids. The three conserved amino acid residues (S, R, and D) identified in all filamentous plant virus coat proteins are in bold (Dolja et al., "Phylogeny of Capsid Proteins of Rod-shaped and Filamentous RNA Plant Viruses: Two Families with Distinct Patterns of Sequence and Probably Structure Conservation," *Virology,* 184:79–86 (1991)).

FIG. 12 is a phylogenetic tree generated by the Clustal Method of MegAlign program in DNASTAR for the coat protein of GLRaV-3 with respect to that of other filamentous plant viruses. The coat protein of GLRaV-3 was incorporated into a previously described alignment (Dolja et al., "Molecular Biology and Evolution of Closteroviruses: Sophisticated Build-up of Large RNA Genomes," *Annual Review of Phytopathology,* 32:261–285 (1994) ("Dolja (1994)")) for comparison. The other virus sequences were obtained from current databases: apple chlorotic leafspot virus ("ACLSV"); apple stem grooving virus ("ASGV"); apple stem pitting virus ("ASPV"); barley yellow mosaic virus ("BaMV"); beet yellows closterovirus ("BYV"); diverged copies of BYV and CTV coat proteins ("BYV p24" and "CTV p27", respectively); citrus tristeza virus ("CTV"); grapevine virus A ("GVA"); grapevine virus B ("GVB"); lily symptomless virus ("LSV"); lily virus X ("LVX"); narcissus mosaic virus ("NMV"); pepper mottle virus ("PeMV"); papaya mosaic virus ("PMV"); potato virus T ("PVT"); potato virus S ("PVS"); potato virus M ("PVM"); potato virus X ("PVX"); tobacco etch virus ("TEV"); tobacco vein mottle virus ("TVMV"); and white clover mosaic virus ("WcMV").

FIG. 13 depicts an analysis of reverse transcription polymerase chain reaction ("RT-PCR") to detect GLRaV-3 in a partially purified virus preparation. The original sample concentration is equivalent to 50 mg/μl of phloem tissue (lane 1) which was diluted by 10-fold series as $10^{-1}$ (lane 2), 10$^{-2}$ (lane 3), 10$^{-3}$ (lane 4), 10$^{-4}$ (lane 5), and 10$^{-5}$ (lane 6), respectively. The expected size of 219 bp PCR product was clearly observed up to lane 4 which is equivalent to a detection limit of 10 μg of phloem tissue. Lane 7 was a healthy control. Lane 8 was dsRNA for positive control. Lanes 9–11 were also used for positive controls of purified viral RNA (lane 9), dsRNA (lane 10), and plasmid DNA (pC4) (lane 11) as templates, respectively. Lane M contains a molecular weight marker of Hae III digested fX 174 DNA.

Figure 14:
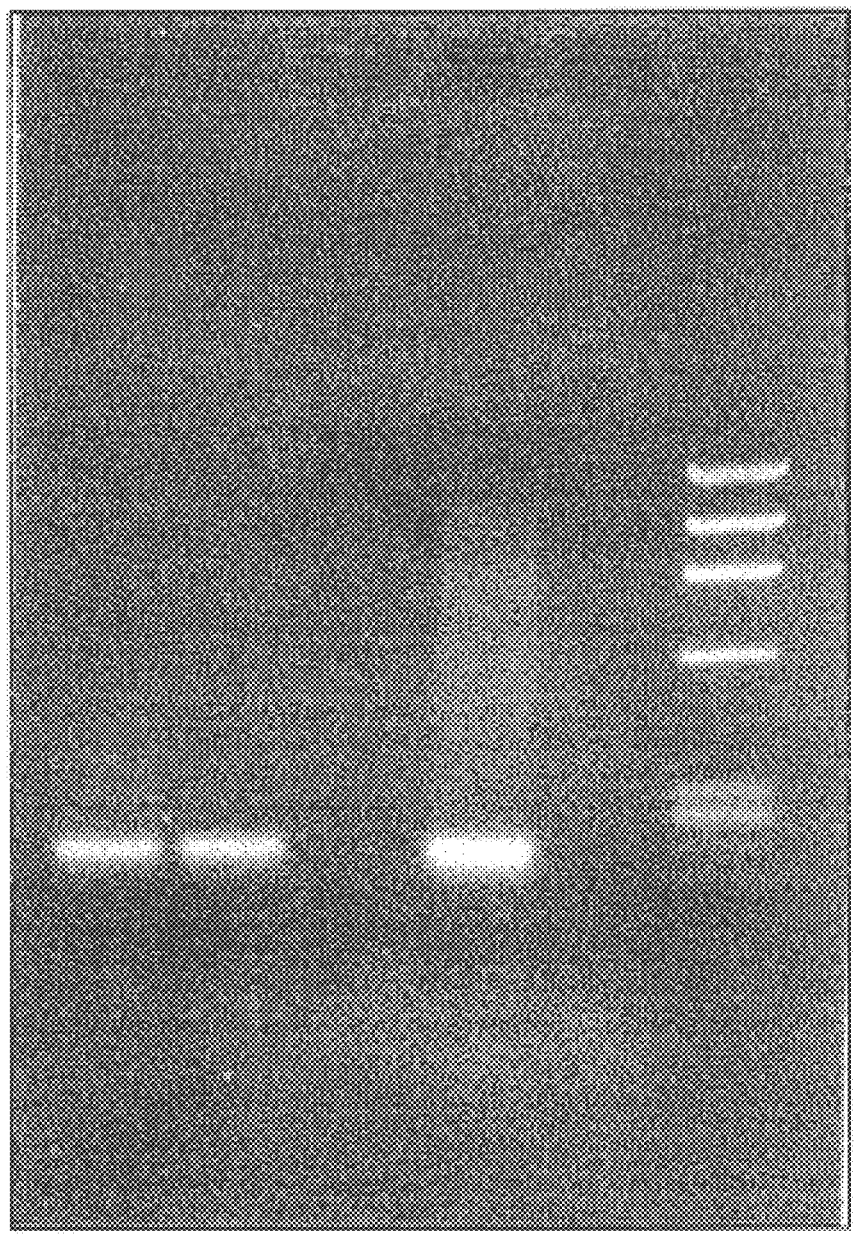

FIG. 14 shows the enzymatic inhibition in RT-PCR with proteinase K treated samples. By increasing amount of proteinase K treated sample in each 100 μl PCR reaction from 0.1 μl (lane 1) to 1 μl (lane 2) and to 10 μl (lane 3), an expected PCR product of 219 bp was readily observed in lane 1 (0.1 μl) and lane 2 (1 μl), but not in lane 3 (10 μl). The expected size of PCR product (219 bp) was also observed in GLRaV-3 dsRNA as positive control (lane 4), but not from proteinase K treated healthy grapevine tissue as negative control (lane 5). Lane M was the molecular weight standard of Hae III digested fX 174 DNA.

FIGS. 15A and 15B depict a comparative analysis of Nested PCR with immuno-capture preparations on field collected samples. Using a polyclonal antibody to GLRaV-3 for immuno-capture, the expected PCR product of 648 bp was not consistently observable in the first round of PCR amplification with external primers over a range of samples (lanes 1–7, panel A). However, the expected PCR product of 219 bp amplified by internal primers was consistently observed over all seven samples (lanes 1–7, panel B). A similar inconsistency is also shown in a sample prepared by proteinase K-treated crude extract (compare panels A to B on lane 8). With dsRNA as template, the expected PCR products were readily observable in both reactions (compare panels A to B on lane 10). No such products were observed on a healthy sample (lane 9). Lane M was a molecular weight marker of Hae III digested fX 174 DNA.

Figure 16A:
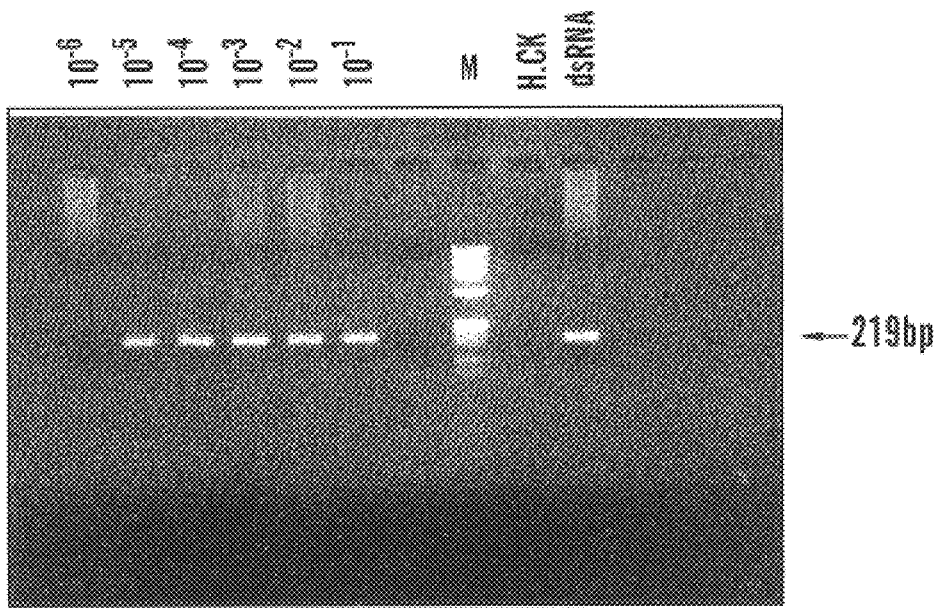
Figure 16B:
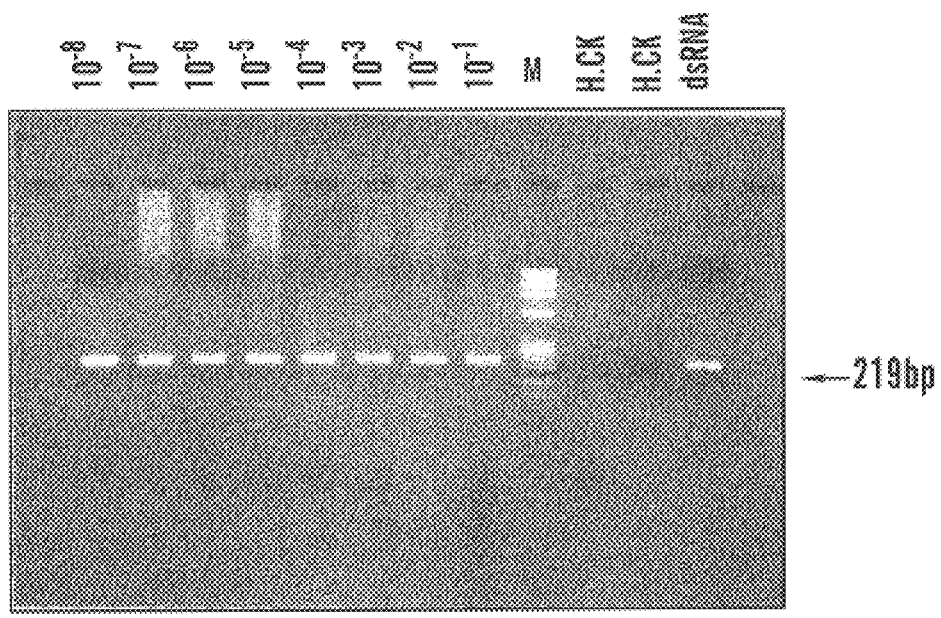

FIGS. 16A and 16B depict comparative studies on the sensitivity of Nested PCR with samples prepared by proteinase K-treated crude extract (panel A, PK Nested PCR) and by immuno-capture preparation (panel B, IC Nested PCR). Nested PCR was performed on samples with serial 10-fold dilutions of up to 10$^{-6}$ in a proteinase K-treated (panel A) and 10$^{-8}$ in an immuno-capture preparation (panel B). The expected PCR product of 219 bp was observable up to 10$^{-5}$ in PK Nested PCR and over 10$^{-8}$ (the highest dilution used in this test) in IC Nested PCR. A similar PCR product was also observed with dsRNA template but not from healthy grape tissues (H. CK). Lane M was a molecular weight marker of Hae III digested fX 174 DNA.

Figure 17:
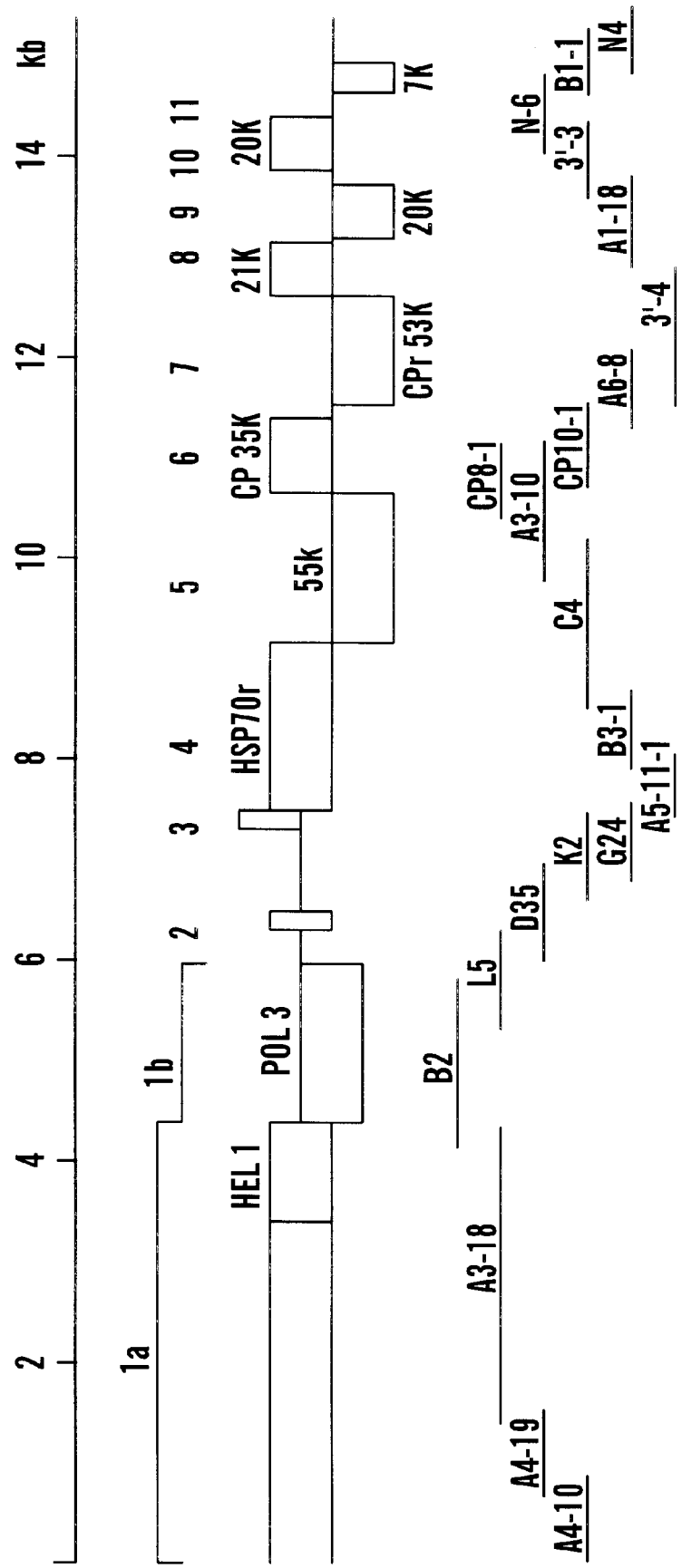

FIG. 17 shows the partial genome organization of GLRaV-3 and the cDNA clones used to determine the nucleotide sequences. Numbered lines represent nucleotide coordinates in kilobases(kb).

FIGS. 18A to W show the nucleotide sequence and partial genome organization of GLRaV-3.

Figure 19:
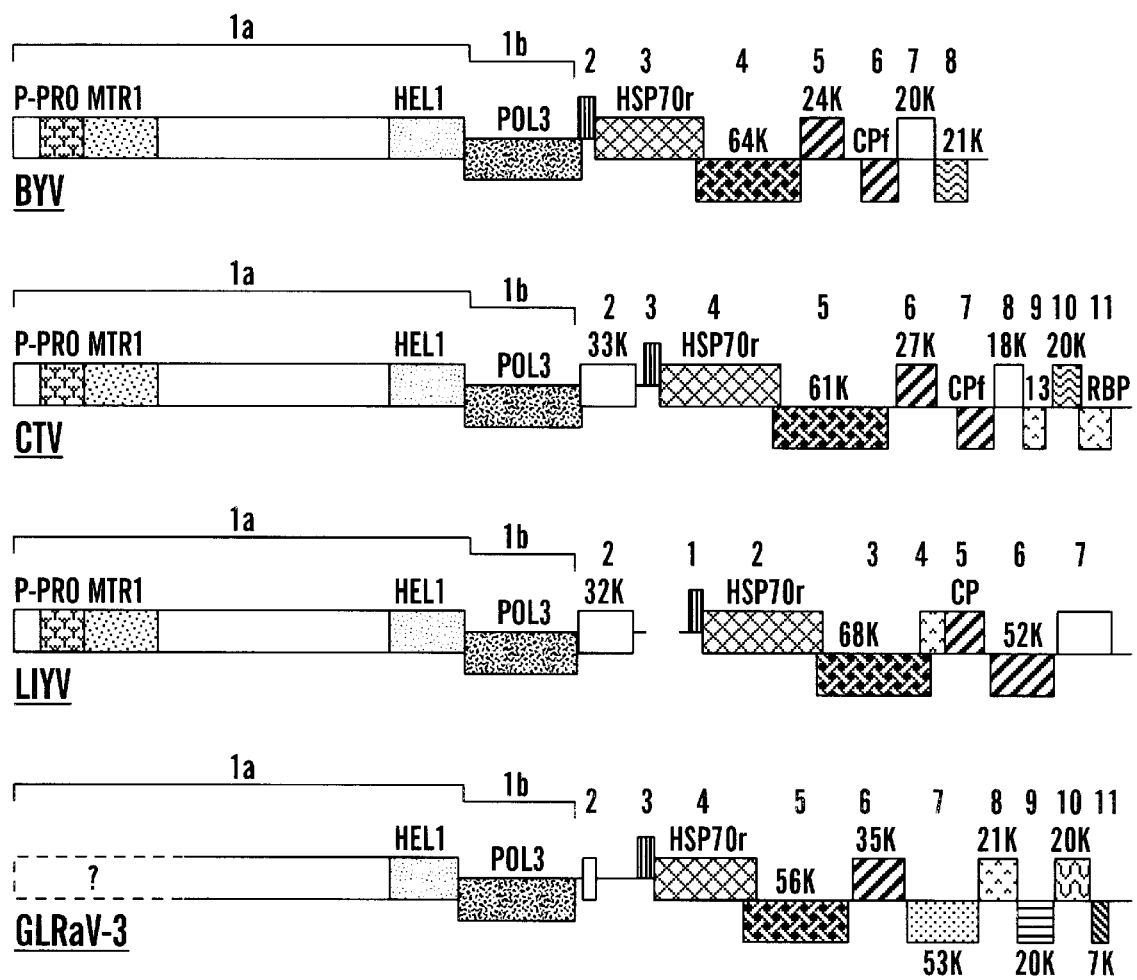

FIG. 19 depicts the proposed genome organization of the GLRaV-3 in comparison with three other closterovirus genomes, BYV, CTV, and LIYV (Dolja (1994)). Homologous proteins are shown by identical patterns. Papain-like proteinase ("P-PRO"); methyltransferase of type 1 ("MTR1"); RNA helicase of superfamily 1 ("HEL1"); RNA polymerase of supergroup 3 ("PLO3"); HSP70-related protein ("HSP70r"); and capsid protein forming filamentous virus particle ("CPf").

FIG. 20 compares the amino acid sequence alignment of the helicase of GLRaV-3 with respect to BYV, CTV, and LIYV. Consensus amino acid residues are shown. Uppercase letters indicate identical amino acids, lowercase letters indicate at least three identical or functionally similar amino acids. Six conserved motifs (I to VI) that are conserved among the Superfamily 1 helicase (Koonin et al., "Evolution and Taxonomy of Positive-strand RNA Viruses: Implications of Comparative Analysis of Amino Acid Sequences," *Critical Reviews in Biochemistry and Molecular Biology*, 28:375–430 (1993)) of the positive-strand RNA viruses are overlined.

Figure 21:
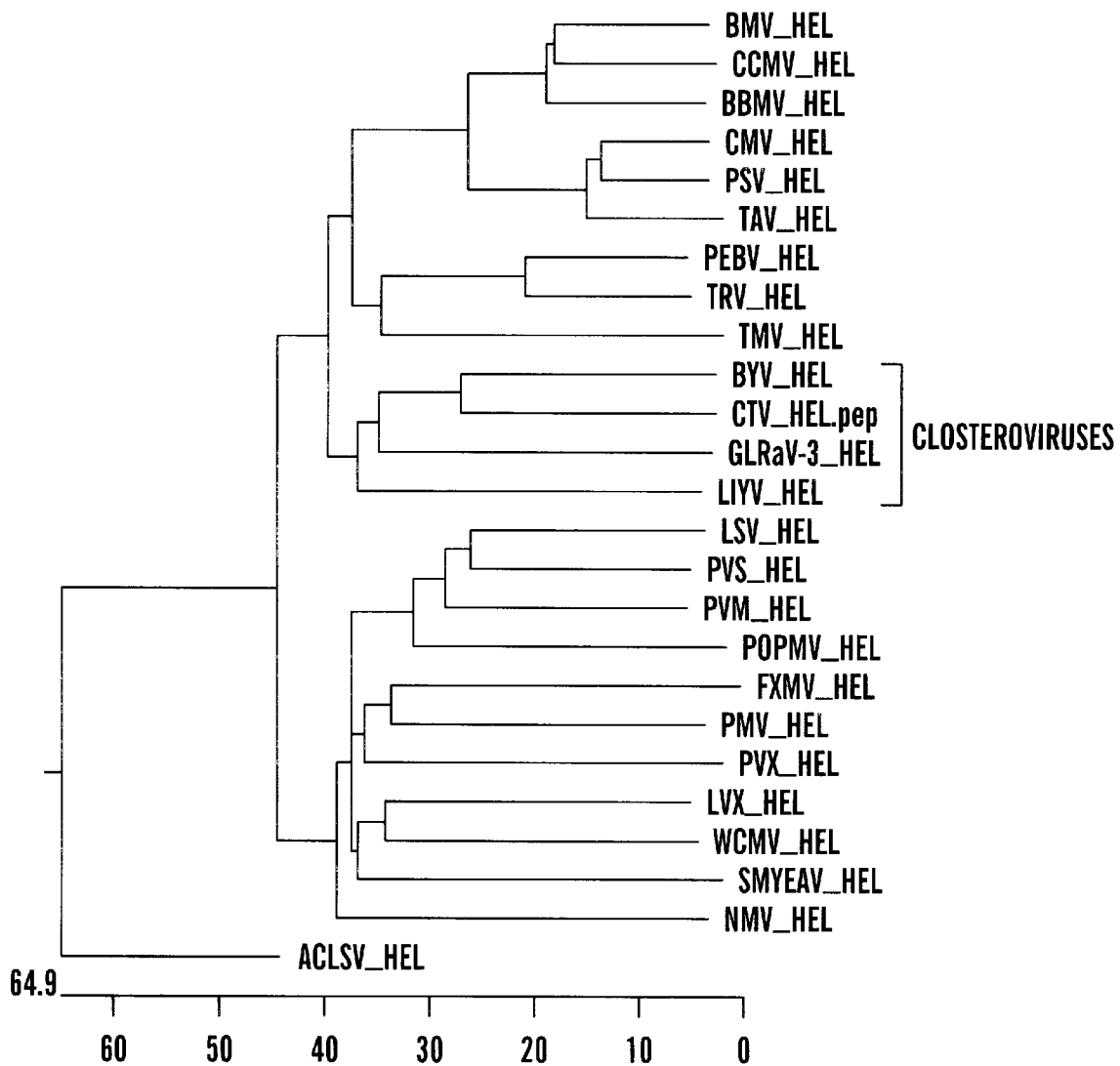

FIG. 21 is a phylogenetic tree showing the amino acid sequence relationship of helicase of alphaviruses. The helicase domain of GLRaV-3 (291 aa) from the present study is used. The other virus sequences were obtained from current databases (Swiss-Prot and GenBank, release 84.0). Apple chlorotic leafspot virus ("ACLSV"); broad bean mottle virus ("BbMV"); brome mosaic virus ("BMV"); beet yellow closterovirus ("BYV"); cowpea chlorotic mottle virus ("CcMV"); cucumber mosaic virus ("CMV"); fox mosaic virus ("FxMV"); lily symptomless virus ("LSV"); lily virus X ("LXV"); narcissus mosaic virus ("NMV"); pea early browning virus ("PeBV"); papaya mosaic virus ("PMV"); poplar mosaic virus ("PopMV"); peanut stunt virus ("PSV"); potato virus S ("PVS"); potato virus M ("PVM"); potato virus X ("PVX"); strawberry mild yellow edge-associated virus ("Sm Yea V"); tomato aspermy virus ("TAV"); tobacco mosaic virus ("TMV"); tobacco rattle virus ("TRV"); and white clover mosaic virus ("WcMV").

FIG. 22 compares the amino acid sequence alignment of the RNA dependent RNA polymerase (RdRp) of GLRaV-3 with respect to BYV, CTV, and LIYV. Consensus amino acid residues are shown. Uppercase letters indicate identical amino acids, and lowercase letters indicate at least three identical or functionally similar amino acids. The motifs (I to VIII) that are conserved among the Supergroup 3 RNA polymerase of positive-strand RNA viruses are overlined.

Figure 23:
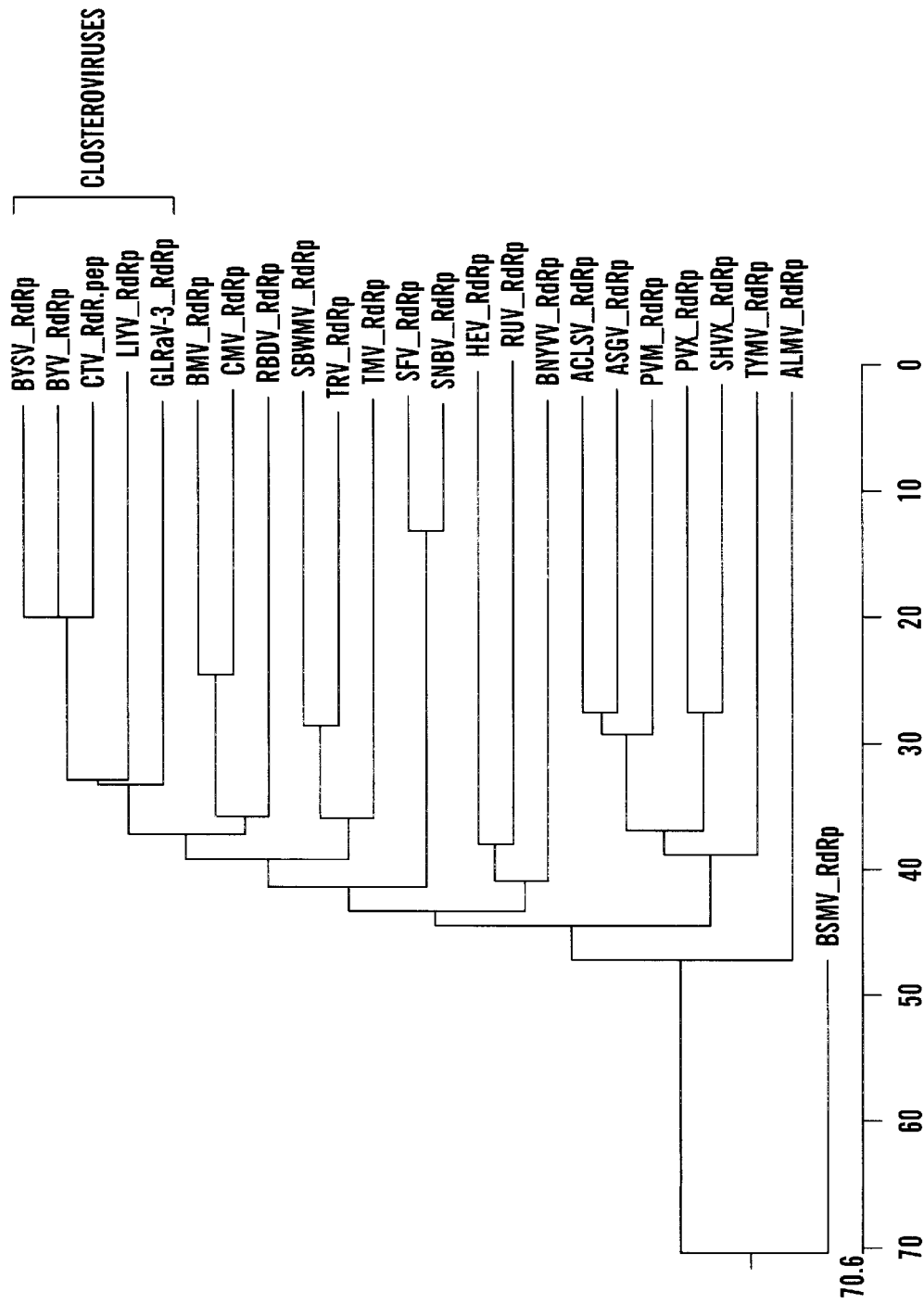

FIG. 23 shows the phylogenetic tree for the RNA dependent RNA polymerases (RdRp) of the alpha-like supergroup of positive strand RNA viruses. RdRp of GLRaV-3 was incorporated into a previously described alignment (Dolja (1994)) for comparison. The other virus sequences were obtained from current databases: Apple chlorotic leafspot virus ("ACLSV"); alfalfa mosaic virus ("AlMV"); apple stem grooving virus ("ASGV"); brome mosaic virus ("BMV"); beet necrotic yellow vein virus ("BNYVV"); beet yellow virus ("BYV"); barley stripe mosaic virus ("BSMV"); beet yellow stunt virus ("BYSV"); cucumber mosaic virus ("CMV"); citrus tristeza virus ("CTV"); hepatitis E virus ("HEV"); potato virus M ("PVM"); potato virus X ("PVX"); raspberry bushy dwarf virus ("RBDV"); shallot virus X ("SHVX"); Sinbis virus ("SNBV"); tobacco mosaic virus ("TMV"); tobacco rattle virus ("TRV"); and turnip yellow mosaic virus ("TYMV").

FIG. 24 compares the alignment of the GLRaV-3 and LIYV nucleotide sequences (presented as DNA) in the vicinity of the proposed frameshift, nt 4,099–4,165 in GLRaV-3 and nt 5,649–5,715 in LIYV. Identical nucleotides are typed in uppercase letters. LIYV +1 frameshift region (aAAG) and the corresponding GLRaV-3 (cACA) are bold and italic. The encoded C-terminus of HEL and N-terminus of RdRp are presented above (GLRaV-3) and below (LIYV) the nucleotide alignment. Repeat sequences are underlined.

FIG. 25 compares the amino acid alignment of the small hydrophobic transmembrane protein of GLRaV-3 p5K with respect to BYV (p6K), CTV (p6K), and LIYV (p5K). Consensus amino acid residues are shown. Lowercase letters indicate at least three identical or functionally similar amino acids. The transmembrane domain that has been identified in several other closteroviruses, BYV, CTV, and LIYV (Karasev et al., "Complete Sequence of the Citrus Tristeza Virus RNA Genome," Virology, 208:511–520 (1995)), is overlined.

FIGS. 26 A to B present the amino acid sequence alignment of the HSP70-related protein of GLRaV-3 (p59K) with respect to BYV (p65K), CTV (p65K), and LIYV (p62K). The eight conserved motifs (A to H) of cellular HSP70 are overlined. Consensus amino acid residues are shown. Uppercase letters indicate identical amino acids, and lowercase letters indicate at least three identical or functionally similar amino acids.

Figure 27:
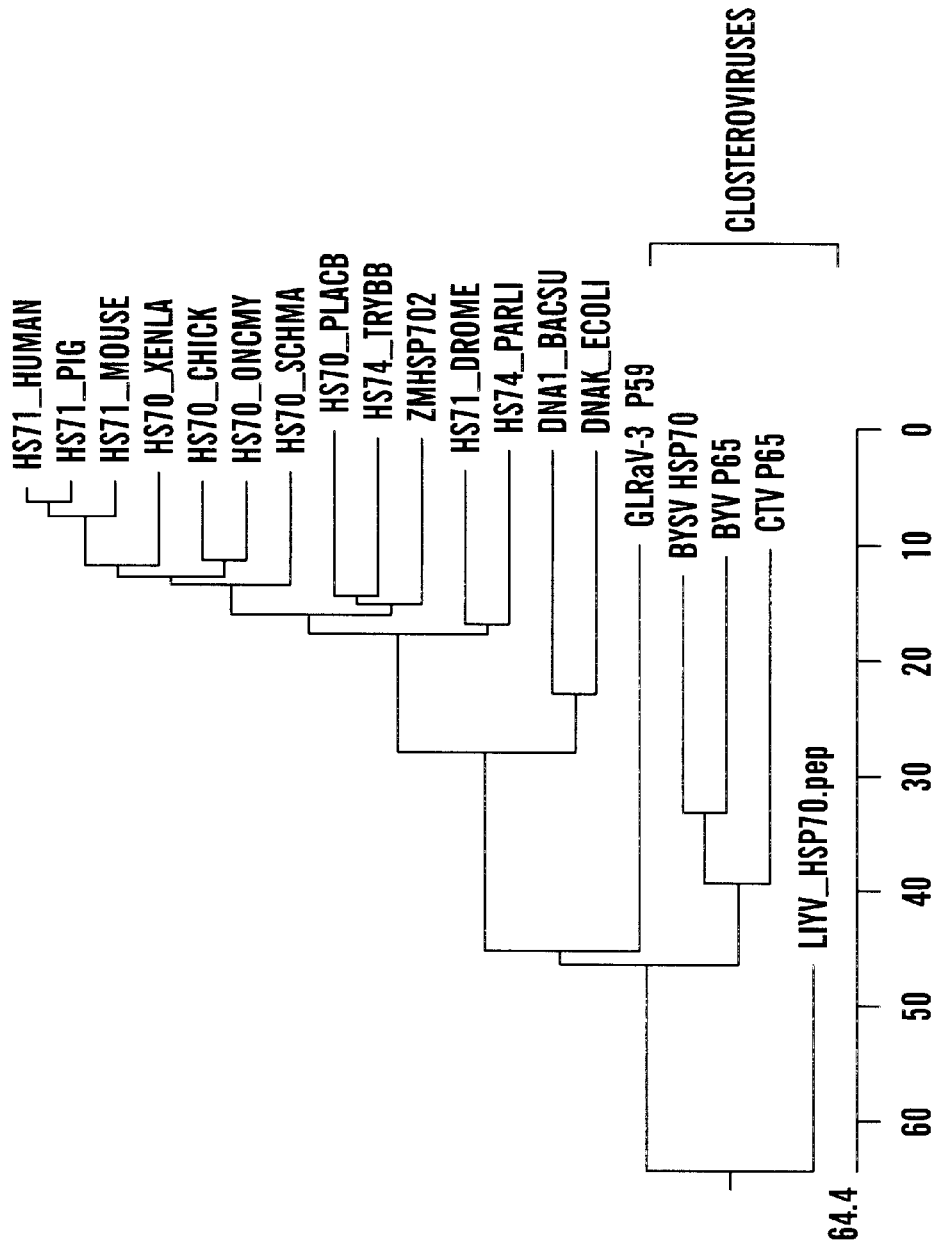
Figure 30:
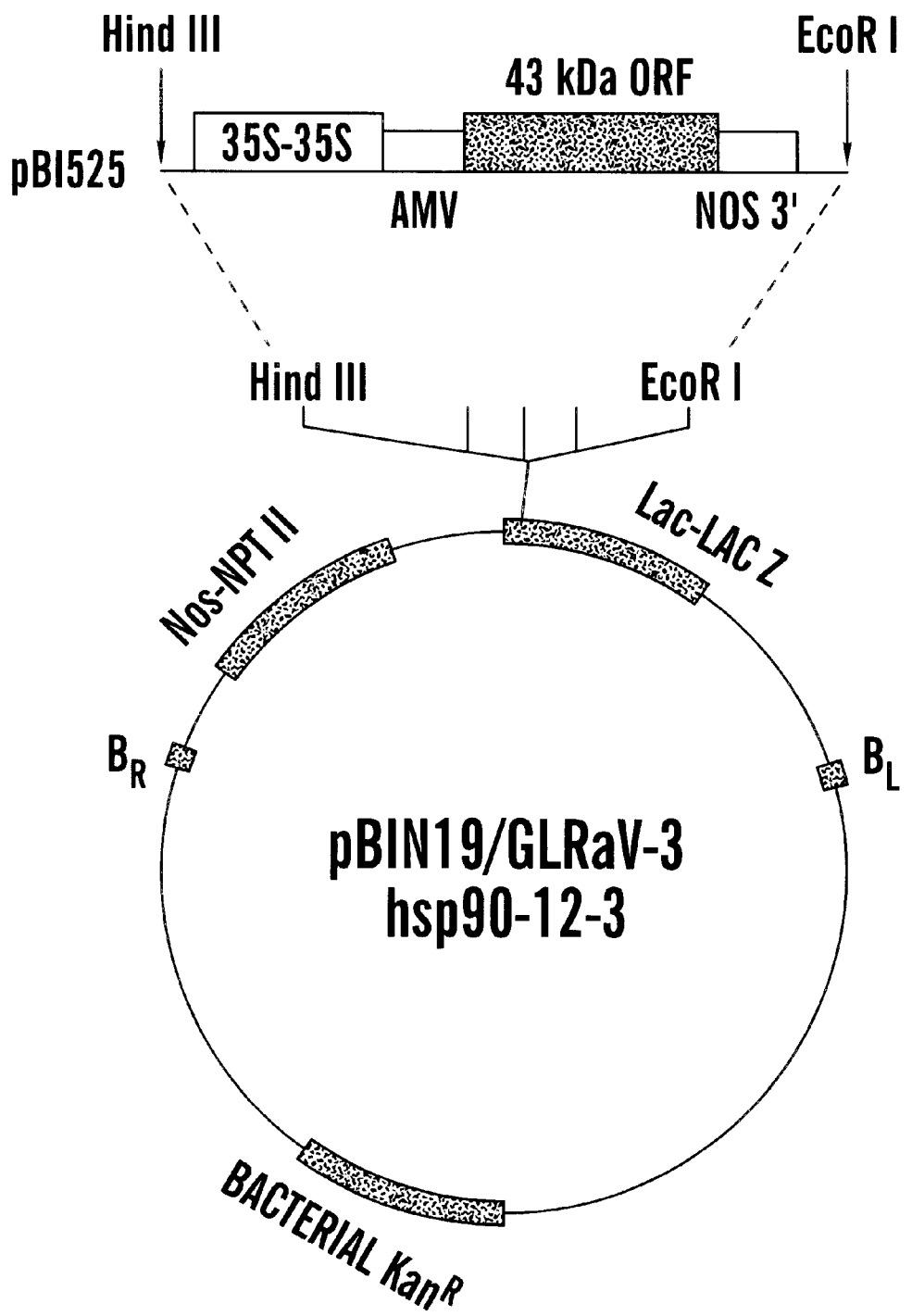
Figure 31:
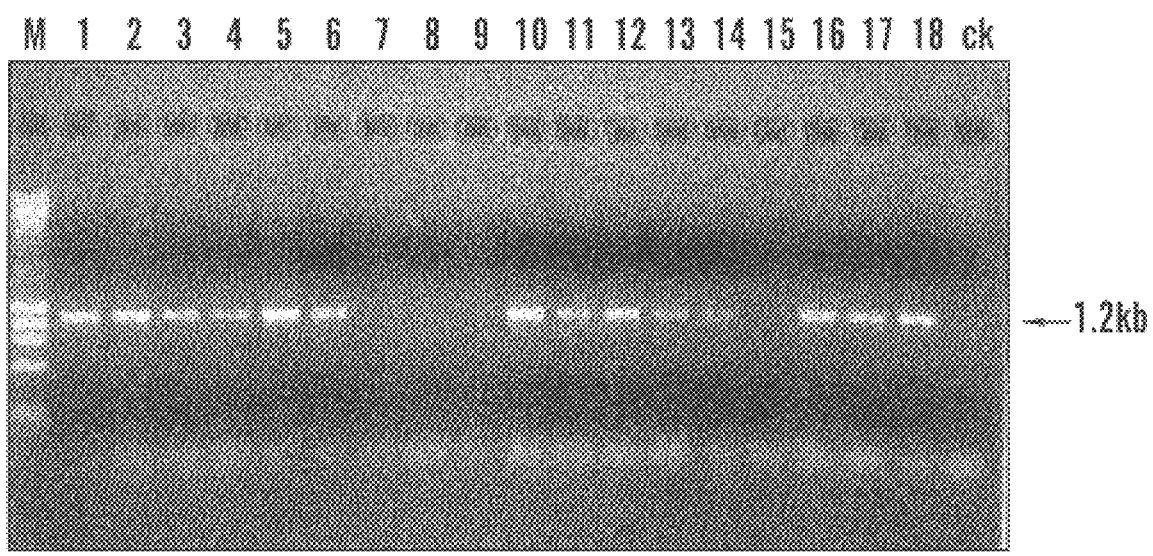

FIG. 27 is a phylogenetic relationship for viral and cellular HSP70 proteins. HSP70-related protein of GLRaV-3 (p59) was incorporated into a previously described alignment (Dolja (1994)) for comparison. The sequences of BYV, CTV, and LIYV proteins were from Agranovsky et al., "Putative 65-kDa protein of Beet Yellows Closterovirus is a Homologue of HSP70 Heat Shock Proteins," Journal of General Virology, 217:603–610 (1991), Pappu et al., "Nucleotide Sequence and Organization of Eight 3' Open Reading Frames of the Citrus Tristeza Closterovirus Genome," Virology, 199:35–46 (1994), and Klaassen et al., "Genome Structure and Phylogenetic Analysis of Lettuce Infectious Yellows Virus, a Whitefly-transmitted, Bipartite Closterovirus," Virology, 208:99–110 (1995), respectively. Only N-terminal half of beet yellow stunt virus HSP70-related protein (Karasev et al., "Screening of the Closterovirus Genome by Degenerate Primer-mediated Polymerase Chain Reaction," Journal of General Virology, 75:1415–1422 (1994)) is used. Other sequences were obtained from the Swiss-Prot database; their accession numbers are as follows: DNA1_BACSU, Bacillus subtilis (P13343); DNAK_ECOLI, Escherichia coli (P04475); HS70_CHICK (P08106); HS70_ONCMY, Oncorhynchus mykiss (P08108); HS70_PLACB, Plasmodium cynomolgi (Q05746); HS70_SCHMA, Schistosoma mansoni (P08418); HS70_XENLA, Xenopus laevis (P02827); HS71_DROME, Drosophila melanogaster (P02825); HS71_HUMAN (P08107); HS71_MOUSE (P17879); HS71_PIG (P34930); HS74_PARLI, Paracentrotus lividus (Q06248); HS74_TRYBB, Trypanosoma brucei (P11145); and ZMHSP702, maize gene for heat shock protein 70 exon 2 (X03697).

FIGS. 28 A to B compare the amino acid sequence alignment of the HSP90-related proteins of GLRaV-3 (p55K) with respect to BYV (p64K), CTV (p61K), and LIYV (p59K). Two domains, I and II, which have been identified on CTV (p61K) are overlined. Consensus amino acid residues are shown. Uppercase letters indicate identical amino acids; lowercase letters indicate at least three identical or functionally similar amino acids.

FIGS. 29 A to B show a nucleotide sequence fragment containing the 43 kDa open reading frame that was used to engineer a plant expression cassette, pBI525GLRaV-3hsp90. This sequence fragment (from nucleotides 9,404 to 10,503 of the partial GLRaV-3 genome sequence, FIG. 18) was later proven to be located in the 3' portion of GLRaV-3 HSP90-related gene. Nucleotides in the lower case were designed to facilitate engineering by addition of NcoI restriction sites.

FIG. 30 is a diagram summarizing the strategies employed in the construction of the plant transformation vector pBin19GLRaV-3hsp90-12-3. A plant expression cassette, in the Hind III-EcoR I fragment containing CaMV 35S—35S promoters-AMV 5' untranslated sequence-43K ORF-Nos 3' untranslated region, was excised from pBI525GLRaV-3hsp90 and cloned into the similar restriction enzyme treated plant transformation vector pBin19. The resulting clone, pBin19GLRaV-3hsp90-12-3, is shown. Locations of important genetic elements within the binary plasmid are indicated: BR, right border; BL, left border; Nos-NPT II, plant expressible neomycin phosphotransferase gene; Lac-LAC Z, plant expressible Lac Z gene; and Bacterial Kan, bacterial kanamycin resistant gene.

FIG. 31 presents an analysis of transgenic tobacco plants with PCR. Using primers flanking the 43K ORF, the proper size of PCR product (1.2 kb) was readily observed from 14 of the 18 kanamycin resistant plants. Lane ck shows a healthy control of nontransformed tobacco. Lane M shows a Mr marker of λ Hind III and fx174 Hae III.

FIG. 32 shows the Agrobacterium-binary vector pGA482G/cpGLRaV-3, which was constructed by cloning the HindIII fragment of pEPT8cpGLRaV-3 into a derivative of pGA482 and used for transformation via Agrobacterium or Biolistic approach.

DETAILED DESCRIPTION OF THE INVENTION

The present invention relates to isolated DNA molecules encoding for the proteins or polypeptides of a grapevine leafroll virus. Applicants have sequenced a substantial portion of the grapevine leafroll virus genome within which are a plurality of open reading frames, each containing DNA molecules in accordance with the present invention. One such DNA molecule constitutes an open reading frame which codes for a grapevine leafroll virus helicase and comprises the nucleotide sequence corresponding to SEQ. ID. No. 1 as follows:

| | | | | |
|---|---|---|---|---|
| GTGTCTACTT | ACGCGAAGAG | TGTGATGAAC | GACAATTTCA | ATATCCTTGA |
| GACCCTGGTA | ACTTTGCCCA | AGTCCTTTAT | AGTCAAAGTA | CCTGGTTCGG |
| TGCTGGTTAG | CATAACCACT | TCGGGCATTT | CCGACAAACT | TGAACTTCGG |
| GGCGCGTTCG | ACGTTTCTAA | AAAGAATTTC | TCCAGGAGGT | TACGTTCGAG |
| TCGTTTGCGC | GTATTTTCTA | GGGCTATTGT | GGAGGATACG | ATCAAGGTTA |
| TGAAGGGCAT | GAAATCAGAG | GATGGTAAAC | CACTCCCTAT | AGCCGAGGAT |
| TCCGTGTACG | CGTTCATGAC | AGGCAATATG | TCAAACGTTC | ATTGCACTAG |
| GGCTGGTTTG | CTCGGGGGCT | CAAAGGCTTG | CGCGGCTTCT | TTAGCTGTGA |
| AGGGTGCAGC | TTCACGCGCT | ACTGGAACAA | AACTCTTTTC | AGGTCTCACA |
| TCCTTTCTTT | CCGCCGGTGG | TCTGTTTTAC | GATGAAGGCT | TGACGCCCGG |
| AGAGAGGCTT | GATGCACTAA | CGCGCCGTGA | ACATGCTGTG | AATTCACCTG |
| TAGGCCTCTT | AGAACCTGGA | GCTTCGGTTG | CGAAGCGGGT | CGTTTCCGGA |
| ACGAAAGCTT | TTCTGTCAGA | ATTGTCATTG | GAGGACTTCA | CCACTTTCGT |
| CATAAAAAAT | AGGGTGCTTA | TTGGTGTTTT | TACTCTTTCC | ATGGCTCTCA |
| CTCCGGTGGT | CTGGAAGTAC | AGAAGGAATA | TCGCGCGAAC | TGGCGTGGAT |

-continued

| | | | | |
|---|---|---|---|---|
| GTTTTCCACC | GTGCTCGTTC | GGGTACCGCG | GCCATCGGTT | TACAATGTCT |
| TAGTGGAGGA | AGGTCGTTAG | CTGGTGACGC | TGCTCGTGGC | GCQTTAACAG |
| TGACTCGAGG | AGGGCTATCT | TCGGCGGTTG | CGGTGACCAG | AAATACAGTG |
| GCTAGGCGTC | AGGTACCATT | GGCGTTGCTT | TCGTTTTCCA | CGTCTTACGC |
| AGTCAGTGGT | TGCACTTTGT | TAGGTATTTG | GGCTCATGCT | CTCCCTAGGC |
| ATTTGATGTT | CTTCTTTGGC | CTAGGGACQC | TCTTCGGGGT | GAGTGCCAGT |
| ACCAATTCTT | GGTCGCTTGG | GGGCTATACG | AACAGTCTGT | TCACCGTACC |
| GGAATTAACT | TGGGAAGGGA | GGAGTTACAG | ATCTTTATTG | CCCCAAGCAG |
| CTTTAGGTAT | TTCTCTCGTT | GTGCGCGGGT | TGTTAAGTGA | AACTGTGCCA |
| CAACTAACGT | ACGTACCGCC | GATTGAAGGT | CGGAATGTTT | ATGATCAGGC |
| ACTAAATTTT | TATCGCGACT | TTGACTATGA | CGATGGTGCA | GGCCCATCCG |
| GGACGGCTGG | TCAAAGCGAT | CCTGGAACCA | ATACTTCGGA | TACTTCTTCG |
| GTTTTCTCTG | ACGATGGTTT | GCCCGCTAGT | GGCGGTGGCT | TCGACGCGCG |
| CGTTGAGGCA | GGTCCCAGCC | ATGCTGTTGA | TGAATCACCA | AGGGGTAGTG |
| TTGAGTTCGT | CTACAGAGAA | CGTGTAGATG | AACATCCGGC | GTGTGGTGAA |
| GCTGAAGTTG | AAAAGGATCT | AATAACACCA | CTTGGTACAG | CTGTCTTAGA |
| GTCGCCCCCC | GTAGGTCCTG | AAGCTGGGAG | CGCGCCCAAC | GTCGAGGACG |
| GTTGTCCGGA | GGTTGAAGCT | GAGAAATGTT | CGGAGGTCAT | CGTTGACGTT |
| CCTAGTTCAG | AACCGCCGGT | ACAAGAAGTC | CTTGAATCAA | CCAATGGTGT |
| CCAAGCTGCA | AGAACTGAAG | AGGTTGTGCA | GGGCGACACA | TGTGGAGCTG |
| GGGTAGCTAA | ATCAGAAGTG | AGTCAACGTG | TGTTTCCTGC | GCAAGTACCC |
| GCACATGAAG | CTGGTCTTGA | GGCATCTAGT | GGCGCGGTCG | TGGAGCCATT |
| GCAAGTTTCT | GTGCCAGTAG | CCGTAGAGAA | AACTGTTTTA | TCTGTCGAGA |
| AGGCGCGTGA | GCTAAAGGCG | GTAGATAAGG | GCAAGGCGGT | CGTGCACGCA |
| AAGGAAGTCA | AGAATGTACC | GGTTAAGACG | TTACCACGAG | GGGCTCTAAA |
| AATTAGTGAG | GATACCGTTC | GTAAGGAATT | GTGCATGTTT | AGAACGTGTT |
| CCTGCGGCGT | GCAGTTGGAC | GTGTACAATG | AAGCGACCAT | CGCCACTAGG |
| TTCTQAAATG | CGTTTACCTT | TGTCGATAGC | TTGAAAGGGA | GGAGTGCGGT |
| TTTCATCAGG | GTGGCCTCGT | GCCCTAGAGG | ATATCTTAAC | GGCAATTAAG |
| TACCCAAGCG | TCTTCGACCA | CTGTTTAGTG | CAGAAGTACA | AGATGGGTGG |
| AGGCGTACCA | TTCCACGCTG | ATGACGAGGA | GTGCTATCCA | TCAGATAACQ |
| CTATCTTGAC | GGTCAATCTC | GTGGGGAAGG | CAAACTTCTC | GACTAAGTGC |
| AGGAAGGGTG | GTAAGGTCAT | GGTCATAAAC | GTAGCTTCGG | GTGACTATTT |
| TCTTATGCCT | TGCGGTTTTC | AAAGGACGCA | CTTGCATTCA | GTAAACTCCA |
| TCGACGAAGG | GCGCATCAGT | TTGACGTTCA | GGGCAACTCG | GCGCGTCTTT |
| GGTGTAGGCA | GGATGTTGCA | GTTAGCGGC | GGCGTGTCGG | ATGAGAAGTC |
| ACCAGGTGTT | CCAAACCAGC | AACCACAGAG | CCAAGGTGCT | ACCAGAACAA |
| TCACACCAAA | ATCGGGGGGC | AAGGCTCTAT | CTGAGGGAAG | TGGTAGGGAA |
| GTCAAGGGGA | GGTCGACATA | CTCGATATGG | TGCAACAAG | ATTACGTTAG |
| GAAGTGTGAG | TGGCTCAGGG | CTGATAATCC | AGTGATGGCT | CTTAAACCTG |
| GCTACACCCC | AATGACATTT | GAAGTGGTTA | AAGCCGGGAC | CTCTGAAGAT |
| GCCGTCGTGG | AGTACTTGAA | GTATCTGGCT | ATAGGCATTG | GGAGGACATA |
| CAGGGCGTTG | CTTATGGCTA | GAAATATTGC | CGTCACTACC | GCCGAAGGTG |
| TTCTGAAAGT | ACCTAATCAA | GTTTATGAAT | CACTACCGGG | CTTTCACGTT |
| TACAAGTCGG | GCACAGATCT | CATTTTTCAT | TCAACACAAG | ACGGCTTGCG |
| TGTGAGAGAC | CTACCGTACG | TATTCATAGC | TGAGAAAGGT | ATTTTTATCA |
| AGGGCAAAGA | TGTCGACGCG | GTAGTAGCTT | TGGGCGACAA | TCTGTCCGTA |
| TGTGATGATA | TATTGGTTTT | CCATGATGCT | ATTAATTTGA | TGGGTGCACT |
| GAAAGTTGCT | CGATGTGGTA | TGGTGGGTGA | ATCATTTAAG | TCGTTCGAAT |
| ACAAATGCTA | TAATGCTCCC | CCAGGTGGCG | GTAAGACGAC | GATGCTAGTG |
| GACGAATTTG | TCAAGTCACC | CAATAGCACG | GCCACCATTA | CGGCTAACGT |
| GGGAAGTTCT | GAGGACATAA | ATATGGCGGT | GAAGAAGAGA | GATCCGAATT |
| TGGAAGGTCT | CAACAGTGCT | ACCACAGTTA | ACTCCAGGGT | GGTTAACTTT |
| ATTGTCAGGG | GAATGTATAA | AAGGGTTTTG | GTGGATGAGG | TGTACATGAT |
| GCATCAAGGC | TTACTACAAC | TAGGCGTCTT | CGCAACCGGC | GCGTCGGAAG |
| GCCTCTTTTT | TGGAGACATA | AATCAGATAC | CATTCATAAA | CCGGGAGAAG |
| GTGTTTAGGA | TGGATTGTGC | TGTATTTGTT | CCAAAGAAGG | AAAGCGTTGT |
| ATACACTTCT | AAATCATACA | GGTGTCCGTT | AGATGTTTGC | TACTTGTTGT |
| CCTCAATGAC | CGTAAGGGGA | ACGGAAAAGT | GTTACCCTGA | AAAGGTCGTT |
| AGCGGTAAGG | ACAAACCAGT | AGTAAGATCG | CTGTCCAAAA | GGCCAATTGG |
| AACCACTGAT | GACGTAGCTG | AAATAAACGC | TGACGTGTAC | TTGTGCATGA |
| CCCAGTTGGA | GAAGTCGGAT | ATGAAGAGGT | CGTTGAAGGG | AAAAGGAAAA |
| GAAACACCAG | TGATGACAGT | GCATGAAGCA | CAGGGAAAAA | CATTCAGTGA |
| TGTGGTATTG | TTTAGGACGA | AGAAAGCCGA | TGACTCCCTA | TTCACTAAAC |
| AACCGCATAT | ACTTGTTGGT | TTGTCGAGAC | ACACACGCTC | ACTGGTTTAT |
| GCCGCTCTGA | GCTCAGAGTT | GGACGATAAG | GTCGGCACAT | ATATTAGCGA |
| CGCGTCGCCT | CAATCAGTAT | CCGACGCTTT | GCTTCACACG | TTCGCCCCGG |
| CTGGTTGCTT | TCGAGGTATA | TGA. | | |

The helicase has an amino acid sequence corresponding to
SEQ. ID. No. 2 as follows:

| | | | | |
|---|---|---|---|---|
| VSTYAKSVMN | DNFNILETLV | TLPKSFIVKV | PGSVLVSITT | SGISDKLELR |
| GAFDVSKKNF | SRRLRSSRLR | VFSRAIVEDT | IKVMKGMKSE | DGKPLPIAED |
| SVYAFMTGNM | SNVHCTRAGL | LGGSKACAAS | LAVKGAASRA | TGTKLFSGLT |

-continued

| | | | | |
|---|---|---|---|---|
| SFLSAGGLFY | DEGLTPGERL | DALTRREHAV | NSPVGLLEPG | ASVAKRVVSG |
| TKAFLSELSL | EDFTTFVIkN | RVLIGVFTLS | MALTPVVWKY | RRNIARTGVD |
| VFHRARSGTA | AIGLQCLSGG | RSLAGDAARG | ALTVTRGGLS | SAVAVTRNTV |
| ARRQVPLALL | SFSTSYAVSG | CTLLGIWAHA | LPRHLMFFFG | LGTLFGVSAS |
| TNSWSLGGYT | NSLFTVPELT | WEGRSYRSLL | PQAALGISLV | VRGLLSETVP |
| QLTYVPPIEG | RNVYDQALNF | YRDFDYDDGA | GPSGTAGQSD | PGTNTSDTSS |
| VFSDDGLPAS | GGGFDARVEA | GPSHAVDESP | RGSVEFVYRE | RVDEHPACGE |
| AEVEKDLITP | LGTAVLESPP | VGPEAGSAPN | VEDGCPEVEA | EKCSEVIVDV |
| PSSEPPVQEV | LESTNGVQAA | RTEEVVQGDT | CGAGVAKSEV | SQRVFPAQVP |
| AHEAGLEASS | GAVVEPLQVS | VPVAVEKTVL | SVEKARELKA | VDKGKAVVHA |
| KEVKNVPVKT | LPRGALKISE | DTVRKELCMF | RTCSCGVQLD | VYNEATIATR |
| FSNAFTFVDS | LKGRSAVFFS | KLGEGYTYNG | GSHVSSGWPR | ALEDILTAIK |
| YPSVFDHCLV | QKYKMGGGVP | FHADDEECYP | SDNPILTVNL | VGKANFSTKC |
| RKGGKVMVIN | VASGDYFLMP | CGFQRTHLHS | VNSIDEGRIS | LTFRATRRVF |
| GVGRMLQLAG | GVSDEKSPGV | PNQQPQSQGA | TRTITPKSGG | KALSEGSGRE |
| VKGRSTYSIW | CEQDYVRKCE | WLRADNPVMA | LKPGYTPMTF | EVVKAGTSED |
| AVVEYLKYLA | IGIGRTYRAL | LMARNIAVTT | AEGVLKVPNQ | VYESLPGFHV |
| YKSGTDLIFH | STQDGLRVRD | LPYVFIAEKG | IFIKQKDVDA | VVALGDNLSV |
| CDDILVFHDA | INLMGALKVA | RCGMVGESFK | SFEYKCYNAP | PGGGKTTMLV |
| DEFVKSPNST | AITTANVGSS | EDINMAVKKR | DPNLEGLNSA | TTVNSRVVNF |
| IVRGMYKRVL | VDEVYMMHQG | LLQLGVFATG | ASEGLFFGDI | NQIPFINREK |
| VFRMDCAVFV | PKKESVVYTS | KSYRCPLDVC | YLLSSMTVRG | TEKCYPEKVV |
| SGKDKPVVRS | LSKRPIGTTD | DVAEINADVY | LCMTQLEKSD | MKRSLKGKGK |
| ETPVMTVHEA | QGKTFSDVVL | FRTKKADDSL | FTKQPHILVG | LSRHTRSLVY |
| AALSSELDDK | VGTYISDASP | QSVSDALLHT | FAPAGCFRGI | | and a molecular weight from about 146 to about 151 kDa, preferably about 148.5 kDa.

Another such DNA molecule constitutes an open reading frame which codes for a grapevine leafroll virus RNA-dependent RNA polymerase and comprises the nucleotide sequence corresponding to SEQ. ID. No. 3 as follows:

| | | | | |
|---|---|---|---|---|
| ATGAATTTTG | GACCGACCTT | CGAAGGGGAG | TTGGTACGGA | AGATACCAAC |
| AAGTCATTTT | GTAGCCGTGA | ATGGGTTTCT | CGAGGACTTA | CTCGACGGTT |
| GTCCGGCTTT | CGACTATGAC | TTCTTTGAGG | ATGATTTCGA | AACTTCAGAT |
| CAGTCTTTCC | TCATAGAAGA | TGTGCGCATT | TCTGAATCTT | TTTCTCATTT |
| TGCGTCGAAA | ATAGAGGATA | GGTTTTACAG | TTTTATTAGG | TCTAGCGTAG |
| GTTTACCAAA | GCGCAACACC | TTGAAGTGTA | ACCTCGTCAC | GTTTGAAAAT |
| AGGAATTCCA | ACGCCGATCG | CGGTTGTAAC | GTGGGTTGTG | ACGACTCTGT |
| GGCGCATGAA | CTGAAGGAGA | TTTTCTTCGA | GGAGGTCGTT | AACAAAGCTC |
| GTTTAGCAGA | GGTGACGGAA | AGCCATTTGT | CCAGCAACAC | GATGTTGTTA |
| TCAGATTGGT | TGGACAAAAG | GGCACCTAAC | GCTTACAAGT | CTCTCAAGCG |
| GGCTTTAGGT | TCGGTTGTCT | TTCATCCGTC | TATGTTGACG | TCTTATACGC |
| TCATGGTGAA | AGCAGACGTA | AAACCCAAGT | TGGACAATAC | GCCATTGTCG |
| AAGTACGTAA | CGGGGCAGAA | TATAGTCTAC | CACGATAGGT | GCGTAACTGC |
| GCTTTTTTCT | TGCATTTTA | CTGCGTGCGT | AGAGCGCTTA | AAATACGTAG |
| TGGACGAAAG | GTGGCTCTTC | TACCACGGGA | TGGACACTGC | GGAGTTGGCG |
| GCTGCATTGA | GGAACAATTT | GGGGGACATC | CGGCAATACT | ACACCTATGA |
| ACTGGATATC | AGTAAGTACG | ACAAATCTCA | GAGTGCTCTC | ATGAAGCAGG |
| TGGAGGAGTT | GATACTCTTG | ACACTTGGTG | TTGATAGAGA | AGTTTTGTCT |
| ACTTTCTTTT | GTGGTGAGTA | TGATAGCGTC | GTGAGAACGA | TGACGAAGGA |
| ATTGGTGTTG | TCTGTCGGCT | CTCAGAGGCG | CAGTGGTGGT | GCTAACACGT |
| GGTTGGGAAA | TAGTTTAGTC | TTGTGCACCT | TGTTGTCCGT | AGTACTTAGG |
| GGATTAGATT | ATAGTTATAT | TGTAGTTAGC | GGTGATGATA | GCCTTATATT |
| TAGTCGGCAG | CCGTTGGATA | TTGATACGTC | GGTTCTGAGC | GATAATTTTG |
| GTTTGACGT | AAAGATTTTT | AACCAAGCTG | CTCCATATTT | TTGTTCTAAG |
| TTTTTAGTTC | AAGTCGAGGA | TAGTCTCTTT | TTTGTTCCCG | ATCCACTTAA |
| ACTCTTCGTT | AAGTTTGGAG | CTTCCAAAAC | TTCAGATATC | GACCTTTTAC |
| ATGAGATTTT | TCAATCTTTC | GTCGATCTTT | CGAAGGGTTT | CAATAGAGAG |
| GACGTCATCC | AGGAATTAGC | TAAGCTGGTG | ACGCGGAAAT | ATAAGCATTC |
| GGGATGGACC | TACTCGGCTT | TGTGTGTCTT | GCACGTTTTA | AGTGCAAATT |
| TTTCGCAGTT | CTGTAGGTTA | TATTACCACA | ATAGCGTGAA | TCTCGATGTG |
| CGCCCTATTC | AGAGGACCGA | GTCGCTTTCC | TTGCTGGCCT | TGAAGGCAAG |
| AATTTTAAGG | TGGAAAGCTT | CTCGTTTTGC | CTTTTCGATA | AAGAGGGGTT |
| AA. | | | | |

The RNA-dependent RNA polymerase has an amino acid sequence corresponding to SEQ. ID. No. 4 as follows:

| | | | | |
|---|---|---|---|---|
| MNFGPTFEGE | LVRKIPTSHF | VAVNGFLEDL | LDGCPAFDYD | FFEDDFETSD |
| QSFLIEDVRI | SESFSHFASK | IEDRFYSFIR | SSVGLPKRNT | LKCNLVTFEN |
| RNSNADRGCN | VGCDDSVAHE | LKEIFFEEVV | NKARLAEVTE | SHLSSNTMLL |
| SDWLDKRAPN | AYKSLKRALG | SVVFHPSMLT | SYTLMVKADV | KPKLDNTPLS |
| KYVTGQNIVY | HDRCVTALFS | CIFTACVERL | KYVVDERWLF | YHGMDTAELA |
| AALRNNLGDI | RQYYTYELDI | SKYDKSQSAL | MKQVEELILL | TLGVDREVLS |
| TFFCGEYDSV | VRTMTKELVL | SVGSQRRSGG | ANTWLGNSLV | LCTLLSVVLR |
| GLDYSYIVVS | GDDSLIFSRQ | PLDIDTSVLS | DNFGFDVKIF | NQAAPYFCSK |
| FLVQVEDSLF | FVPDPLKLFV | KFGASKTSDI | DLLHEIFQSF | VDLSKGFNRE |
| DVIQELAKLV | TRKYKHSGWT | YSALCVLHVL | SANFSQFCRL | YYHNSVNLDV |
| RPIQRTESLS | LLALKARILR | WKASRFAFSI | KRG | | and a molecular weight from about 59 to about 63 kDa, preferably about 61 kDa.

Another such DNA molecule constitutes an open reading frame which codes for a grapevine leafroll virus hsp70-related protein or polypeptide and comprises the nucleotide sequence corresponding to SEQ. ID. No. 5 as follows:

and a molecular weight from about 57 to about 61 kDa, preferably about 59 kDa.

Another such DNA molecule constitutes an open reading frame which codes for a grapevine leafroll virus hsp90-related protein or polypeptide and comprises the nucleotide sequence corresponding to SEQ. ID. No. 7 as follows:

| | | | | |
|---|---|---|---|---|
| ATGGAAGTAG | GTATAGATTT | TGGAACCACT | TTCAGCACAA | TCTGCTTTTC |
| CCCATCTGGG | GTCAGCGGTT | GTACTCCTGT | GGCCGGTAGT | GTTTACGTTG |
| AAACCCAAAT | TTTTATACCT | GAAGGTAGCA | GTACTTACTT | AATTGGTAAA |
| GCTGCGGGGA | AAGCTTATCG | TGACGGTGTA | GAGGGAAGGT | TGTATGTTAA |
| CCCGAAAAGG | TGGGCAGGTG | TGACGAGGGA | TAACGTCGAA | CGCTACGTCG |
| AGAAATTAAA | ACCTACATAC | ACCGTGAAGA | TAGACAGCGG | AGGCGCCTTA |
| TTAATTGGAG | GTTTAGGTTC | CGGACCAGAC | ACCTTATTGA | GGGTCGTTGA |
| CGTAATATGT | TTATTCTTGA | GAGCCTTGAT | ACTGGAGTGC | GAAAQGTATA |
| CGTCTACGAC | GGTTACAGCA | GCTGTTGTAA | CGGTACCGGC | TGACTATAAC |
| TCCTTTAAAC | GAAGCTTCGT | TGTTGAGGCG | CTAAAAGGTC | TTGGTATACC |
| GGTTAGAGGT | GTTGTTAACG | AACCGACGGC | CGCAGCCCTC | TATTCCTTAG |
| CTAAGTCGCG | AGTAGAAGAC | CTATTATTAG | CGGTTTTTGA | TTTTGGGGGA |
| GGGACTTTCG | ACGTCTCATT | CGTTAAGAAG | AAGGGAAATA | TACTATGCGT |
| CATCTTTTCA | GTGGGTGATA | ATTTCTTGGG | TGGTAGAGAT | ATTGATAGAG |
| CTATCGTGGA | AGTTATCAAA | CAAAAGATCA | AAGGAAAGGC | GTCTGATGCC |
| AAGTTAGGGA | TATTCGTATC | CTCGATGAAG | GAAGACTTGT | CTAACAATAA |
| CGCTATAACG | CAACACCTTA | TCCCCGTAGA | AGGGGGTGTG | GAGGTTGTGG |
| ATTTGACTAG | CGACGAACTG | GACGCAATCG | TTGCACCATT | CAGCGCTAGG |
| GCTGTGGAAG | TATTCAAAAC | TGGTCTTGAC | AACTTTTACC | CAGACCCGGT |
| TATTGCCGTT | ATGACTGGGG | GGTCAAGTGC | TCTAGTTAAG | GTCAGGAGTG |
| ATGTGGCTAA | TTTGCCGCAG | ATATCTAAAG | TCGTGTTCGA | CAGTACCGAT |
| TTTAGATGTT | CGGTGGCTTG | TGGGGCTAAG | GTTTACTGCG | ATACTTTGGC |
| AGGTAATAGC | GGACTGAGAC | TGGTGGACAC | TTTAACGAAT | ACGCTAACGG |
| ACGAGGTAGT | GGGTCTTCAG | CCGGTGGTAA | TTTTCCCGAA | AGGTAGTCCA |
| ATACCCTGTT | CATATACTCA | TAGATACACA | GTGGGTGGTG | GAGATGTGGT |
| ATACGGTATA | TTTGAAGGGG | AGAATAACAG | AGCTTTTCTA | AATGAGCCGA |
| CGTTCCGGGG | CGTATCGAAA | CGTAGGGGAG | ACCCAGTAGA | GACCGACGTG |
| GCGCAGTTTA | ATCTCTCCAC | GGACGGAACG | GTGTCTGTTA | TCGTTAATGG |
| TGAGGAAGTA | AAGAATGAAT | ATCTGGTACC | CGGGACAACA | AACGTACTGG |
| ATTCATTGGT | CTATAAATCT | GGGAGAGAAG | ATTTAGAGGC | TAAGGCAATA |
| CCAGAGTACT | TGACCACACT | GAATATTTTG | CACGATAAGG | CTTTCACGAG |
| GAGAAACCTG | GGTAACAAAG | ATAAGGGGTT | CTCGGATTTA | AGGATAGAAG |
| AAAATTTTTT | AAAATCCGCC | GTAGATACAG | ACACGATTTT | GAATGGATAA. |

The hsp70-related protein or polypeptide has an amino acid sequence corresponding to SEQ. ID. No. 6 as follows:

| | | | | |
|---|---|---|---|---|
| MEVGIDFGTT | FSTICFSPSG | VSGCTPVAGS | VYVETQIFIP | EGSSTYLIGK |
| AAGKAYRDGV | EGRLYVNPKR | WAGVTRDNVE | RYVEKLKPTY | TVKIDSGGAL |
| LIGGLGSGPD | TLLRVVDVIC | LFLRALILEC | ERYTSTTVTA | AVVTVPADYN |
| SFKRSFVVEA | LKGLGIPVRG | VVNEPTAAAL | YSLAKSRVED | LLLAVFDFGG |
| GTFDVSFVKK | KGNILCVIFS | VGDNFLGGRD | IDRAIVEVIK | QKIKGKASDA |
| KLGIFVSSMK | EDLSNNNAIT | QHLIPVEGGV | EVVDLTSDEL | DAIVAPFSAR |
| AVEVFKTGLD | NFYPDPVIAV | MTGGSSALVK | VRSDVANLPQ | ISKVVFDSTD |
| FRCSVACGAK | VYCDTLAGNS | GLRLVDTLTN | TLTDEVVGLQ | PVVIFPKGSP |
| IPCSYTHRYT | VGGGDVVYGI | FEGENNRAFL | NEPTFRGVSK | RRGDPVETDV |
| AQFNLSTDGT | VSVIVNGEEV | KNEYLVPGTT | NVLDSLVYKS | GREDLEAKAI |
| PEYLTTLNIL | HDKAFTRRNL | GNKDKGFSDL | RIEENFLKSA | VDTDTILNG |

| | | | | |
|---|---|---|---|---|
| ATGGATAAAT | ATATTTATGT | AACGGGGATA | TTAAACCCTA | ACGAGGCTAG |
| AGACGAGGTA | TTCTCGGTAG | TGAATAAGGG | ATATATTGGA | CCGGGAGGGC |
| GCTCCTTTTC | GAATCGTGGT | AGTAAGTACA | CCGTCGTCTG | GGAAAACTCT |
| GCTGCGAGGA | TTAGTGGATT | TACGTCGACT | TCGCAATCTA | CGATAGATGC |
| TTTCGCGTAT | TTCTTGTTGA | AAGGCGGATT | GACTACCACG | CTCTCTAACC |
| CAATAAACTG | TGAGAATTGG | GTCAGGT6AT | CTAAGGATTT | AAGCGCGTTT |
| TTCAGGACCC | TAATTAAAGG | TAAGATTTAT | GCATCGCGTT | CTGTGGACAG |
| CAATCTTCCA | AAGAAAGACA | GGGATGACAT | CATGGAAGCG | AGTCGACGAC |
| TATCGCCATC | GGACGCCGCC | TTTTGCAGAG | CAGTGTCGGT | TCAGGTAGGG |
| AAGTATGTGG | ACGTAACGCA | GAATTTAGAA | AGTACGATCG | TGCCGTTAAG |
| AGTTATGGAA | ATAAAGAAAA | GACGAGGATC | AGCACATGTT | AGTTTACCGA |
| AGGTGGTATC | CGCTTACGTA | GATTTTTATA | CGAACTTGCA | GGAATTGCTG |
| TCGGATGAAG | TAACTAGGGC | CAGAACCGAT | ACAGTTTCGG | CATACGCTAC |
| CGACTCTATG | GCTTTCTTAG | TTAAGATGTT | ACCCCTGACT | GCTCGTGAGC |
| AGTGGTTAAA | AGACGTGCTA | GGATATCTGC | TGGTACGGAG | ACGACCAGCA |
| AATTTTTCCT | ACGACGTAAG | AGTAGCTTGG | GTATATGACG | TGATCGCTAC |
| GCTCAAGCTG | GTCATAAGAT | TGTTTTTCAA | CAAGGACACA | CCCGGGGGTA |
| TTAAAGACTT | AAAACCGTGT | GTGCCTATAG | AGTCATTCGA | CCCCTTTCAC |
| GAGCTTTCGT | CCTATTTCTC | TAGGTTAAGT | TACGAGATGA | CGACAGGTAA |
| AGGGGGAAAG | ATATGCCCGG | AGATCGCCGA | GAAGTTGGTG | CGCCGTCTAA |
| TGGAGGAAAA | CTATAAGTTA | AGATTGACCC | CAGTGATGGC | CTTAATAATT |
| ATACTGGTAT | ACTACTCCAT | TTACGGCACA | AACGCTACCA | GGATTAAAAG |
| ACGCCCGGAT | TTCCTCAATG | TGAGGATAAA | GGGAAGAGTC | GAGAAGGTTT |
| CGTTACGGGG | GGTAGAAGAT | CGTGCCTTTA | GAATATCAGA | AAAGCGCGGG |
| ATAAACGCTC | AACGTGTATT | ATGTAGGTAC | TATAGCGATC | TCACATGTCT |
| GGCTAGGCGA | CATTACGGCA | TTCGCAGGAA | CAATTGGAAG | ACGCTGAGTT |
| ATGTAGACGG | GACGTTAGCG | TATGACACGG | CTGATTGTAT | AACTTCTAAG |
| GTGAGAAATA | CGATCAACAC | CGCAGATCAC | GCTAGCATTA | TACACTATAT |
| CAAGACGAAC | GAAAACCAGG | TTACCGGAAC | TACTCTACCA | CACCAGCTTT |
| AA. | | | | |

The hsp90-related protein or polypeptide has an amino acid sequence corresponding to SEQ. ID. No. 8 as follows:

| | | | | |
|---|---|---|---|---|
| MDKYIYVTGI | LNPNEARDEV | FSVVNKGYIG | PGGRSFSNRG | SKYTVVWENS |
| AARISGFTST | SQSTIDAFAY | FLLKGGLTTT | LSNPINCENW | VRSSKDLSAF |
| FRTLIKGKIY | ASRSVDSNLP | KKDRDDIMEA | SRRLSPSDAA | FCRAVSVQVG |
| KYVDVTQNLE | STIVPLRVME | IKKRRGSAHV | SLPKVVSAYV | DFYTNLQELL |
| SDEVTRARTD | TVSAYATDSM | AFLVKMLPLT | AREQWLKDVL | GYLLVRRRPA |
| NFSYDVRVAW | VYDVIATLKL | VIRLFFNKDT | PGGIKDLKPC | VPIESFDPFH |
| ELSSYFSRLS | YEMTTGKGGK | ICPEIAEKLV | RRLMEENYKL | RLTPVMALII |
| ILVYYSIYGT | NATRIKRRPD | FLNVRIKGRV | EKVSLRGVED | RAFRISEKRG |
| INAQRVLCRY | YSDLTCLARR | HYGIRRNNWK | TLSYVDGTLA | YDTADCITSK |
| VRNTINTADH | ASIIHYIKTN | ENQVTGTTLP | HQL | | and a molecular weight from about 53 to about 57 kDa, preferably about 55 kDa.

Another such DNA molecule constitutes an open reading frame which codes for a grapevine leafroll virus coat protein or polypeptide. The DNA molecule comprises the nucleotide sequence corresponding to SEQ. ID. No. 9 as follows:

| | | | | |
|---|---|---|---|---|
| ATGGCATTTG | AACTGAAATT | AGGGCAGATA | TATGAAGTCG | TCCCCGAAAA |
| TAATTTGAGA | GTTAGAGTGG | GGGATGCGGC | ACAAGGAAAA | TTTAGTAAQG |
| CGAGTTTCTT | AAAGTACGTT | AAGGACGGGA | CACAGGCGGA | ATTAACGGGA |
| ATCGCCGTAG | TGCCCGAAAA | ATACGTATTC | GCCACAGCAG | CTTTGGCTAC |
| AGCGGCGCAG | GAGCCACCTA | GGCAGCCACC | AGCGCAAGTG | GCGGAACCAC |
| ATGGCATTTG | AACTGAAATT | AGGGCAGATA | TATGAAGTCG | TCCCCGAAAA |
| TAATTTGAGA | GTTAGAGTGG | GGGATGCGGC | ACAAGGAAAA | TTTAGTAAQG |
| CGAGTTTCTT | AAAGTACGTT | AAGGACGGGA | CACAGGCGGA | ATTAACGGGA |
| ATCGCCGTAG | TGCCCGAAAA | ATACGTATTC | GCCACAGCAG | CTTTGGCTAC |
| AGCGGCGCAG | GAGCCACCTA | GGCAGCCACC | AGCGCAAGTG | GCGGAACCAC |
| AGGAAACCGA | TATAGGGGTA | GTGCCGGAAT | CTGAGACTCT | CACACCAAAT |
| AAGTTGGTTT | TCGAGAAAGA | TCCAGACAAG | TTCTTGAAGA | CTATGGGCAA |
| GGGAATAGCT | TTGGACTTGG | CGGGAGTTAC | CCACAAACCG | AAAGTTATTA |
| ACGAGCCAGG | GAAAGTATCA | GTAGAGGTGG | CAATGAAGAT | TAATGCCGCA |
| TTGATGGAGC | TGTGTAAGAA | GGTTATGGGC | GCCGATGACG | CAGCAACTAA |
| GACAGAATTC | TTCTTGTACG | TGATGCAGAT | TGCTTGCACG | TTCTTTACAT |
| CGTCTTCGAC | GGAGTTCAAA | GAGTTTGACT | ACATAGAAAC | CGATGATGGA |
| AAGAAGATAT | ATGCGGTGTG | GGTATATGAT | TGCATTAAAC | AAGCTGCTGC |
| TTCGACGGGT | TATGAAAACC | CGGTAAGGCA | GTATCTAGCG | TACTTCACAC |
| CAACCTTCAT | CACGGCGACC | CTGAATGGTA | AACTAGTGAT | GAACGAGAAG |

| | | | | |
|---|---|---|---|---|
| GTTATGGCAC | AGCATGGAGT | ACCACCGAAA | TTCTTTCCGT | ACACGATAGA |
| CTGCGTTCGT | CCGACGTACG | ATCTGTTCAA | CAACGACGCA | ATATTAGCAT |
| GGAATTTAGC | TAGACAGCAG | GCGTTTAGAA | ACAAGACGGT | AACGGCCGAT |
| AACACCTTAC | ACAACGTCTT | CCAACTATTG | CAAAAGAAGT | AG. |

The coat protein or polypeptide has an amino acid sequence corresponding to SEQ. ID. No. 10 as follows:

| | | | | |
|---|---|---|---|---|
| MAFELKLGQI | YEVVPENNLR | VRVGDAAQGK | FSKASFLKYV | KDGTQAELTG |
| IAVVPEKYVF | ATAALATAAQ | EPPRQPPAQV | AEPQETDIGV | VPESETLTPN |
| KLVFEKDPDK | FLKTMGKGIA | LDLAGVTHKP | KVINEPGKVS | VEVAMKINAA |
| LMELCKKVMG | ADDAATKTEF | FLYVMQIACT | FFTSSSTEFK | EFDYIETDDG |
| KKIYAVWVYD | CIKQAAASTG | YENPVRQYLA | YFTPTFITAT | LNGKLVMNEK |
| VMAQHGVPPK | FFPYTIDCVR | PTYDLFNNDA | ILAWNLARQQ | AFRNKTVTAD |
| NTLHNVFQLL | QKK | | | | and a molecular weight from about 33 to about 43 kDa, preferably about 35 kDa.

Alternatively, the DNA molecule of the present invention can constitute an open reading frame which codes for a first undefined protein or polypeptide. This DNA molecule comprises the nucleotide sequence corresponding to SEQ. ID. No. 11 as follows:

| | | | | |
|---|---|---|---|---|
| ATGTACAGTA | GAGGGTCTTT | CTTTAAGTCT | CGGGTTACCC | TTCCTACTCT |
| TGTCGGAGCA | TACATGTGGG | AGTTTGAACT | CCCGTATCTT | ACGGACAAGA |
| GACACATCAG | CTATAGCGCG | CCAAGTGTCG | CGACTTTTAG | CCTTGTGTCG |
| AGGTAG. | | | | |

The first undefined protein or polypeptide has an amino acid sequence corresponding to SEQ. ID. No. 12 as follows:

| | | | | |
|---|---|---|---|---|
| MYSRGSFFKS R | RVTLPTLVGA | YMWEFELPYL | TDKRHISYSA | PSVATFSLVS | and a molecular weight from about 5 to about 7 kDa, preferably about 6 kDa.

Another such DNA molecule constitutes an open reading frame which codes for a second undefined grapevine leafroll virus protein or polypeptide and comprises the nucleotide sequence corresponding to SEQ. ID. No. 13 as follows:

| | | | | |
|---|---|---|---|---|
| ATGGATGATT | TTAAACAGGC | AATACTGTTG | CTAGTAGTCG | ATTTTGTCTT |
| CGTGATAATT | CTGCTGCTGG | TTCTTACGTT | CGTCGTCCCG | AGGTTACAGC |
| AAAGCTCCAC | CATTAATACA | GGTCTTAGGA | CAGTGTGA. | |

The second undefined protein or polypeptide has an amino acid sequence corresponding to SEQ. ID. No. 14 as follows:

| | | | | |
|---|---|---|---|---|
| MDDFKQAILL | LVVDFVFVII | LLLVLTFVVP | RLQQSSTINT | GLRTV | and a molecular weight from about 4 to about 6 kDa, preferably about 5 kDa.

Another such DNA molecule constitutes an open reading frame which codes for a grapevine leafroll virus coat protein or polypeptide repeat and comprises the nucleotide sequence corresponding to SEQ. ID. No. 15 as follows:

| | | | | |
|---|---|---|---|---|
| ATGGGAGCTT | ATACACATGT | AGACTTTCAT | GAGTCGCGGT | TGCTGAAAGA |
| CAAACAAGAC | TATCTTTCTT | TCAAGTCAGC | GGATGAAGCT | CCTCCTGATC |
| CTCCCGGATA | CGTTCGCCCA | GATAGTTATG | TGAGGGCTTA | TTTGATACAA |
| AGAGCAGACT | TTCCCAATAC | TCAAAGCTTA | TCAGTTACGT | TATCGATAGC |
| CAGTAATAAG | TTAGCTTCAG | GTCTTATGGG | AAGCGACGCA | GTATCATCGT |
| CGTTTATGCT | GATGAACGAC | GTGGGAGATT | ACTTCGAGTG | CGGCGTGTGT |
| CACAACAAAC | CCTACTTAGG | ACGGGAAGTT | ATCTTCTGTA | GGAAATACAT |
| AGGTGGGAGA | GGAGTGGAGA | TCACCACTGG | TAAGAACTAC | ACGTCGAACA |
| ATTGGAACGA | GGCGTCGTAC | GTAATACAAG | TGAACGTAGT | CGATGGGTTA |
| GCACAGACCA | CTGTTAATTC | TACTTATACG | CAAACGGACG | TTAGTGGTCT |
| ACCCAAAAAT | TGGACGCGTA | TCTACAAAAT | AACAAAGATA | GTGTCCGTGA |
| ATCAGAACCT | CTACCCTGGT | TGTTTCTCAG | ACTCGAAACT | GGGTGTAATG |
| CGTATAAGGT | CACTGTTAGT | TTCCCCAGTG | CGCATCTTCT | TTAGGGATAT |
| CTTATTGAAA | CCTTTGAAGA | AATCGTTCAA | CGCAAGAATC | GAGGATGTGC |
| TGAATATTGA | CGACACGTCG | TTGTTAGTAC | CGAGTCCTGT | CGTACCAGAG |
| TCTACGGGAG | GTGTAGGTCC | ATCAGAGCAG | CTGGATGTAG | TGGCTTTAAC |
| GTCCGACGTA | ACGGAATTGA | TCAACACTAG | GGGGCAAGGT | AAGATATGTT |
| TTCCAGACTC | AGTGTTATCG | ATCAATGAAG | CGGATATCTA | CGATGAGCGG |
| TATTTGCCGA | TAACGAAGC | TCTACAGATA | AACGCAAGAC | TACGCAGACT |
| CGTTCTTTCG | AAAGGCGGGA | GTCAAACACC | ACGAGATATG | GGGAATATGA |
| TAGTGGCCAT | GATACAACTT | TTCGTACTCT | ACTCTACTGT | AAAGAATATA |
| AGCGTCAAAG | ACGGGTATAG | GGTGGAGACC | GAATTAGGTC | AAAAGAGAGT |
| CTACTTAAGT | TATTCQGAAG | TAAGGGAAGC | TATATTAGGA | GGGAAATACG |
| GTGCGTCTCC | AACCAACACT | GTGCGATCCT | TCATGAGGTA | TTTTGCTCAC |
| ACCACTATTA | CTCTACTTAT | AGAGAAGAAA | ATTCAGCCAG | CGTGTACTGC |
| CCTAGCTAAG | CACGGCGTCC | CGAAGAGGTT | CACTCCGTAC | TGCTTCGACT |
| TCGCACTACT | GGATAACAGA | TATTACCCGG | CGGACGTGTT | GAAGGCTAAC |
| GCAATGGCTT | GCGCTATAGC | GATTAAATCA | GCTAATTTAA | GGCGTAAAGG |
| TTCGGAGACG | TATAACATCT | TAGAAAGCAT | TTGA. | |

The grapevine leafroll virus coat protein or polypeptide repeat has an amino acid sequence corresponding to SEQ. ID. No. 16 as follows:

| | | | | |
|---|---|---|---|---|
| MGAYTHVDFH | ESRLLKDKQD | YLSFKSADEA | PPDPPGYVRP | DSYVRAYLIQ |
| RADFPNTQSL | SVTLSIASNK | LASGLMGSDA | VSSSFMLMND | VGDYFECGVC |
| HNKPYLGREV | IFCRKYIGGR | GVEITTGKNY | TSNNWNEASY | VIQVNVVDGL |
| AQTTVNSTYT | QTDVSGLPKN | WTRIYKITKI | VSVDQNLYPG | CFSDSKLGVM |
| RIRSLLVSPV | RIFFRDILLK | PLKKSFNARI | EDVLNIDDTS | LLVPSPVVPE |
| STGGVGPSEQ | LDVVALTSDV | TELINTRGQG | KICFPDSVLS | INEADIYDER |
| YLPITEALQI | NARLRRLVLS | KGGSQTPRDM | GNMIVAMIQL | FVLYSTVKNI |
| SVKDGYRVET | ELGQKRVYLS | YSEVREAILG | GKYGASPTNT | VRSFMRYFAH |
| TTITLLIEKK | IQPACTALAK | HGVPKRFTPY | CFDFALLDNR | YYPADVLKAN |
| AMACAIAIKS | ANLRRKGSET | YNILESI | | | and a molecular weight from about 51 to about 55 kDa, preferably about 53 kDa.

Yet another such DNA molecule constitutes an open reading frame which codes for a third undefined grapevine leafroll virus protein or polypeptide and comprises the nucleotide sequence corresponding to SEQ. ID. No. 17 as follows:

| | | | | |
|---|---|---|---|---|
| ATGGAATTCA | GACCAGTTTT | AATTACAGTT | CGCCGTGATC | CCGGCGTAAA |
| CACTGGTAGT | TTGAAAGTGA | TAGCTTATGA | CTTACACTAC | GACAATATAT |
| TCGATAACTG | CGCGGTAAAG | TCGTTTCGAG | ACACCGACAC | TGGATTCACT |
| GTTATGAAAG | AATACTCGAC | GAATTCAGCG | TTCATACTAA | GTCCTTATAA |
| ACTGTTTTCC | GCGGTCTTTA | ATAAGGAAGG | TGAGATGATA | AGTAACGATG |
| TAGGATCGAG | TTTCAGGGTT | TACAATATCT | TTTCGCAAAT | GTGTAAAGAT |
| ATCAACGAGA | TCAGCGAGAT | ACAACGCQCC | GGTTACCTAG | AAACATATTT |
| AGGAGACGGG | CAGGCTGACA | CTGATATATT | TTTTGATGTC | TTAACCAACA |
| ACAAAGCAAA | GGTAAGGTGG | TTAGTTAATA | AAGACCATAG | CGCGTGGTGT |
| GGGATATTGA | ATGATTTGAA | GTGGGAAGAG | AGCAACAAGG | AGAAATTTAA |
| GGGGAGAGAC | ATACTAGATA | CTTACGTTTT | ATCGTCTGAT | TATCCAGGGT |
| TTAAATGA. | | | | |

The third undefined protein or polypeptide has an amino acid sequence corresponding to SEQ. ID. No. 18 as follows:

| | | | | |
|---|---|---|---|---|
| MEFRPVLITV | RRDPGVNTGS | LKVIAYDLHY | DNIFDNCAVK | SFRDTDTGFT |
| VMKEYSTNSA | FILSPYKLFS | AVFNKEGEMI | SNDVGSSFRV | YNIFSQMCKD |
| INEISEIQRA | GYLETYLGDG | QADTDIFFDV | LTNNKAKVRW | LVNKDHSAWC |
| GILNDLKWEE | SNKEKFKGRD | ILDTYVLSSD | YPGFK | | and a molecular weight from about 33 to about 39 kDa, preferably about 36 kDa.

Yet another such DNA molecule constitutes an open reading frame which codes for a fourth undefined grapevine leafroll virus protein or polypeptide and comprises the nucleotide sequence corresponding to SEQ. ID. No. 19 as follows:

| | | | | |
|---|---|---|---|---|
| ATGAAGTTGC | TTTCGCTCCG | CTATCTTATC | TTAAGGTTGT | CAAAGTCGCT |
| TAGAACGAAC | GATCACTTGG | TTTTAATACT | TATAAAGGAG | GCGCTTATAA |
| ACTATTACAA | CGCCTCTTTC | ACCGATGAGG | GTGCCGTATT | AAGAGACTCT |
| CGCGAAAGTA | TAGAGAATTT | TCTCGTAGCC | AGGTGCGGTT | CGCAAAATTC |
| CTGCCGAGTC | ATGAAGGCTT | TGATCACTAA | CACAGTCTGT | AAGATGTCGA |
| TAGAAACAGC | CAGAAGTTTT | ATCGGAGACT | TAATACTCGT | CGCCGACTCC |
| TCTGTTTCAG | CGTTGGAAGA | AGCGAAATCA | ATTAAAGATA | ATTTCCGCTT |
| AAGAAAAAGG | AGAGGCAAGT | ATTATTATAG | TGGTGATTGT | GGATCCGACG |
| TTGCGAAAGT | TAAGTATATT | TTGTCTGGGG | AGAATCGAGG | ATTGGGGTGC |
| GTAGATTCCT | TGAAGCTAGT | TTGCGTAGGT | AGACAAGGAG | GTGGAAACGT |
| ACTACAGCAC | CTACTAATCT | CATCTCTGGG | TTAA. | |

The fourth undefined protein or polypeptide has an amino acid sequence corresponding to SEQ. ID. No. 20 as follows:

| | | | | |
|---|---|---|---|---|
| MKLLSLRYLI | LRLSKSLRTN | DHLVLILIKE | ALINYYNASF | TDEGAVLRDS |
| RESIENFLVA | RCGSQNSCRV | MKALITNTVC | KMSIETARSF | IGDLILVADS |
| SVSALEEAKS | IKDNFRLRKR | RGKYYYSGDC | GSDVAKVKYI | LSGENRGLGC |
| VDSLKLVCVG | RQGGGNVLQH | LLISSLG | | | and a molecular weight from about 17 to about 23 kDa, preferably about 20 kDa.

Yet another such DNA molecule constitutes an open reading frame which codes for a fifth undefined grapevine leafroll virus protein or polypeptide and comprises the nucleotide sequence corresponding to SEQ. ID. No. 21 as follows:

| | | | | |
|---|---|---|---|---|
| ATGGACCTAT | CGTTTATTAT | TGTGCAGATC | CTTTCCGCCT | CGTACAATAA |
| TGACGTGACA | GCACTTTACA | CTTTGATTAA | CGCGTATAAT | AGCGTTGATG |
| ATACGACGCG | CTGGGCAGCG | ATAAACGATC | CGCAAGCTGA | GGTTAACGTC |
| GTGAAGGCTT | ACGTAGCTAC | TACAGCGACG | ACTGAGCTGC | ATAGAACAAT |
| TCTCATTGAC | AGTATAGACT | CCGCCTTCGC | TTATGACCAA | GTGGGGTGTT |
| TGGTGGGCAT | AGCTAGAGGT | TTGCTTAQAC | ATTCGGAAGA | TGTTCTGGAG |
| GTCATCAAGT | CGATGGAGTT | ATTCGAAGTG | TGTCGTGGAA | AGAGGGGAAG |
| CAAAAGATAT | CTTGGATACT | TAAGTGATCA | ATGCACTAAC | AAATACATGA |
| TGCTAACTCA | GGCCGGACTG | GCCGCAGTTG | AAGGAGCAGA | CATACTACGA |
| ACGAATCATC | TAGTCAGTGG | TAATAAGTTC | TCTCCAAATT | TCGGGATCGC |
| TAGGATGTTG | CTCTTGACGC | TTTGTTGCGG | AGCACTATAA. | |

The fifth undefined protein or polypeptide has an amino acid sequence corresponding to SEQ. ID. No. 22 as follows:

| | | | | |
|---|---|---|---|---|
| MDLSFIIVQI | LSASYNNDVT | ALYTLINAYN | SVDDTTRWAA | INDPQAEVNV |
| VKAYVATTAT | TELHRTILID | SIDSAFAYDQ | VGCLVGIARG | LLRHSEDVLE |
| VIKSMELFEV | CRGKRGSKRY | LGYLSDQCTN | KYMMLTQAGL | AAVEGADILR |
| TNHLVSGNKF | SPNFGIARML | LLTLCCGAL | | | and a molecular weight from about 17 to about 23 kDa, preferably about 20 kDa.

Yet another such DNA molecule constitutes an open reading frame which codes for a sixth undefined grapevine leafroll virus protein or polypeptide and comprises the nucleotide sequence corresponding to SEQ. ID. No. 23 as follows:

| | | | | |
|---|---|---|---|---|
| ATGAGGCACT | TAGAAAAACC | CATCAGAGTA | GCGGTACACT | ATTQQGTCGT |
| GCGAAGTGAC | GTTTGTGACG | GGTGGGATGT | ATTTATAGGC | GTAACGTTAA |
| TCGGTATGTT | TATTAGTTAC | TATTTATATG | CTCTAATTAG | CATATGTAGA |
| AAAGGAGAAG | GTTTAACAAC | CAGTAATGGG | TAA. | |

The sixth undefined protein or polypeptide has an amino acid sequence corresponding to SEQ. ID. No. 24 as follows:

| | | | | |
|---|---|---|---|---|
| MRHLEKPIRV | AVHYCVVRSD | VCDGWDVFIG | VTLIGMFISY | YLYALISICR |
| KGEGLTTSNG | | | | | and a molecular weight from about 5 to about 9 kDa, preferably about 7 kDa.

Also encompassed by the present invention are fragments of the DNA molecules of the present invention. Suitable fragments capable of imparting grapevine leafroll resistance to grape plants are constructed by using appropriate restriction sites, revealed by inspection of the DNA molecule's sequence, to: (i) insert an interposon (Felley et al., "Interposon Mutagenesis of Soil and Water Bacteria: a Family of DNA Fragments Designed for in vitro Insertion Mutagenesis of Gram-negative Bacteria," Gene, 52:147–15 (1987), which is hereby incorporated by reference) such that truncated forms of the grapevine leafroll virus coat polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Variants may also (or alternatively) be modified by, for example, the deletion or addition of nucleotides that have minimal influence on the properties, secondary structure and hydropathic nature of the encoded polypeptide. For example, the nucleotides encoding a polypeptide may be conjugated to a signal (or leader) sequence at the N-terminal end of the protein which co-translationally or post-translationally directs transfer of the protein. The nucleotide sequence may also be altered so that the encoded polypeptide is conjugated to a linker or other sequence for ease of synthesis, purification, or identification of the polypeptide.

The protein or polypeptide of the present invention is preferably produced in purified form (preferably, at least about 80%, more preferably 90%, pure) by conventional techniques. Typically, the protein or polypeptide of the present invention is isolated by lysing and sonication. After washing, the lysate pellet is resuspended in buffer containing Tris-HCl. During dialysis, a precipitate forms from this protein solution. The solution is centrifuged, and the pellet is washed and resuspended in the buffer containing Tris-HCl. Proteins are resolved by electrophoresis through an SDS 12% polyacrylamide gel.

The DNA molecule encoding the grapevine leafroll virus protein or polypeptide of the present invention can be incorporated in cells using conventional recombinant DNA technology. Generally, this involves inserting the DNA molecule into an expression system to which the DNA molecule is heterologous (i.e. not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eucaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/- or KS +/- (see "Stratagene Cloning Systems" Catalog (1993) from Stratagene, La Jolla, Calif., which is hereby incorporated by reference), pQE, pIH821, PGEX, pET series (see Studier et. al., "Use of T7 RNA Polymerase to Direct Expression of Cloned Genes," Gene Expression Technology, vol. 185 (1990), which is hereby incorporated by reference), and any derivatives thereof. Recombinant molecules can be introduced into cells via transformation, transduction, conjugation, mobilization, or electroporation. The DNA sequences are cloned into the vector using standard cloning procedures in the art, as described by Maniatis et al., Molecular Cloning: A Laboratory Manual, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promotor which is a DNA sequence that directs the binding of RNA polymerase and thereby promotes mRNA synthesis. The DNA sequences of eucaryotic promoters differ from those of procaryotic promoters. Furthermore, eucaryotic promoters and accompanying genetic signals may not be recognized in or may not function in a procaryotic system, and, further, procaryotic promoters are not recognized and do not function in eucaryotic cells.

Similarly, translation of mRNA in procaryotes depends upon the presence of the proper procaryotic signals which differ from those of eucaryotes. Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology*, 68:473 (1979), which is hereby incorporated by reference.

Promotors vary in their "strength" (i.e. their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli*, its bacteriophages, or plasmids, promoters such as the T7 phage promoter, lac promotor, trp promotor, recA promotor, ribosomal RNA promotor, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promotor or other *E. coli* promoters produced by recombinant DNA or other synthetic DNA techniques may be used to provide for transcription of the inserted gene.

Bacterial host cell strains and expression vectors may be chosen which inhibit the action of the promotor unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promotor, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various grapevine leafroll virus proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various grapevine leafroll virus proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a grapevine leafroll virus to transform grape plants in order to impart grapevine leafroll resistance to the plants. The mechanism by which resistance is imparted in not known. In one hypothetical mechanism, the transformed plant can express the coat protein or polypeptide, and, when the transformed plant is inoculated by a grapevine leafroll virus, such as GLRaV-1, GLRaV-2, GLRav-3, GLRaV-4, GLRaV-5, or GLRaV-6, or combinations of these, the expressed coat protein or polypeptide surrounds the virus, thereby preventing translation of the viral DNA.

In this aspect of the present invention the subject DNA molecule incorporated in the plant can be constitutively expressed. Alternatively, expression can be regulated by a promoter which is activated by the presence of grapevine leafroll virus. Suitable promoters for these purposes include those from genes expressed in response to grapevine leafroll virus infiltration.

The isolated DNA molecules of the present invention can be utilized to impart grapevine leafroll resistance for a wide variety of grapevine plants. The DNA molecules are particularly well suited to imparting resistance to Vitis scion or rootstock cultivars. Scion cultivars which can be protected include those commonly referred to as Table on Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A x R #1), Harmony, Kober 5BB, LN33, Millardet & de Grasset 41B, Millardet & de Grasset 420A, Millardet & de Grasset 101-14, Oppenheim 4 (SO4), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis california,* and *Vitis girdiana.*

There exists an extensive similarity in the hsp70-related sequence regions of GLRaV-3 and other closteroviruses, such as tristeza virus. Consequently, the GLRaV-3 hsp70-related gene can also be used to produce transgenic cultivars other than grape, such as citrus, which are resistant to closteroviruses other than grapevine leafroll, such as tristeza virus. These include cultivars of lemon, lime, orange, grapefruit, pineapple, tangerine, and the like, such as Joppa, Maltaise Ovale, Parson (Parson Brown), Pera, Pineapple, Queen, Shamouti, Valencia, Tenerife, Imperial Doblefina, Washington Sanguine, Moro, Sanguinello Moscato, Spanish Sanguinelli, Tarocco, Atwood, Australian, Bahia, Baiana, Cram, Dalmau, Eddy, Fisher, Frost Washington, Gillette, LengNavelina, Washington, Satsuma Mandarin, Dancy, Robinson, Ponkan, Duncan, Marsh, Pink Marsh, Ruby Red, Red Seedless, Smooth Seville, Orlando Tangelo, Eureka, Lisbon, Meyer Lemon', Rough Lemon, Sour Orange, Persian Lime, West Indian Lime, Bearss, Sweet Lime, Troyer Citrange, and Citrus trifoliata.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart grapevine leafroll virus resistance. Transformed cells can be regenerated into whole plants such that the protein or polypeptide imparts resistance to grapevine leafroll virus in the intact transgenic plants. In either case, the plant cells transformed with the recombinant DNA expression system of the present invention are grown and caused to express that DNA molecule to produce one of the above-described grapevine leafroll virus proteins or polypeptides and, thus, to impart grapevine leafroll resistance.

One technique of transforming plants with the DNA molecules in accordance with the present invention is by contacting the tissue of such plants with an inoculum of a bacteria transformed with a vector comprising a gene in accordance with the present invention which imparts grapevine leafroll resistance. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes. Agrobacterium tumefaciens* (e.g., strains C58, LBA4404, or EHA105) is particularly useful due to its well-known ability to transform plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports,* 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Once a grape plant tissue is transformed in accordance with the present invention, it is regenerated to form a transgenic grape plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop tissue culture and are screened for marker gene activity.

The DNA molecules of the present invention can be made capable of transcription to a messenger RNA, which, although encoding for a grapevine leafroll virus protein or polypeptide, does not translate to the protein. This is known as RNA-mediated resistance. When a Vitis scion or rootstock cultivar is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

The grapevine leafroll virus protein or polypeptide can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature,* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.*, 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 μl per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthenized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, F(ab')$_2$ fragments, and Fv fragments. These antibody fragments can be made by conventional procedures, such as proteolytic fragmentation procedures, as described in Goding, *Monoclonal Antibodies: Principles and Practice*, New York:Academic Press, pp. 98–118 (1983), which is hereby incorporated by reference.

The present invention also relates to probes found either in nature or prepared synthetically by recombinant DNA procedures or other biological procedures. Suitable probes are molecules which bind to grapevine leafroll viral antigens identified by the monoclonal antibodies of the present invention. Such probes can be, for example, proteins, peptides, lectins, or nucleic acid probes.

The antibodies or binding portions thereof or probes can be administered to grapevine leafroll virus infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by grapevine leafroll virus. In either case, the antibody or binding portion thereof or probe will bind to the virus and help prevent the usual leafroll response.

Antibodies raised against the proteins or polypeptides of the present invention or binding portions of these antibodies can be utilized in a method for detection of grapevine leafroll virus in a sample of tissue, such as tissue from a grape scion or rootstock. Antibodies or binding portions thereof suitable for use in the detection method include those raised against a helicase, an RNA-dependent RNA polymerase, an hsp70-related, an hsp90-related, or a coat protein or polypeptide in accordance with the present invention Any reaction of the sample with the antibody is detected using an assay system which indicates the presence of grapevine leafroll virus in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, grapevine leafroll virus can be detected in such a sample using a nucleotide sequence of the DNA molecule, or a fragment thereof, encoding for a protein or polypeptide of the present invention. The nucleotide sequence is provided as a probe in a nucleic acid hybridization assay or a gene amplification detection procedure (e.g., using a polymerase chain reaction procedure). Any reaction with the probe is detected so that the presence of grapevine leafroll virus in the sample is indicated.

The following examples are provided to illustrate embodiments of the present invention but are by no means intended to limit its scope.

EXAMPLES

Example 1

Materials and Methods

Virus purification and dsRNA isolation. The NY1 isolate, which is also referred to as isolate GLRaV 109 by Golino, "The Davis Grapevine Virus Collection," *Amer. J. Enol. Vitic,* 43:200–205 (1992), a member of GLRaV-3 (Hu et al., "Characterization of Closterovirus-like Particles Associated with Grapevine Leafroll Disease," *J. Phytopathol. (Berl.)*, 128:1–14 (1990) ("Hu (1990)") and Zee et al., "Cytopathology of Leafroll-Diseased Grapevines and the Purification and Serology of Associated Closteroviruslike Particles," *Phytopathology,* 77:1427–1434 (1987) ("Zee (1987)"), which are hereby incorporated by reference) was used throughout this work. Leafroll-diseased canes and mature leaves were collected from a vineyard in central New York State, and kept at −20° C. until used. GLRaV-3 virus particles were purified according to the method described by Zee (1987), which is hereby incorporated by reference, and modified later by Hu (1990), which is incorporated by reference. After two cycles of $Cs_2SO_4$ gradient purification, virus particles were observable from virus-enriched fractions by negative staining on an electron microscope.

The dsRNA was extracted from scraped bark/phloem tissue of canes as described in Hu (1990), which is hereby incorporated by reference. Briefly, total nucleic acid was extracted with phenol/chloroform; dsRNA was absorbed on a CF-11 cellulose column under 17% ethanol and eluted without ethanol. After two cycles of ethanol precipitation, dsRNA was analyzed by electrophoresis on a 6% polyacrylamide or 1% agarose gel. A high Mr dsRNA (~16 kb) along with several smaller Mr dsRNAs was consistently identified in leafroll diseased but not in healthy samples (Hu (1990), which is hereby incorporated by reference). The 16 kb dsRNA, which was presumably a replicative form of the virus, was purified further following separation on a low melting temperature-agarose gel (Sambrook et al., *Molecu-* lar *Cloning, A Laboratory Manual*, 2nd Ed., Cold Spring Harbor Laboratory Press (1989) ("Sambrook (1989)"), which is hereby incorporated by reference). The double-stranded nature of the dsRNA was confirmed after it was demonstrated to be resistant to DNase and RNase in high salt but sensitive to RNase in water (Hu (1990), which is hereby incorporated by reference).

cDNA synthesis and molecular cloning. Complementary DNA (cDNA) was prepared by the procedure of Gubler et al., "A Simple and Very Efficient Method for Generating cDNA Libraries," *Gene*, 25:263 (1983), which is hereby incorporated by reference, and modified for dsRNA by Jelkmann et al., "Cloning of Four Plant Viruses from Small Quantities of Double-Stranded RNA," *Phytopathology*, 79:1250–1253 (1989), which is hereby incorporated by reference. Briefly, following denaturation of about 2 μg of dsRNA in 20 mM methylmercuric hydroxide (MeHg) for 10 min, the first-strand cDNA was synthesized by avian myeloblastosis virus ("AMV")-reverse transcriptase using random primers (Boehringer Mannheim, Indianapolis, Ind.). The second-strand cDNA was synthesized with DNA polymerase I while RNA templates were treated with RNase H. The cDNA was size-fractionated on a CL-4B Sepharose column and peak fractions, which contained larger molecular weight cDNA, were pooled and used for cloning. Complimentary DNA ends were blunted with T4 DNA polymerase, and Eco RI adapters were ligated onto a portion of the blunt-ended cDNA. After treatment with T4 polynucleotide kinase and removal of unligated adapters by spin column chromatography, the cDNA was ligated with lambda ZAPII/EcoR I prepared arms (Stratagene, La Jolla, Calif.). These recombinant DNAs were packaged in vitro with GIGAPACK II GOLD™ packaging extract according to the manufacturer's instruction (Stratagene). The packaged phage particles were used to infect bacteria, XL1-blue cells.

Screening the cDNA library. To select GLRaV-3 dsRNA specific cDNA clones, probes were prepared from UNI-AMP™ (Clontech, Palo Alto, Calif.) PCR-amplified cDNA. PCR-amplified GLRaV-3 cDNA was labeled with $^{32}$P [a-dATP] by Klenow fragment of *E. coli* DNA polymerase I with random primers and used as a probe for screening the library (Feinberg et al., "A Technique for Radiolabeling DNA Restriction Endonuclease Fragments to High Specific Activity," *Analytic Biochem.*, 132:6–13 (1983) ("Feinberg (1983)"), which is hereby incorporated by reference). Library screening was carried out by transferring plaques grown overnight onto GENESCREEN PLUS™ filters, following the manufacturer's instructions for denaturation, prehybridization, and hybridization (Dupont, Boston, Mass.). After washing, an autoradiograph was developed after exposing Kodak X-OMAT film to the washed filters overnight at –80° C. Bacteriophage recombinants were converted into plasmids (in vivo excision) following the manufacturer's instruction (Stratagene).

Identification of the coat protein gene was done by immunoscreening the cDNA library with GLRaV-3 specific polyclonal (Zee (1987), which is hereby incorporated by reference) and monoclonal (Hu (1990), which is hereby incorporated by reference) antibodies. Degenerate primer (5'GGNGGNGGNACNTTYGAYGTNTCN (SEQ. ID. No. 25), I=inosine, Y=T or C) generated from a conserved amino acid sequence in Motif C of the BYV HSP70 gene (p65) was used to select HSP70 positive clones. Further sequence extension was made possible by the clone walking strategy, which used sequences that flanked the sequence contig to probe the library for a clone that might contain an insert extending farther in either 5' or 3' direction.

Northern blot hybridization. Inserts from selected clones were labeled with $^{32}$P[a-dATP] by Klenow fragment of *E. coli* DNA polymerase I (Feinberg (1983), which is hereby incorporated by reference) and used as probes to test their specific reactions to dsRNAs isolated from leafroll infected tissues. Double-stranded RNA isolated from GLRaV-3 infected vines was separated by electrophoresis on a 1% agarose gel (nondenatured condition), denatured with 50 mM NaOH, 0.6 M NaCl for 30 min at room temperature, and neutralized with 1.5 M NaCl, 0.5 M Tris-HCl, pH 7.5 for another 30 min. Denatured dsRNA was sandwich-blotted onto a GENESCREEN PLUS™ membrane. Prehybridization and hybridization were carried out in a manner similar to that described above. The membrane was washed and exposed to Kodak X-OMAT film, and an autoradiograph was developed.

Identification of immunopositive clones. For immunoscreening, plates with plaques appearing after 8–12 h incubation at 37° C. were overlaid with a 10 mM isopropyl-β-D-thio-galactopyranoside ("IPTG") impregnated Nylon filters (GENESCREEN PLUS™) and incubated for an additional 3–4 h. After blocking with 3% bovine serum albumin ("BSA"), the blotted filter was incubated in a 1:1000 dilution of alkaline phosphatase-conjugated GLRaV-3 polyclonal antibody for 3 h at 37° C. Positive signals (purple dots) were developed by incubation of washed filters in a freshly prepared nitroblue tetrazolium ("NBT") and 5-bromo-4-chloro-3-indolyl phosphate ("BCIP") solution. To further confirm whether or not a true GLRaV-3 coat protein expression plaque was selected, a secondary immunoscreening was carried out by reinfection of bacterial XL1 Blue cells with an earlier selected plaque.

Western blot analysis. After secondary immunoscreening, GLRaV-3 antibody positive plaques were converted into plasmid, the pBluescript, by in vivo excision. Single colonies were picked up and cultured in LB medium with 100 μg/ml of ampicillin until mid-log growth. Fusion protein expression was induced by addition of 10 mM IPTG with an additional 3 h of incubation at 37° C. Bacteria was pelleted and denatured by boiling in protein denaturation buffer (Sambrook (1989), which is hereby incorporated by reference). An aliquot of 5 μl denatured sample was loaded and separated by electrophoresis on a 12% SDS-polyacrylamide gel along with a prestained protein molecular weight marker (Bio-Rad, Hercules, Calif.). The separated proteins were transferred onto an Immobulon membrane (Millipore) with an electroblotting apparatus (Bio-Rad). After blocking with 3% BSA, the transferred membrane was incubated with 1:1,000 dilution of either GLRaV-3 polyclonal or monoclonal antibody alkaline phosphatase conjugate. A positive signal was developed after incubation of the washed membrane in NBT and BCIP.

PCR analysis. To analyze a cloned insert, an aliquot of a bacterial culture was used directly in PCR amplification with common vector primers (SK and KS). PCR-amplified product was analyzed by electrophoresis on an agarose gel.

Nucleotide sequencing and computer sequence analysis. Plasmid DNA, purified by either a CsCl method (Sambrook (1989), which is hereby incorporated by reference) or a modified mini alkaline-lysis/PEG precipitation procedure (Applied Biosystems' Instruction), was sequenced either with Sequenase version 2 kit following the manufacturer's instruction (US Biochemical, Cleveland, Ohio) or with Taq DYEDEOXY™ terminator cycle sequencing kit (Applied Biosystems, Inc.). Automated sequencing was conducted on an ABI373 automated sequencer at the New York State Agricultural Experiment Station in Geneva, N.Y.

Nucleotide sequences were analyzed using a Genetics Computer Group (GCG) sequence analysis software package (Madison, Wis.). Sequence fragments were assembled using Newgelstart to initiate the GCG fragment assembly system and to support automated fragment assembly in GCG Version 7.2.

Computer-assisted analysis of phylogenetic relationship. Amino acid sequences were either obtained from database Swiss-Prot or translated from nucleotide sequences obtained from GenBank. A phylogenetic tree depicting a relationship in the evolution of the GLRaV-3 coat protein sequence with respect to those of other filamentous plant viruses was generated using the Clustal Method of the DNASTAR's MegAlign program (Madison, Wis.). With the Clustal method, a preliminary phylogeny is derived from the distances between pairs of input sequences and the application of the UPGMA algorithm (Sneath et al., *Numerical Taxonomy—The Principles and Practice of Numerical Taxonomy,* Freeman Press (1973), which is hereby incorporated by reference) which guides the alignment of ancestral sequences. The final phylogeny is produced by applying the neighborhood joining method of Saitou et al., "The Neighbor Joining Method: A New Method for Reconstructing Phylogenetic Trees," *Mol. Biol. Evol.,* 4:406–425 (1987), which is hereby incorporated by reference, to the distance and alignment data.

Figure 2:

Nucleotide sequence and primer selection. The sequence fragment (FIG. 2) selected for PCR has now been identified to be from nucleotides 9,364 to 10,011 of the incomplete GLRaV-3 genome (FIG. 18). This sequence region encodes a short peptide which shares sequence similarity to HSP90 homologues of other closteroviruses (FIG. 3). Selected primers and their designations are shown in FIG. 2.

Sample preparation. These include 1) dsRNA, 2) purified virus, 3) partially purified virus, 4) proteinase K treated crude extract, and 5) immuno-capture preparation.

Isolation of dsRNA from leafroll infected grapevine tissues followed the procedure developed by Hu (1990), which is hereby incorporated by reference.

Virus purification was effected by the following procedure. An aliquot of 500 $\mu$l GLRaV-3-enriched fractions after two cycles of $Cs_2SO_4$ gradient was diluted with two volumes of TE buffer (10 mM Tris, 1 mM EDTA, pH 8.0) and incubated on ice for 5 min. The reaction was then adjusted to a final concentration of 200 mM NaAc, pH 5.0, 0.5% SDS, and 200 $\mu$g/ml proteinase K and incubated at 37° C. for 3 h. Viral RNA was extracted with phenol and chloroform, ethanol-precipitated, and resuspended in 50 $\mu$l of diethyl pyrocarbonate ("DEPC")-treated $H_2O$. For each 100 $\mu$l PCR reaction mixture, 1 $\mu$l of purified viral RNA was used as template.

Partially purified virus was prepared according to the virus purification procedure described in Hu (1990), which is hereby incorporated by reference, but only to the high speed centrifugation (27,000 rpm, 2 h) step without further $Cs_2SO_4$ gradient centrifugation. The pellet was resuspended in TE buffer and subjected to proteinase K treatment as described above. Viral RNA was extracted with phenol/chloroform and precipitated by ethanol. From 10 g of starting material, the pellet was resuspended in 200 $\mu$l of DEPC treated $H_2O$. A 1 $\mu$l aliquot of extracted RNA or its 10-fold dilution series (up to $10^{-5}$) was used for reverse transcription-PCR ("RT-PCR").

Crude extract was treated with Proteinase K using the following procedure. Liquid nitrogen powdered grapevine bark/phloem tissue (100 mg) was macerated in 1 ml of virus extraction buffer (0.5 M Tris-HCl, pH 9.0, 0.01 M $MgSO_4$, 4% water insoluble polyvinyl pyrrolidone ("PVP40"), 0.5% bentonite, 0.2% 2-mercaptoethanol, and 5% Triton X-100) (Zee (1987), which is hereby incorporated by reference). After a brief centrifugation (5,000 rpm, 2 min), 500 $\mu$l of supernatant was transferred into a new tube, adjusted to 100 $\mu$g/ml proteinase K, and incubated for 1 h at 55° C. (Kawasaki, "Sample Preparation from Blood, Cells, and Other Fluids," in Innis et al., eds, *PCR Protocols: A Guide to Methods and Applications,* Academic Press, Inc. (1990), which is hereby incorporated by reference). Following incubation, the preparation was boiled for 10 min to inactivate proteinase K and to denature the viral RNA. The upper clear phase was transferred into a new tube after a brief centrifugation. The viral RNA was precipitated with ethanol and resuspended in 100 $\mu$l of DEPC-treated $H_2O$. An aliquot of 1 $\mu$l proteinase K-treated crude extract or its 10-fold dilution series (up to $10^{-6}$) was used.

The immuno-capture procedure was adapted from the method described by Wetzel et al., "A Highly Sensitive Immunocapture Polymerase Chain Reaction Method for Plum Pox Potyvirus Detection," *J. Virol. Meth.* 39:27–37 (1992) ("Wetzel (1992)"), which is hereby incorporated by reference. A 0.5 ml thin wall PCR tube was coated directly with 100 $\mu$l of 10 $\mu$g/ml purified gamma-globulin from GLRaV-3 antiserum (Zee (1987), which is hereby incorporated by reference) in ELISA coating buffer (15 mM $Na_2CO_3$, 35 mM $NaHCO_3$, pH 9.6, and 0.02% $NaN_3$) and incubated for 4 h at 30° C. After washing 3 times with PBS-Tween-20, the antibody coated tube was loaded with 100 $\mu$l of crude extract (1:10 or its 10-fold dilution series, up to $10^{-8}$) prepared in ELISA extraction buffer (50 mM sodium citrate, pH 8.3, 20 mM sodium diethyldithiocarbonate ("DIECA"), 2% PVP 40K) and incubated at 30° C. for 4 h. After washing, a 25 $\mu$l aliquot of transfer buffer (10 mM Tris, pH 8.0, 1% Triton X-100) was added to the tube and vortexed thoroughly to release viral RNA.

RT-PCR. Initially, reverse transcription ("RT") and polymerase chain reaction ("PCR") were performed in two separate reactions. An aliquot of 20 $\mu$l of reverse transcription reaction mixture was prepared to contain 2 $\mu$l of 10× PCR buffer (Promega) (10 mM Tris-HCl, pH 8.3, 500 mM KCl, and 0.01% gelatin), 50 mM $MgCl_2$, 2 $\mu$l of 10 mM dNTP, 150 ng of 5' and 3' primers, 16 units of RNasin, 25 units of avian myeloblastosis virus ("AMV") reverse transcriptase, and 1 $\mu$l of a denatured sample preparation. The reverse transcription reaction was carried out at 37° C. for 30 min. After denaturation by heating at 95° C. for 5 min, an aliquot of PCR reaction mixture was added. This PCR reaction mixture (80 $\mu$l) contained 8 $\mu$l of 10× PCR buffer (Promega), 150 mM $MgCl_2$, 250 ng of each 5' and 3' primer, 1 $\mu$l of 10 mM dNTP, and 2.5 units of Taq DNA polymerase. The thermal cycling program was set as follows: a precycle at 92° C. for 3 min; followed by 35 cycles of denaturation at 92° C., 1 min; annealing at 50° C., 1 min; and extension at 72° C., 2.5 min. The final extension cycle was set at 72° C. for 5 min.

Because reverse transcriptase can work under the PCR buffer system, combination of RT and PCR would make RT-PCR in a single reaction (Ali et al., "Direct Detection of Hepatitis C Virus RNA in Serum by Reverse Transcription PCR," *Biotechniques,* 15:40–42 (1993) and Goblet et al., "One-Step Amplification of Transcripts in Total RNA Using the Polymerase Chain Reaction," *Nucleic Acids Research,* 17:2144 (1989), which are hereby incorporated by reference). The RT-PCR reaction mixture of 100 $\mu$l contains 10 $\mu$l of 10× PCR amplification buffer (Promega), 200 mM MgCl$_2$, 250 ng each of primers, 3 µl of 10 mM dNTPs, 40 units of RNasin, 25 units of AMV or moloney-murine leukemia virus ("M-MLV") reverse transcriptase, 2.5 units of Taq DNA polymerase, and 1 µl of denatured sample preparation. The thermal cycling program was set as follows: one cycle of cDNA synthesis step at 37° C. for 30 min, immediately followed by the PCR cycling parameters described above.

Nested PCR. Inconsistent results obtained from a single round of PCR amplification prompted an investigation into the feasibility of Nested PCR. Initial PCR amplification was performed with an external primer set (93-110 & 92-98) (FIG. 2). A PCR product of 648 bp was consistently observed from dsRNA as template, but the expected PCR product was not consistently observed in samples prepared from proteinase K-treated crude extract or immuno-capture sample preparation. Consequently, additional PCR amplification with an internal primer set (93-25 & 93-40) was carried out by adding 5 µl of the first external primer-amplified PCR product into a freshly prepared 100 µl PCR reaction mixture. The PCR cycling parameters were the same as described above.

Example 2

Virus Purification and dsRNA Isolation

Figure 5:
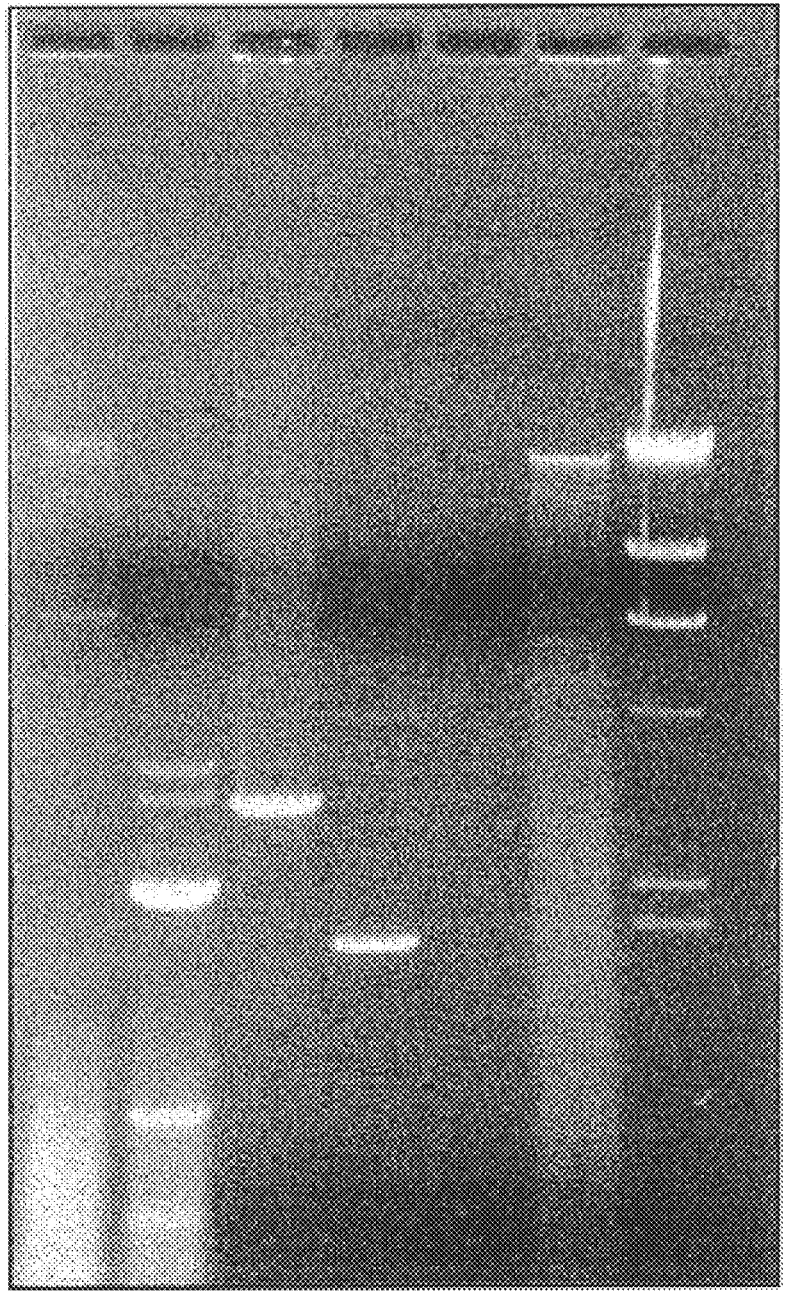

GLRaV-3 virus particles were purified directly from field collected samples of infected grapevines. Attempts to use genomic RNA for cDNA cloning failed due to low yield of virus particles with only partial purity (FIG. 1). However, under an electron microscope, virus particles were shown to be decorated by GLRaV-3 antibody. The estimated coat protein molecular weight of 41K agreed with an earlier study (Hu (1990), which is hereby incorporated by reference). Because of low yield in virus purification, dsRNA isolation was further pursued. Based on the assumption that high Mr dsRNA (16 kb) is the replicative form of the GLRaV-3 genomic RNA, this high Mr dsRNA was separated from other smaller ones by electrophoresis (FIG. 5), purified from a low melting temperature agarose gel, and used for cDNA synthesis.

Example 3 cDNA Synthesis, Molecular Cloning, and Analysis of cDNA Clones

First-strand cDNA was synthesized with AMV reverse transcriptase from purified 16 kb dsRNA which had been denatured with 10 mM MeHg. Only random primers were used to prime the denatured dsRNA because several other closteroviruses (BYV, CTV, and LIYV) have been shown to have no polyadenylated tail on the 3' end (Agranovsky et al., "Nucleotide Sequence of the 3'-Terminal Half of Beet Yellows Closterovirus RNA Genome Unique Arrangement of Eight Virus Genes," *Journal of General Virology*, 72:15–24 (1991) ("Agranovsky (1991)"), Agranovsky et al., "Beet Yellows Closterovirus: Complete Genome Structure and Identification of a Papain-like Thiol Protease," *Virology*, 198:311–324 (1994) ("Agranovsky (1994)"), Karasev et al., "Complete Sequence of the Citrus Tristeza Virus RNA Genome," *Virology*, 208:511–520 (1995) ("Karasev (1995)"), Klaassen et al., "Genome Structure and Phylogenetic Analysis of Lettuce Infectious Yellows Virus, A Whitefly-Transmitted, Bipartite Closterovirus," *Virology*, 208:99–110 (1995) ("Klaassen (1995)"), and Pappu et al., "Nucleotide Sequence and Organization of Eight 3' Open Reading Frames of the Citrus Tristeza Closterovirus Genome," *Virology*, 199:35–46 (1994) ("Pappu (1994)"), which are hereby incorporated by reference). After second-strand cDNA synthesis, the cDNA was size-fractionated on a CL-4B Sepharose column and peak fractions which contained larger molecular weight cDNA were pooled and used for cloning. An autoradiograph of this pooled cDNA revealed cDNA of up to 4 kb in size. A bacteriophage cDNA library was prepared after cloning of the synthesized cDNA into the cloning vector, lambda ZAPII.

A lambda ZAPII library was prepared from cDNA that was synthesized with random primed, reverse transcription of GLRaV-3 specific dsRNA. Initially, white/blue color selection in IPTG/X-gal containing plates was used to estimate the ratio of recombination. There were 15.7% white plaques or an estimate of 7×10$^4$ GLRaV-3 specific recombinants in this cDNA library. The library was screened with probes prepared from UNI-AMP™ PCR-amplified GLRaV-3 cDNA. More than 300 clones with inserts of up to 3 kb were selected after screening the cDNA library with probe prepared from UNI-AMP™ PCR-amplified GLRaV-3 cDNA. In Northern blot hybridization, a probe prepared from a clone insert, pC4, reacted strongly to the 16 kb dsRNA as well as to several other smaller Mr dsRNAs. Such a reaction was not observed with nucleic acids from healthy grape nor to dsRNA of CTV (FIG. 4).

Example 4

Selection and Characterization of Immunopositive Clones

Figure 6:
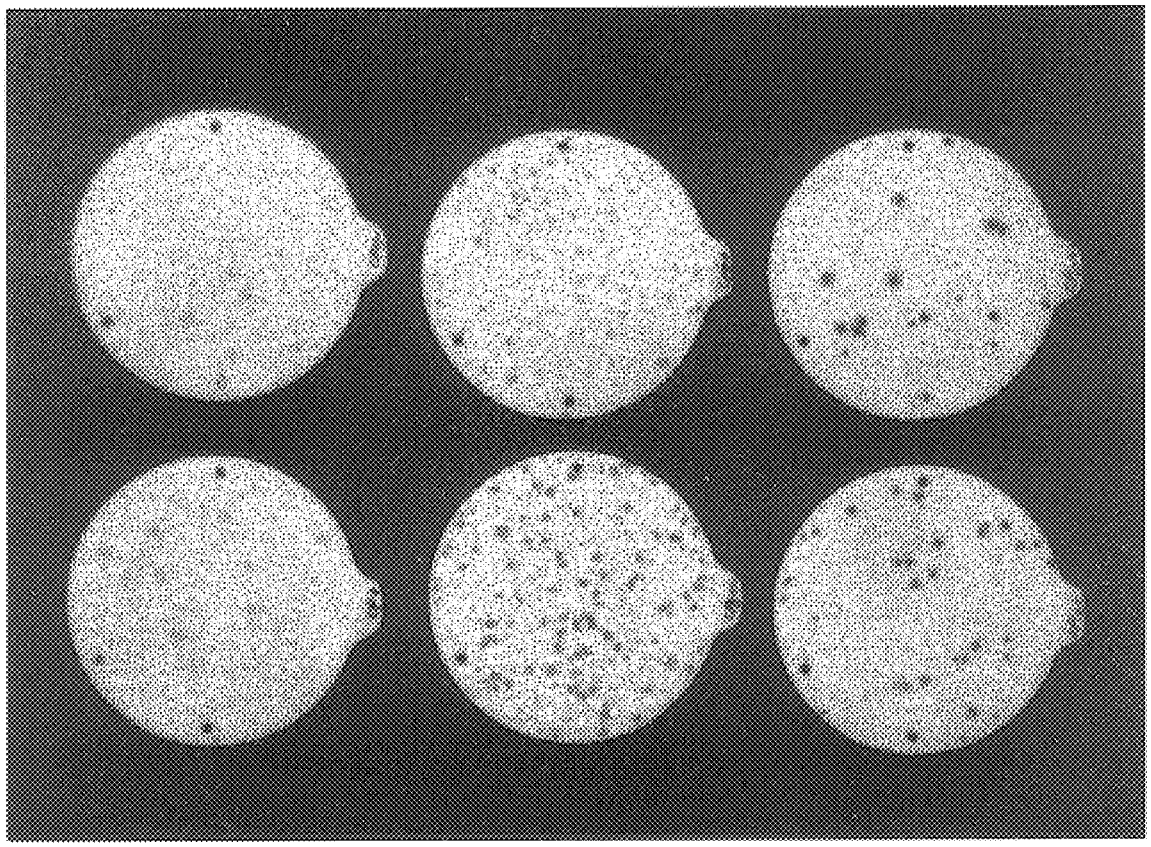
Figure 7:
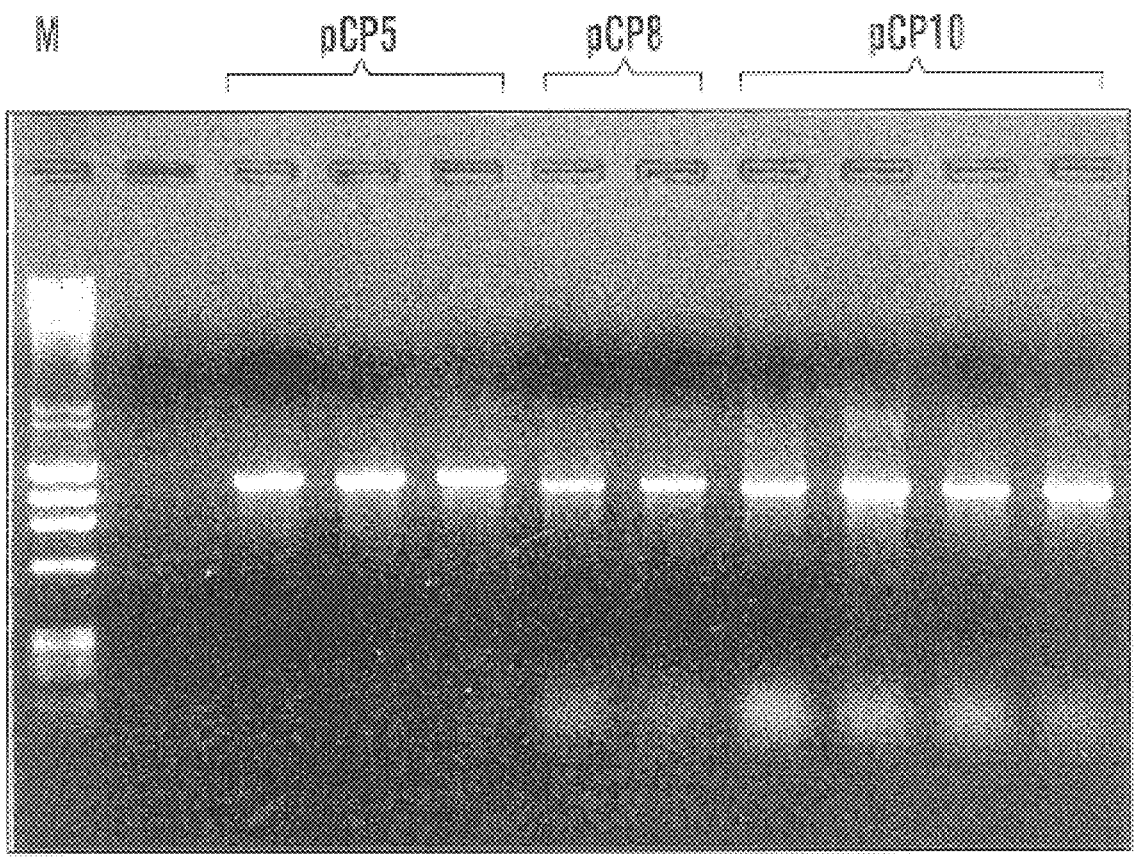

A total of 6×10$^4$ plaques were immunoscreened with GLRaV-3 specific polyclonal antibody. Three cDNA clones, designated pCP5, pCP8-4, and pCP10-1, produced proteins that reacted to the polyclonal antibody to GLRaV-3 (FIG. 6). GLRaV-3 antibody specificity of the clones was further confirmed by their reaction to GLRaV-3 monoclonal antibody. PCR analysis of cloned inserts showed that a similar size of PCR product (1.0–1.1 kb) was cloned in each immunopositive clone (FIG. 7). However, various sizes of antibody-reacting protein were produced from each clone, which suggested that individual clones were independent and contained different segments of the coat protein gene (FIG. 8). The Mr of immunopositive fusion protein from clone pCP10-1 was estimated to be 50K in SDS-PAGE, which was greater than the native coat protein of 41K (compare lanes 1 to 4 in FIG. 8). Immunopositive proteins produced in clone pCP5 (FIG. 8, lane 2) and pCP8 (FIG. 8, lane 3) were different in size and smaller than the native coat protein. Clone pCP5 produced a GLRaV-3 antibody-reacting protein of 29K. Clone pCP8-4, however, produced an antibody-reacted protein of 27K. Similar banding patterns were observed when either polyclonal (FIG. 8 A) or monoclonal (FIG. 8 B) antibodies were used in Western blots. These results further substantiated the proposition that these cDNA clones contained coding sequences of the GLRaV-3 coat protein gene.

Example 5

Nucleotide Sequencing and Identification of the Coat Protein Gene

Figure 9:
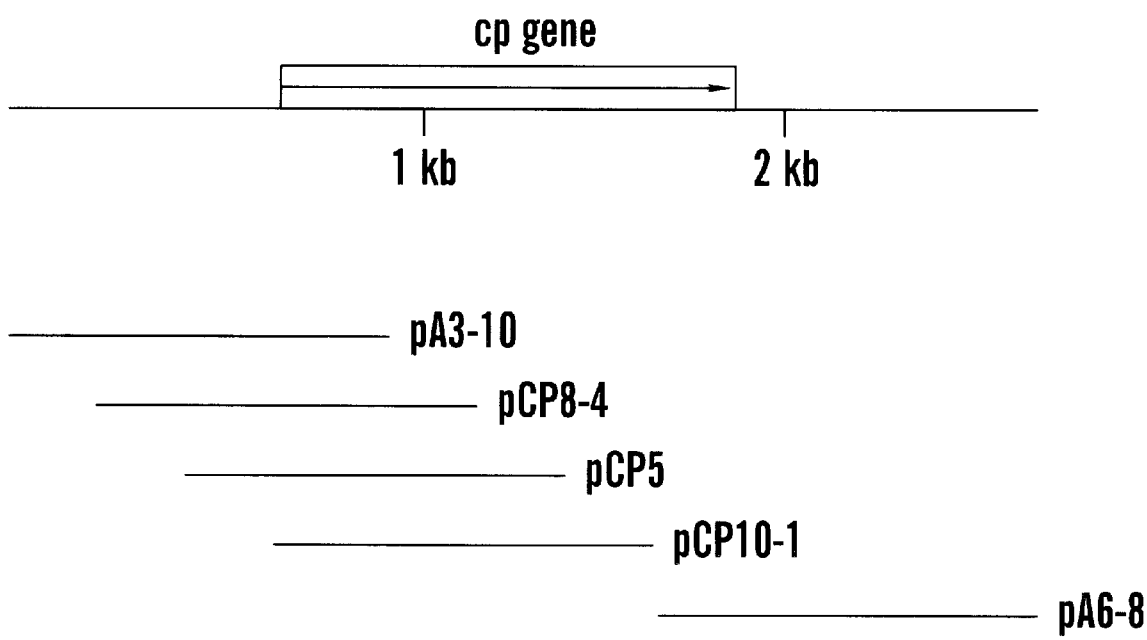
Figure 12:
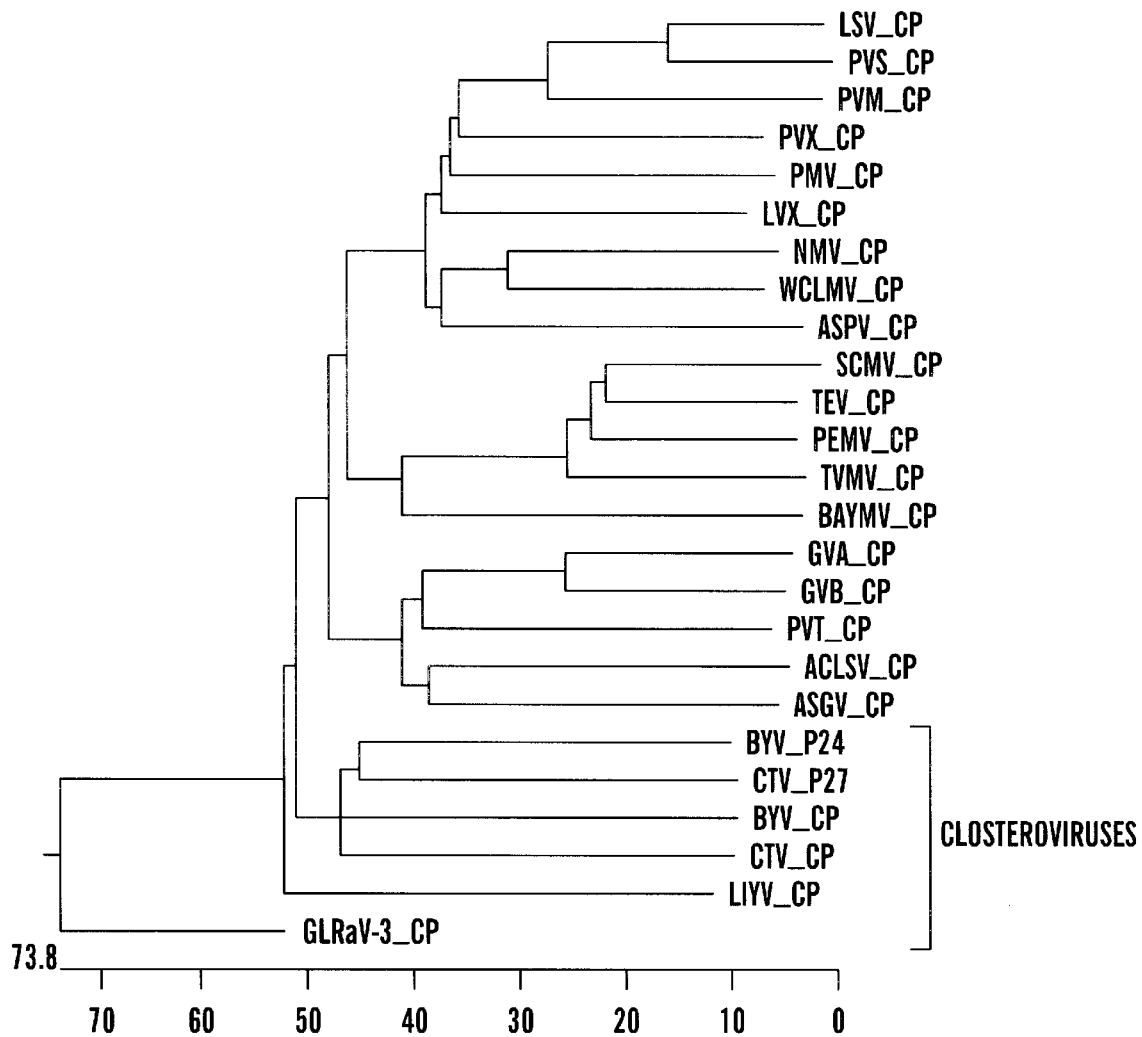

Both strands of the three immunopositive clones were sequenced at least twice. A multiple sequence alignment of these three clones overlapped and contained an incomplete ORF lacking the 3' terminal sequence region. The complete sequence of this ORF was obtained by sequencing an additional clone, pA6-8, which was selected by using the clone walking strategy. The complete ORF potentially encoded a protein of 313 amino acids with a calculated Mr of 34,866 (p35) (FIGS. 9 and 10). Because this ORF was derived from three independent clones after screening with GLRaV-3 coat protein specific antibody, it was identified as the coat protein gene of GLRaV-3. A multiple amino acid sequence alignment of p35 with the coat proteins of other closteroviruses, including BYV, CTV, and LIYV, is presented in FIG. 11. The typical consensus amino acid residues (S, R, and D) of the coat proteins of the filamentous plant viruses (Dolja et al., "Phylogeny of Capsid Proteins of Rod-Shaped and Filamentous RNA Plant Viruses Two Families with Distinct Patterns of Sequence and Probably Structure Conservation," *Virology*, 184:79–86 (1991) ("Dolja (1991)"), which is hereby incorporated by reference), which may be involved in salt bridge formation and the proper folding of the most conserved core region (Boyko et al., "Coat Protein Gene Duplication in a Filamentous RNA Virus of Plants," *Proc. Natl. Acad. Sci. U.S.A.*, 89:9156–9160 (1992) ("Boyko (1992)"), which is hereby incorporated by reference), were also preserved in the p35. Phylogenetic analysis of the GLRaV-3 coat protein amino acid sequence with respect to the other filamentous plant viruses placed GLRaV-3 into a separate but closely related branch of the closterovirus (FIG. 12). Direct sequence comparison of GLRaV-3 coat protein with respect to other closterovirus coat proteins or their diverged copies by the GCG Pileup program demonstrated that at the nucleotide level, GLRaV-3 had its highest homology to BYV (41.5%) and CTV (40.3%). At the amino acid level, however, the highest percentage similarity were to the diverged copies of coat protein, with 23.5% identity (46.5% similarity) to CTV p26 and 22.6% (44.3% similarity) to BYV p24.

Example 6

Identification of a Possible Coat Protein Translation Initiation Site

Various sizes of GLRaV-3 specific antibody-reacted proteins were produced by three immunopositive clones in *E. coli* (FIG. 8). Sequences of these clones overlapped and encoded a common ORF that was identified as the coat protein gene (FIG. 9). In searching for possible translation regulatory elements, sequence analysis beyond the coat protein coding region revealed a purine rich sequence, -uGAGuGAAcgcgAUG-(SEQ. ID. No. 26), which was similar to the Shine-Dalgarno sequence (uppercase letters) (Shine et al., "The 3'-Terminal Sequence of *Escherichia Coli* 16S Ribosomal RNA: Complementarity to Nonsense Triplets and Ribosome Binding Sites," *Proc. Nat. Acad. Sci. U.S.A.*, 71:1342–1346 (1974), which is hereby incorporated by reference), upstream from the coat protein initiation site (AUG). This purine rich sequence may serve as an alternative ribosome entry site for the translation of the GLRaV-3 coat protein gene in *E. coli*. If this first AUG in the ORF was to serve for the actual coat protein translation, the ribosomal entry site must be located in this purine rich region because an in-frame translation stop codon (UGA) was only nine nucleotides upstream from the coat protein gene translation initiation site (AUG). Analysis of nucleotide sequence beyond the cloned insert into the vector sequence of clone pCP8-4 and pCP10-1 provided direct evidence that the fusion protein was made from the N-terminal portion of coat protein and C-terminal portion of β-galactosidase (16.5K). Further analysis of sequence around the selected AUG initiation codon of the coat protein gene revealed a consensus sequence (-GnnAUGG-) that favored the expression of eucaryotic mRNAs (Kozak, "Comparison of Initiation of Protein Synthesis in Procaryotes, Eucaryotes, and Organelles," *Microbiological Reviews*, 47:1–45 (1983) and Kozak, "Point Mutations Define a Sequence Flanking the AUG Initiator Codon that Modulates Translation by Eukaryotic Ribosomes," *Cell*, 44:283–292 (1986), which are hereby incorporated by reference).

Nucleotide sequence analysis of three immunopositive clones revealed overlapping sequences and an ORF that covers about 96% of the estimated coat protein gene (FIG. 9). The complete ORF was obtained after sequencing of an additional clone (pA6-8) that was selected by the clone walking strategy. Identification of this ORF as the coat protein gene was based upon its immunoreactivity to GLRaV-3 polyclonal and monoclonal antibodies, the presence of filamentous virus coat protein consensus amino acid residues (S, R, and D), and the identification of a potential translation initiation site. The calculated coat protein molecular weight (35K) is smaller than what was estimated on SDS-PAGE (41K). This discrepancy in molecular weight between computer-calculated and SDS-PAGE estimated falls in the expected range. However, direct evidence by micro-sequencing of the N-terminal coat protein sequence was not possible due to the difficulties in obtaining sufficient amounts of purified virus.

The estimated coat protein Mr of GLRaV-3 and another grape closterovirus-like designated GLRaV-1 are larger than the 22–28K coat protein range reported for other well characterized closteroviruses, such as BYV, CTV, and LIYV (Agranovsky (1991); Bar-Joseph et al., "Closteroviruses," *CMI/AAB*, No. 260 (1982), Klaassen et al., "Partial Characterization of the Lettuce Infectious Yellows Virus Genomic RNAs, Identification of the Coat Protein Gene and Comparison of its Amino Acid Sequence with Those of Other Filamentous RNA Plant Viruses," *Journal of General Virology*, 75:1525–1533 (1994); (Martelli et al., "Closterovirus, Classification and Nomenclature of Viruses, Fifth Report of the International Committee on Taxonomy of Viruses," in *Archieves of Virology Supplementum* 2, Martelli et al., eds., New York: Springer-Verlag Wein, pp. 345–347 (1991) ("Martelli (1991)"); and Sekiya et al., "Molecular Cloning and Nucleotide Sequencing of the Coat Protein Gene of Citrus Tristeza Virus," *Journal of General Virology*, 72:1013–1020 (1991), which are hereby incorporated by reference). Hu (1990), which is hereby incorporated by reference, suggested a possible coat protein dimer. Our sequence data, however, do not support this suggestion. First, the size of the coat protein is only 35K, which is smaller than what would be expected as a coat protein dimer. Second, a multiple sequence alignment of N-terminal half and C-terminal half of GLRaV-3 coat protein with the coat proteins of other closteroviruses showed that the filamentous virus coat protein consensus amino acid residues (S, R, and D) are only present in the C-terminal portion, but not in the N-terminal portion of the coat protein.

Example 7

Primer Selection

Figure 13:
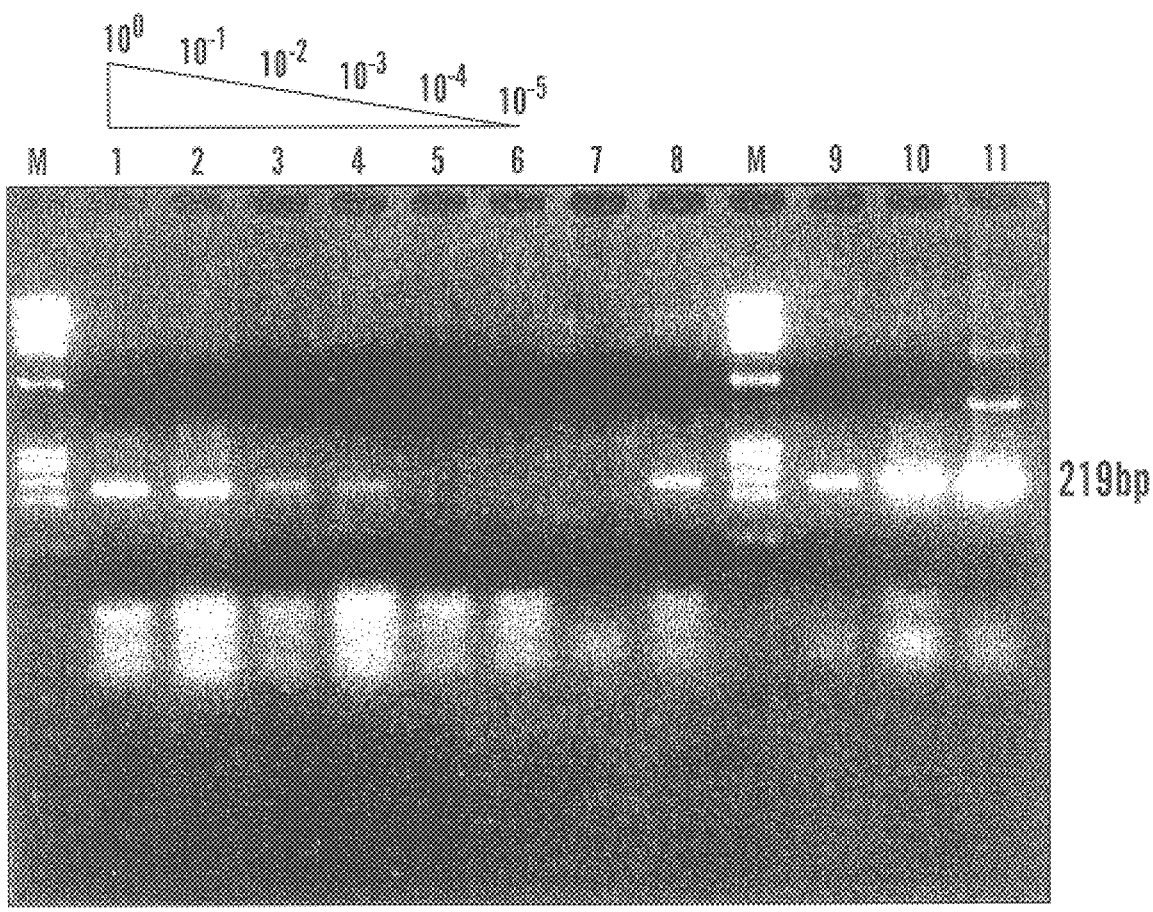

Primers were selected based on the nucleotide sequence of clone pC4 that had been shown to hybridize to GLRaV-3 dsRNAs on a Northern hybridization (FIG. 4). The 648 bp sequence amplified by PCR was identified as nucleotides 9,364 to 10,011 of the incomplete GLRaV-3 genome (FIG. 18). This sequence fragment encodes a short peptide which shows some degree of amino acid sequence similarity to heat shock protein 90 (HSP90) homologues of other closteroviruses, BYV, CTV, and LIYV (FIG. 3). Two sets of primer sequences and their designations (external, 93-110 & 92-98, and internal, 93-25 & 93-40) are shown in FIG. 2. Effectiveness of synthesized primers to amplify the expected PCR product was first evaluated on its respective cDNA clone, pC4 (FIG. 13, lane 11).

Example 8

Development of a Simple and Effective PCR Sample Preparation

Initially, purified dsRNA was used in a RT-PCR reaction. Expected size of PCR product of 219 bp was consistently observed with the internal set of primers (FIG. 13, lane 10). To test whether or not these primers derived from GLRaV-3 specific dsRNA sequence is in fact the GLRaV-3 genome sequence, RNA extracted from a highly purified virus preparation was included in an assay. As expected, PCR products with similar size (219 bp) were observed in cloned plasmid DNA (pC4) (FIG. 13, lane 11), dsRNA (FIG. 13, lane 10) as well as purified viral RNA (FIG. 13, lane 9). This PCR result was encouraging as it was the first evidence to suggest that dsRNA isolated from leafroll-infected tissue may actually be derived from the GLRaV-3 genome. However, PCR sample preparations from the purified virus procedure are too complicated to be used for leafroll diagnosis. Further simplification of sample preparations was made possible by using viral RNA extracted from a partially purified virus preparation. This partially purified virus preparation was again shown to be effective in RT-PCR (FIG. 13). Sensitivity of RT-PCR was further evaluated with 10-fold serial dilution (up to $10^{-5}$) of a sample. The expected PCR product of 219 bp in a partially purified virus preparation was observable up to the $10^{-3}$ dilution (FIG. 13, lane 4). Although RT-PCR was shown again to work with partially purified virus preparations, this method of sample preparation was still too complicated to be used in a routine disease diagnosis. However, over 10 attempts to directly use crude extract for RT-PCR were unsuccessful. Proteinase K-treated crude extract was by far the most simple and still effective for RT-PCR. Therefore, the proteinase K-treated crude extract was used to evaluate RT-PCR for its ability to detect GLRaV-3.

Example 9

RT-PCR

With proteinase K-treated crude extract prepared from scraped phloem tissue collected from a typical leafroll infected vine (Doolittle's vineyard, New York), a PCR product of 219 bp was readily observable. However, application of this sample preparation method to test other field collected samples (USDA, PGRU, Geneva, N.Y.) was disappointing. With different batches of sample preparations, a range of 3 to 10 out of 12 ELISA positive samples were shown to have the expected PCR products. To determine whether or not these inconsistent results were due to some kinds of enzyme (reverse transcriptase or Taq DNA polymerase) inhibition presented in the proteinase K-treated crude extract, increasing amounts of a sample were added into an aliquot of 100 μl PCR reaction mixture. FIG. 14 shows that PCR products of 219 bp were readily observed from samples of 0.1 μl (lane 1) and 1 μl (lane 2) but not from 10 μl (lane 3). Presumably, sufficient amount of enzyme inhibitors was present in the 10 μl of this sample.

Example 10

Immuno-capture RT-PCR

Figure 15:
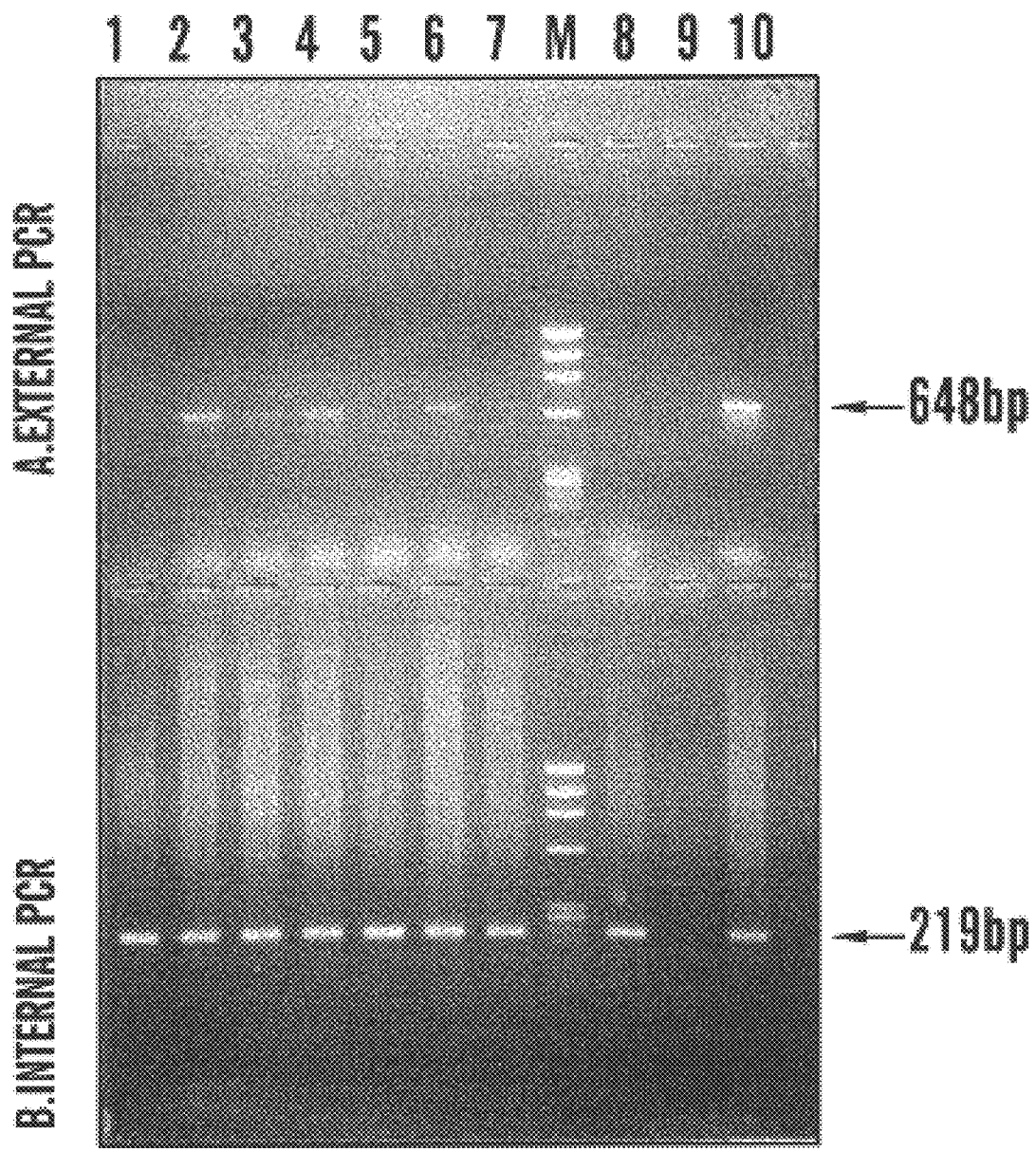

The immuno-capture method further simplified sample preparation by directly using crude extracts that were prepared in the standard ELISA extraction buffer. Immuno-capture RT-PCR ("IC RT-PCR") tests were initially performed with the internal primer set, and the expected PCR product of 219 bp was observable from a typical leafroll infected sample. However, using this PCR method to test a range of field collected ELISA positive samples, inconsistent results were again experienced. In a PCR test performed with the external primer set, only five out of seven field collected ELISA positive samples were shown to amplify the expected PCR product (648 bp) (FIG. 15 A). Meanwhile, the expected PCR product was consistently observed in dsRNA (FIG. 15 A, lane 10), but such product was never observed in the healthy control (FIG. 15 A, lane 9). In this case, however, the expected PCR product was not observable in a sample prepared by proteinase K-treated crude extract (FIG. 15 A, lane 8).

Example 11

Nested PCR

As described above, inconsistency of RT-PCR was experienced with samples prepared either by the proteinase K-treated or by the immuno-capture methods. If this PCR technique is to be used in the practical disease diagnosis, a consistent and repetitive result is desirable. Thus, the Nested PCR method was introduced. Although an expected PCR product of 648 bp from the first PCR amplification with the external primer set was not always observable (FIG. 15 A), in a Nested PCR amplification with the internal primer set, the expected 219 bp PCR product was consistently observed from all seven ELISA positive samples (FIG. 15 B). These similar products were also observed either in dsRNA (FIG. 15 B, lane 10) or in the proteinase K-treated crude extract (FIG. 15 B, lane 8) but, again, not in a healthy control (FIG. 15 B, lane 9). To determine the sensitivity of Nested PCR with samples prepared either by proteinase K-treated or by immuno-capture methods, Nested PCR and ELISA were performed simultaneously with samples prepared from a 10-fold dilution series. The sensitivity of Nested PCR was shown to be $10^{-5}$ in proteinase K-treated crude extract (FIG. 16 A), and was more than $10^{-8}$ (the highest dilution point in this test) in an immuno-capture preparation (FIG. 16 B). With similar sample preparations, sensitivity for ELISA was only $10^{-2}$.

Example 12

Validation of PCR with ELISA and Indexing

To determine whether or not the PCR-based GLRaV-3 detection method described in this study has a potential practical implication for grapevine leafroll disease diagnosis, a validation experiment with plants characterized thoroughly by ELISA and indexing is necessary. Several grapevines collected at USDA-PGRU at Geneva, N.Y. that have been well characterized by 3-year biological indexing and by ELISA were selected for validation tests. A perfect correlation was observed between ELISA positive and PCR positive samples, although there was some discrepancy over indexing which suggested that other types of closteroviruses may also be involved in the grapevine leafroll disease (Table 2).

TABLE 2

| Sample # | Accession # | ELISA * | RT-PCR | Indexing |
|---|---|---|---|---|
| 1 | 476.01 | 1.424 (+) | + | + |
| 2 | 447.01 | 0.970 (+) | + | + |
| 3 | 123.01 | 1.101 (+) | + | + |
| 4 | 387.01 | >1.965 (+) | + | + |
| 5 | 80.01 | >2.020 (+) | + | + |
| 6 | 244.01 | >2.000 (+) | + | + |
| 7 | 441.01 | >2.000 (+) | + | + |
| 8 | 510.01 | 0.857 (+) | + | + |
| 9 | 536.01 | 0.561 (+) | + | + |
| 10 | 572.01 | >2.000 (+) | + | + |
| 11 | 468.01 | >2.000 (+) | + | + |
| 12 | 382.01 | >2.000 (+) | + | + |
| 13 | NY1 | 0.656 (+) | + | + |
| 14 | Healthy | 0.002 (−) | − | − |

Plus (+) and Minus (−) represent positive and negative reactions, respectively. For ELISA an $OD_{405nm}$ that was at least twice higher than a healthy control, and more than 0.100 was regarded as positive.

PCR technology has been applied to detect viruses, viroids and phytoplasmas in the field of plant pathology (Levy et al., "Simple and Rapid Preparation of Infected Plant Tissue Extracts for PCR Amplification of Virus, Viroid and MLO Nucleic Acids," *Journal of Virological Methods*, 49:295–304 (1994), which is hereby incorporated by reference). However because of the presence of enzyme inhibitors (reverse transcriptase and/or Taq DNA polymerase) in many plant tissues, a lengthy and complicated procedure is usually required to prepare a sample for PCR. In studies of PCR detection of grapevine fanleaf virus, Rowhani et al., "Development of a Polymerase Chain Reaction Technique for the Detection of Grapevine Fanleaf Virus in Grapevine Tissue," *Phytopathology*, 83:749–753 (1993), which is hereby incorporated by reference, have already observed an enzyme inhibitory phenomenon. Substances such as phenolic compounds and polysaccharides in grapevine tissues were suggested to be involved in enzyme inhibition. Present work further confirmed this observation. One of the objectives in the present study was to develop a sound practical procedure of sample preparation to eliminate this inhibitory problem for PCR detection of GLRaV-3 in grapevine tissues. Although the expected PCR product was consistently observed from samples of dsRNA, purified virus and partial purified virus, proteinase K-treated crude extract and immuno-capture methods were the simplest and were still effective. Samples prepared with proteinase K-treated crude extract have an advantage over others in that hazardous organic solvents, such as phenol and chloroform, are avoided. However, care must be taken in the sample concentration because the reaction can be inhibited by adding too much grapevine tissue (see lane 3 in FIG. 14). Minafra et al., "Sensitive Detection of Grapevine Virus A, B, or Leafroll-Associated III from Viruliferous Mealybugs and Infected Tissue by cDNA Amplification," *Journal of Virological Methods*, 47:175–188 (1994) ("Minafra (1994)"), which is hereby incorporated by reference, reported the successful PCR detection of grapevine virus A, grapevine virus B, and GLRaV-3 with crude saps prepared from infected grapevine tissues; this method of sample preparation was, however, not effective in the present study. The similar primers used by Minafra (1994), which is hereby incorporated by reference, were, however, able to amplify the expected size of PCR products from dsRNA of the NY1 isolate of GLRaV-3.

Immuno-capture is another simple and efficient method of sample preparation (Wetzel (1992), which is hereby incorporated by reference). First, crude ELISA extracts can be used directly for RT-PCR. Second, it provides not only a definitive answer, but may also be an indication to a virus serotype. Third, with an immuno-capture step, virus particles are trapped by an antibody, and inhibitory substances may be washed away. Nested PCR with samples prepared by the immuno-capture method is $10^3$ times more sensitive than with samples prepared by proteinase K-treated crude extract. However, this approach requires a virus specific antibody. For some newly discovered or hard to purify viruses, a virus specific antibody might not be always available. More specifically, there are at least six serologically distinctive closteroviruses associated with grapevine leafroll disease (Boscia (1995)), which is hereby incorporated by reference).

Example 13

Nucleotide Sequence and Open Reading Frames

A lambda ZAPII library was prepared from cDNA that was synthesized with random primed, reverse transcription of GLRaV-3 specific dsRNA. Initially, white/blue color selection in IPTG/X-gal containing plates was used to estimate the ratio of recombination. There were 15.7% white plaques or an estimate of $7 \times 10^4$ GLRaV-3 specific recombinants in this cDNA library. The library was screened with probes prepared from UNI-AMP™ PCR-amplified GLRaV-3 cDNA. More than 300 clones with inserts of up to 3 kb were selected after screening the cDNA library with probe prepared from UNI-AMP™ PCR-amplified GLRaV-3 cDNA. In Northern blot hybridization, a probe prepared from a clone insert, pC4, reacted strongly to the 16 kb dsRNA as well as to several other smaller Mr dsRNAs. Such a reaction was not observed with nucleic acids from healthy grape nor to dsRNA of CTV (FIG. 4).

Sequencing work began with clone pB3-1 that was selected after screening the library with HSP70 degenerated primer (5'-G-G-I-G-G-I-G-G-I-A-C-I-T-T-Y-G-A-Y-G-T-I-T-C-I (SEQ. ID. No. 25)). Other clones that were chosen for nucleotide sequencing were selected by the clone walking strategy. The nucleotide sequencing strategy employed was based on terminal sequencing of random selected clones assisted with GCG fragment assembly program to assemble and extend the sequence contig. The step-by-step primer extension method was used to sequence the internal region of a selected clone. A total of 54 clones were selected for sequencing. Among them, 16 clones were completely sequenced on both DNA strands (FIG. 17).

A total of 15,227 nucleotides were sequenced so far (FIG. 18), which potentially encompass nine open reading frames (ORFs) (FIG. 19), designated as ORFs 1a, 1b, and 2 to 8. The sequenced region was estimated to cover about 80% of the complete GLRaV-3 genome. Major genetic components, such as helicase (ORF 1a), RdRp (ORF 1b), HSP70 homologue (ORF 4), HSP90 homologue (ORF 5) and coat protein (ORF 6) were identified.

ORF 1a was an incomplete ORF from which the 5' terminal portion has yet to be cloned and sequenced. The sequenced region presented in FIGS. 18 and 19 represents approximately two-thirds of the expected ORF 1a, as compared to the ORF 1a from BYV, CTV, and LIYV. The partial ORF 1a was terminated by the UGA stop codon at positions 4,165–4,167; the respective product consisted of 1,388 amino acid residues and had a deduced Mr of 148,603. Database searching indicated that the C-terminal portion of this protein shared significant similarity with the Superfamily 1 helicase of positive-strand RNA viruses. Comparison of the conserved domain region (291 amino acids) showed a 38.4% identity with an additional 19.7% similarity between GLRaV-3 and BYV and a 32.4% identity with an additional 21.1% similarity between GLRaV-3 and LIYV (Table 3). Six helicase conserved motifs of Superfamily 1 helicase of positive-strand RNA viruses (Hodgman, "A New Superfamily of Replicative Proteins," *Nature,* 333:22–23 (Erratum 578) (1988) and Koonin et al., "Evolution and Taxonomy of Positive-Strand RNA Viruses: Implications of Comparative Analysis of Amino Acid Sequences," *Critical Reviews in Biochemistry and Molecular Biology,* 28:375–430 (1993), which are hereby incorporated by reference) were also retained in GLRaV-3 (FIG. 20). Analysis of the phylogenetic relationship in helicase domains between GLRaV-3 and the other positive-strand RNA viruses placed GLRaV-3 along with the other closteroviruses, including BYV, CTV, and LIYV, into the "tobamo" branch of the alphavirus-like supergroup (FIG. 21).

involved in the BYV frameshift was absent from the GLRaV-3 ORF1a/1b overlap. The frameshift within the GLRaV-3 ORF 1a/1b overlap was selected based on an inspection of the C-terminal portion of the helicase alignment and the N-terminal portion of the RdRp alignment between GLRaV-3 and LIYV (FIG. 24). The GLRaV-3 ORF 1a/1b frameshift was predicted to occur in the homologous region of the LIYV genome, and was also preceded by a repeat sequence (GCTT) (FIG. 24). Unlike LIYV, this repeat sequence was not a tandem repeat and was separated by one nucleotide (T) in GLRaV-3. The frameshift was predicted to occur at CACA (from His to Thr) in GLRaV-3 rather than slippery sequence AAAG in LIYV. However, additional experiments on in vitro expression of GLRaV-3 genomic RNA are needed in order to determine whether or not a large fusion protein is actually produced.

ORF 2 potentially encoded a small peptide of 51 amino acids with a calculated Mr of 5,927. Database searching did

TABLE 3

| Virus | Helicase | | RdRp | | p5K | | HSP70 | | HSP90 | | CP | |
|---|---|---|---|---|---|---|---|---|---|---|---|---|
| | nt | aa | nt | aa | nt | aa | nt | aa | nt | aa | nt | aa |
| BYV | 37.7 | 38.4 (58.1) | 44.5 | 41.2 (61.0) | 42.0 | 30.4 (47.8) | 43.5 | 28.6 (48.0) | 40.5 | 21.7 (51.0) | 41.5 | 20.3 (43.7) |
| CTV | 45.3 | 36.3 (55.2) | 44.0 | 40.1 (62.2) | 42.8 | 20.0 (48.9) | 43.7 | 28.7 (49.3) | 38.6 | 17.5 (43.5) | 40.3 | 20.5 (41.9) |
| LIYV | 44.9 | 32.4 (53.5) | 46.2 | 35.9 (56.4) | 45.8 | 17.9 (46.2) | 43.9 | 28.2 (46.9) | 39.3 | 16.7 (36.8) | 36.3 | 17.8 (41.1) |

Nucleotide ("nt") and amino acid ("aa") sequence similarity was calculated from perfect matches after aligning with the GCG program GAP; the percentages in parentheses are the percentages calculated by the GAP program, which employs a matching table based on evolutionary conservation of amino acids (Devereux et al., "A Comprehensive Set of Sequence Analysis Programs for the VAX," Nucleic Acids Res.,12:387–395 (1984), which is hereby incorporated by reference). The sources for the BYV, CTV, and LIYV sequences were, respectively, Agranovsky (1994), Karasev (1995), and Klaassen (1995), which are hereby incorporated by reference.

ORF 1b overlapped the last 113 nucleotides of ORF 1a and terminated at the UAG codon at positions 5780 to 5782. This ORF encoded a protein of 536 amino acid residues, counting from the first methionine codon and had a calculated Mr of 61,050 (FIGS. 18 and 19). Database screening of this protein revealed a significant similarity to the Supergroup 3 RdRp of the positive-strand RNA viruses. Sequence comparison of GLRaV-3 with BYV, LIYV, and CTV over a 313-amino acid sequence fragment revealed a striking amino acid sequence similarity among eight conserved motifs (FIG. 22). The best alignment was with BYV, with 41.2% identity and 19.8% additional similarity while the least alignment was with LIYV, with 35.9% identity and 20.5% additional similarity (Table 3). Analysis of phylogenetic relationships of the RdRp domains of the alphavirus-like supergroup viruses again placed GLRaV-3 into a "tobamo" branch along with other closteroviruses, BYV, CTV, BYSV, and LIYV (FIG. 23).

Publications on BYV, CTV, and LIYV have proposed that ORF 1b is expressed via a +1 ribosomal frameshift (Agranovsky (1994), Dolja et al., "Molecular Biology and Evolution of Closteroviruses: Sophisticated Build-up of Large RNA Genomes," *Annual Review of Phytopathology,* 32:261–285 (1994) ("Dolja (1994)"), Karasev (1995), and Klaassen (1995), which are hereby incorporated by reference). Direct nucleotide sequence comparison was performed within the ORF1a/1b overlap of GLRaV-3 with respect to BYV, CTV, or LIYV. An apparently significant similarity was observed only to LIYV (FIG. 24), and not to BYV or CTV. The so-called "slippery" GGGUUU sequence and the stem-and-loop structure that were proposed to be not reveal any obvious protein matches within the existing Genbank (Release 84.0).

Intergenic regions of 220 bp between ORF 1b and ORF 2 and 1,065 bp between ORF 2 and ORF 3 were identified. There is no counterpart in BYV or LIYV genomes; instead, an ORF of 33K in CTV (Karasev et al., "Screening of the Closterovirus Genome by Degenerate Primer-Mediated Polymerase Chain Reaction," *Journal of General Virology,* 75:1415–1422 (1994), which is hereby incorporated by reference) or 32K in LIYV (Klaassen (1995), which is hereby incorporated by reference) is observed over this similar region.

ORF 3 encoded a small peptide of 45 amino acids with a calculated Mr of 5,090 (p5K). Database searching revealed that it was most closely related to the small hydrophobic, transmembrane proteins of BYV (6.4K), CTV (6K), and LIYV (5K) (FIG. 25). Individual comparison (Table 3) showed that LIYV was its most close relative (45.8%) at the nucleotide level and BYV was the most homologous (30.4%) at the amino acid level.

ORF 4 potentially encoded a protein of 549 amino acids with a calculated Mr of 59,113 (p59) (FIGS. 18 and 19). Database screening revealed a significant similarity to the HSP70 family, the p65 protein of BYV, the p65 protein of CTV, and the p62 protein of LIYV. A multiple amino acid sequence alignment of GLRaV-3 p59 with HSP70 analogs of other closteroviruses showed a striking sequence similarity among eight conserved motifs (A–H) (FIG. 26). Functionally important motifs (A–C) that are characteristic of all proteins containing the ATPase domain of the HSP70 type (Bork et al., "An ATPase Domain Common to Prokaryotic Cell Cycle Proteins, Sugar Kinases, Actin, and HSP70 Heat Shock Proteins," Proc. Natl. Acad. Sci. U.S.A., 89:7290–7294 (1992), which is hereby incorporated by reference) were also preserved in GLRaV-3 p59 (FIG. 26), which suggested that this HSP70 chaperon-like protein may also possess ATPase activity on its N-terminal domain and protein-protein interaction on its C-terminal domain (Dolja (1994), which is hereby incorporated by reference). Analysis of the phylogenetic relationship of p59 of GLRaV-3 with HSP70-related proteins of other closteroviruses (BYV, CTV, and BYSV) and cellular HSP70s again placed the four closteroviruses together and the rest of the cellular HSP70s on the other branches (FIG. 27). Although several closterovirus HSP70-related proteins are closely related to each other and distant from other cellular members of this family, inspection of the phylogenetic tree (FIG. 27) suggested that GLRaV-3 may be an ancestral closterovirus relatively early in evolution as predicted by Dolja (1994), which is hereby incorporated by reference, because GLRaV-3 was placed in between closteroviruses and the other cellular HSP70 members.

ORF 5 encoded a protein of 483 amino acids with a calculated Mr of 54,852 (p55) (FIGS. 18 and 19). No significant sequence homology with other proteins was observed in the current database (GenBank, release 84.0). Direct comparison with other counterparts (p61 of CTV, p64 of BYV, and p59 of LIYV) of closteroviruses revealed some degree of amino acid sequence similarity, with 21.7% to BYV, 17.5% to CTV, and 16.7% to LIYV, respectively (Table 3, FIG. 28). Two conserved regions of HSP90 previously described in BYV and CTV (Pappu (1994), which is hereby incorporated by reference) were identified in the p55 of GLRaV-3 (FIG. 28).

The data in this ORF has been extensively described. ORF 6 encoded a protein of 313 amino acids with a calculated Mr of 34,866 (p35) (FIGS. 18 and 19). The fact that this ORF was encoded by three overlapping GLRaV-3 immunpositive clones suggests that it may contain the coat protein gene of GLRaV-3. Alignment of the product of ORF 6 (p35) with respect to BYV, CTV, and LIYV, is presented in FIG. 11. The typical consensus amino acid residues (S, R, and D) of the coat protein of the filamentous plant viruses (Dolja (1991), which is hereby incorporated by reference), which may be involved in salt bridge formation and the proper folding of the most conserved core region (Boyko (1992), which is hereby incorporated by reference), were also retained in the p35 (FIG. 11). Individual sequence comparison showed the highest similarity to CTV (20.5%) and BYV (20.3%), and the lowest similarity to LIYV (17.8%). Analysis of phylogenetic relationships with other filamentous plant viruses placed GLRaV-3 into a separate, but a closely related branch of closteroviruses (FIG. 12).

ORF 7 encoded a protein of 477 amino acids with a calculated Mr of 53,104 (p53) (FIGS. 18 and 19). Based on the presence of conserved amino acid sequences, this protein is designated as grapevine leafroll coat protein repeat (p53).

ORF 8 encoded an unidentified polypeptide having a calculated Mr of 21,148 (p21).

ORF 9 encoded an unidentified polypeptide having a calculated Mr of 19,588 (p20).

ORF 10 encoded an unidentified polypeptide having a calculated Mr of 19,653 (p20).

ORF 11 encoded an unidentified polypeptide having a calculated Mr of 6,963 (p7).

In the present study, many GLRaV-3 dsRNA specific cDNA clones were identified using a probe generated from UNI-AMP™ PCR-amplified cDNA. Using UNI-AMP™ adapters and primers (Clontech) in PCR has several advantages. First, it is not necessary to know the nucleotide sequence of an amplified fragment. Second, cDNA can be amplified in sufficient amounts for specific probe preparation. In general, cDNA amplified by PCR using UNI-AMP™ primers and adapters could be used for cloning as well as a probe for screening of cDNA libraries. However, low abundance of the starting material and many cycles of PCR amplification often incorporate errors into the nucleotide sequence (Keohavong et al., "Fidelity of DNA Polymerases in DNA Amplification," Proc. Natl. Acad. Sci. U.S.A., 86:9253–9257 (1989) and Saiki et al., "Primer-Directed Enzymatic Amplification of DNA with a Thermostable DNA Polymerase," Science, 239:487–491 (1988), which are hereby incorporated by reference). In the present study, only UNI-AMP™ PCR amplified cDNA was used as a probe for screening. The cDNA library was generated by direct cloning of the cDNA that was synthesized by AMV reverse transcriptase. Therefore, the cDNA cloned inserts are believed to more accurately reflect the actual sequence of the dsRNA and the genomic RNA of GLRaV-3.

A total of 15,227 nucleotides or about 80% of the estimated 16 kb GLRaV-3 dsRNA was cloned and sequenced. Identification of this sequence fragment as the GLRaV-3 genome was based on its sequence alignment with the coat protein gene of GLRaV-3. This is the first direct evidence showing that high molecular weight dsRNA (~16 kb) isolated from GLRaV-3 infected vines is derived from GLRaV-3 genomic RNA. Based upon the nine ORFs identified, the genome organization of GLRaV-3 bears significant similarity to the other closteroviruses sequenced (BYV, CTV, and LIYV) (FIG. 19).

Dolja (1994), which is hereby incorporated by reference, divided the closterovirus genome into four modules. For GLRaV-3, the 5' accessory module including protease and vector transmission factor is yet to be identified. The core module, including key domains in RNA replication machinery (MET-HEL-RdRp) that is conserved throughout the alphavirus supergroup, has been revealed in parts of the HEL and RdRp domains. The MET domain has not yet been identified for GLRaV-3. The chaperon module, including three ORFs coding for the small transmembrane protein, the HSP70 homologue, and the distantly related HSP90 homologue, has been fully sequenced. The last module includes coat protein and its possible diverged copy and is also preserved in GLRaV-3. Overall similarity of the genome organization of GLRaV-3 with other closteroviruses further support the inclusion of GLRaV-3 as a member of closteroviruses (Hu (1990) and Martelli (1991), which are hereby incorporated by reference). However, observation of a ambisense gene on its 3' terminal region may separate GLRaV-3 from other closteroviruses. Further comparative sequence analysis (Table 3) as well as phylogenetic observation of GLRaV-3 with respect to other closteroviruses over the entire genome sequence region suggested that GLRaV-3 is most closely related to BYV, followed by CTV, and LIYV.

As suggested by others (Agranovsky (1994), Dolja (1994), Karasev (1995), and Klaassen (1995), which are hereby incorporated by reference), expression of ORF 1b in closteroviruses may be via a +1 ribosomal frameshift mechanism. In GLRaV-3, a potential translation frameshift of ORF 1b could make a fusion HEL-RdRp protein of over 1,926 amino acid residues with a capacity to encode a protein of more than 210K Comparative study of GLRaV-3 with respect to other closteroviruses over the ORF 1a/1b overlap revealed a significant sequence similarity to LIYV, but not to BYV or to CTV. The so-called slippery sequence (GGGUUU) and stem-loop and pseudoknot structures identified in BYV (Agranovsky (1994), which is hereby incorporated by reference) is not present in GLRaV-3. Thus, a frameshift mechanism that is similar to LIYV may be employed for GLRaV-3. However, protein analysis is necessary in order to determine the protein encoding capacities of these ORFs.

Differing from BYV, both CTV and LIYV have an extra ORF (ORF 2) in between RdRp (ORF 1b) and the small membrane protein (ORF 3) and potentially encoding a protein of 33K or 32K, respectively. However, in GLRaV-3, there is a much smaller ORF 2 (7K) followed by a long intergenic region of 1,065 bp. Thus, nucleotide sequencing of additional clones around this region may be necessary to resolve this discrepancy.

So far, among all plant viruses described, the HSP70 related gene is present only in the closteroviruses (Dolja (1994), which is hereby incorporated by reference). Identification of the GLRaV-3 HSP70 gene was based on an assumption that this gene should also be present in the closterovirus associated with grapevine leafroll disease, specifically GLRaV-3. Thus, cDNA clones that reacted with HSP70-degenerated primers were identified for sequence analysis. The identification of subsequent clones for sequencing was based on the gene-walking methodology. However, identification of immunopositive clones enabled identification of the coat protein gene of GLRaV-3 and proved that the HSP70-containing sequence fragment is present in the GLRaV-3 RNA genome.

The 16 kb dsRNA used for cDNA synthesis was assumed to be a virus replicative form (Hu (1990), which is hereby incorporated by reference). Identification of the virus coat protein from this study further supports this assumption. Several lines of evidence show that the partial genome of GLRaV-3 has been cloned and sequenced. First, selected clones have been shown by Northern hybridization to hybridize to the 16 kb dsRNA and several smaller RNAs (presumably subgenomic RNAs) (FIG. 4). Second, three GLRaV-3 antibody-reacting clones were identified after immuno-screening of the protein expressive library with both GLRaV-3 polyclonal (Zee (1987), which is hereby incorporated by reference) and monoclonal (Hu (1990), which is hereby incorporated by reference) antibodies. After nucleotide sequencing, these three antibody-reacting clones were shown to overlap one another and contain a common ORF which potentially encodes a protein with calculated Mr of 35K. This is in general agreement with the Mr estimated on SDS-PAGE (41K). Third, analysis of the partial genome sequence of GLRaV-3 suggested a close similarity in genome organization and gene sequences to the other closteroviruses (Dolja (1994), which is hereby incorporated by reference).

Information regarding the genome of GLRaV-3 provides a better understanding of this and related viruses and adds to the fundamental knowledge of closteroviruses. Present work on the nucleotide sequence and genome organization (about 80% of the estimated genome sequence) has provided direct evidence of a close relationship between GLRaV-3 and other closteroviruses. It has also made it possible, for the first time, to thoroughly evaluate a phylogenetic relationship of GLRaV-3 based on a wide range of genes and gene products (helicase, polymerase, HSP70 homologue, HSP90 homologue, and coat protein). Based upon major differences in genome format and organization between BYV, CTV, and LIYV, along with phylogenetic analysis, Dolja (1994), which is hereby incorporated by reference, proposed the establishment of the new family Closteroviridae with three new genera of Closterovirus (BYV), Citrivirus (CTV), and Biclovirus (LIYV). This work on genome organization and phylogenetic analysis, along with evidence that this virus is transmitted by mealybugs (Engelbrecht et al., "Association of a Closterovirus with Grapevines Indexing Positive for Grapevine Leafroll Disease and Evidence for its Natural Spread in Grapevines," *Phytopathol. Mediter.*, 24:101–105 (1990), Engelbrecht et al., "Field Spread of Corky Bark Fleck Leafroll and Shiraz Decline Diseases and Associated Viruses in South African Grapevines," *Phytophylactica*, 22:347–354 (1990), Engelbrecht et al., "Transmission of Grapevine Leafroll Disease and Associated Closteroviruses by the Vine Mealybug *Planococcus-Ficus*," *Phytophylactica*, 22:341–346 (1990), Rosciglione et al., "Transmission of Grapevine Leafroll Disease and an Associated Closterovirus to Healthy Grapevine by the Mealybug *Planococcus Ficus* (Abstract)," *Phytoparasitica*, 17:63–63 (1989), and Tanne et al., "Transmission of Closterolike Particles Associated with Grapevine Leafroll by Mealybugs (Abstract)," *Phytoparasitica*, 17:55 (1989), which are hereby incorporated by reference), suggest that a new genus under Closteroviridae family should be established. Thus, GLRaV-3 (the NY1 isolate) is proposed to be the type representative of the new genus, Graclovirus (grapevine clo-sterovirus). Further sequencing of other grapevine leafroll associated closteroviruses may add more members to this genus.

Another cDNA library of GLRaV-3 has been established recently from dsRNA of an Italian isolate of GLRaV-3 (Saldarelli et al., "Detection of Grapevine Leafroll-Associated Closterovirus III by Molecular Hybridization," *Plant Pathology (Oxford)*, 43:91–96 (1994), which is hereby incorporated by reference). Selected clones react specifically to GLRaV-3 dsRNA on a Northern blot; however, no direct evidence was provided to suggest that those clones were indeed from GLRaV-3 genomic RNA. Meanwhile, a small piece of sequence information from one of those cDNA clones was used to synthesize primers for the development of a PCR detection method (Minafra (1994), which is hereby incorporated by reference). Direct sequence comparison of these primer sequences to GLRaV-3 genome sequence obtained in the present study, showed that one of the primers (H229, 5'-A-T-A-A-G-C-A-T-T-C-g-G-G-A-T-G-G-A-C-C (SEQ. ID. No. 27)) is located at nucleotides 5562–5581 and the other (C547, 5'-A-T-T-A-A-C-t-T-g-A-C-G-G-A-T-G-G-C-A-C-G-C (SEQ. ID. No. 28)) is in reverse direction and is the complement of nucleotides 5880–5901. Mismatching nucleotides between the primers and GLRaV-3 sequence are shown in lowercase letters. Sequence comparison over these short primer regions to GLRaV-3 (isolate NY1) genome sequence showed a 90–95% identity, which suggested that these two isolates belong to the same virus (GLRaV-3). Moreover, the primers prepared by Minafra (1994), which is hereby incorporated by reference, from the Italian isolate of GLRaV-3 produced an expected size of PCR product with templates prepared from the NY1 isolate of GLRaV-3.

The reminder of the GLRaV-3 genome can be sequenced using the methods described herein.

Example 14

Identification and Characterization of the 43 K ORF

The complete nucleotide sequence of the GLRaV-3 HSP90 gene is given in FIG. 18. Initial sequencing work indicated that a open reading frame ("ORF") potentially encoding for a protein with a calculated Mr of 43K (FIG. 29) was downstream of the HSP70-related gene. This gene was selected for engineering because the size of its encoded product is similar to the GLRaV-3 coat protein gene. However, after sequence editing, this incomplete ORF was proven to be located in the 3' terminal region of the HSP90-related gene. It is referred to herein as the incomplete GLRaV-3 HSP90 gene or as the 43K ORF.

Example 15

Custom-PCR Engineering the Incomplete GLRaV-3 HSP90 Gene for Expression in Plant Tissues Two custom synthesized oligonucleotide primers, 5' primer (93–224, t-a-c-t-t-a-t-c-t-a-g-a-a-c-c-A-T-G-G-A-A-G-C-G-A-G-T-C-G-A-C-G-A-C-T-A (SEQ. ID. No. 29)) and 3' complimentary primer (93–225, t-c-t-t-g-a-g-g-a-t-c-c-a-t-g-g-A-G-A-A-A-C-A-T-C-G-T-C-G-C-A-T-A-C-T-A (SEQ. ID. No. 30)) that flank the 43K ORF were designed to amplify the incomplete HSP90 gene fragment by polymerase chain reaction ("PCR"). Addition of a restriction enzyme Nco I site in the primer is for the convenience of cloning and for protein expression (FIG. 29) (Slightom, "Custom Polymerase-Chain-Reaction Engineering of a Plant Expression Vector," *Gene,* 100:251–255 (1991), which is hereby incorporated by reference). Using these primers, a product of the proper size (1.2 kb) was amplified by reverse transcription PCR ("RT-PCR") using GLRaV-3 double-stranded RNA ("dsRNA") as template. The PCR amplified product was treated with Nco I, isolated from a low-melting temperature agarose gel, and cloned into the same restriction enzyme treated binary vector pBI525 (obtained from William Crosby, Plant Biotechnology Institute, Saskatoon, Sask., Canada), resulting in a clone pBI525GLRaV-3hsp90 (FIG. 30). A plant expression cassette, the EcoR I and Hind III fragment of clone pBI525GLRaV-3hsp90, which contains proper engineered CaMV 35S promoters and a Nos 3' untranslated region, was excised and cloned into a similar restriction enzyme digested plant transformation vector, pBin19 (FIG. 30) (Clontech Laboratories, Inc.). Two clones, pBin19GLRaV-3hsp90-12-3 and pBin19GLRaV-3hsp90-12-4 that were shown by PCR to contain the proper size of the incomplete HSP90 gene were used to transform the avirulent *Agrobacterium tumefaciens,* strain LBA4404 via electroporation (Bio-Rad). The potentially transformed Agrobacterium was plated on selective media with 75 μg/ml of kanamycin. Agrobacterium lines which contain the HSP90 gene sequence were used to transform tobacco (*Nicotiana tobaccum* cv. Havana 423) using standard procedures (Horsch et al., "A Simple and General Method for Transferring Genes into Plants," *Science,* 227:1229–1231 (1985) ("Horsch (1985)"), which is hereby incorporated by reference). Kanamycin resistant tobacco plants were analyzed by PCR for the presence of the transgene. Transgenic tobacco plants with the transgene were self pollinated and seed was harvested.

Example 16

Custom-PCR Engineering of the 43K ORF

The complete sequence of the GLRaV-3 hsp90 gene was reported in FIG. 18. However, in the present study, using two custom synthesized oligo primers (93–224, tacttatctagaaccATGGAAGCGAGTCGACGACTA (SEQ. ID. No. 29) and 93–225, tcttgaggatccatggAGAAACATCGTCGCATACTA (SEQ. ID. No. 30)) and GLRaV-3 dsRNA as template, the incomplete HSP90 related gene sequence was amplified by RT-PCR which added an Nco I restriction enzyme recognition sequence (CCATGG) around the potential translation initiation codon (ATG) and another Nco I site, 29 nt downstream from the translation termination codon (TAA) (FIG. 29). The PCR amplified fragment was digested with Nco I, and cloned into the same restriction enzyme treated plant expression vector, pBI525. Under ampicillin selective conditions, hundreds of antibiotic resistant, transformants of *E. coli* strain DH5a were generated. Clones derived from five colonies were selected for further analysis. Restriction enzyme mapping (Nco I or BamH I and EcoR V) showed that three out of five clones contained the proper size of the incomplete GLRaV-3 HSP90 sequence. Among them, two clones were engineered in the correct 5'–3' orientation with respect to the CaMV-AMV gene regulatory elements in the plant expression vector, pBI525. A graphical structure in the region of the plant expression cassette of clone pBI525GLRaV-3hsp90-12 is presented in FIG. 30.

The GLRaV-3 HSP90 expression cassette was removed from clone pBI525GLRaV-3hsp90-12 by a complete digestion with Hind III and EcoR I and cloned into the similar restriction enzyme treated plant transformation vector pBin19. A clone designated as pBin19GLRaV-3hsp90-12 was then obtained (FIG. 30) and was subsequently mobilized into the avirulent Agrobacterium strain LBA4404 using a standard electroporation protocol (Bio-Rad). Potentially transformed Agrobacteria were then plated on a selective medium (75 μg/ml kanamycin), and antibiotic resistant colonies were analyzed further by PCR with specific synthesized primers (93–224 and 93–225) to see whether or not the incomplete HSP90 gene was still present. After analysis, clone LBA4404/pBin19GLRaV-3hsp90-12 was selected and used to transform tobacco tissues.

Example 17

Transformation and Characterization of Transgenic Plants

The genetically engineered *Agrobacterium tumefaciens* strain, LBA4404/pBin19GLRaV-3hsp90-12, was co-cultivated with tobacco leaf discs as described (Horsch (1985), which is hereby incorporated by reference). Potentially transformed tobacco tissues were selected on MS regeneration medium (Murashige et al., "A Revised Medium for Rapid Growth and Bioassays with Tobacco Tissue Cultures," *Physiologia Plantarum,* 15:473–497 (1962), which is hereby incorporated by reference) containing 300 μg/ml of kanamycin. Numerous shoots developed from kanamycin resistant calli in about 6 weeks. Rooted tobacco plants were obtained following growth of developed shoots on a rooting medium (MS without hormones) containing 300 μg/ml of kanamycin. Eighteen independent, regenerated kanamycin resistant plants were transplanted in a greenhouse and tested for the presence of the HSP90-related gene by PCR. Fourteen out of eighteen selected kanamycin resistant transgenic lines were shown to contain a PCR product with the expected size (FIG. 31).

The genetically engineered *Agrobacterium tumefaciens* strain LBA4404/pBin19GLRaV-3hsp90-12 was also used to transform the grapevines rootstock Couderc 3309 (*Vitis riparia×Vitis rupestris*). Embryogenic calli of Couderc 3309 were obtained by culturing anthers on MSE media. (MSE media contained Murashige and Skoog salts plus 0.2% sucrose, 1.1 mg/L 2,-4-D, and 0.2 mg/L BA. The media were adjusted to pH 6.5, and 0.8% Noble agar was added. After autoclaving, 100 ml M-0654, 100 ml M-0529, and 1 ml vitamin M-3900 were added to the media). After 60 days, primary calli were induced and transferred to hormone-free HMG medium (½ Murashige salts with 10 g/L sucrose, 4.6 g/L glycerol and 0.8% Noble agar) for embryogenesis. Calli with globular or heart-shaped embryos were immersed for 15 minutes in *Agrobacterium tumefaciens* LBA4404/ pBin19GLRaV-3hsp90-12 that was suspended in MS liquid medium. The embryos were blotted on filter paper to remove excess liquid and transferred to HMG medium with acetosyringone (100 µM) and kept for 48 hours in the dark at 28° C. The calli were then washed 2–3 times in MS liquid medium plus cefotaxime (300 µg/ml) and carbenicillin (200 µg/ml) and transferred to HMG medium with the same antibiotics for 1–2 weeks. Subsequently, the embryogenic calli were transferred to HMG medium containing 20 or 40 mg/L kanamycin and 300 mg/L cefotaxime plus 200 mg/L carbenicillin to select transgenic embryos. After being on selection medium for 3–4 months, growing embryos were transferred to HMG, MGC (full-strength MS salts amended with 20 g/L sucrose, 4.6 g/L glycerol, 1 g/L casein hydrolysate, and 0.8% Noble agar), or MSE medium with kanamycin. After 4 months, germinated embryos were transferred to baby food jars containing rooting medium, such as a woody plant medium described, for example, in Lloyd et al., "Commercially Feasible Micropropogation of Mountain Laurel. *Kalmia latifolia,* By Use of Shoot Tip Culture," *Proc. Intl. Plant Prop. Soc.,* 30:421–427 (1981), which is hereby incorporated by reference, that was supplemented with 0.1 mg/L BA, 3 g/L activated charcoal and 1.5% sucrose. The pH was adjusted to 5.8 and Noble agar was added to 0.7%]. Plantlets with roots were transplanted to pots with artificial soil mix and grown in greenhouses. In this manner, 88 grapevine plants were transferred to the greenhouse. The 43K protein gene has been detected by PCR in a number of them.

Using the methods described above, engineering of the incomplete HSP90 gene of GLRaV-3 into plant expression and transformation vectors has been effected. The targeted gene sequence was shown to be integrated into the plant genome by PCR analysis of the transgenic tobacco plants. The engineered *Agrobacterium tumefaciens* strain LBA4404/pBin19GLRaV-3hsp90-12 has been used to transform grapes and tobacco. Furthermore, success in the genetic engineering of a plant transformation vector may serve as a model for further construction of other GLRaV-3 genes, such as coat protein, RdRp, and HSP70 that are now available.

Since the first demonstration of transgenic tobacco plants expressing the coat protein gene of TMV resulted in resistance against TMV infection (Powell-Abel et al., "Delay of Disease Development in Transgenic Plants that Express the Tobacco Mosaic Virus Coat Protein Gene," *Science,* 232:738–743 (1986), which is hereby incorporated by reference), the phenomenon of the coat protein-mediated protection has been observed for over 20 viruses in at least 10 different taxonomic groups in a wide variety of dicotyledonous plant species (Beachy et al., "Coat Protein-Mediated Resistance Against Virus Infection," *Annu. Rev. Phytopathol.,* 28:451–74 (1990) ("Beachy (1990)") and Wilson, "Strategies to Protect Crop Plants Against Viruses: Pathogen-Derived Resistance Blossoms," *Proc. Natl. Acad. Sci., U.S.A.,* 90:3134–3141 (1993) ("Wilson (1993)", which are hereby incorporated by reference). If gene silencing (or co-suppression) (Finnegan et al., "Transgene Inactivation: Plants Fight Back!" *Bio/Technology,* 12:883–888 (1994) and Flavell, "Inactivation of Gene Expression in Plants as a Consequence of Specific Sequence Duplication," *Proc. Natl. Acad. Sci. U.S.A.,* 91:3490–3496 (1994), which are hereby incorporated by reference) is one of the resistance mechanisms (Lindbo et al., "Induction of a Highly Specific Antiviral State in Transgenic Plants: Implications for Regulation of Gene Expression and Virus Resistance," *The Plant Cell,* 5:1749–1759 (1993), Pang et al., "Different Mechanisms Protect Transgenic Tobacco Against Tomato Spotted Wilt and Impatiens Necrotic Spot Tospoviruses," *Bio/ Technology,* 11:819–824 (1993) ("Pang (1993)"), and Smith et al., "Transgenic Plant Virus Resistance Mediated by Untranslatable Sense RNAs: Expression, Regulation, and Fate of Nonessential RNAs," *The Plant Cell,* 6:1441–1453 (1994), which are hereby incorporated by reference), then one would expect to generate transgenic plants expressing any part of a viral genome sequence to protect plants from that virus infection. Thus, in the present study, trangenic plants expressing the 43K ORF (or the incomplete hsp90 gene) may be protected from GLRaV-3 infection.

Since tobacco (*Nicotiana tobaccum* cv. Havana 423) is not the host of GLRaV-3, direct evaluation of the virus resistance was not possible. However, recently, after a mechanical inoculation of *N. benthamiana* with grapevine leafroll infected tissue, Boscia (1995), which is hereby incorporated by reference, have recovered a long closterovirus from *N. benthamiana* which is probably GLRaV-2. Thus, it is believed that other types of grapevine leafroll associated closteroviruses can also be mechanically transmitted to *N. benthamiana*. If the 43K ORF from GLRaV-3 can also be transferred to *N. benthamiana,* it might be possible to evaluate the resistance of those plants against GLRaV-2 infection. However, the resistance of the transgenic grape rootstock Couderc 3309 against leafroll infection can be presently evaluated.

Example 18

Coat Protein-mediated Protection and Other Forms of Pathogen-derived Resistance

Figure 32:
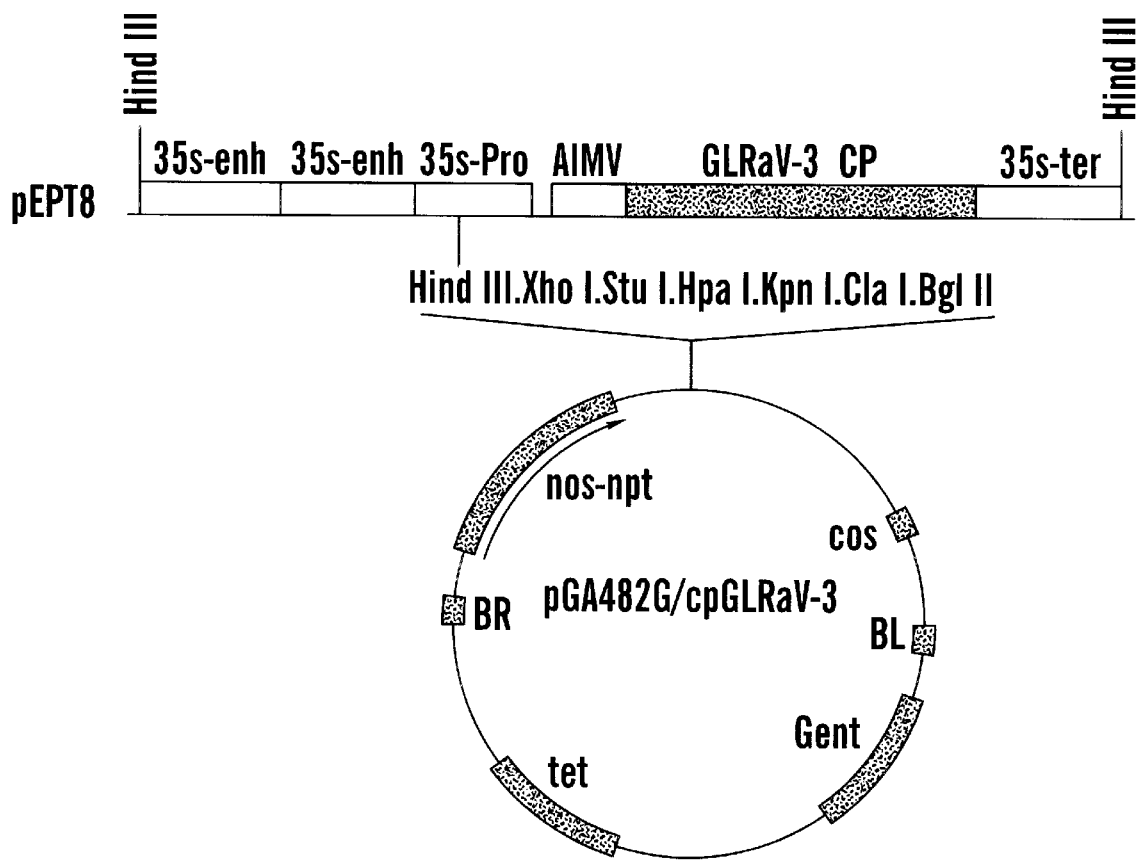

The successful engineering technique used in the above work could be utilized to engineer other gene sequences of GLRaV-3 which have since been identified. Among these, the coat protein gene of GLRaV-3 is the primary candidate since coat protein-mediated protection (Beachy (1990), Hull et al., "Approaches to Nonconventional Control of Plant Virus Diseases," *Crit. Rev. Plant Sci.,* 11:17–33 (1992), and Wilson (1993), which are hereby incorporated by reference) has been the most successful example in the application of the concept of pathogen-derived resistance (Sanford et al., "The Concept of Parasite-Derived Resistance—Deriving Resistance Genes from the Parasite's Own Genome," *J. Theor. Biol.,* 113:395–405 (1985), which is hereby incorporated by reference). Construction of plant expression vector (pEPT8/cpGLRaV-3) and Agrobacterium binary vector (pGA482pEPT8/cpGLRaV-3) was done following a strategy similar to the above. The GLRaV-3 coat protein gene was PCR amplified with primers (KSL95-5, a-c-t-a-t-t-t-c-t-a-g-a-a-c-c-A-T-G-G-C-A-T-T-T-G-A-A-C-T-G-A-A-A-T-T (SEQ. ID. No. 31), and KSL95-6, t-t-c-t-g-a-g-g-a-t-c-c-a-t-g-g-T-A-T-A-A-G-C-T-C-C-C-A-T-G-A-A-T-T-A-T (SEQ. ID. No. 32)) and cloned into pEPT8 after NcoI treatment. The expression cassette from pEPT8/cpGLRaV-3 (including double CaMV 35S enhancers, 35S promotor, alfalfa mosaic virus leader sequence, GLRaV-3 coat protein gene, and 35S terminator) was digested with HindIII and cloned into pGA482G (FIG. 32). Resulting Agrobacterium binary vector (pGA482GpEPT8/cpGLRaV-3) was mobilized into *Agrobacterium tumerfaciens* strain C58Z707 and used for transformation of grapevines.

Other gene sequence (ORF 1b, the RNA dependent RNA polymerase) may also be used, as replicase-mediated protection has been effectively used to protect plants from virus infection (Carr et al., "Replicase-Mediated Resistance," *Seminars in Virology,* 4:339–347 (1993) and Golemboski et al., "Plants Transformed with a Tobacco Mosaic Virus Nonstructural Gene Sequence are Resistant to the Virus," *Proc. Natl. Acad. Sci. U.S.A.,* 87:6311–6315 (1990), which are hereby incorporated by reference). The HSP70 homologue may also be used to generate transgenic plants that are resistant against all types of grapevine leafroll associated closteroviruses since significant consensus sequences are observed over HSP70 conserved domains. Moreover, the phenomenon of RNA-mediated protection has also been observed (de Haan et al., "Characterization of RNA-Mediated Resistance to Tomato Spotted Wilt Virus in Transgenic Tobacco Plants," *Bio/Technology,* 10:1133–1137 (1992), Farinelli et al., "Coat Protein Gene-Mediated Resistance to Potato Virus Y in Tobacco Examination of the Resistance Mechanisms is the Transgenic Coat Protein Required for Protection?" *Mol. Plant Microbe Interact.,* 6:284–292 (1993), ("Farinelli (1993)"), Kawchuk et al., "Sense and Antisense RNA-Mediated Resistance to Potato Leafroll Virus in Russet Burbank Potato Plants," *Mol. Plant Microbe Interact,* 4:247–253 (1991) ("Kawchuk (1991)"), Lindbo et al., "Untranslatable Transcripts of the Tobacco Etch Virus Coat Protein Gene Sequence Can Interfere with Tobacco Etch Virus Replication in Transgenic Plants and Protoplasts," *Virology,* 189:725–733 (1992), Lindbo et al., "Pathogen-Derived Resistance to a Potyvirus Immune and Resistant Phenotypes in Transgenic Tobacco Expressing Altered Forms of a Potyvirus Coat Protein Nucleotide Sequence," *Mol. Plant Microbe Interact,* 5:144–153 (1992), Lindbo et al., "Pathogen Derived Resistance to Potyviruses: Working, But Why?" *Seminars in Virology,* 4:369–379 (1993), Pang (1993), and Van Der Wilk et al., "Expression of the Potato Leafroll Luteovirus Coat Protein Gene in Transgenic Potato Plants Inhibits Viral Infection," *Plant Mol. Biol.,* 17:431–440 (1991), which are hereby incorporated by reference). Thus, untranslatable transcript versions of the above mentioned GLRaV-3 genes might also produce leafroll resistant transgenic plants.

Another form of pathogen-derived resistance that has also been shown to be effective in control of plant viral disease is through the use of antisense RNA. Transgenic tobacco plants expressing the antisense sequence of the coat protein gene of cucumber mosaic virus ("CMV") showed a delay in symptom expression by CMV infection (Cuozzo et al., "Viral Protection in Transgenic Tobacco Plants Expressing the Cucumber Mosaic Virus Coat Protein or its Antisense RNA," *Bio/Technology,* 6:549–554 (1988), which is hereby incorporated by reference). Transgenic plants expressing either potato virus X ("PVX") coat protein or its antisense transcript were protected from infection by PVX. However, plants expressing antisense RNA were protected only at low inoculum concentration. The extent of this protection mediated by antisense transcript is usually lower than transgenic plants expressing the coat protein (Hemenway et al., "Analysis of the Mechanism of Protection in Transgenic Plants Expressing the Potato Virus X Coat Protein or its Antisense RNA," *Embo.* (*Eur. Mol. Biol. Organ.*) *J.,* 7:1273–1280 (1988), which is hereby incorporated by reference). This type of resistance has also been observed in bean yellow mosaic virus (Hammond et al., "Expression of Coat Protein and Antisense RNA of Bean Yellow Mosaic Virus in Transgenic *Nicotiana-Benthamiana,*" *Phytopathology,* 81:1174 (1991), which is hereby incorporated by reference, tobacco etch virus (Lindbo et al., "Untranslatable Transcripts of the Tobacco Etch Virus Coat Protein Gene Sequence Can Interfere with Tobacco Etch Virus Replication in Transgenic Plants and Protoplasts," *Virology,* 189:725–733 (1992), which is hereby incorporated by reference), potato virus Y (Farinelli (1993), which is hereby incorporated by reference), and zucchini yellow mosaic virus (Fang et al., "Genetic Engineering of Potyvirus Resistance Using Constructs Derived from the Zucchini Yellow Mosaic Virus Coat Protein Gene," *Mol. Plant Microbe Interact.,* 6:358–367 (1993), which is hereby incorporated by reference). However, high level of resistance mediated by antisense sequence was observed to be similar to potato plants (Russet Burbank) expressing potato leafroll virus coat protein (Kawchuk (1991), which is hereby incorporated by reference). Besides using antisense transcript of the virus coat protein gene, other virus genome sequences have also been demonstrated to be effective. These included the 51-nucleotide sequences near the 5' end of TMV RNA (Nelson et al., "Tobacco Mosaic Virus Infection of Transgenic *Nicotiana-Tabacum* Plants is Inhibited by Antisense Constructs Directed at the 5' Region of Viral RNA," *Gene* (Abst), 127:227–232 (1993), which is hereby incorporated by reference) and noncoding region of turnip yellow mosaic virus genome (Zaccomer et al., "Transgenic Plants that Express Genes Including the 3' Untranslated Region of the Turnip Yellow Mosaic Virus (TYMV) Genome are Partially Protected Against TYMV Infection," *Gene,* 87–94 (1993), which is hereby incorporated by reference).

GLRaV-3 has been shown to be transmitted by mealybugs and in some cases it has been shown to spread rapidly in vineyards (Engelbrecht et al., "Field Spread of Corky Bark Fleck Leafroll and Shiraz Decline Diseases and Associated Viruses in South African Grapevines," *Phytophylactica,* 22:347–354 (1990), Engelbrecht et al., "Transmission of Grapevine Leafroll Disease and Associated Closteroviruses by the Vine Mealybug *Planococcus-Ficus,*" *Phytophylactica,* 22:341–346 (1990), and Jordan et al., "Spread of Grapevine Leafroll and its Associated Virus in New Zealand Vineyards," *11th Meeting of the International Council for the Study of Viruses and Virus Diseases of the Grapevine,* pp. 113–114 (1993), which are hereby incorporated by reference). This disease may become more of a problem if mealybugs become difficult to control due to the lack of insecticides. In this scenario, the development of leafroll resistant grapevines becomes very attractive. Although grapevine is a natural host of Agrobacterium (*A. vitis* is the causal agent of the grapevine crown gall disease), transformation of grapevine has proven to be difficult (Baribault et al., "Transgenic Grapevines: Regeneration of Shoots Expressing β-glucuronidase," *J. Exp. Bot.,* 41:1045–1049 (1990), Baribault et al., "Genetic Transformation of Grapevine Cells," *Plant Cell Reports,* 8:137–140 (1989), Colby et al., "Cellular Differences in Agrobacterium Susceptibility and Regenerative Capacity Restrict the Development of Transgenic Grapevines," *J. Am. Soc. Hort. Sci.,* 116:356–361 (1991), Guellec et al., "Agrobacterium-Rhizogenes Mediated Transformation of Grapevine *Vitis-Vinifera* 1, Agrobacterium-Rhizogenes Mediated Transformation of Grapevine *Vitis-Vinifera* 1," *Plant Cell Tissue Organ Cult.,* 20:211–216 (1990), Hebert et al., "Optimization of Biolistic Transformation of Embryogenic Grape Cell Suspensions," *Plant Cell Reports,* 12:585–589 (1993), Le Gall et al., "Agrobacterium-Mediated Genetic Transformation of Grapevine Somatic Embryos and Regeneration of Transgenic Plants Expressing the Coat Protein of Grapevine Chrome Mosaic Nepovirus (GCMV)," *Plant Science,*

102:161–170 (1994), Martinelli et al., "Genetic Transformation and Regeneration of Transgenic Plants in Grapevine (*Vitis Rupestris* S.)," *Theoretical and Applied Genetics*, 88:621–628 (1994), and Mullins et al., "Agrobacterium-Mediated Genetic Transformation of Grapevines: Transgenic Plants of *Vitis rupestris* Scheele and Buds of *Vitis vinifera* L.," *Bio/Technology*, 8:1041–1045 (1990), which are hereby incorporated by reference). Recently, an efficient regeneration system using proliferative somatic embryogenesis and subsequent plant development has been developed from zygotic embryos of stenospermic seedless grapes (Mozsar, J. et al., "A Rapid Method for Somatic Embryogenesis and Plant Regeneration from Cultured Anthers of *Vitis Riparia*," *Vitis*, 33:245–246 (1994), and Emerschad (1995), which are hereby incorporated by reference). Using this regeneration system, Scorza et al., "Transformation of Grape (*Vitis vinifera* L.) Zygotic-Derived Somatic Embryos and Regeneration of Transgenic Plants," *Plant Cell Reports*, 14:589–592 (1995) ("Scorza (1995)"), which is hereby incorporated by reference, succeeded in obtaining transgenic grapevines through zygotic-derived somatic embryos after particle-wounding/*A. tumefaciens* treatment. Using a Biolistic device, tiny embryos were shot with gold particles (1.0 μm in diameter). The wounded embryos were then co-cultivated with *A. tumefaciens* containing engineered plasmids carrying the selection marker of kanamycin resistance and β-glucuronidase ("GUS") genes. Selection of transgenic grapevines was carried out with 20 μg/ml kanamycin in the initial stage and then 40 μg/ml for later proliferation. Small rooted seedlings were obtained from embryogenic culture within 5 months of bombardment/*A. tumefaciens* (Scorza (1995), which is hereby incorporated by reference). Transgenic grapevines were analyzed by PCR and Southern hybridization, and shown to carry the transgenes. The above-mentioned grapevine transformation approach has been carried out in the current investigation to generate transgenic grapevines expressing GLRaV-3 genes. Evaluation of any potential leafroll resistance on transgenic grapevines may be carried out by insect vectors or grafting.

Example 19

Production of Antibodies Recognizing GLRaV3

The clone pCP10-1 which was shown to contain the major portion of the coat protein gene of GLRaV3 (FIG. 9) was used to express the coat protein and the β-galactosidase fusion protein. About 500 ml of LB medium containing 50 μg/ml of ampicilian was inoculated with a pCP10-1 single colony and incubated with rigorous shaking for overnight until log-phase growth. Expression of the fusion protein was further induced by the addition of 1 mM IPTG. Bacteria were harvested by centrifugation at 5,000 rpm for 10 min. The bacterial cell wall was broken by sonication. After low speed centrifugation to get rid of cell debris, the fusion protein was precipitated by the addition of saturated ammonium sulfate, then resuspended in PBS buffer and electrophoresced in a SDS-polyacrylamide gel ("SDS-PAGE"). The fusion protein band was excised after soaking the SDS-PAGE gel in 0.25M KCl to locate the protein band. The protein was eluted with buffer (0.05M Tris-HCl, pH7.9, 0.1% SDS, 0.1 mM EDT and 0.15M NaCl) and precipitated by trichoroacetic acid to a final concentration of 20%.

An antiserum was prepared by immunization of a rabbit with 0.5–1 mg of the purified protein emulsified with Freund's completed adjuvant followed by two more weekly injections of 0.5–1 mg protein emulsified with Freund's incomplete adjuvant. After the last injection, antisera were collected from blood taken from the rabbit every week for a period of 4 months.

On Western blot analysis, the antibody gave a specific reaction to the 41K protein from GLRaV3 infected tissue as well as to the fusion protein itself (50K) and generated a pattern similar to the pattern seen in FIG. 8. This antibody was also successfully used as a coating antibody and as an antibody-conjugate in enzyme linked immunosorbent assay ("ELISA").

The above method of producing antibody to GLRaV3 can also be applied to other gene sequences of the present invention. The method affords a large amount of highly purified protein from *E. coli* from which antibodies can be readily obtained. It is particularly useful in the common case where it is rather difficult to obtain sufficient amount of purified virus from GLRaV3 infected grapevine tissues.

Although the invention has been described in detail for the purpose of illustration, it is understood that such detail is solely for that purpose, and variations can be made therein by those skilled in the art without departing from the spirit and scope of the invention which is defined by the following claims.

SEQUENCE LISTING (1) GENERAL INFORMATION:

(iii) NUMBER OF SEQUENCES: 32

(2) INFORMATION FOR SEQ ID NO:1:

(i) SEQUENCE CHARACTERISTICS:
      (A) LENGTH: 4173 base pairs
      (B) TYPE: nucleic acid
      (C) STRANDEDNESS: single
      (D) TOPOLOGY: linear (ii) MOLECULE TYPE: cDNA (xi) SEQUENCE DESCRIPTION: SEQ ID NO:1:

```
GTGTCTACTT ACGCGAAGAG TGTGATGAAC GACAATTTCA ATATCCTTGA GACCCTGGTA     60
```

-continued

| | |
|---|---|
| ACTTTGCCCA AGTCCTTTAT AGTCAAAGTA CCTGGTTCGG TGCTGGTTAG CATAACCACT | 120 |
| TCGGGCATTT CCGACAAACT TGAACTTCGG GGCGCGTTCG ACGTTTCTAA AAAGAATTTC | 180 |
| TCCAGGAGGT TACGTTCGAG TCGTTTGCGC GTATTTTCTA GGGCTATTGT GGAGGATACG | 240 |
| ATCAAGGTTA TGAAGGGCAT GAAATCAGAG GATGGTAAAC CACTCCCTAT AGCCGAGGAT | 300 |
| TCCGTGTACG CGTTCATGAC AGGCAATATG TCAAACGTTC ATTGCACTAG GGCTGGTTTG | 360 |
| CTCGGGGGCT CAAAGGCTTG CGCGGCTTCT TTAGCTGTGA AGGGTGCAGC TTCACGCGCT | 420 |
| ACTGGAACAA AACTCTTTTC AGGTCTCACA TCCTTTCTTT CCGCCGGTGG TCTGTTTTAC | 480 |
| GATGAAGGCT TGACGCCCGG AGAGAGGCTT GATGCACTAA CGCGCCGTGA ACATGCTGTG | 540 |
| AATTCACCTG TAGGCCTCTT AGAACCTGGA GCTTCGGTTG CGAAGCGGGT CGTTTCCGGA | 600 |
| ACGAAAGCTT TTCTGTCAGA ATTGTCATTG GAGGACTTCA CCACTTTCGT CATAAAAAAT | 660 |
| AGGGTGCTTA TTGGTGTTTT TACTCTTTCC ATGGCTCTCA CTCCGGTGGT CTGGAAGTAC | 720 |
| AGAAGGAATA TCGCGCGAAC TGGCGTGGAT GTTTTCCACC GTGCTCGTTC GGGTACCGCG | 780 |
| GCCATCGGTT TACAATGTCT TAGTGGAGGA AGGTCGTTAG CTGGTGACGC TGCTCGTGGC | 840 |
| GCGTTAACAG TGACTCGAGG AGGGCTATCT TCGGCGGTTG CGGTGACCAG AAATACAGTG | 900 |
| GCTAGGCGTC AGGTACCATT GGCGTTGCTT TCGTTTTCCA CGTCTTACGC AGTCAGTGGT | 960 |
| TGCACTTTGT TAGGTATTTG GGCTCATGCT CTCCCTAGGC ATTTGATGTT CTTCTTTGGC | 1020 |
| CTAGGGACGC TCTTCGGGGT GAGTGCCAGT ACCAATTCTT GGTCGCTTGG GGGCTATACG | 1080 |
| AACAGTCTGT TCACCGTACC GGAATTAACT TGGGAAGGGA GGAGTTACAG ATCTTTATTG | 1140 |
| CCCCAAGCAG CTTTAGGTAT TTCTCTCGTT GTGCGCGGGT TGTTAAGTGA AACTGTGCCA | 1200 |
| CAACTAACGT ACGTACCGCC GATTGAAGGT CGGAATGTTT ATGATCAGGC ACTAAATTTT | 1260 |
| TATCGCGACT TTGACTATGA CGATGGTGCA GGCCCATCCG GGACGGCTGG TCAAAGCGAT | 1320 |
| CCTGGAACCA ATACTTCGGA TACTTCTTCG GTTTTCTCTG ACGATGGTTT GCCCGCTAGT | 1380 |
| GGCGGTGGCT TCGACGCGCG CGTTGAGGCA GGTCCCAGCC ATGCTGTTGA TGAATCACCA | 1440 |
| AGGGGTAGTG TTGAGTTCGT CTACAGAGAA CGTGTAGATG AACATCCGGC GTGTGGTGAA | 1500 |
| GCTGAAGTTG AAAAGGATCT AATAACACCA CTTGGTACAG CTGTCTTAGA GTCGCCCCCC | 1560 |
| GTAGGTCCTG AAGCTGGGAG CGCGCCCAAC GTCGAGGACG TTGTCCGGA GGTTGAAGCT | 1620 |
| GAGAAATGTT CGGAGGTCAT CGTTGACGTT CCTAGTTCAG AACCGCCGGT ACAAGAAGTC | 1680 |
| CTTGAATCAA CCAATGGTGT CCAAGCTGCA AGAACTGAAG AGGTTGTGCA GGGCGACACA | 1740 |
| TGTGGAGCTG GGGTAGCTAA ATCAGAAGTG AGTCAACGTG TGTTTCCTGC GCAAGTACCC | 1800 |
| GCACATGAAG CTGGTCTTGA GGCATCTAGT GGCGCGGTCG TGGAGCCATT GCAAGTTTCT | 1860 |
| GTGCCAGTAG CCGTAGAGAA AACTGTTTTA TCTGTCGAGA AGGCGCGTGA GCTAAAGGCG | 1920 |
| GTAGATAAGG GCAAGGCGGT CGTGCACGCA AAGGAAGTCA AGAATGTACC GGTTAAGACG | 1980 |
| TTACCACGAG GGGCTCTAAA AATTAGTGAG GATACCGTTC GTAAGGAATT GTGCATGTTT | 2040 |
| AGAACGTGTT CCTGCGGCGT GCAGTTGGAC GTGTACAATG AAGCGACCAT CGCCACTAGG | 2100 |
| TTCTCAAATG CGTTTACCTT TGTCGATAGC TTGAAAGGGA GGAGTGCGGT CTTTTTCTCA | 2160 |
| AAGCTGGGTG AGGGGTATAC CTATAATGGT GGTAGCCATG TTTCATCAGG GTGGCCTCGT | 2220 |
| GCCCTAGAGG ATATCTTAAC GGCAATTAAG TACCCAAGCG TCTTCGACCA CTGTTTAGTG | 2280 |
| CAGAAGTACA AGATGGGTGG AGGCGTACCA TTCCACGCTG ATGACGAGGA GTGCTATCCA | 2340 |
| TCAGATAACC CTATCTTGAC GGTCAATCTC GTGGGGAAGG CAAACTTCTC GACTAAGTGC | 2400 |
| AGGAAGGGTG GTAAGGTCAT GGTCATAAAC GTAGCTTCGG GTGACTATTT CTTATGCCT | 2460 |

-continued

```
TGCGGTTTTC AAAGGACGCA CTTGCATTCA GTAAACTCCA TCGACGAAGG GCGCATCAGT      2520

TTGACGTTCA GGGCAACTCG GCGCGTCTTT GGTGTAGGCA GGATGTTGCA GTTAGCCGGC      2580

GGCGTGTCGG ATGAGAAGTC ACCAGGTGTT CCAAACCAGC AACCACAGAG CCAAGGTGCT      2640

ACCAGAACAA TCACACCAAA ATCGGGGGGC AAGGCTCTAT CTGAGGGAAG TGGTAGGGAA      2700

GTCAAGGGGA GGTCGACATA CTCGATATGG TGCGAACAAG ATTACGTTAG GAAGTGTGAG      2760

TGGCTCAGGG CTGATAATCC AGTGATGGCT CTTAAACCTG GCTACACCCC AATGACATTT      2820

GAAGTGGTTA AAGCCGGGAC CTCTGAAGAT GCCGTCGTGG AGTACTTGAA GTATCTGGCT      2880

ATAGGCATTG GGAGGACATA CAGGGCGTTG CTTATGGCTA GAAATATTGC CGTCACTACC      2940

GCCGAAGGTG TTCTGAAAGT ACCTAATCAA GTTTATGAAT CACTACCGGG CTTTCACGTT      3000

TACAAGTCGG GCACAGATCT CATTTTTCAT TCAACACAAG ACGGCTTGCG TGTGAGAGAC      3060

CTACCGTACG TATTCATAGC TGAGAAAGGT ATTTTTATCA AGGGCAAAGA TGTCGACGCG      3120

GTAGTAGCTT TGGGCGACAA TCTGTCCGTA TGTGATGATA TATTGGTTTT CCATGATGCT      3180

ATTAATTTGA TGGGTGCACT GAAAGTTGCT CGATGTGGTA TGGTGGGTGA ATCATTTAAG      3240

TCGTTCGAAT ACAAATGCTA TAATGCTCCC CCAGGTGGCG GTAAGACGAC GATGCTAGTG      3300

GACGAATTTG TCAAGTCACC CAATAGCACG GCCACCATTA CGGCTAACGT GGGAAGTTCT      3360

GAGGACATAA ATATGGCGGT GAAGAAGAGA GATCCGAATT TGGAAGGTCT CAACAGTGCT      3420

ACCACAGTTA ACTCCAGGGT GGTTAACTTT ATTGTCAGGG GAATGTATAA AGGGTTTTG      3480

GTGGATGAGG TGTACATGAT GCATCAAGGC TTACTACAAC TAGGCGTCTT CGCAACCGGC      3540

GCGTCGGAAG GCCTCTTTTT TGGAGACATA AATCAGATAC CATTCATAAA CCGGGAGAAG      3600

GTGTTTAGGA TGGATTGTGC TGTATTTGTT CCAAAGAAGG AAAGCGTTGT ATACACTTCT      3660

AAATCATACA GGTGTCCGTT AGATGTTTGC TACTTGTTGT CCTCAATGAC CGTAAGGGGA      3720

ACGGAAAAGT GTTACCCTGA AAAGGTCGTT AGCGGTAAGG ACAAACCAGT AGTAAGATCG      3780

CTGTCCAAAA GGCCAATTGG AACCACTGAT GACGTAGCTG AAATAAACGC TGACGTGTAC      3840

TTGTGCATGA CCCAGTTGGA GAAGTCGGAT ATGAAGAGGT CGTTGAAGGG AAAAGGAAAA      3900

GAAACACCAG TGATGACAGT GCATGAAGCA CAGGGAAAAA CATTCAGTGA TGTGGTATTG      3960

TTTAGGACGA AGAAAGCCGA TGACTCCCTA TTCACTAAAC AACCGCATAT ACTTGTTGGT      4020

TTGTCGAGAC ACACACGCTC ACTGGTTTAT GCCGCTCTGA GCTCAGAGTT GGACGATAAG      4080

GTCGGCACAT ATATTAGCGA CGCGTCGCCT CAATCAGTAT CCGACGCTTT GCTTCACACG      4140

TTCGCCCCGG CTGGTTGCTT TCGAGGTATA TGA                                  4173
```

(2) INFORMATION FOR SEQ ID NO:2:

(i) SEQUENCE CHARACTERISTICS:
        (A) LENGTH: 1390 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:2:

```
Val Ser Thr Tyr Ala Lys Ser Val Met Asn Asp Asn Phe Asn Ile Leu
 1               5                  10                  15

Glu Thr Leu Val Thr Leu Pro Lys Ser Phe Ile Val Lys Val Pro Gly
             20                  25                  30

Ser Val Leu Val Ser Ile Thr Thr Ser Gly Ile Ser Asp Lys Leu Glu
         35                  40                  45
```

```
Leu Arg Gly Ala Phe Asp Val Ser Lys Lys Asn Phe Ser Arg Arg Leu
 50                  55                  60

Arg Ser Ser Arg Leu Arg Val Phe Ser Arg Ala Ile Val Glu Asp Thr
 65                  70                  75                  80

Ile Lys Val Met Lys Gly Met Lys Ser Glu Asp Gly Lys Pro Leu Pro
                 85                  90                  95

Ile Ala Glu Asp Ser Val Tyr Ala Phe Met Thr Gly Asn Met Ser Asn
                100                 105                 110

Val His Cys Thr Arg Ala Gly Leu Leu Gly Gly Ser Lys Ala Cys Ala
                115                 120                 125

Ala Ser Leu Ala Val Lys Gly Ala Ser Arg Ala Thr Gly Thr Lys
130                 135                 140

Leu Phe Ser Gly Leu Thr Ser Phe Leu Ser Ala Gly Gly Leu Phe Tyr
145                 150                 155                 160

Asp Glu Gly Leu Thr Pro Gly Glu Arg Leu Asp Ala Leu Thr Arg Arg
                165                 170                 175

Glu His Ala Val Asn Ser Pro Val Gly Leu Leu Glu Pro Gly Ala Ser
                180                 185                 190

Val Ala Lys Arg Val Ser Gly Thr Lys Ala Phe Leu Ser Glu Leu
                195                 200                 205

Ser Leu Glu Asp Phe Thr Thr Phe Val Ile Lys Asn Arg Val Leu Ile
210                 215                 220

Gly Val Phe Thr Leu Ser Met Ala Leu Thr Pro Val Val Trp Lys Tyr
225                 230                 235                 240

Arg Arg Asn Ile Ala Arg Thr Gly Val Asp Val Phe His Arg Ala Arg
                245                 250                 255

Ser Gly Thr Ala Ala Ile Gly Leu Gln Cys Leu Ser Gly Gly Arg Ser
                260                 265                 270

Leu Ala Gly Asp Ala Ala Arg Gly Ala Leu Thr Val Thr Arg Gly Gly
                275                 280                 285

Leu Ser Ser Ala Val Ala Val Thr Arg Asn Thr Val Ala Arg Arg Gln
290                 295                 300

Val Pro Leu Ala Leu Leu Ser Phe Ser Thr Ser Tyr Ala Val Ser Gly
305                 310                 315                 320

Cys Thr Leu Leu Gly Ile Trp Ala His Ala Leu Pro Arg His Leu Met
                325                 330                 335

Phe Phe Phe Gly Leu Gly Thr Leu Phe Gly Val Ser Ala Ser Thr Asn
                340                 345                 350

Ser Trp Ser Leu Gly Gly Tyr Thr Asn Ser Leu Phe Thr Val Pro Glu
                355                 360                 365

Leu Thr Trp Glu Gly Arg Ser Tyr Arg Ser Leu Leu Pro Gln Ala Ala
                370                 375                 380

Leu Gly Ile Ser Leu Val Val Arg Gly Leu Leu Ser Glu Thr Val Pro
385                 390                 395                 400

Gln Leu Thr Tyr Val Pro Pro Ile Glu Gly Arg Asn Val Tyr Asp Gln
                405                 410                 415

Ala Leu Asn Phe Tyr Arg Asp Phe Asp Tyr Asp Asp Gly Ala Gly Pro
                420                 425                 430

Ser Gly Thr Ala Gly Gln Ser Asp Pro Gly Thr Asn Thr Ser Asp Thr
                435                 440                 445

Ser Ser Val Phe Ser Asp Asp Gly Leu Pro Ala Ser Gly Gly Phe
450                 455                 460

Asp Ala Arg Val Glu Ala Gly Pro Ser His Ala Val Asp Glu Ser Pro
465                 470                 475                 480
```

```
Arg Gly Ser Val Glu Phe Val Tyr Arg Glu Arg Val Asp Glu His Pro
                485                 490                 495

Ala Cys Gly Glu Ala Glu Val Glu Lys Asp Leu Ile Thr Pro Leu Gly
            500                 505                 510

Thr Ala Val Leu Glu Ser Pro Pro Val Gly Pro Glu Ala Gly Ser Ala
            515                 520                 525

Pro Asn Val Glu Asp Gly Cys Pro Glu Val Glu Ala Glu Lys Cys Ser
530                 535                 540

Glu Val Ile Val Asp Val Pro Ser Ser Glu Pro Pro Val Gln Glu Val
545                 550                 555                 560

Leu Glu Ser Thr Asn Gly Val Gln Ala Ala Arg Thr Glu Glu Val Val
                565                 570                 575

Gln Gly Asp Thr Cys Gly Ala Gly Val Ala Lys Ser Glu Val Ser Gln
            580                 585                 590

Arg Val Phe Pro Ala Gln Val Pro Ala His Glu Ala Gly Leu Glu Ala
            595                 600                 605

Ser Ser Gly Ala Val Val Glu Pro Leu Gln Val Ser Val Pro Val Ala
            610                 615                 620

Val Glu Lys Thr Val Leu Ser Val Glu Lys Ala Arg Glu Leu Lys Ala
625                 630                 635                 640

Val Asp Lys Gly Lys Ala Val Val His Ala Lys Glu Val Lys Asn Val
                645                 650                 655

Pro Val Lys Thr Leu Pro Arg Gly Ala Leu Lys Ile Ser Glu Asp Thr
            660                 665                 670

Val Arg Lys Glu Leu Cys Met Phe Arg Thr Cys Ser Cys Gly Val Gln
            675                 680                 685

Leu Asp Val Tyr Asn Glu Ala Thr Ile Ala Thr Arg Phe Ser Asn Ala
690                 695                 700

Phe Thr Phe Val Asp Ser Leu Lys Gly Arg Ser Ala Val Phe Phe Ser
705                 710                 715                 720

Lys Leu Gly Glu Gly Tyr Thr Tyr Asn Gly Gly Ser His Val Ser Ser
                725                 730                 735

Gly Trp Pro Arg Ala Leu Glu Asp Ile Leu Thr Ala Ile Lys Tyr Pro
            740                 745                 750

Ser Val Phe Asp His Cys Leu Val Gln Lys Tyr Lys Met Gly Gly Gly
            755                 760                 765

Val Pro Phe His Ala Asp Asp Glu Glu Cys Tyr Pro Ser Asp Asn Pro
            770                 775                 780

Ile Leu Thr Val Asn Leu Val Gly Lys Ala Asn Phe Ser Thr Lys Cys
785                 790                 795                 800

Arg Lys Gly Gly Lys Val Met Val Ile Asn Val Ala Ser Gly Asp Tyr
                805                 810                 815

Phe Leu Met Pro Cys Gly Phe Gln Arg Thr His Leu His Ser Val Asn
            820                 825                 830

Ser Ile Asp Glu Gly Arg Ile Ser Leu Thr Phe Arg Ala Thr Arg Arg
            835                 840                 845

Val Phe Gly Val Gly Arg Met Leu Gln Leu Ala Gly Gly Val Ser Asp
850                 855                 860

Glu Lys Ser Pro Gly Val Pro Asn Gln Gln Pro Gln Ser Gln Gly Ala
865                 870                 875                 880

Thr Arg Thr Ile Thr Pro Lys Ser Gly Gly Lys Ala Leu Ser Glu Gly
                885                 890                 895
```

```
Ser Gly Arg Glu Val Lys Gly Arg Ser Thr Tyr Ser Ile Trp Cys Glu
            900                 905                 910

Gln Asp Tyr Val Arg Lys Cys Glu Trp Leu Arg Ala Asp Asn Pro Val
            915                 920                 925

Met Ala Leu Lys Pro Gly Tyr Thr Pro Met Thr Phe Glu Val Val Lys
            930                 935                 940

Ala Gly Thr Ser Glu Asp Ala Val Val Glu Tyr Leu Lys Tyr Leu Ala
945                 950                 955                 960

Ile Gly Ile Gly Arg Thr Tyr Arg Ala Leu Leu Met Ala Arg Asn Ile
            965                 970                 975

Ala Val Thr Thr Ala Glu Gly Val Leu Lys Val Pro Asn Gln Val Tyr
            980                 985                 990

Glu Ser Leu Pro Gly Phe His Val Tyr Lys Ser Gly Thr Asp Leu Ile
            995                 1000                1005

Phe His Ser Thr Gln Asp Gly Leu Arg Val Arg Asp Leu Pro Tyr Val
            1010                1015                1020

Phe Ile Ala Glu Lys Gly Ile Phe Ile Lys Gly Lys Asp Val Asp Ala
1025                1030                1035                1040

Val Val Ala Leu Gly Asp Asn Leu Ser Val Cys Asp Asp Ile Leu Val
            1045                1050                1055

Phe His Asp Ala Ile Asn Leu Met Gly Ala Leu Lys Val Ala Arg Cys
            1060                1065                1070

Gly Met Val Gly Glu Ser Phe Lys Ser Phe Glu Tyr Lys Cys Tyr Asn
            1075                1080                1085

Ala Pro Pro Gly Gly Lys Thr Thr Met Leu Val Asp Glu Phe Val
            1090                1095                1100

Lys Ser Pro Asn Ser Thr Ala Thr Ile Thr Ala Asn Val Gly Ser Ser
1105                1110                1115                1120

Glu Asp Ile Asn Met Ala Val Lys Lys Arg Asp Pro Asn Leu Glu Gly
            1125                1130                1135

Leu Asn Ser Ala Thr Thr Val Asn Ser Arg Val Val Asn Phe Ile Val
            1140                1145                1150

Arg Gly Met Tyr Lys Arg Val Leu Val Asp Glu Val Tyr Met Met His
            1155                1160                1165

Gln Gly Leu Leu Gln Leu Gly Val Phe Ala Thr Gly Ala Ser Glu Gly
            1170                1175                1180

Leu Phe Phe Gly Asp Ile Asn Gln Ile Pro Phe Ile Asn Arg Glu Lys
1185                1190                1195                1200

Val Phe Arg Met Asp Cys Ala Val Phe Val Pro Lys Lys Glu Ser Val
            1205                1210                1215

Val Tyr Thr Ser Lys Ser Tyr Arg Cys Pro Leu Asp Val Cys Tyr Leu
            1220                1225                1230

Leu Ser Ser Met Thr Val Arg Gly Thr Glu Lys Cys Tyr Pro Glu Lys
            1235                1240                1245

Val Val Ser Gly Lys Asp Lys Pro Val Val Arg Ser Leu Ser Lys Arg
            1250                1255                1260

Pro Ile Gly Thr Thr Asp Asp Val Ala Glu Ile Asn Ala Asp Val Tyr
1265                1270                1275                1280

Leu Cys Met Thr Gln Leu Glu Lys Ser Asp Met Lys Arg Ser Leu Lys
            1285                1290                1295

Gly Lys Gly Lys Glu Thr Pro Val Met Thr Val His Glu Ala Gln Gly
            1300                1305                1310

Lys Thr Phe Ser Asp Val Val Leu Phe Arg Thr Lys Lys Ala Asp Asp
            1315                1320                1325
```

```
         Ser Leu Phe Thr Lys Gln Pro His Ile Leu Val Gly Leu Ser Arg His
             1330                1335                1340

Thr Arg Ser Leu Val Tyr Ala Ala Leu Ser Ser Glu Leu Asp Asp Lys
         1345                1350                1355                1360

Val Gly Thr Tyr Ile Ser Asp Ala Ser Pro Gln Ser Val Ser Asp Ala
                         1365                1370                1375

Leu Leu His Thr Phe Ala Pro Ala Gly Cys Phe Arg Gly Ile
                     1380                1385                1390

(2) INFORMATION FOR SEQ ID NO:3:

(i) SEQUENCE CHARACTERISTICS:
        (A) LENGTH: 1602 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:3:

ATGAATTTTG GACCGACCTT CGAAGGGGAG TTGGTACGGA AGATACCAAC AAGTCATTTT     60

GTAGCCGTGA ATGGGTTTCT CGAGGACTTA CTCGACGGTT GTCCGGCTTT CGACTATGAC    120

TTCTTTGAGG ATGATTTCGA AACTTCAGAT CAGTCTTTCC TCATAGAAGA TGTGCGCATT    180

TCTGAATCTT TTTCTCATTT TGCGTCGAAA ATAGAGGATA GGTTTTACAG TTTTATTAGG    240

TCTAGCGTAG GTTTACCAAA GCGCAACACC TTGAAGTGTA ACCTCGTCAC GTTTGAAAAT    300

AGGAATTCCA ACGCCGATCG CGGTTGTAAC GTGGGTTGTG ACGACTCTGT GGCGCATGAA    360

CTGAAGGAGA TTTTCTTCGA GGAGGTCGTT AACAAAGCTC GTTTAGCAGA GGTGACGGAA    420

AGCCATTTGT CCAGCAACAC GATGTTGTTA TCAGATTGGT TGGACAAAAG GCACCTAAC    480

GCTTACAAGT CTCTCAAGCG GCTTTAGGT TCGGTTGTCT TTCATCCGTC TATGTTGACG    540

TCTTATACGC TCATGGTGAA AGCAGACGTA AAACCCAAGT TGGACAATAC GCCATTGTCG    600

AAGTACGTAA CGGGGCAGAA TATAGTCTAC ACGATAGGT GCGTAACTGC GCTTTTTTCT    660

TGCATTTTTA CTGCGTGCGT AGAGCGCTTA AAATACGTAG TGGACGAAAG GTGGCTCTTC    720

TACCACGGGA TGGACACTGC GGAGTTGGCG GCTGCATTGA GGAACAATTT GGGGGACATC    780

CGGCAATACT ACACCTATGA ACTGGATATC AGTAAGTACG ACAAATCTCA GAGTGCTCTC    840

ATGAAGCAGG TGGAGGAGTT GATACTCTTG ACACTTGGTG TTGATAGAGA AGTTTTGTCT    900

ACTTTCTTTT GTGGTGAGTA TGATAGCGTC GTGAGAACGA TGACGAAGGA ATTGGTGTTG    960

TCTGTCGGCT CTCAGAGGCG CAGTGGTGGT GCTAACACGT GGTTGGGAAA TAGTTTAGTC   1020

TTGTGCACCT TGTTGTCCGT AGTACTTAGG GGATTAGATT ATAGTTATAT TGTAGTTAGC   1080

GGTGATGATA GCCTTATATT TAGTCGGCAG CCGTTGGATA TTGATACGTC GGTTCTGAGC   1140

GATAATTTTG GTTTTGACGT AAAGATTTTT AACCAAGCTG CTCCATATTT TTGTTCTAAG   1200

TTTTTAGTTC AAGTCGAGGA TAGTCTCTTT TTTGTTCCCG ATCCACTTAA ACTCTTCGTT   1260

AAGTTTGGAG CTTCCAAAAC TTCAGATATC GACCTTTTAC ATGAGATTTT TCAATCTTTC   1320

GTCGATCTTT CGAAGGGTTT CAATAGAGAG GACGTCATCC AGGAATTAGC TAAGCTGGTG   1380

ACGCGGAAAT ATAAGCATTC GGGATGGACC TACTCGGCTT TGTGTGTCTT GCACGTTTTA   1440

AGTGCAAATT TTTCGCAGTT CTGTAGGTTA TATTACCACA ATAGCGTGAA TCTCGATGTG   1500

CGCCCTATTC AGAGGACCGA GTCGCTTTCC TTGCTGGCCT TGAAGGCAAG AATTTTAAGG   1560

TGGAAAGCTT CTCGTTTTGC CTTTTCGATA AAGAGGGGTT AA                      1602
```

(2) INFORMATION FOR SEQ ID NO:4:

(i) SEQUENCE CHARACTERISTICS:
        (A) LENGTH: 533 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:4:

```
Met Asn Phe Gly Pro Thr Phe Glu Gly Glu Leu Val Arg Lys Ile Pro
 1               5                  10                  15

Thr Ser His Phe Val Ala Val Asn Gly Phe Leu Glu Asp Leu Leu Asp
                20                  25                  30

Gly Cys Pro Ala Phe Asp Tyr Asp Phe Phe Glu Asp Asp Phe Glu Thr
                35                  40                  45

Ser Asp Gln Ser Phe Leu Ile Glu Asp Val Arg Ile Ser Glu Ser Phe
50                  55                  60

Ser His Phe Ala Ser Lys Ile Glu Asp Arg Phe Tyr Ser Phe Ile Arg
65                  70                  75                  80

Ser Ser Val Gly Leu Pro Lys Arg Asn Thr Leu Lys Cys Asn Leu Val
                85                  90                  95

Thr Phe Glu Asn Arg Asn Ser Asn Ala Asp Arg Gly Cys Asn Val Gly
               100                 105                 110

Cys Asp Asp Ser Val Ala His Glu Leu Lys Glu Ile Phe Phe Glu Glu
               115                 120                 125

Val Val Asn Lys Ala Arg Leu Ala Glu Val Thr Glu Ser His Leu Ser
130                 135                 140

Ser Asn Thr Met Leu Leu Ser Asp Trp Leu Asp Lys Arg Ala Pro Asn
145                 150                 155                 160

Ala Tyr Lys Ser Leu Lys Arg Ala Leu Gly Ser Val Val Phe His Pro
                165                 170                 175

Ser Met Leu Thr Ser Tyr Thr Leu Met Val Lys Ala Asp Val Lys Pro
                180                 185                 190

Lys Leu Asp Asn Thr Pro Leu Ser Lys Tyr Val Thr Gly Gln Asn Ile
                195                 200                 205

Val Tyr His Asp Arg Cys Val Thr Ala Leu Phe Ser Cys Ile Phe Thr
210                 215                 220

Ala Cys Val Glu Arg Leu Lys Tyr Val Val Asp Glu Arg Trp Leu Phe
225                 230                 235                 240

Tyr His Gly Met Asp Thr Ala Glu Leu Ala Ala Ala Leu Arg Asn Asn
                245                 250                 255

Leu Gly Asp Ile Arg Gln Tyr Tyr Thr Tyr Glu Leu Asp Ile Ser Lys
                260                 265                 270

Tyr Asp Lys Ser Gln Ser Ala Leu Met Lys Gln Val Glu Glu Leu Ile
                275                 280                 285

Leu Leu Thr Leu Gly Val Asp Arg Glu Val Leu Ser Thr Phe Phe Cys
290                 295                 300

Gly Glu Tyr Asp Ser Val Val Arg Thr Met Thr Lys Glu Leu Val Leu
305                 310                 315                 320

Ser Val Gly Ser Gln Arg Arg Ser Gly Ala Asn Thr Trp Leu Gly
                325                 330                 335

Asn Ser Leu Val Leu Cys Thr Leu Ser Val Val Leu Arg Gly Leu
                340                 345                 350
```

```
          Asp Tyr Ser Tyr Ile Val Val Ser Gly Asp Asp Ser Leu Ile Phe Ser
                  355                 360                 365

Arg Gln Pro Leu Asp Ile Asp Thr Ser Val Leu Ser Asp Asn Phe Gly
              370                 375                 380

Phe Asp Val Lys Ile Phe Asn Gln Ala Ala Pro Tyr Phe Cys Ser Lys
          385                 390                 395                 400

Phe Leu Val Gln Val Glu Asp Ser Leu Phe Val Pro Asp Pro Leu
                              405                 410                 415

Lys Leu Phe Val Lys Phe Gly Ala Ser Lys Thr Ser Asp Ile Asp Leu
                      420                 425                 430

Leu His Glu Ile Phe Gln Ser Phe Val Asp Leu Ser Lys Gly Phe Asn
                  435                 440                 445

Arg Glu Asp Val Ile Gln Glu Leu Ala Lys Leu Val Thr Arg Lys Tyr
              450                 455                 460

Lys His Ser Gly Trp Thr Tyr Ser Ala Leu Cys Val Leu His Val Leu
          465                 470                 475                 480

Ser Ala Asn Phe Ser Gln Phe Cys Arg Leu Tyr Tyr His Asn Ser Val
                              485                 490                 495

Asn Leu Asp Val Arg Pro Ile Gln Arg Thr Glu Ser Leu Ser Leu Leu
                          500                 505                 510

Ala Leu Lys Ala Arg Ile Leu Arg Trp Lys Ala Ser Arg Phe Ala Phe
                      515                 520                 525

Ser Ile Lys Arg Gly
                  530

(2) INFORMATION FOR SEQ ID NO:5:

(i) SEQUENCE CHARACTERISTICS:
          (A) LENGTH: 1650 base pairs
          (B) TYPE: nucleic acid
          (C) STRANDEDNESS: single
          (D) TOPOLOGY: linear (ii) MOLECULE TYPE: cDNA (xi) SEQUENCE DESCRIPTION: SEQ ID NO:5:

ATGGAAGTAG GTATAGATTT TGGAACCACT TTCAGCACAA TCTGCTTTTC CCCATCTGGG        60

GTCAGCGGTT GTACTCCTGT GGCCGGTAGT GTTTACGTTG AAACCCAAAT TTTTATACCT       120

GAAGGTAGCA GTACTTACTT AATTGGTAAA GCTGCGGGGA AAGCTTATCG TGACGGTGTA       180

GAGGGAAGGT TGTATGTTAA CCCGAAAAGG TGGGCAGGTG TGACGAGGGA TAACGTCGAA       240

CGCTACGTCG AGAAATTAAA ACCTACATAC ACCGTGAAGA TAGACAGCGG AGGCGCCTTA       300

TTAATTGGAG GTTTAGGTTC CGGACCAGAC ACCTTATTGA GGGTCGTTGA CGTAATATGT       360

TTATTCTTGA GAGCCTTGAT ACTGGAGTGC GAAAGGTATA CGTCTACGAC GGTTACAGCA       420

GCTGTTGTAA CGGTACCGGC TGACTATAAC TCCTTTAAAC GAAGCTTCGT TGTTGAGGCG       480

CTAAAAGGTC TTGGTATACC GGTTAGAGGT GTTGTAACG AACCGACGGC CGCAGCCCTC        540

TATTCCTTAG CTAAGTCGCG AGTAGAAGAC CTATTATTAC GGTTTTTGA TTTTGGGGGA        600

GGGACTTTCG ACGTCTCATT CGTTAAGAAG AAGGGAAATA TACTATGCGT CATCTTTTCA       660

GTGGGTGATA ATTTCTTGGG TGGTAGAGAT ATTGATAGAG CTATCGTGGA AGTTATCAAA       720

CAAAAGATCA AGGAAAGGC GTCTGATGCC AAGTTAGGGA TATTCGTATC CTCGATGAAG        780

GAAGACTTGT CTAACAATAA CGCTATAACG CAACACCTTA TCCCCGTAGA AGGGGGTGTG       840

GAGGTTGTGG ATTTGACTAG CGACGAACTG GACGCAATCG TTGCACCATT CAGCGCTAGG      900

GCTGTGGAAG TATTCAAAAC TGGTCTTGAC AACTTTTACC CAGACCCGGT TATTGCCGTT       960
```

```
ATGACTGGGG GGTCAAGTGC TCTAGTTAAG GTCAGGAGTG ATGTGGCTAA TTTGCCGCAG    1020

ATATCTAAAG TCGTGTTCGA CAGTACCGAT TTTAGATGTT CGGTGGCTTG TGGGGCTAAG    1080

GTTTACTGCG ATACTTTGGC AGGTAATAGC GGACTGAGAC TGGTGGACAC TTTAACGAAT    1140

ACGCTAACGG ACGAGGTAGT GGGTCTTCAG CCGGTGGTAA TTTTCCCGAA AGGTAGTCCA    1200

ATACCCTGTT CATATACTCA TAGATACACA GTGGGTGGTG GAGATGTGGT ATACGGTATA    1260

TTTGAAGGGG AGAATAACAG AGCTTTTCTA AATGAGCCGA CGTTCCGGGG CGTATCGAAA    1320

CGTAGGGGAG ACCCAGTAGA GACCGACGTG GCGCAGTTTA ATCTCTCCAC GGACGGAACG    1380

GTGTCTGTTA TCGTTAATGG TGAGGAAGTA AAGAATGAAT ATCTGGTACC CGGGACAACA    1440

AACGTACTGG ATTCATTGGT CTATAAATCT GGGAGAGAAG ATTTAGAGGC TAAGGCAATA    1500

CCAGAGTACT TGACCACACT GAATATTTTG CACGATAAGG CTTTCACGAG GAGAAACCTG    1560

GGTAACAAAG ATAAGGGGTT CTCGGATTTA AGGATAGAAG AAAATTTTTT AAAATCCGCC    1620

GTAGATACAG ACACGATTTT GAATGGATAA                                    1650

(2) INFORMATION FOR SEQ ID NO:6:

(i) SEQUENCE CHARACTERISTICS:
        (A) LENGTH: 549 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:6:

Met Glu Val Gly Ile Asp Phe Gly Thr Thr Phe Ser Thr Ile Cys Phe
    1               5                   10                  15

Ser Pro Ser Gly Val Ser Gly Cys Thr Pro Val Ala Gly Ser Val Tyr
                20                  25                  30

Val Glu Thr Gln Ile Phe Ile Pro Glu Gly Ser Ser Thr Tyr Leu Ile
                35                  40                  45

Gly Lys Ala Ala Gly Lys Ala Tyr Arg Asp Gly Val Glu Gly Arg Leu
    50                  55                  60

Tyr Val Asn Pro Lys Arg Trp Ala Gly Val Thr Arg Asp Asn Val Glu
    65                  70                  75                  80

Arg Tyr Val Glu Lys Leu Lys Pro Thr Tyr Thr Val Lys Ile Asp Ser
                    85                  90                  95

Gly Gly Ala Leu Leu Ile Gly Gly Leu Gly Ser Gly Pro Asp Thr Leu
                100                 105                 110

Leu Arg Val Val Asp Val Ile Cys Leu Phe Leu Arg Ala Leu Ile Leu
                115                 120                 125

Glu Cys Glu Arg Tyr Thr Ser Thr Thr Val Thr Ala Ala Val Val Thr
    130                 135                 140

Val Pro Ala Asp Tyr Asn Ser Phe Lys Arg Ser Phe Val Val Glu Ala
    145                 150                 155                 160

Leu Lys Gly Leu Gly Ile Pro Val Arg Gly Val Val Asn Glu Pro Thr
                    165                 170                 175

Ala Ala Ala Leu Tyr Ser Leu Ala Lys Ser Arg Val Glu Asp Leu Leu
                180                 185                 190

Leu Ala Val Phe Asp Phe Gly Gly Gly Thr Phe Asp Val Ser Phe Val
                195                 200                 205

Lys Lys Lys Gly Asn Ile Leu Cys Val Ile Phe Ser Val Gly Asp Asn
                210                 215                 220
```

```
Phe Leu Gly Gly Arg Asp Ile Asp Arg Ala Ile Val Glu Val Ile Lys
225                 230                 235                 240

Gln Lys Ile Lys Gly Lys Ala Ser Asp Ala Lys Leu Gly Ile Phe Val
            245                 250                 255

Ser Ser Met Lys Glu Asp Leu Ser Asn Asn Ala Ile Thr Gln His
            260                 265                 270

Leu Ile Pro Val Glu Gly Gly Val Glu Val Val Asp Leu Thr Ser Asp
        275                 280                 285

Glu Leu Asp Ala Ile Val Ala Pro Phe Ser Ala Arg Ala Val Glu Val
    290                 295                 300

Phe Lys Thr Gly Leu Asp Asn Phe Tyr Pro Asp Pro Val Ile Ala Val
305                 310                 315                 320

Met Thr Gly Gly Ser Ser Ala Leu Val Lys Val Arg Ser Asp Val Ala
                325                 330                 335

Asn Leu Pro Gln Ile Ser Lys Val Val Phe Asp Ser Thr Asp Phe Arg
            340                 345                 350

Cys Ser Val Ala Cys Gly Ala Lys Val Tyr Cys Asp Thr Leu Ala Gly
            355                 360                 365

Asn Ser Gly Leu Arg Leu Val Asp Thr Leu Thr Asn Thr Leu Thr Asp
370                 375                 380

Glu Val Val Gly Leu Gln Pro Val Ile Phe Pro Lys Gly Ser Pro
385                 390                 395                 400

Ile Pro Cys Ser Tyr Thr His Arg Tyr Thr Val Gly Gly Asp Val
            405                 410                 415

Val Tyr Gly Ile Phe Glu Gly Glu Asn Asn Arg Ala Phe Leu Asn Glu
            420                 425                 430

Pro Thr Phe Arg Gly Val Ser Lys Arg Gly Asp Pro Val Glu Thr
            435                 440                 445

Asp Val Ala Gln Phe Asn Leu Ser Thr Asp Gly Thr Val Ser Val Ile
450                 455                 460

Val Asn Gly Glu Glu Val Lys Asn Glu Tyr Leu Val Pro Gly Thr Thr
465                 470                 475                 480

Asn Val Leu Asp Ser Leu Val Tyr Lys Ser Gly Arg Glu Asp Leu Glu
            485                 490                 495

Ala Lys Ala Ile Pro Glu Tyr Leu Thr Thr Leu Asn Ile Leu His Asp
            500                 505                 510

Lys Ala Phe Thr Arg Arg Asn Leu Gly Asn Lys Asp Lys Gly Phe Ser
            515                 520                 525

Asp Leu Arg Ile Glu Glu Asn Phe Leu Lys Ser Ala Val Asp Thr Asp
        530                 535                 540

Thr Ile Leu Asn Gly
545
```

(2) INFORMATION FOR SEQ ID NO:7:

(i) SEQUENCE CHARACTERISTICS:
        (A) LENGTH: 1452 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:7:

```
ATGGATAAAT ATATTTATGT AACGGGGATA TTAAACCCTA ACGAGGCTAG AGACGAGGTA        60

TTCTCGGTAG TGAATAAGGG ATATATTGGA CCGGGAGGGC GCTCCTTTTC GAATCGTGGT       120
```

```
AGTAAGTACA CCGTCGTCTG GGAAAACTCT GCTGCGAGGA TTAGTGGATT TACGTCGACT    180

TCGCAATCTA CGATAGATGC TTTCGCGTAT TTCTTGTTGA AAGGCGGATT GACTACCACG    240

CTCTCTAACC CAATAAACTG TGAGAATTGG GTCAGGTCAT CTAAGGATTT AAGCGCGTTT    300

TTCAGGACCC TAATTAAAGG TAAGATTTAT GCATCGCGTT CTGTGGACAG CAATCTTCCA    360

AAGAAAGACA GGGATGACAT CATGGAAGCG AGTCGACGAC TATCGCCATC GGACGCCGCC    420

TTTTGCAGAG CAGTGTCGGT TCAGGTAGGG AAGTATGTGG ACGTAACGCA GAATTTAGAA    480

AGTACGATCG TGCCGTTAAG AGTTATGGAA ATAAAGAAAA GACGAGGATC AGCACATGTT    540

AGTTTACCGA AGGTGGTATC CGCTTACGTA GATTTTTATA CGAACTTGCA GGAATTGCTG    600

TCGGATGAAG TAACTAGGGC CAGAACCGAT ACAGTTTCGG CATACGCTAC CGACTCTATG    660

GCTTTCTTAG TTAAGATGTT ACCCCTGACT GCTCGTGAGC AGTGGTTAAA AGACGTGCTA    720

GGATATCTGC TGGTACGGAG ACGACCAGCA AATTTTTCCT ACGACGTAAG AGTAGCTTGG    780

GTATATGACG TGATCGCTAC GCTCAAGCTG GTCATAAGAT TGTTTTTCAA CAAGGACACA    840

CCCGGGGGTA TTAAAGACTT AAAACCGTGT GTGCCTATAG AGTCATTCGA CCCCTTTCAC    900

GAGCTTTCGT CCTATTTCTC TAGGTTAAGT TACGAGATGA CGACAGGTAA AGGGGGAAAG    960

ATATGCCCGG AGATCGCCGA GAAGTTGGTG CGCCGTCTAA TGGAGGAAAA CTATAAGTTA   1020

AGATTGACCC CAGTGATGGC CTTAATAATT ATACTGGTAT ACTACTCCAT TTACGGCACA   1080

AACGCTACCA GGATTAAAAG ACGCCCGGAT TTCCTCAATG TGAGGATAAA GGGAAGAGTC   1140

GAGAAGGTTT CGTTACGGGG GGTAGAAGAT CGTGCCTTTA GAATATCAGA AAAGCGCGGG   1200

ATAAACGCTC AACGTGTATT ATGTAGGTAC TATAGCGATC TCACATGTCT GGCTAGGCGA   1260

CATTACGGCA TTCGCAGGAA CAATTGGAAG ACGCTGAGTT ATGTAGACGG GACGTTAGCG   1320

TATGACACGG CTGATTGTAT AACTTCTAAG GTGAGAAATA CGATCAACAC CGCAGATCAC   1380

GCTAGCATTA TACACTATAT CAAGACGAAC GAAAACCAGG TTACCGAAAC TACTCTACCA   1440

CACCAGCTTT AA                                                      1452
```

(2) INFORMATION FOR SEQ ID NO:8:

(i) SEQUENCE CHARACTERISTICS:
        (A) LENGTH: 483 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:8:

```
Met Asp Lys Tyr Ile Tyr Val Thr Gly Ile Leu Asn Pro Asn Glu Ala
1               5                   10                  15

Arg Asp Glu Val Phe Ser Val Val Asn Lys Gly Tyr Ile Gly Pro Gly
            20                  25                  30

Gly Arg Ser Phe Ser Asn Arg Gly Ser Lys Tyr Thr Val Val Trp Glu
        35                  40                  45

Asn Ser Ala Ala Arg Ile Ser Gly Phe Thr Ser Thr Ser Gln Ser Thr
    50                  55                  60

Ile Asp Ala Phe Ala Tyr Phe Leu Leu Lys Gly Gly Leu Thr Thr Thr
65                  70                  75                  80

Leu Ser Asn Pro Ile Asn Cys Glu Asn Trp Val Arg Ser Ser Lys Asp
                85                  90                  95

Leu Ser Ala Phe Phe Arg Thr Leu Ile Lys Gly Lys Ile Tyr Ala Ser
            100                 105                 110
```

```
Arg Ser Val Asp Ser Asn Leu Pro Lys Lys Asp Arg Asp Asp Ile Met
        115                 120                 125

Glu Ala Ser Arg Arg Leu Ser Pro Ser Asp Ala Ala Phe Cys Arg Ala
130                 135                 140

Val Ser Val Gln Val Gly Lys Tyr Val Asp Val Thr Gln Asn Leu Glu
145                 150                 155                 160

Ser Thr Ile Val Pro Leu Arg Val Met Glu Ile Lys Lys Arg Arg Gly
                165                 170                 175

Ser Ala His Val Ser Leu Pro Lys Val Val Ser Ala Tyr Val Asp Phe
            180                 185                 190

Tyr Thr Asn Leu Gln Glu Leu Leu Ser Asp Glu Val Thr Arg Ala Arg
        195                 200                 205

Thr Asp Thr Val Ser Ala Tyr Ala Thr Asp Ser Met Ala Phe Leu Val
210                 215                 220

Lys Met Leu Pro Leu Thr Ala Arg Glu Gln Trp Leu Lys Asp Val Leu
225                 230                 235                 240

Gly Tyr Leu Leu Val Arg Arg Pro Ala Asn Phe Ser Tyr Asp Val
                245                 250                 255

Arg Val Ala Trp Val Tyr Asp Val Ile Ala Thr Leu Lys Leu Val Ile
                260                 265                 270

Arg Leu Phe Phe Asn Lys Asp Thr Pro Gly Gly Ile Lys Asp Leu Lys
        275                 280                 285

Pro Cys Val Pro Ile Glu Ser Phe Asp Pro Phe His Glu Leu Ser Ser
290                 295                 300

Tyr Phe Ser Arg Leu Ser Tyr Glu Met Thr Thr Gly Lys Gly Gly Lys
305                 310                 315                 320

Ile Cys Pro Glu Ile Ala Glu Lys Leu Val Arg Arg Leu Met Glu Glu
                325                 330                 335

Asn Tyr Lys Leu Arg Leu Thr Pro Val Met Ala Leu Ile Ile Ile Leu
                340                 345                 350

Val Tyr Tyr Ser Ile Tyr Gly Thr Asn Ala Thr Arg Ile Lys Arg Arg
            355                 360                 365

Pro Asp Phe Leu Asn Val Arg Ile Lys Gly Arg Val Glu Lys Val Ser
        370                 375                 380

Leu Arg Gly Val Glu Asp Arg Ala Phe Arg Ile Ser Glu Lys Arg Gly
385                 390                 395                 400

Ile Asn Ala Gln Arg Val Leu Cys Arg Tyr Tyr Ser Asp Leu Thr Cys
                405                 410                 415

Leu Ala Arg Arg His Tyr Gly Ile Arg Arg Asn Asn Trp Lys Thr Leu
                420                 425                 430

Ser Tyr Val Asp Gly Thr Leu Ala Tyr Asp Thr Ala Asp Cys Ile Thr
            435                 440                 445

Ser Lys Val Arg Asn Thr Ile Asn Thr Ala Asp His Ala Ser Ile Ile
        450                 455                 460

His Tyr Ile Lys Thr Asn Glu Asn Gln Val Thr Gly Thr Thr Leu Pro
465                 470                 475                 480

His Gln Leu
```

(2) INFORMATION FOR SEQ ID NO:9:

(i) SEQUENCE CHARACTERISTICS:
        (A) LENGTH: 942 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:9:

```
ATGGCATTTG AACTGAAATT AGGGCAGATA TATGAAGTCG TCCCCGAAAA TAATTTGAGA      60

GTTAGAGTGG GGGATGCGGC ACAAGGAAAA TTTAGTAAGG CGAGTTTCTT AAAGTACGTT     120

AAGGACGGGA CACAGGCGGA ATTAACGGGA ATCGCCGTAG TGCCCGAAAA ATACGTATTC     180

GCCACAGCAG CTTTGGCTAC AGCGGCGCAG GAGCCACCTA GGCAGCCACC AGCGCAAGTG     240

GCGGAACCAC AGGAAACCGA TATAGGGGTA GTGCCGGAAT CTGAGACTCT CACACCAAAT     300

AAGTTGGTTT TCGAGAAAGA TCCAGACAAG TTCTTGAAGA CTATGGGCAA GGGAATAGCT     360

TTGGACTTGG CGGGAGTTAC CCACAAACCG AAAGTTATTA ACGAGCCAGG GAAAGTATCA     420

GTAGAGGTGG CAATGAAGAT TAATGCCGCA TTGATGGAGC TGTGTAAGAA GGTTATGGGC     480

GCCGATGACG CAGCAACTAA GACAGAATTC TTCTTGTACG TGATGCAGAT TGCTTGCACG     540

TTCTTTACAT CGTCTTCGAC GGAGTTCAAA GAGTTTGACT ACATAGAAAC CGATGATGGA     600

AAGAAGATAT ATGCGGTGTG GGTATATGAT TGCATTAAAC AAGCTGCTGC TTCGACGGGT     660

TATGAAAACC CGGTAAGGCA GTATCTAGCG TACTTCACAC CAACCTTCAT CACGGCGACC     720

CTGAATGGTA AACTAGTGAT GAACGAGAAG GTTATGGCAC AGCATGGAGT ACCACCGAAA     780

TTCTTTCCGT ACACGATAGA CTGCGTTCGT CCGACGTACG ATCTGTTCAA CAACGACGCA     840

ATATTAGCAT GGAATTTAGC TAGACAGCAG GCGTTTAGAA ACAAGACGGT AACGGCCGAT     900

AACACCTTAC ACAACGTCTT CCAACTATTG CAAAAGAAGT AG                        942
```

(2) INFORMATION FOR SEQ ID NO:10:

(i) SEQUENCE CHARACTERISTICS:
      (A) LENGTH: 313 amino acids
      (B) TYPE: amino acid
      (C) STRANDEDNESS:
      (D) TOPOLOGY: linear (ii) MOLECULE TYPE: protein (xi) SEQUENCE DESCRIPTION: SEQ ID NO:10:

```
Met Ala Phe Glu Leu Lys Leu Gly Gln Ile Tyr Glu Val Val Pro Glu
 1               5                  10                  15

Asn Asn Leu Arg Val Arg Val Gly Asp Ala Ala Gln Gly Lys Phe Ser
             20                  25                  30

Lys Ala Ser Phe Leu Lys Tyr Val Lys Asp Gly Thr Gln Ala Glu Leu
         35                  40                  45

Thr Gly Ile Ala Val Val Pro Glu Lys Tyr Val Phe Ala Thr Ala Ala
     50                  55                  60

Leu Ala Thr Ala Ala Gln Glu Pro Pro Arg Gln Pro Pro Ala Gln Val
 65                  70                  75                  80

Ala Glu Pro Gln Glu Thr Asp Ile Gly Val Val Pro Glu Ser Glu Thr
                 85                  90                  95

Leu Thr Pro Asn Lys Leu Val Phe Glu Lys Asp Pro Asp Lys Phe Leu
            100                 105                 110

Lys Thr Met Gly Lys Gly Ile Ala Leu Asp Leu Ala Gly Val Thr His
        115                 120                 125

Lys Pro Lys Val Ile Asn Glu Pro Gly Lys Val Ser Val Glu Val Ala
    130                 135                 140

Met Lys Ile Asn Ala Ala Leu Met Glu Leu Cys Lys Lys Val Met Gly
145                 150                 155                 160
```

```
    Ala Asp Asp Ala Ala Thr Lys Thr Glu Phe Phe Leu Tyr Val Met Gln
                    165                 170                 175

Ile Ala Cys Thr Phe Phe Thr Ser Ser Thr Glu Phe Lys Glu Phe
                180                 185                 190

Asp Tyr Ile Glu Thr Asp Asp Gly Lys Lys Ile Tyr Ala Val Trp Val
                    195                 200                 205

Tyr Asp Cys Ile Lys Gln Ala Ala Ser Thr Gly Tyr Glu Asn Pro
    210                 215                 220

Val Arg Gln Tyr Leu Ala Tyr Phe Thr Pro Thr Phe Ile Thr Ala Thr
    225                 230                 235                 240

Leu Asn Gly Lys Leu Val Met Asn Glu Lys Val Met Ala Gln His Gly
                    245                 250                 255

Val Pro Pro Lys Phe Phe Pro Tyr Thr Ile Asp Cys Val Arg Pro Thr
                    260                 265                 270

Tyr Asp Leu Phe Asn Asn Asp Ala Ile Leu Ala Trp Asn Leu Ala Arg
                    275                 280                 285

Gln Gln Ala Phe Arg Asn Lys Thr Val Thr Ala Asp Asn Thr Leu His
                    290                 295                 300

Asn Val Phe Gln Leu Leu Gln Lys Lys
    305                 310
```

(2) INFORMATION FOR SEQ ID NO:11:

(i) SEQUENCE CHARACTERISTICS:
        (A) LENGTH: 156 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:11:

```
ATGTACAGTA GAGGGTCTTT CTTTAAGTCT CGGGTTACCC TTCCTACTCT TGTCGGAGCA    60

TACATGTGGG AGTTTGAACT CCCGTATCTT ACGGACAAGA GACACATCAG CTATAGCGCG   120

CCAAGTGTCG CGACTTTTAG CCTTGTGTCG AGGTAG                             156
```

(2) INFORMATION FOR SEQ ID NO:12:

(i) SEQUENCE CHARACTERISTICS:
        (A) LENGTH: 51 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:12:

```
    Met Tyr Ser Arg Gly Ser Phe Phe Lys Ser Arg Val Thr Leu Pro Thr
    1               5                   10                  15

Leu Val Gly Ala Tyr Met Trp Glu Phe Glu Leu Pro Tyr Leu Thr Asp
                    20                  25                  30

Lys Arg His Ile Ser Tyr Ser Ala Pro Ser Val Ala Thr Phe Ser Leu
                    35                  40                  45

Val Ser Arg
        50
```

(2) INFORMATION FOR SEQ ID NO:13:

(i) SEQUENCE CHARACTERISTICS:
        (A) LENGTH: 138 base pairs
        (B) TYPE: nucleic acid (C) STRANDEDNESS: single
            (D) TOPOLOGY: linear (ii) MOLECULE TYPE: cDNA (xi) SEQUENCE DESCRIPTION: SEQ ID NO:13:

ATGGATGATT TTAAACAGGC AATACTGTTG CTAGTAGTCG ATTTTGTCTT CGTGATAATT        60

CTGCTGCTGG TTCTTACGTT CGTCGTCCCG AGGTTACAGC AAAGCTCCAC CATTAATACA       120

GGTCTTAGGA CAGTGTGA                                                    138

(2) INFORMATION FOR SEQ ID NO:14:

(i) SEQUENCE CHARACTERISTICS:
        (A) LENGTH: 45 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:14:

Met Asp Asp Phe Lys Gln Ala Ile Leu Leu Val Val Asp Phe Val
    1               5                  10                  15

Phe Val Ile Ile Leu Leu Leu Val Leu Thr Phe Val Val Pro Arg Leu
                    20                  25                  30

Gln Gln Ser Ser Thr Ile Asn Thr Gly Leu Arg Thr Val
            35                  40                  45

(2) INFORMATION FOR SEQ ID NO:15:

(i) SEQUENCE CHARACTERISTICS:
        (A) LENGTH: 1434 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:15:

ATGGGAGCTT ATACACATGT AGACTTTCAT GAGTCGCGGT TGCTGAAAGA CAAACAAGAC        60

TATCTTTCTT TCAAGTCAGC GGATGAAGCT CCTCCTGATC CTCCCGGATA CGTTCGCCCA       120

GATAGTTATG TGAGGGCTTA TTTGATACAA AGAGCAGACT TTCCCAATAC TCAAAGCTTA       180

TCAGTTACGT TATCGATAGC CAGTAATAAG TTAGCTTCAG GTCTTATGGG AAGCGACGCA       240

GTATCATCGT CGTTTATGCT GATGAACGAC GTGGGAGATT ACTTCGAGTG CGGCGTGTGT       300

CACAACAAAC CCTACTTAGG ACGGGAAGTT ATCTTCTGTA GGAAATACAT AGGTGGGAGA       360

GGAGTGGAGA TCACCACTGG TAAGAACTAC ACGTCGAACA ATTGGAACGA GGCGTCGTAC       420

GTAATACAAG TGAACGTAGT CGATGGGTTA GCACAGACCA CTGTTAATTC TACTTATACG       480

CAAACGGACG TTAGTGGTCT ACCCAAAAAT TGGACGCGTA TCTACAAAAT AACAAAGATA       540

GTGTCCGTAG ATCAGAACCT CTACCCTGGT TGTTTCTCAG ACTCGAAACT GGGTGTAATG       600

CGTATAAGGT CACTGTTAGT TTCCCCAGTG CGCATCTTCT TTAGGGATAT CTTATTGAAA       660

CCTTTGAAGA AATCGTTCAA CGCAAGAATC GAGGATGTGC TGAATATTGA CGACACGTCG       720

TTGTTAGTAC CGAGTCCTGT CGTACCAGAG TCTACGGGAG TGTAGGTCC ATCAGAGCAG        780

CTGGATGTAG TGGCTTTAAC GTCCGACGTA ACGGAATTGA TCAACACTAG GGGGCAAGGT       840

AAGATATGTT TTCCAGACTC AGTGTTATCG ATCAATGAAG CGGATATCTA CGATGAGCGG       900

TATTTGCCGA TAACGGAAGC TCTACAGATA AACGCAAGAC TACGCAGACT CGTTCTTTCG       960

```
AAAGGCGGGA GTCAAACACC ACGAGATATG GGGAATATGA TAGTGGCCAT GATACAACTT    1020

TTCGTACTCT ACTCTACTGT AAAGAATATA AGCGTCAAAG ACGGGTATAG GGTGGAGACC    1080

GAATTAGGTC AAAAGAGAGT CTACTTAAGT TATTCGGAAG TAAGGGAAGC TATATTAGGA    1140

GGGAAATACG GTGCGTCTCC AACCAACACT GTGCGATCCT TCATGAGGTA TTTTGCTCAC    1200

ACCACTATTA CTCTACTTAT AGAGAAGAAA ATTCAGCCAG CGTGTACTGC CCTAGCTAAG    1260

CACGGCGTCC CGAAGAGGTT CACTCCGTAC TGCTTCGACT TCGCACTACT GGATAACAGA    1320

TATTACCCGG CGGACGTGTT GAAGGCTAAC GCAATGGCTT GCGCTATAGC GATTAAATCA    1380

GCTAATTTAA GGCGTAAAGG TTCGGAGACG TATAACATCT TAGAAAGCAT TTGA          1434
```

(2) INFORMATION FOR SEQ ID NO:16:

(i) SEQUENCE CHARACTERISTICS:
        (A) LENGTH: 477 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:16:

```
Met Gly Ala Tyr Thr His Val Asp Phe His Glu Ser Arg Leu Leu Lys
 1               5                  10                  15

Asp Lys Gln Asp Tyr Leu Ser Phe Lys Ser Ala Asp Glu Ala Pro Pro
            20                  25                  30

Asp Pro Pro Gly Tyr Val Arg Pro Asp Ser Tyr Val Arg Ala Tyr Leu
        35                  40                  45

Ile Gln Arg Ala Asp Phe Pro Asn Thr Gln Ser Leu Ser Val Thr Leu
    50                  55                  60

Ser Ile Ala Ser Asn Lys Leu Ala Ser Gly Leu Met Gly Ser Asp Ala
65                  70                  75                  80

Val Ser Ser Ser Phe Met Leu Met Asn Asp Val Gly Asp Tyr Phe Glu
                85                  90                  95

Cys Gly Val Cys His Asn Lys Pro Tyr Leu Gly Arg Glu Val Ile Phe
            100                 105                 110

Cys Arg Lys Tyr Ile Gly Gly Arg Gly Val Glu Ile Thr Thr Gly Lys
        115                 120                 125

Asn Tyr Thr Ser Asn Asn Trp Asn Glu Ala Ser Tyr Val Ile Gln Val
    130                 135                 140

Asn Val Val Asp Gly Leu Ala Gln Thr Thr Val Asn Ser Thr Tyr Thr
145                 150                 155                 160

Gln Thr Asp Val Ser Gly Leu Pro Lys Asn Trp Thr Arg Ile Tyr Lys
                165                 170                 175

Ile Thr Lys Ile Val Ser Val Asp Gln Asn Leu Tyr Pro Gly Cys Phe
            180                 185                 190

Ser Asp Ser Lys Leu Gly Val Met Arg Ile Arg Ser Leu Leu Val Ser
        195                 200                 205

Pro Val Arg Ile Phe Phe Arg Asp Ile Leu Leu Lys Pro Leu Lys Lys
    210                 215                 220

Ser Phe Asn Ala Arg Ile Glu Asp Val Leu Asn Ile Asp Asp Thr Ser
225                 230                 235                 240

Leu Leu Val Pro Ser Pro Val Pro Glu Ser Thr Gly Gly Val Gly
                245                 250                 255

Pro Ser Glu Gln Leu Asp Val Val Ala Leu Thr Ser Asp Val Thr Glu
            260                 265                 270
```

```
Leu Ile Asn Thr Arg Gly Gln Gly Lys Ile Cys Phe Pro Asp Ser Val
    275                 280                 285

Leu Ser Ile Asn Glu Ala Asp Ile Tyr Asp Glu Arg Tyr Leu Pro Ile
    290                 295                 300

Thr Glu Ala Leu Gln Ile Asn Ala Arg Leu Arg Leu Val Leu Ser
305                 310                 315                 320

Lys Gly Gly Ser Gln Thr Pro Arg Asp Met Gly Asn Met Ile Val Ala
                325                 330                 335

Met Ile Gln Leu Phe Val Leu Tyr Ser Thr Val Lys Asn Ile Ser Val
                340                 345                 350

Lys Asp Gly Tyr Arg Val Glu Thr Glu Leu Gly Gln Lys Arg Val Tyr
            355                 360                 365

Leu Ser Tyr Ser Glu Val Arg Glu Ala Ile Leu Gly Gly Lys Tyr Gly
    370                 375                 380

Ala Ser Pro Thr Asn Thr Val Arg Ser Phe Met Arg Tyr Phe Ala His
385                 390                 395                 400

Thr Thr Ile Thr Leu Leu Ile Glu Lys Lys Ile Gln Pro Ala Cys Thr
                405                 410                 415

Ala Leu Ala Lys His Gly Val Pro Lys Arg Phe Thr Pro Tyr Cys Phe
                420                 425                 430

Asp Phe Ala Leu Leu Asp Asn Arg Tyr Tyr Pro Ala Asp Val Leu Lys
                435                 440                 445

Ala Asn Ala Met Ala Cys Ala Ile Ala Ile Lys Ser Ala Asn Leu Arg
            450                 455                 460

Arg Lys Gly Ser Glu Thr Tyr Asn Ile Leu Glu Ser Ile
465                 470                 475
```

(2) INFORMATION FOR SEQ ID NO:17:

(i) SEQUENCE CHARACTERISTICS:
        (A) LENGTH: 558 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:17:

```
ATGGAATTCA GACCAGTTTT AATTACAGTT CGCCGTGATC CCGGCGTAAA CACTGGTAGT    60

TTGAAAGTGA TAGCTTATGA CTTACACTAC GACAATATAT TCGATAACTG CGCGGTAAAG   120

TCGTTTCGAG ACACCGACAC TGGATTCACT GTTATGAAAG AATACTCGAC GAATTCAGCG   180

TTCATACTAA GTCCTTATAA ACTGTTTTCC GCGGTCTTTA ATAAGGAAGG TGAGATGATA   240

AGTAACGATG TAGGATCGAG TTTCAGGGTT TACAATATCT TTTCGCAAAT GTGTAAAGAT   300

ATCAACGAGA TCAGCGAGAT ACAACGCGCC GGTTACCTAG AAACATATTT AGGAGACGGG   360

CAGGCTGACA CTGATATATT TTTTGATGTC TTAACCAACA ACAAAGCAAA GGTAAGGTGG   420

TTAGTTAATA AAGACCATAG CGCGTGGTGT GGGATATTGA ATGATTTGAA GTGGGAAGAG   480

AGCAACAAGG AGAAATTTAA GGGGAGAGAC ATACTAGATA CTTACGTTTT ATCGTCTGAT   540

TATCCAGGGT TTAAATGA                                                 558
```

(2) INFORMATION FOR SEQ ID NO:18:

(i) SEQUENCE CHARACTERISTICS:
        (A) LENGTH: 185 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:18:

```
Met Glu Phe Arg Pro Val Leu Ile Thr Val Arg Arg Asp Pro Gly Val
  1               5                  10                  15

Asn Thr Gly Ser Leu Lys Val Ile Ala Tyr Asp Leu His Tyr Asp Asn
               20                  25                  30

Ile Phe Asp Asn Cys Ala Val Lys Ser Phe Arg Asp Thr Asp Thr Gly
               35                  40                  45

Phe Thr Val Met Lys Glu Tyr Ser Thr Asn Ser Ala Phe Ile Leu Ser
 50                  55                  60

Pro Tyr Lys Leu Phe Ser Ala Val Phe Asn Lys Glu Gly Glu Met Ile
 65                  70                  75                  80

Ser Asn Asp Val Gly Ser Ser Phe Arg Val Tyr Asn Ile Phe Ser Gln
                    85                  90                  95

Met Cys Lys Asp Ile Asn Glu Ile Ser Glu Ile Gln Arg Ala Gly Tyr
                   100                 105                 110

Leu Glu Thr Tyr Leu Gly Asp Gly Gln Ala Asp Thr Asp Ile Phe Phe
               115                 120                 125

Asp Val Leu Thr Asn Asn Lys Ala Lys Val Arg Trp Leu Val Asn Lys
130                 135                 140

Asp His Ser Ala Trp Cys Gly Ile Leu Asn Asp Leu Lys Trp Glu Glu
145                 150                 155                 160

Ser Asn Lys Glu Lys Phe Lys Gly Arg Asp Ile Leu Asp Thr Tyr Val
                   165                 170                 175

Leu Ser Ser Asp Tyr Pro Gly Phe Lys
                   180                 185
```

(2) INFORMATION FOR SEQ ID NO:19:

(i) SEQUENCE CHARACTERISTICS:
        (A) LENGTH: 534 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:19:

```
ATGAAGTTGC TTTCGCTCCG CTATCTTATC TTAAGGTTGT CAAAGTCGCT TAGAACGAAC      60

GATCACTTGG TTTTAATACT TATAAAGGAG GCGCTTATAA ACTATTACAA CGCCTCTTTC     120

ACCGATGAGG GTGCCGTATT AAGAGACTCT CGCGAAAGTA TAGAGAATTT TCTCGTAGCC     180

AGGTGCGGTT CGCAAAATTC CTGCCGAGTC ATGAAGGCTT TGATCACTAA CACAGTCTGT     240

AAGATGTCGA TAGAAACAGC CAGAAGTTTT ATCGGAGACT TAATACTCGT CGCCGACTCC     300

TCTGTTTCAG CGTTGGAAGA AGCGAAATCA ATTAAAGATA ATTTCCGCTT AAGAAAAAGG     360

AGAGGCAAGT ATTATTATAG TGGTGATTGT GGATCCGACG TTGCGAAAGT TAAGTATATT     420

TTGTCTGGGG AGAATCGAGG ATTGGGGTGC GTAGATTCCT TGAAGCTAGT TTGCGTAGGT     480

AGACAAGGAG GTGGAAACGT ACTACAGCAC CTACTAATCT CATCTCTGGG TTAA          534
```

(2) INFORMATION FOR SEQ ID NO:20:

(i) SEQUENCE CHARACTERISTICS:
        (A) LENGTH: 177 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:20:

```
Met Lys Leu Leu Ser Leu Arg Tyr Leu Ile Leu Arg Leu Ser Lys Ser
  1               5                  10                  15

Leu Arg Thr Asn Asp His Leu Val Leu Ile Leu Ile Lys Glu Ala Leu
             20                  25                  30

Ile Asn Tyr Tyr Asn Ala Ser Phe Thr Asp Glu Gly Ala Val Leu Arg
         35                  40                  45

Asp Ser Arg Glu Ser Ile Glu Asn Phe Leu Val Ala Arg Cys Gly Ser
     50                  55                  60

Gln Asn Ser Cys Arg Val Met Lys Ala Leu Ile Thr Asn Thr Val Cys
 65                  70                  75                  80

Lys Met Ser Ile Glu Thr Ala Arg Ser Phe Ile Gly Asp Leu Ile Leu
                 85                  90                  95

Val Ala Asp Ser Ser Val Ser Ala Leu Glu Glu Ala Lys Ser Ile Lys
            100                 105                 110

Asp Asn Phe Arg Leu Arg Lys Arg Arg Gly Lys Tyr Tyr Tyr Ser Gly
        115                 120                 125

Asp Cys Gly Ser Asp Val Ala Lys Val Lys Tyr Ile Leu Ser Gly Glu
    130                 135                 140

Asn Arg Gly Leu Gly Cys Val Asp Ser Leu Lys Leu Val Cys Val Gly
145                 150                 155                 160

Arg Gln Gly Gly Gly Asn Val Leu Gln His Leu Leu Ile Ser Ser Leu
                165                 170                 175

Gly
```

(2) INFORMATION FOR SEQ ID NO:21:

(i) SEQUENCE CHARACTERISTICS:
        (A) LENGTH: 540 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:21:

```
ATGGACCTAT CGTTTATTAT TGTGCAGATC CTTTCCGCCT CGTACAATAA TGACGTGACA      60

GCACTTTACA CTTTGATTAA CGCGTATAAT AGCGTTGATG ATACGACGCG CTGGGCAGCG     120

ATAAACGATC CGCAAGCTGA GGTTAACGTC GTGAAGGCTT ACGTAGCTAC TACAGCGACG     180

ACTGAGCTGC ATAGAACAAT TCTCATTGAC AGTATAGACT CCGCCTTCGC TTATGACCAA     240

GTGGGGTGTT TGGTGGGCAT AGCTAGAGGT TTGCTTAGAC ATTCGGAAGA TGTTCTGGAG     300

GTCATCAAGT CGATGGAGTT ATTCGAAGTG TGTCGTGGAA AGAGGGGAAG CAAAAGATAT     360

CTTGGATACT TAAGTGATCA ATGCACTAAC AAATACATGA TGCTAACTCA GGCCGGACTG     420

GCCGCAGTTG AAGGAGCAGA CATACTACGA ACGAATCATC TAGTCAGTGG TAATAAGTTC     480

TCTCCAAATT TCGGGATCGC TAGGATGTTG CTCTTGACGC TTTGTTGCGG AGCACTATAA     540
```

(2) INFORMATION FOR SEQ ID NO:22:

(i) SEQUENCE CHARACTERISTICS:
        (A) LENGTH: 179 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:22:

```
Met Asp Leu Ser Phe Ile Ile Val Gln Ile Leu Ser Ala Ser Tyr Asn
1               5                   10                  15

Asn Asp Val Thr Ala Leu Tyr Thr Leu Ile Asn Ala Tyr Asn Ser Val
            20                  25                  30

Asp Asp Thr Thr Arg Trp Ala Ala Ile Asn Asp Pro Gln Ala Glu Val
        35                  40                  45

Asn Val Val Lys Ala Tyr Val Ala Thr Ala Thr Thr Glu Leu His
    50                  55                  60

Arg Thr Ile Leu Ile Asp Ser Ile Asp Ser Ala Phe Ala Tyr Asp Gln
65                  70                  75                  80

Val Gly Cys Leu Val Gly Ile Ala Arg Gly Leu Leu Arg His Ser Glu
                85                  90                  95

Asp Val Leu Glu Val Ile Lys Ser Met Glu Leu Phe Glu Val Cys Arg
                100                 105                 110

Gly Lys Arg Gly Ser Lys Arg Tyr Leu Gly Tyr Leu Ser Asp Gln Cys
            115                 120                 125

Thr Asn Lys Tyr Met Met Leu Thr Gln Ala Gly Leu Ala Ala Val Glu
        130                 135                 140

Gly Ala Asp Ile Leu Arg Thr Asn His Leu Val Ser Gly Asn Lys Phe
145                 150                 155                 160

Ser Pro Asn Phe Gly Ile Ala Arg Met Leu Leu Leu Thr Leu Cys Cys
                165                 170                 175

Gly Ala Leu
```

(2) INFORMATION FOR SEQ ID NO:23:

(i) SEQUENCE CHARACTERISTICS:
        (A) LENGTH: 183 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:23:

```
ATGAGGCACT TAGAAAAACC CATCAGAGTA GCGGTACACT ATTGCGTCGT GCGAAGTGAC      60

GTTTGTGACG GGTGGGATGT ATTTATAGGC GTAACGTTAA TCGGTATGTT TATTAGTTAC     120

TATTTATATG CTCTAATTAG CATATGTAGA AAAGGAGAAG GTTTAACAAC CAGTAATGGG     180

TAA                                                                    183
```

(2) INFORMATION FOR SEQ ID NO:24:

(i) SEQUENCE CHARACTERISTICS:
        (A) LENGTH: 60 amino acids
        (B) TYPE: amino acid
        (C) STRANDEDNESS:
        (D) TOPOLOGY: linear (ii) MOLECULE TYPE: protein (xi) SEQUENCE DESCRIPTION: SEQ ID NO:24:

```
Met Arg His Leu Glu Lys Pro Ile Arg Val Ala Val His Tyr Cys Val
1               5                   10                  15

Val Arg Ser Asp Val Cys Asp Gly Trp Asp Val Phe Ile Gly Val Thr
            20                  25                  30
```

```
        Leu Ile Gly Met Phe Ile Ser Tyr Tyr Leu Tyr Ala Leu Ile Ser Ile
             35                  40                  45

Cys Arg Lys Gly Glu Gly Leu Thr Thr Ser Asn Gly
         50                  55                  60
```

(2) INFORMATION FOR SEQ ID NO:25:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:25:

GGGGGGGGGA CGTTGGAGGT GTCG                                      24

(2) INFORMATION FOR SEQ ID NO:26:

(i) SEQUENCE CHARACTERISTICS:
        (A) LENGTH: 15 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:26:

GGAGGGAACG CGAGG                                                15

(2) INFORMATION FOR SEQ ID NO:27:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:27:

ATAAGCATTC GGGATGGACC                                      20

(2) INFORMATION FOR SEQ ID NO:28:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:28:

ATTAACTTGA CGGATGGCAC GC                                    22

(2) INFORMATION FOR SEQ ID NO:29:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:29:

TACTTATCTA GAACCATGGA AGCGAGTCGA CGACTA                  36

-continued (2) INFORMATION FOR SEQ ID NO:30:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:30:

TCTTGAGGAT CCATGGAGAA ACATCGTCGC ATACTA          36

(2) INFORMATION FOR SEQ ID NO:31:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:31:

ACTATTTCTA GAACCATGGC ATTTGAACTG AAATT          35

(2) INFORMATION FOR SEQ ID NO:32:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO:32:

TTCTGAGGAT CCATGGTATA AGCTCCCATG AATTAT          36

What is claimed:

1. A transgenic Vitis scion cultivar or rootstock cultivar comprising a DNA molecule encoding a protein or polypeptide of a grapevine leafroll virus.

2. A transgenic Vitis scion cultivar or rootstock cultivar according to claim 1, wherein the protein or polypeptide is selected from a group consisting of a helicase, an RNA-dependent RNA polymerase, an hsp70-related, an hsp90-related, and a coat protein or polypeptide.

3. A transgenic Vitis scion cultivar or rootstock cultivar according to claim 2, wherein the protein or polypeptide is a helicase having a molecular weight of from about 146 to about 151 kDa.

4. A transgenic Vitis scion cultivar or rootstock cultivar according to claim 2, wherein the protein or polypeptide is an RNA-dependent RNA polymerase having a molecular weight of from about 59 to about 63 kDa.

5. A transgenic Vitis scion cultivar of rootstock cultivar according to claim 4, wherein the protein or polypeptide comprises an amino acid sequence corresponding to SEQ. ID. No. 4.

6. A transgenic Vitis scion cultivar or rootstock cultivar according to claim 5, wherein the DNA molecule comprises a nucleotide sequence corresponding to SEQ. ID. No. 3.

7. A transgenic Vitis scion cultivar or rootstock cultivar according to claim 2, wherein the protein or polypeptide is an hsp70-related protein or polypeptide having a molecular weight of from about 57 to about 61 kDa.

8. A transgenic Vitis scion cultivar or rootstock cultivar according to claim 7, wherein the protein or polypeptide comprises an amino acid sequence corresponding to SEQ. ID. No. 6.

9. A transgenic Vitis scion cultivar or rootstock cultivar according to claim 8, wherein the DNA molecule comprises a nucleotide sequence corresponding to SEQ. ID. No. 5.

10. A transgenic Vitis scion cultivar or rootstock cultivar according to claim 2, wherein the protein or polypeptide is an hsp90-related protein or polypeptide having a molecular weight of from about 53 to about 57 kDa.

11. A transgenic Vitis scion cultivar or rootstock cultivar according to claim 10, wherein the protein or polypeptide comprises an amino acid sequence corresponding to SEQ. ID. No. 8.

12. A transgenic Vitis scion cultivar or rootstock cultivar according to claim 11, wherein the DNA molecule comprises a nucleotide sequence corresponding to SEQ. ID. No. 7.

13. A transgenic Vitis scion cultivar or rootstock cultivar according to claim 2, wherein the protein or polypeptide is a coat protein or polypeptide having a molecular weight of from about 33 to about 43 kDa.

14. A transgenic Vitis scion cultivar or rootstock cultivar according to claim 13, wherein the protein or polypeptide comprises an amino acid sequence corresponding to SEQ. ID. No. 10.

15. A transgenic Vitis scion cultivar or rootstock cultivar according to claim 14, wherein the DNA molecule comprises a nucleotide sequence corresponding to SEQ. ID. No. 9.

16. A transgenic Vitis scion cultivar or rootstock cultivar according to claim 1, wherein the protein or polypeptide comprises an amino acid sequence corresponding to SEQ. ID. No. 12.

17. A transgenic Vitis scion cultivar or rootstock cultivar according to claim 16, wherein the DNA molecule comprises a nucleotide sequence corresponding to SEQ. ID. No. 11.

18. A transgenic Vitis scion cultivar or rootstock cultivar according to claim 1, wherein the protein or polypeptide comprises an amino acid sequence corresponding to SEQ. ID. No. 14.

19. A transgenic Vitis scion cultivar or rootstock cultivar according to claim 18, wherein the DNA molecule comprises a nucleotide sequence corresponding to SEQ. ID. No. 13.

20. A transgenic Vitis scion cultivar or rootstock cultivar according to claim 1, wherein the protein or polypeptide comprises an amino acid sequence corresponding to SEQ. ID. No. 16.

21. A transgenic Vitis scion cultivar or rootstock cultivar according to claim 20, wherein the DNA molecule comprises a nucleotide sequence corresponding to SEQ. ID. No. 15.

22. A transgenic Vitis scion cultivar or rootstock cultivar according to claim 1, wherein the protein or polypeptide comprises an amino acid sequence corresponding to SEQ. ID. No. 18.

23. A transgenic Vitis scion cultivar or rootstock cultivar according to claim 22, wherein the DNA molecule comprises a nucleotide sequence corresponding to SEQ. ID. No. 17.

24. A transgenic Vitis scion cultivar or rootstock cultivar according to claim 1, wherein the protein or polypeptide comprises an amino acid sequence corresponding to SEQ. ID. No. 20.

25. A transgenic Vitis scion cultivar or rootstock cultivar according to claim 24, wherein the DNA molecule comprises a nucleotide sequence corresponding to SEQ. ID. No. 19.

26. A transgenic Vitis scion cultivar or rootstock cultivar according to claim 1, wherein the protein or polypeptide comprises an amino acid sequence corresponding to SEQ. ID. No. 22.

27. A transgenic Vitis scion cultivar or rootstock cultivar according to claim 26, wherein the DNA molecule comprises a nucleotide sequence corresponding to SEQ. ID. No. 21.

28. A transgenic Vitis scion cultivar or rootstock cultivar according to claim 1, wherein the protein or polypeptide comprises an amino acid sequence corresponding to SEQ. ID. No. 24.

29. A transgenic Vitis scion cultivar or rootstock cultivar according to claim 28, wherein the DNA molecule comprises a nucleotide sequence corresponding to SEQ. ID. No. 23.

30. A transgenic Vitis scion cultivar or rootstock cultivar according to claim 1, wherein the grapevine leafroll virus is GLRaV-3.

31. A transgenic Vitis scion cultivar or rootstock cultivar comprising a DNA molecule for a grapevine leafroll virus protein or polypeptide selected from the group consisting of a helicase, an RNA-dependent RNA polymerase, an hsp70-related protein or polypeptide, and a coat protein or polypeptide.

32. A transgenic Vitis scion cultivar or rootstock cultivar according to claim 31, wherein the grapevine leafroll virus protein or polypeptide is an RNA-dependent RNA polymerase.

33. A transgenic Vitis scion cultivar or rootstock cultivar according to claim 31, wherein the grapevine leafroll virus protein or polypeptide is an hsp70-related protein or polypeptide.

34. A transgenic Vitis scion cultivar or rootstock cultivar according to claim 31, wherein the grapevine leafroll virus protein or polypeptide is a coat protein or polypeptide.

* * * * *